United States Patent
Clapham et al.

(10) Patent No.: US 9,012,651 B2
(45) Date of Patent: Apr. 21, 2015

(54) TRPV3 MODULATORS

(75) Inventors: Bruce Clapham, Lindenhurst, IL (US); Phil B. Cox, Grayslake, IL (US); Michael J. Dart, Highland Park, IL (US); Arthur Gomtsyan, Vernon Hills, IL (US); Tammie K. Jinkerson, Pleasant Prairie, WI (US); Ryan G. Keddy, Beach Park, IL (US); Michael E. Kort, Lake Bluff, IL (US); Philip R. Kym, Libertyville, IL (US); Mark Matulenko, Libertyville, IL (US); Robert G. Schmidt, Antioch, IL (US); Clara I. Villamil, Glenview, IL (US); Eric A. Voight, Pleasant Prairie, WI (US); Kevin R. Woller, Antioch, IL (US)

(73) Assignee: AbbVie Inc., North Chicago, IL (US)

( * ) Notice: Subject to any disclaimer, the term of this patent is extended or adjusted under 35 U.S.C. 154(b) by 281 days.

(21) Appl. No.: 13/428,259

(22) Filed: Mar. 23, 2012

(65) Prior Publication Data
US 2012/0245124 A1     Sep. 27, 2012

Related U.S. Application Data

(60) Provisional application No. 61/467,143, filed on Mar. 24, 2011.

(51) Int. Cl.
| | | |
|---|---|---|
| *C07D 401/04* | (2006.01) | |
| *C07D 401/14* | (2006.01) | |
| *C07D 409/04* | (2006.01) | |
| *C07D 417/04* | (2006.01) | |
| *A61K 31/444* | (2006.01) | |
| *A61P 29/00* | (2006.01) | |
| *C07D 213/61* | (2006.01) | |
| *A61K 31/44* | (2006.01) | |
| *A61K 31/505* | (2006.01) | |
| *C07D 211/06* | (2006.01) | |
| *C07D 239/28* | (2006.01) | |
| *C07D 239/30* | (2006.01) | |
| *C07D 401/12* | (2006.01) | |
| *C07D 413/12* | (2006.01) | |
| *C07D 413/14* | (2006.01) | |
| *C07D 417/12* | (2006.01) | |
| *C07D 405/14* | (2006.01) | |
| *C07D 213/74* | (2006.01) | |
| *C07D 401/10* | (2006.01) | |
| *C07D 405/04* | (2006.01) | |
| *C07D 239/26* | (2006.01) | |
| *C07D 417/10* | (2006.01) | |
| *C07D 213/38* | (2006.01) | |
| *C07D 213/64* | (2006.01) | |

(52) U.S. Cl.
CPC .............. *C07D 213/61* (2013.01); *A61K 31/44* (2013.01); *A61K 31/505* (2013.01); *C07D 211/06* (2013.01); *C07D 239/28* (2013.01); *C07D 239/30* (2013.01); *C07D 401/12* (2013.01); *C07D 413/12* (2013.01); *C07D 413/14* (2013.01); *C07D 417/12* (2013.01); *C07D 405/14* (2013.01); *C07D 213/74* (2013.01); *C07D 401/04* (2013.01); *C07D 401/10* (2013.01); *C07D 405/04* (2013.01); *C07D 239/26* (2013.01); *C07D 409/04* (2013.01); *C07D 417/04* (2013.01); *C07D 417/10* (2013.01); *C07D 213/38* (2013.01); *C07D 213/64* (2013.01)

(58) Field of Classification Search
USPC ........................................ 546/268.1; 514/336
See application file for complete search history.

(56) References Cited

U.S. PATENT DOCUMENTS

| | | |
|---|---|---|
| 5,112,828 A | 5/1992 | Zipperer et al. |
| 6,114,532 A | 9/2000 | Ries et al. |
| 7,396,910 B2 | 7/2008 | Bevan et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |

(Continued)

FOREIGN PATENT DOCUMENTS

| | | |
|---|---|---|
| CN | 101883772 A | 11/2010 |
| EP | 0400344 A1 | 12/1990 |

(Continued)

OTHER PUBLICATIONS

Alexander et al., "The Photochemical Synthesis of a Tricyclo[2.2.0. 02,5]hexane," J. American Chem. Soc., 1976, 98(14): 4324-4325.

(Continued)

*Primary Examiner* — Venkataraman Balasubramanian

(57) ABSTRACT

Disclosed herein are modulators of TRPV3 of formula (I)

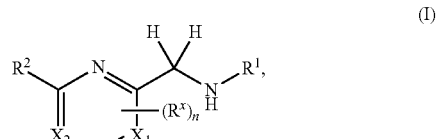

wherein $X_1$, $X_2$, $R^1$, $R^2$, $R^x$, and n are as defined in the specification. Compositions comprising such compounds and methods for treating conditions and disorders using such compounds and compositions are also presented.

9 Claims, No Drawings

(56) References Cited

U.S. PATENT DOCUMENTS

| | | | |
|---|---|---|---|
| 7,531,685 B2 | 5/2009 | Czarnik | |
| 7,534,814 B2 | 5/2009 | Ascher et al. | |
| 7,538,189 B2 | 5/2009 | Naicker et al. | |
| 2004/0019044 A1* | 1/2004 | Dorsch et al. | 514/227.8 |
| 2007/0167491 A1* | 7/2007 | Mansfield et al. | 514/340 |
| 2008/0153871 A1 | 6/2008 | Bayburt et al. | |
| 2008/0280868 A1* | 11/2008 | Eatherton et al. | 514/210.2 |
| 2009/0082471 A1 | 3/2009 | Czarnik | |
| 2009/0088416 A1 | 4/2009 | Czarnik | |
| 2009/0088456 A1* | 4/2009 | Coqueron et al. | 514/332 |
| 2009/0093422 A1 | 4/2009 | Tung et al. | |
| 2009/0093516 A1 | 4/2009 | Li et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2012/0010190 A1 | 1/2012 | Bissantz et al. | |

FOREIGN PATENT DOCUMENTS

| | | |
|---|---|---|
| IN | 200900517 A2 | 11/2010 |
| WO | 9429281 A1 | 12/1994 |
| WO | 9504042 A1 | 2/1995 |
| WO | 9507271 A1 | 3/1995 |
| WO | 9710223 A1 | 3/1997 |
| WO | 9940072 A1 | 8/1999 |
| WO | 0222572 A2 | 3/2002 |
| WO | 03086294 A2 | 10/2003 |
| WO | 03086294 A3 | 10/2003 |
| WO | 2004043958 A1 | 5/2004 |
| WO | 2005099353 A2 | 10/2005 |
| WO | 2006008754 A1 | 1/2006 |
| WO | 2006122156 A2 | 11/2006 |
| WO | 2007056124 A2 | 5/2007 |
| WO | WO-2008075196 A1 | 6/2008 |
| WO | 2010004379 A2 | 1/2010 |
| WO | 2010070452 A1 | 6/2010 |
| WO | WO-2010063634 A1 | 6/2010 |
| WO | 2012019315 A1 | 2/2012 |
| WO | 2013062966 A2 | 5/2012 |
| WO | 2013062964 A2 | 5/2013 |

OTHER PUBLICATIONS

Aley et al., "Nitric oxide signaling in pain and nociceptor sensitization in the rat," J Neurosci., 1998, 18(17): 7008-7014.
Berge et al., "Pharmaceutical salts," J. Pharm Sci., 1977, 66(1): 1-19.
Beylot et al., "In vivo studies of intrahepatic metabolic pathways," Diabetes Metab., 1997, 23(3): 251-257.
Blagojevic et al., "Role of Heavy Water in Boron Neutron Capture Therapy," Topics in Dosimetry & Treatment Planning for Neutron Capture Therapy, R. Zamenhoff, G. Solares, O. Harling, Editors, 1994, Advanced Medical Publishing, Madison Wisconsin, pp. 125-134.
Blake et al., "Studies with deuterated drugs," J Pharm Sci., 1975, 64(3): 367-391.
Brickner et al., "Synthesis and antibacterial activity of U-100592 and U-100766, two oxazolidinone antibacterial agents for the potential treatment of multidrug-resistant gram-positive bacterial infections," J Med Chem., 1996, 39(3): 673-679.
Caterina, MJ, "Transient receptor potential ion channels as participants in thermosensation and thermoregulation," Am J Physiol Regul Integr Comp Physiol., 2007, 292(1): R64-R76.
Caterina et al., "A capsaicin-receptor homologue with a high threshold for noxious heat," Nature, 1999, 398(6726): 436-441.
Chung et al., "2-aminoethoxydiphenyl borate activates and sensitizes the heat-gated ion channel TRPV3," J Neurosci. 2004, 24(22):5177-5182.
Chung et al., "Biphasic currents evoked by chemical or thermal activation of the heat-gated ion channel, TRPV3," J Biol Chem., 2005, 280(16): 15928-15941.
Chung et al., "Warm temperatures activate TRPV4 in mouse 308 keratinocytes," J Biol Chem., 2003, 278(34): 32037-32046.
Chung et al., "TRPV3 and TRPV4 mediate warmth-evoked currents in primary mouse keratinocytes," J Biol Chem., 2004, 279(20): 21569-21575.
Coppi et al., "2-Lithiated-2-phenyloxetane: a new attractive synthon for the preparation of oxetane derivatives," Chem. Commun (Camb)., 2011, 47(35): 9918-9920.
Cross, LC. et al., "IUPAC Commission on Nomenclature of Organic Chemistry: Rules for the Nomenclature of Organic Chemistry, Section E: Stereochemistry," Pure and Applied Chemistry. 1976, vol. 45, pp. 13-30.
Czajka et al., "Effect of deuterium oxide on the reproductive potential of mice," Ann N Y Acad Sci., 1960, 84: 770-779.
Czajka et al., "Physiological effects of deuterium on dogs," Am J Physiol. 1961, 201(2): 357-362.
Dörwald, FZ, "1.3 Hard and Soft Acids and Bases," Side Reactions in Organic Synthesis, 2005, Wiley-VCH, Weinheim, 390 pages.
Drug labeling information or Tylenol® with codeine, Revised Aug. 2010, taken from PDR®3D™ (Digital Drug Database) available at www.pdrnetwork.com, printed Mar. 22, 2013 (9 pages).
Facer et al., "Differential expression of the capsaicin receptor TRPV1 and related novel receptors TRPV3, TRPV4 and TRPM8 in normal human tissues and changes in traumatic and diabetic neuropathy," BMC Neurol., 2007, 7: 11-22.
Foster et al., "Deuterium Isotope Effects in the Metabolism of Drugs and Xenobiotics: Implications for Drug Design," Advances in Drug Research, 1985, vol. 14 Academic press, London, pp. 2-36.
Greene, T. et al., Editor, Protective Groups in Organic Synthesis (3rd ed.), John Wiley & Sons, NY, 1999, (20 pages, Table of Contents).
Güler et al., "Heat-evoked activation of the ion channel, TRPV4," J Neurosci., 2002, 22(15): 6408-6414.
Hailes et al., "2.05—Oxetanes and Oxetenes: Monocyclic" Comprehensive Heterocyclic Chemistry III, Elsevier, Oxford, 2008, pp. 321-364.
Hardouin et al, "BF3•OEt2-Mediated Rearrangement of Cyclopropyl Carbinols: A Concise Route to Polycyclic Cyclobutanes," J. Org. Chem., 2001, 66(12): 4450-4452.
Harper et al., "1-3,4-Dichlorobenzamidomethyl)cyclohexyldimethylamine and Related Compounds as Potential Analgesics," Journal of Medicinal Chemistry, 1974, 17(11): 1188-1193.
Hattersley et al., "Some Reactions with 4-Cyano-4-phenyltetrahydropyran" Journal of Medicinal Chemistry, 1967, 10(1): 128-129.
Hu et al., "2-aminoethoxydiphenyl borate is a common activator of TRPV1, TRPV2, and TRPV3," J Biol Chem., 2004, 279(34): 35741-35748.
Hu et al., "Potentiation of TRPV3 channel function by unsaturated fatty acids," J Cell Physiol. 2006, 208(1): 201-212.
Kanemoto et al., "Novel Synthesis of Monofluorocyclobutanes by the Ring Expansion Fluorination of Cyclopropylmethanols With an Amine-Metal, Fluoride-Pyridinium Poly(Hydrogen Fluoride)-Complex," Tetrahedron Letters, 1987, 28(5): 6313-6316.
Kato et al., "Synthesis of Deuterated Mosapride Citrate," J Labelled Compd Rad., 1995, 36(10): 927-932.
Kushner et al., "Pharmacological uses and perspectives of heavy water and deuterated compounds," Can J Physiol Pharmacol., 1999, 77(2): 79-88.
Lee et al., "TRPV channels as thermosensory receptors in epithelial cells," Pflugers Arch.—Eur J Physiol. 2005, 451(1): 160-167.
Lee-Ruff et al., "Enantiomerically pure cyclobutane derivatives and their use in organic synthesis," Chem Rev., 2003, 103(4): 1449-1483.
Lizondo et al., "Linezolid. Oxazolidinone Antibacterial," Drugs Fut., 1996, 21(11): 1116-1123.
MacPherson et al., "More than cool: promiscuous relationships of menthol and other sensory compounds" Mol Cell Neurosci. 2006, 32(4): 335-343.

(56) References Cited

OTHER PUBLICATIONS

Mallesham et al., "Highly efficient CuI-catalyzed coupling of aryl bromides with oxazolidinones using Buchwald's protocol: a short route to linezolid and toloxatone," Org Lett., 2003, 5(7): 963-965.
McCarty et al., "Central Stimulants. α,α-Disubstituted 2-Piperidinemethanols and 1,1-Disubstitued Heptahydrooxazolo [3,4-a]pyridines," J. Am. Chem. Soc., 1957, 179(2): 472-480.
Montell, C. "Preventing a Perm with TRPV3," Cell, 2010, 141(2): 218-220.
Moqrich, A. et al., "Impaired thermosensation in mice lacking TRPV3, a heat and camphor sensor in the skin," Science 2005, 307(5714): 1468-1472.
Moussaieff et al., "Incensole acetate, an incense component, elicits psychoactivity by activating TRPV3 channels in the brain," FASEB J., 2008, 22(8): 3024-3034.
Nilius et al., "Transient receptor potential cation channels in disease," Physiol Rev., 2007, 87(1): 165-217.
Okuhara et al., "Transient receptor potential channels as drug targets," Expert Opin Ther Targets, 2007, 11(3): 391-401.
Ong et al., "Novel Tetracyclic Spiropiperidines. II. Synthesis of 2-Aryl-2,3-dihydrospiro[benzofuran-3,4'-piperidines] (1,2)," Journal of Heterocyclic Chemistry, 1981, 18(4): 815-820.
Peier et al., "A heat-sensitive TRP channel expressed in keratinocytes," Science, 2002, 296(5575): 2046-2049.
Prescott, D.M., Editor, "Methods in Cell Biology," vol. XIV, Academic Press, New York, N.Y. 1976, 12 pages.
Smith et al., "TRPV3 is a temperature-sensitive vanilloid receptor-like protein," Nature 2002, 418(6894): 186-190.
Stewhoff et al., "A TR(I)P to pruritus research: role of TRPV3 in inflammation and itch," J. Invest. Dermatology, 2009, 129(3): 531-535.
Thomson JF, "Physiological effects of D20 in mammals," Ann NY Acad Sci., 1960, 84: 736-744.
Vogt-Eisele et al., "Monoterpenoid agonists of TRPV3," Br J Pharmacol. 2007, 151(4): 530-540.
Wermuth Editor, The Practice of Medicinal Chemistry, 3rd Edition, Elsevier, 2008, pp. 126, 276, 294, 328, 343, 350, 431, 432, 440, 452, 533, 535, 536, 724 and 725.
Wissenbach et al., "TRP channels as potential drug targets," Biology of the Cell, (2004), 96(1): 47-54.
Xu et al., "Camphor activates and strongly desensitizes the transient receptor potential vanilloid subtype 1 channel in a vanilloid-independent mechanism," J Neurosci. 2005, 25(39): 8924-8937.
Xu et al., "Oregano, thyme and clove-derived flavors and skin sensitizers activate specific TRP channels," Nat Neurosci. 2006, 9(5): 628-635.
Xu et al., "TRPV3 is a calcium-permeable temperature-sensitive cation channel," Nature, 2002, 418(6894): 181-186.
Yoshida et al., Editors, "Nitric oxide activates TRP channels by cysteine 5-nitrosylation," Nat Chem Biol., 2006, 2(11): 596-607.
Yus et al., "Intramolecular carbolithiation promoted by a DTBB-catalysed chlorine-lithium exchange," Tetrahedron, 2003, 59(43):8525-8542.
Zhang et al., "Cyclization reactions of 3,3-dimethyl-1-(1H-1,2,4-triazolo-1-yl)-2-butanone or substituted 1-(1H-1,2,4-triazolo-1-yl)acetophenone with dibromide compounds and its biological activities," Gaodeng Xuexiao Huaxue Xuebao, 24(3): 431-435 (retrieved from STN Database accession No. 2003:247751 abstract).
International Search Report for PCT/US2012/030096, dated Jul. 4, 2012.

* cited by examiner

TRPV3 MODULATORS

RELATED APPLICATION INFORMATION

This application claims the benefit of U.S. Patent Application No. 61/467,143 filed on Mar. 24, 2011, the contents of which are herein incorporated by reference.

TECHNICAL FIELD

Compounds that are Transient Receptor Potential Vanilloid 3 (TRPV3) modulators, compositions comprising such compounds, and methods for treating conditions and disorders using such compounds and compositions, are disclosed herein.

BACKGROUND OF THE INVENTION

A subset of the vanilloid channels (TRPV1-4) are referred to as thermoTRPs to reflect the observation that heat elicits channel opening across a continuum of temperatures with thresholds ranging from 25° C. to 52° C. (Caterina, M. J.; Rosen, T. A.; Tominaga, M.; Brake, A. J.; Julius, D., *Nature* 1999, 398, 436-441). TRPV3 characteristically responds to innocuous heat >31° C., exhibits exquisite sensitivity around the physiological temperature of humans, 37° C., and sensitizes dramatically following repetitive heating (Smith, G. D.; Gunthorpe, M. J.; Kelsell, R. E.; Hayes, P. D.; Reilly, P.; Facer, P.; Wright, J. E.; Jerman, J. C.; Walhin, J. P.; Ooi, L.; Egerton, J.; Charles, K. J.; Smart, D.; Randall, A. D.; Anand, P.; Davis, J. B., *Nature* 2002, 418, 186-190.; Xu, H.; Ramsey, I. S.; Kotecha, S. A.; Moran, M. M.; Chong, J. A.; Lawson, D.; Ge, P.; Lilly, J.; Silos-Santiago, I.; Xie, Y.; DiStefano, P. S.; Curtis, R.; Clapham, D. E., *Nature* 2002, 418, 181-186; Peier, A. M.; Reeve, A. J.; Andersson, D. A.; Moqrich, A.; Earley, T. J.; Hergarden, A. C.; Story, G. M.; Colley, S.; Hogenesch, J. B.; McIntyre, P.; Bevan, S.; Patapoutian, A., *Science* 2002, 296, 2046-2049).

TRPV3 is a nonselective cation channel with permeability for calcium, but also to other cations, for example sodium. Multiple compounds that have been shown to activate TRPV3, include: monoterpenes, camphor (Peier, A. M. et al., 2002; Moqrich, A.; Hwang, S. W.; Earley, T. J.; Petrus, M. J.; Murray, A. N.; Spencer, K. S.; Andahazy, M.; Story, G. M.; Patapoutian, A., *Science* 2005, 307, 1468-1472; Xu, H.; Blair, N. T.; Clapham, D. E., *J Neurosci.* 2005, 25, 8924-8937), carvacrol, and thymol (Xu, H.; Delling, M.; Jun, J. C.; Clapham, D. E. *Nat Neurosci.* 2006, 9, 628-635; Vogt-Eisele, A. K.; Weber, K.; Sherkheli, M. A.; Vielhaber, G.; Panten, J.; Gisselmann, G.; Hatt, H., *Br J Pharmacol.* 2007, 151, 530-540; Earley, S.; Gonzales, A. L.; Garcia, Z. I., *Mol Pharmacol.* 2010, Jan. 19); menthol (Macpherson, L. J.; Hwang, S. W.; Miyamoto, T.; Dubin, A. E.; Patapoutian, A; Story, G. M., *Mol Cell Neurosci.* 2006, 32, 335-343; Vogt-Eisele, A. K. et al., 2007); cinnamaldehyde (Macpherson, L. J. et al., 2006); incensole acetate (Moussaieff, A.; Rimmerman, N.; Bregman, T.; Straiker, A.; Felder, C. C.; Shoham, S.; Kashman, Y.; Huang, S. M.; Lee, H.; Shohami, E.; Mackie, K.; Caterina, M. J.; Walker, J. M.; Fride, E.; Mechoulam, R., *FASEB J.* 2008, 22, 3024-3034.); and vanilloid analogs, eugenol and ethyl vanillin (Hu, H. Z.; Gu, Q.; Wang, C.; Colton, C. K.; Tang, J.; Kinoshita-Kawada, M.; Lee, L. Y.; Wood, J. D.; Zhu, M. X., *J Biol Chem.* 2004, 279, 35741-35748; Vogt-Eisele, A. K. et al., 2007; Xu, H. et al., 2006). Though relatively weak ($EC_{50}$, ~40 μM) and nonspecific across TRPs, 2-aminoethoxydiphenylborate (2-APB) and diphenylboronic anhydride (DPBA) have been widely and productively used to characterize key attributes of TRPV3 in cellular assays and electrophysiology (Hu, H. Z. et al., 2004; Chung, M. K.; Lee, H.; Mizuno, A.; Suzuki, M.; Caterina, M. J. *J Neurosci.* 2004, 24, 5177-5182; Chung, M. K.; Giller, A. D.; Caterina, M. J., *J Biol Chem.* 2005, 280, 15928-15941). While heat and direct ligand binding are clearly central to TRPV3 pharmacology, accumulating evidence of potentiation by arachidonic acid, other unsaturated fatty acid derivatives (Hu, H. Z.; Xiao, R.; Wang, C.; Gao, N.; Colton, C. K.; Wood, J. D.; Zhu, M. X., *J Cell Physiol.* 2006, 208, 201-212), and nitric oxide (Aley, K. O.; McCarter, G.; Levine, J. D., *J Neurosci.* 1998, 18, 7008-7014; Yoshida, T.; Inoue, R.; Morii, T.; Takahashi, N.; Yamamoto, S.; Hara, Y.; Tominaga, M.; Shimizu, S.; Sato, Y.; Mori, Y., *Nat Chem Biol.* 2006, 2, 596-607) suggests that authentic activation involves stimulation of G protein-coupled receptors and downstream second messenger signal cascades (e.g., phospholipase C, protein kinase C) that mediate local inflammatory responses and nociceptor sensitization that could enhance TRPV3 function (Xu, H. et al., 2006) in a pathophysiological, as compared to basal, state.

Evidence suggests that transcriptional regulation of the TRPV3 gene restricts its basal expression and is responsible for enhanced expression following nerve injury. Levels of TRPV3 mRNA recovered from rat L4 and L5 DRG neurons is elevated in the spinal nerve ligation model of neuropathic pain, as compared to uninjured rats (U.S. Pat. No. 7,396,910). Similar upregulation of TRPV3 has been observed in sensory neurons following peripheral nerve injury in humans (Facer, P.; Casula, M. A.; Smith, G. D.; Benham, C. D.; Chessell, I.P.; Bountra, C.; Sinisi, M.; Birch, R.; Anand, P., *BMC Neurol.* 2007, 7, 11-22; Smith G. D. et al., 2002).

One feature that distinguishes TRPV3 from the other thermoTRPs is its relatively prominent localization in skin (Peier, A. M. et al., 2002; Xu, H. et al., 2002). TRPV3 is also expressed in dorsal root ganglion, trigeminal ganglion, spinal cord and brain (Xu, H. et al., 2002; Smith G. D. et al., 2002). Its distinctive tissue profile, with significant expression in keratinocytes proximal to nociceptive neurons (Chung, M. K.; Lee, H.; Caterina, M. J., *J Biol Chem.* 2003, 278, 32037-32046; Chung, M. K.; Lee, H.; Mizuno, A.; Suzuki, M.; Caterina, M. J. *J Biol Chem.* 2004, 279, 21569-21575; Peier, A. M. et al., 2002; Xu, H. et al., 2002) as well as upregulation of TRPV3 in disease states is consistent with a likely role of TRPV3 in pain (Caterina M J., *Am J Physiol Regul Integr Comp Physiol.* 2007, 292, R64-R76; Lee, H.; Caterina, M. J., *Pflugers Arch.* 2005, 451, 160-167; Giller, A. D.; Lee, H.; Iida, T.; Shimizu, I.; Tominaga, M.; Caterina, M., *J Neurosci.* 2002, 22, 6408-6414; Chung, M. K. et al., 2003; Chung, M. K.; Lee, H.; Mizuno, A.; Suzuki, M.; Caterina, M. J. *J Biol Chem.* 2004, 279, 21569-21575). In a keratinocyte cell line, stimulation of TRPV3 leads to release of inflammatory mediators including interleukin-1. Thus TRPV3 may also play an important role in regulating inflammation, itch (Steinhoff, M. and Biro, T. *J. Invest. Dermatology,* 2009, 129, 531-535) and pain that results from the release of inflammatory stimuli. In addition, localization of TRPV3 in non-neuronal tissues, especially skin, suggests also that pharmacological modulation of the channel may provide a therapy to treat diseases that impair the skin barrier (Montell, C. *Cell,* 2010, Apr. 16, 218-220) and have additional, as yet unidentified, benefit for disease states beyond pain. Accordingly, compounds that can modulate one or more functions of TRPV3 can have various therapeutic utilities.

SUMMARY OF THE INVENTION

Disclosed herein are compounds of formula (I)

$$R^2 \underset{X_2}{\overset{N}{\diagdown}} \underset{X_1}{\overset{H}{\diagdown}} \underset{(R^x)_n}{\overset{H}{\diagdown}} \overset{R^1}{\underset{H}{\diagdown}}$$ (I)

or a pharmaceutically acceptable salts, solvates, or salts of a solvates thereof, wherein $X_1$ and $X_2$ are the same or different, and are independently CH or N;

each $R^x$ is an optional substituent on any substitutable carbon atom, and is independently selected from the group consisting of alkyl, alkenyl, alkynyl, halogen, CN, $O(R^{1a})$, $N(R^{1a})(R^{1b})$, $NO_2$, haloalkyl, —($C_1$-$C_6$ alkylenyl)-$O(R^{1a})$, and —($C_1$-$C_6$ alkylenyl)-$N(R^{1a})(R^{1b})$;

n is 0, 1, 2, or 3;

$R^1$ is a monocyclic cycloalkyl, a monocyclic heterocycle, or —$CH_2$-(monocyclic cycloalkyl); wherein the monocyclic cycloalkyl or the monocyclic heterocycle, by itself or as part of the substituent, is substituted with one substituent, $R^y$, selected from the group consisting of OH, —($CH_2$)—OH, and —$C(O)N(R^5)_2$, and is optionally further substituted with 1, 2, 3, 4, or 5 substituents, $R^z$, selected from the group consisting of alkyl, halogen, haloalkyl, and oxo; or $R^1$ is $$\underset{R^4}{\overset{R^3}{\diagdown}} \underset{R^4}{\overset{R^3}{\diagdown}} \overset{G^1}{\underset{m}{\diagdown}}$$

$G^1$ is OH or —$C(O)N(R^5)_2$;

m is 0, 1, or 2; with the proviso that m is 1 or 2 when $G^1$ is OH;

each $R^3$ is independently hydrogen, alkyl, halogen, haloalkyl, —$C(O)R^{3a}$, —$C(O)OR^{3a}$, —$C(O)N(R^{3a})(R^{3b})$, $G^{3a}$, —($C_1$-$C_6$ alkylenyl)-$G^{3a}$, hydroxyalkyl, alkoxyalkyl, or haloalkoxyalkyl; wherein $G^{3a}$ is cycloalkyl, cycloalkenyl, heterocycle, aryl, or heteroaryl; or two $R^3$ together with the carbon atom to which they are attached, form a 3-, 4-, 5-, or 6-membered monocyclic ring wherein said ring optionally contains 1, 2, or 3 heteroatoms selected from the group consisting of S, O, N, and NH, and optionally contains one double bond; said ring is unsubstituted or substituted on any substitutable ring atoms with 1, 2, 3, 4, or 5 substituents independently selected from the group consisting of alkyl, halogen, haloalkyl, and oxo;

$R^{3a}$, at each occurrence, is independently hydrogen, alkyl, or haloalkyl;

$R^{3b}$ is hydrogen, alkyl, haloalkyl, or aryl wherein the aryl is optionally substituted with 1, 2, 3, 4, or 5 substituents independently selected from the group consisting of alkyl, halogen, and haloalkyl;

each $R^4$ is independently hydrogen, alkyl, halogen, phenyl, or haloalkyl; two $R^4$ together with the carbon atom to which they are attached, optionally form a 3-, 4-, 5-, or 6-membered monocyclic ring, said ring optionally contains 1, 2, or 3 heteroatoms selected from the group consisting of S, O, N, and NH, and optionally contains one double bond; said ring is unsubstituted or substituted on any substitutable ring atoms with 1, 2, 3, 4, or 5 substituents independently selected from the group consisting of alkyl, halogen, haloalkyl, and oxo;

each $R^5$ is independently hydrogen or alkyl, or two $R^5$ together with the nitrogen atom to which they are attached, form 3-, 4-, 5-, or 6-membered monocyclic heterocycle ring; wherein said ring optionally contains one additional heteroatom selected from the group consisting of N, NH, O, S, S(O), and $S(O)_2$ and optionally a double bond, and is optionally fused with a monocyclic ring selected from the group consisting of benzo, heteroaryl, heterocycle, cycloalkyl, and cycloalkenyl; said ring is optionally substituted with 1, 2, 3, 4, or 5 substituents independently selected from the group consisting of alkyl, alkenyl, alkynyl, oxo, halogen, and haloalkyl;

$R^2$ is alkyl, —$OR^{2a}$, $G^{2a}$, $C_2$-$C_4$ alkenyl, $C_2$-$C_4$ alkynyl, or —($C_1$-$C_6$ alkylenyl)-$G^{2a}$; wherein $C_2$-$C_4$ alkenyl and $C_2$-$C_4$ alkynyl are each independently unsubstituted or substituted with a $G^{2aa}$;

$G^{2a}$ and $G^{2aa}$, at each occurrence, are each independently aryl, heteroaryl, cycloalkyl, cycloalkenyl, or heterocycle; and are each optionally substituted with 1, 2, 3, 4, or 5 substituents independently selected from the group consisting of alkyl, alkenyl, alkynyl, halogen, haloalkyl, oxo, $G^a$, $NO_2$, CN, —$OR^f$, —$OC(O)R^f$, —$OC(O)N(R^f)_2$, —$Si(alkyl)_3$, —$SF_5$, —$SR^f$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^e$, —$N(R^f)S(O)_2R^e$, —$N(R^f)C(O)O(R^e)$, —$N(R^f)C(O)N(R^f)_2$, —($C_1$-$C_6$ alkylenyl)-$G^a$, —($C_1$-$C_6$ alkylenyl)-$OR^f$, —($C_1$-$C_6$ alkylenyl)—$OC(O)R^f$, —($C_1$-$C_6$ alkylenyl)—$OC(O)N(R^f)_2$, —($C_1$-$C_6$ alkylenyl)-$S(O)_2R^e$, —($C_1$-$C_6$ alkylenyl)-$S(O)_2N(R^f)_2$, —($C_1$-$C_6$ alkylenyl)-$C(O)R^f$, —($C_1$-$C_6$ alkylenyl)-$C(O)OR^f$, —($C_1$-$C_6$ alkylenyl)-$C(O)N(R^f)_2$, —($C_1$-$C_6$ alkylenyl)-$N(R^f)_2$, —($C_1$-$C_6$ alkylenyl)-$N(R^f)C(O)R^e$, —($C_1$-$C_6$ alkylenyl)-$N(R^f)S(O)_2R^e$, —($C_1$-$C_6$ alkylenyl)-$N(R^f)C(O)O(R^e)$, —($C_1$-$C_6$ alkylenyl)-$N(R^f)C(O)N(R^f)_2$, and —($C_1$-$C_6$ alkylenyl)-CN;

$R^f$, at each occurrence, is independently hydrogen, alkyl, haloalkyl, —($C_1$-$C_6$ alkylenyl)-$OR^g$, $G^a$, or —($C_1$-$C_6$ alkylenyl)-$G^a$;

$R^e$, at each occurrence, is independently alkyl, haloalkyl, —($C_1$-$C_6$ alkylenyl)-$OR^g$, $G^a$, or —($C_1$-$C_6$ alkylenyl)-$G^a$;

$R^g$, at each occurrence, is independently hydrogen, alkyl, haloalkyl, monocyclic cycloalkyl, or —($C_1$-$C_6$ alkylenyl)-(monocyclic cycloalkyl); wherein the monocyclic cycloakyl, alone or as part of the group, is optionally substituted with 1, 2, 3, 4, or 5 substituents independently selected from the group consisting of alkyl, haloalkyl, oxo, OH, and alkoxy;

$R^{2a}$ is alkyl, alkenyl, alkynyl, haloalkyl, $G^{2b}$, or —($C_1$-$C_6$ alkylenyl)-$G^{2b}$;

$G^{2b}$ and $G^a$, at each occurrence, are each independently aryl, heteroaryl, cycloalkyl, cycloalkenyl, or heterocycle;

$G^{3a}$, $G^{2b}$, and $G^a$, are each independently unsubstituted or substituted with 1, 2, 3, 4, or 5 substituents independently selected from the group consisting of alkyl, alkenyl, alkynyl, halogen, haloalkyl, oxo, $NO_2$, CN, —$OR^{1a}$, —$OC(O)R^{1c}$, —$OC(O)N(R^{1a})(R^{1b})$, —$SR^{1a}$, —$S(O)_2R^{1a}$, —$S(O)_2N(R^{1a})(R^{1b})$, —$C(O)R^{1a}$, —$C(O)OR^{1a}$, —$C(O)N(R^{1a})(R^{1b})$, —$N(R^{1a})(R^{1b})$, —$N(R^{1a})C(O)R^{1c}$, —$N(R^{1a})S(O)_2R^{1c}$, —$N(R^{1a})C(O)O(R^{1c})$, —$N(R^{1a})C(O)N(R^{1a})(R^{1b})$, —($C_1$-$C_6$ alkylenyl)-$OR^{1a}$, —($C_1$-$C_6$ alkylenyl)—$OC(O)R^{1c}$, —($C_1$-$C_6$ alkylenyl)—$OC(O)N(R^{1a})(R^{1b})$, —($C_1$-$C_6$ alkylenyl)-$S(O)_2R^{1a}$, —($C_1$-$C_6$ alkylenyl)-$S(O)_2N(R^{1a})(R^{1b})$, —($C_1$-$C_6$ alkylenyl)-$C(O)R^{1a}$, —($C_1$-$C_6$ alkylenyl)-$C(O)OR^{1a}$, —($C_1$-$C_6$ alkylenyl)-$C(O)N(R^{1a})(R^{1b})$, —($C_1$-$C_6$ alkylenyl)-N(R$^{1a}$)(R$^{1b}$), —(C$_1$-C$_6$ alkylenyl)-N(R$^{1a}$)C(O)R$^{1c}$, —(C$_1$-C$_6$ alkylenyl)-N(R$^{1a}$)S(O)$_2$R$^{1c}$, —(C$_1$-C$_6$ alkylenyl)-N(R$^{1a}$)C(O)O(R$^{1c}$), —(C$_1$-C$_6$ alkylenyl)-N(R$^{1a}$)C(O)N(R$^{1a}$)(R$^{1b}$), and —(C$_1$-C$_6$ alkylenyl)-CN;

R$^{1a}$ and R$^{1b}$, at each occurrence, are each independently hydrogen, alkyl, or haloalkyl; and R$^{1c}$, at each occurrence, is each independently alkyl or haloalkyl.

Another aspect relates to pharmaceutical compositions comprising therapeutically effective amount of a compound described herein or pharmaceutically acceptable salt, solvate, salt of a solvate, or solvate of a salt thereof, in combination with a pharmaceutically acceptable carrier. Such compositions can be administered in accordance with methods described herein, typically as part of a therapeutic regimen for treatment or prevention of conditions and disorders related to TRPV3 activity. More particularly, the methods are useful for treating conditions related to pain such as, but not limited to, acute pain, chronic pain, neuropathic pain, nociceptive pain, allodynia, migraine, post-stroke pain, HIV-related neuropathy, nerve injury, spinal cord injury, multiple sclerosis pain, rheumatoid arthritic pain, osteoarthritic pain, inflammatory pain, inflammatory hyperalgesia, cancer pain (e.g. bone cancer pain), lower back pain, diabetic neuropathic pain, fibromyalgia, carpal tunnel syndrome, neuritis, sciatica, pelvic hypersensitivity, pelvic pain, post operative pain, post herpatic neuralgia, visceral pain, dental pain, eye pain, and menstrual pain, or combinations thereof.

Further, provided herein are uses of the present compounds or pharmaceutically acceptable salts, solvates, or salts of solvates thereof, in the manufacture of medicaments for the treatment of the disease or conditions described above, alone or in combination with a pharmaceutically acceptable carrier, particularly for the treatment of pain as described herein above.

The compounds, compositions comprising the compounds, pharmaceutically acceptable salts, solvates, salts of the solvates, or solvates of the salts thereof, and methods for treating or preventing conditions and disorders by administering the compounds or compositions thereof, are further described herein.

These and other objectives are described further in the following paragraphs. These objectives should not be deemed to narrow the scope of the invention.

DETAILED DESCRIPTION OF THE INVENTION

Compounds of formula (I)

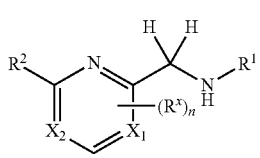

(I)

wherein X$_1$, X$_2$, R$^1$, R$^2$, R$^x$, and n are as defined above in the Summary and below in the Detailed Description are disclosed. Compositions comprising such compounds and methods for treating conditions and disorders using such compounds and compositions are also disclosed.

In various embodiments, compounds described herein may contain variables that occur more than one time in any substituent or in the compound described or any other formula herein. Definition of a variable on each occurrence is independent of its definition at another occurrence. Further, combinations of variables are permissible only if such combinations result in stable compounds. Stable compounds are compounds that can be isolated from a reaction mixture.

a. Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "C$_2$-C$_4$ alkenyl" means an alkenyl group containing 2-4 carbon atoms and a carbon-carbon double bond. Non-limiting examples of alkenyl include buta-1,3-dienyl, ethenyl (vinyl), 3,3-dimethylbutenyl, 2-propenyl, prop-1-en-1-yl, 2-methyl-2-propenyl, prop-1-en-2-yl, 3-butenyl, 4-pentenyl, 5-hexenyl, 2-heptenyl, 2-methyl-1-heptenyl, and 3-decenyl.

The term "alkenylene" or "alkenylenyl" means a divalent group derived from a straight or branched chain hydrocarbon of 2 to 4 carbon atoms and contains at least one carbon-carbon double. Representative examples of alkenylene and alkenylenyl include, but are not limited to, —CH═CH— and —CH$_2$CH═CH—.

The term "alkoxy" as used herein, means an alkyl group, as defined herein, appended to the parent molecular moiety through an oxygen atom. The term "C$_1$-C$_4$ alkoxy" as used herein, means a C$_1$-C$_4$ alkyl group, as defined herein, appended to the parent molecular moiety through an oxygen atom. Representative examples of alkoxy include, but are not limited to, methoxy, ethoxy, propoxy, 2-propoxy, 2-methylpropoxy, butoxy, tert-butoxy, pentyloxy, and hexyloxy.

The term "alkoxyalkyl" as used herein, means an alkoxy group, as defined herein, appended to the parent molecular moiety through an alkylenyl group, as defined herein. Representative examples of alkoxy include, but are not limited to, methoxymethyl, ethoxymethyl, 1-methoxyethyl, propoxymethyl, and 2-propoxymethyl.

The term "alkyl" as used herein, means a straight or branched, saturated hydrocarbon chain containing from 1 to 10 carbon atoms. The term "C$_x$—C$_y$ alkyl" means a straight or branched chain, saturated hydrocarbon containing x to y carbon atoms. For example "C$_1$-C$_4$ alkyl" means a straight or branched chain, saturated hydrocarbon containing 1 to 4 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2,2-dimethylpropyl, 1-methylpropyl, 2-methylpropyl, 1-ethylpropyl, 2,2-dimethylbutyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a straight or branched, saturated hydrocarbon chain, for example, of 1 to 10 carbon atoms or of 1 to 4 (C$_1$-C$_4$ alkylenyl) carbon atoms. The term "C$_1$-C$_6$ alkylene" or "C$_1$-C$_6$ alkylenyl" means a divalent group derived from a straight or branched, saturated hydrocarbon chain, for example, of 1 to 6 carbon atoms. Examples of alkylene and alkylenyl include, but are not limited to, —CH$_2$—, —CH(CH$_3$)—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "C$_2$-C$_4$ alkynyl" means a straight or branched chain hydrocarbon group containing from 2 to 4 carbon atoms and a carbon-carbon triple bond. Representative examples of alkynyl include, but are not limited, to ethynyl, 1-propynyl, 2-propynyl, 3-butynyl, 2-pentynyl, and but-1-yn-1yl.

The term "aryl" as used herein, means phenyl, a bicyclic aryl, and a tricyclic aryl. The bicyclic aryl is naphthyl, or a phenyl fused to a monocyclic cycloalkyl, or a phenyl fused to a monocyclic cycloalkenyl. The tricyclic aryl is a bicyclic aryl fused to a phenyl, or a bicyclic aryl fused to a monocyclic cycloalkyl. Non-limiting examples of the aryl groups include dihydroindenyl (e.g. 2,3-dihydroindenyl), indenyl, naphthyl, dihydronaphthalenyl (e.g. 3,4-dihydronaphthalenyl), 9H-fluoren-2-yl, and tetrahydronaphthalenyl. The aryl groups are attached to the parent molecular moiety through any carbon atom contained within the bicyclic ring system and can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The term "C$_3$-C$_6$ cycloalkyl" means a carbocyclic ring system selected from the group consisting of cyclopropyl, cyclobutyl, cyclopentyl, and cyclohexyl. The bicyclic cycloalkyl is a monocyclic cycloalkyl fused to a monocyclic cycloalkyl ring such as, for example, bicyclo[3.1.0]hexyl. Tricyclic cycloalkyls are exemplified by a bicyclic cycloalkyl fused to a monocyclic cycloalkyl. The monocyclic, bicyclic, and tricyclic cycloalkyls may have one or two alkylenyl bridges of 1, 2, 3, or 4 carbon atoms, each linking two non-adjacent carbon atoms of the ring system. Non-limiting examples of cycloalkyls having one or two alkylenyl bridges include, but not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The cycloalkyls of the present application can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic and the bicyclic cycloalkenyl rings may contain one or two alkylenyl bridges, each consisting of one, two, or three carbon atoms and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five, or six hydrogen atoms are replaced by halogen. The term "C$_1$-C$_4$ haloalkyl" means a C$_1$-C$_4$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloalkoxy" as used herein, means an alkoxy group, as defined herein, in which one, two, three, four, five or six hydrogen atoms are replaced by halogen. The term "C$_1$-C$_4$ haloalkoxy" as used herein, means a C$_1$-C$_4$ alkoxy group, as defined herein, in which one, two, three, four, five or six hydrogen atoms are replaced by halogen. Representative examples of haloalkoxy include, but are not limited to, 2-fluoroethoxy, 2,2,2-trifluoroethoxy, trifluoromethoxy, and difluoromethoxy.

The term "haloalkoxyalkyl" as used herein, means an haloalkoxy group, as defined herein, appended to the parent molecular moiety through an alkylenyl group, as defined herein.

The term "hydroxyalkyl" as used herein, means an hydroxy group, as defined herein, appended to the parent molecular moiety through an alkylenyl group, as defined herein. Examples of hydroxyalkyl include, but are not limited to, 2-hydroxyethyl and hydroxymethyl.

The term "heterocycle" or "heterocyclic" as used herein, means a monocyclic heterocycle, a bicyclic heterocycle, tricyclic heterocycle, and a spiro heterocycle. The monocyclic heterocycle is a three-, four-, five-, six-, seven-, or eight-membered ring containing at least one heteroatom independently selected from the group consisting of O, N, NH, and S. The three- or four-membered ring contains zero or one double bond, and one heteroatom selected from the group consisting of O, N, NH, and S. The five-membered ring contains zero or one double bond and one, two, or three heteroatoms selected from the group consisting of O, N, NH, and S. The six-membered ring contains zero, one, or two double bonds and one, two, or three heteroatoms selected from the group consisting of O, N, NH, and S. The seven- and eight-membered rings contains zero, one, two, or three double bonds and one, two, or three heteroatoms selected from the group consisting of O, N, NH, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 1,3-dihydroisoindolyl, 3,4-dihydroisoquinolinyl, 1,2,3,4-tetrahydroisoquinolinyl, 2,3-dihydrobenzofuranyl, 2,3-dihydrobenzothienyl, and 3,4-dihydro-2H-1,5-benzodioxepin-7-yl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. An example of a tricyclic heterocycle is 9H-carbazol-2-yl. The spiro heterocycle is a monocyclic heterocycle wherein two substituents on the same carbon atom, together with said carbon atom, form a monocyclic cycloalkyl ring. Examples of the spiro heterocycle include, but are not limited to, 1,4-dioxaspiro[4.5]dec-7-yl and 1,4-dioxaspiro[4.5]dec-8-yl. The monocyclic, bicyclic, and tricyclic heterocycle groups of the present application may have one or two alkylenyl bridges of 1, 2, 3, or 4 carbon atoms, or one or two alkenylenyl bridges of two, three, or four carbon atoms, or combinations thereof, each linking two non-adjacent carbon atoms of the ring system. Examples of the heterocycles having such alkylenyl or alkenylenyl bridge(s) include, but are not limited to, azabicyclo[3.2.1]octane, azabicyclo[2.2.1]heptyl (including 2-azabicyclo[2.2.1]hept-2-yl), 2,3-dihydro-1H-indolyl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The heterocycles of the present application can be unsubstituted or substituted, and are connected to the parent molecular moiety through any substitutable carbon atom or any substitutable nitrogen atom contained within the rings. The nitrogen and sulfur heteroatoms in the heterocycle rings may optionally be oxidized (e.g. 1,1-dioxidothiomorpholinyl (thiomorpholine sulfone)), and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, 1,3,4-thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any substitutable carbon atom or any substitutable nitrogen atom contained within the ring systems.

The term "hydroxyl" or "hydroxy" means a —OH group.

The term "oxo" as used herein, means a =O group.

"Treatment" or "treating" pain includes acute or chronic pain and refers to: (1) preventing pain, i.e. causing pain not to develop or occur with less intensity in a subject that may be exposed or predisposed to pain but does not yet experience or display pain, (2) inhibiting pain, i.e., arresting the development or reversing pain, or (3) relieving pain, i.e., decreasing the amount of pain experienced by the subject.

The term "subject" includes animals such as mammals, including, but not limited to, primates (e.g., humans), cows, sheep, goats, horses, dogs, cats, rabbits, rats, mice and the like. In preferred embodiments, the subject is a human.

b. Compounds

Compounds of formula (I) are as described above.

Particular values of variable groups in compounds of formula (I) are as follows. Such values may be used where appropriate with any of the other values, definitions, claims or embodiments defined hereinbefore or hereinafter.

$R^1$ has values as described in the Summary. One subset of compounds of formula (I) is directed to those wherein $R^1$ is monocyclic cycloalkyl, a monocyclic heterocyle, or —CH$_2$—(monocyclic cycloalkyl). One subset of compounds of formula (I) is directed to those wherein $R^1$ is monocyclic cycloalkyl or monocyclic heterocyle. In one embodiment, $R^1$ is a monocyclic cycloalkyl. In yet another embodiment, $R^1$ is cyclopentyl, cyclohexyl, or bicyclo[2.2.1]heptyl. In yet another embodiment, $R^1$ is cyclohexyl. Each monocyclic cycloalkyl (including the exemplary rings) or monocyclic heterocyl, by itself of as part of the substituent, is substituted with one $R^y$ group, and optionally further substituted with 1, 2, 3, 4, or 5 $R^z$ groups, wherein $R^y$ and $R^z$ are as described in the Summary and herein. In conjunction with any of the above and below embodiments, $R^y$, for example, is OH or —(CH$_2$)—OH; or $R^y$, for example, is OH; or $R^y$, for example, is —(CH$_2$)—OH.

Examples of the subset of compounds wherein $R^1$ is monocyclic cycloalkyl or —CH$_2$—(monocyclic cycloalkyl) include, but are not limited to, compounds of formula (I-i)

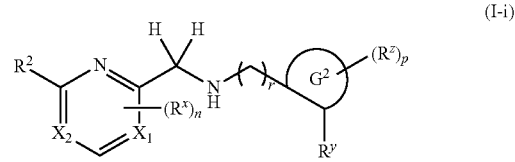

(I-i)

wherein r is 0 or 1.

Examples of a subset of compounds wherein $R^1$ is monocyclic cycloalkyl include, but are not limited to, compounds of formula (I-a)

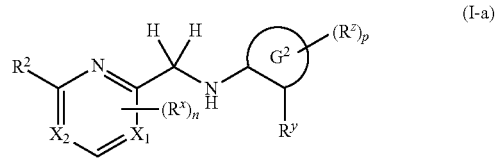

(I-a)

wherein $G^2$ of formula (I-i) and (I-a) is a $C_3$-$C_6$ cycloalkyl wherein two non-adjacent atoms are optionally linked by an alkylenyl bridge of 1 or 2 carbon atoms, $X_1$, $X_2$, $R^x$, $R^2$, n, $R^y$, and $R^z$ of formula (I-i) and (I-a) have values as described in the Summary and embodiments herein above and below, and p is 0, 1, 2, 3, 4, or 5. In certain embodiments, $G^2$ is cyclopentyl, cyclohexyl, or bicyclo[2.2.1]heptyl. In yet other embodiments, $G^2$ is cyclohexyl. In conjunction with any embodiments herein above and below, p, for example, is 0.

Another subset of compounds of formula (I) is directed to those wherein $R^1$ is

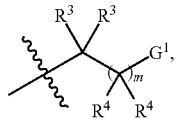

wherein $R^3$, $R^4$, m, and $G^1$ have meanings as disclosed in the Summary and embodiments herein.

In certain embodiments, $G^1$ is OH. In yet other embodiments, $G^1$ is —C(O)N($R^5$)$_2$.

In the embodiments wherein $G^1$ is —C(O)N($R^5$)$_2$, m is 0, and $R^5$ is as defined in the Summary and embodiments herein. For example, in certain embodiments, $R^5$ is hydrogen.

In yet other embodiments wherein $G^1$ is —C(O)N($R^5$)$_2$, m is 0, each $R^3$ is the same or different, and is independently hydrogen or alkyl (e.g. isopropyl, sec-butyl), and $R^5$ is as defined in the Summary and embodiments herein. For example, in certain embodiments, $R^5$ is hydrogen.

In the embodiments wherein $G^1$ is OH, m, for example, is 1 or 2; or m, for example, is 1; or m, for example, is 2. Each $R^4$, for example, is independently hydrogen, alkyl (e.g. methyl, ethyl), phenyl, or haloalkyl (e.g. trifluoromethyl); two $R^4$ together with the carbon atom to which they are attached, optionally form a $C_3$-$C_6$ cycloalkyl, oxetanyl, or tetrahydropyranyl, each of which is optionally substituted. In conjunction with the embodiments herein above and below, each $R^4$, for example, for this subset of compounds of formula (I) is, independently hydrogen or $C_1$-$C_4$ alkyl (e.g. methyl, ethyl).

In conjunction with embodiments herein above and below wherein $R^1$ is —C($R^3$)$_2$(C($R^4$)$_2$)$_m$OH, one $R^3$, for example, is hydrogen or alkyl (e.g. $C_1$-$C_4$ alkyl such as, but not limited to, methyl), and the other $R^3$ is hydrogen, alkyl (e.g. $C_1$-$C_4$ alkyl such as, but not limited to, methyl, ethyl, n-propyl, iso-propyl, iso-butyl, sec-butyl, tert-butyl), alkoxyalkyl (e.g. methoxymethyl), —C(O)N($R^{3a}$)($R^{3b}$) (e.g. C(O)NH$_2$ or C(O)N(H)(naphthyl)), hydroxyalkyl (e.g. hydroxymethyl), $G^{3a}$ (e.g. optionally substituted phenyl or optionally substituted $C_3$-$C_6$ cycloalkyl), or —(C$_1$-C$_6$ alkylenyl)-$G^3$a (e.g. benzyl); or two $R^3$ together with the carbon atom to which they are attached form an optionally substituted $C_3$-$C_6$ cycloalkyl. In certain embodiments, both $R^3$ can be the same or different and for example, are independently hydrogen, alkyl (e.g. $C_1$-$C_4$ alkyl such as, but not limited to, methyl, ethyl, n-propyl, isopropyl, iso-butyl, sec-butyl, tert-butyl), or cyclopropyl. In certain embodiments, both $R^3$ can be the same or different and for example, are independently hydrogen or alkyl (e.g. $C_1$-$C_4$ alkyl such as, but not limited to, methyl, ethyl, n-propyl, isopropyl, iso-butyl, sec-butyl, tert-butyl).

Certain compounds are directed to those wherein m is 1 or 2, $R^4$ is each independently hydrogen or $C_1$-$C_4$ alkyl, and $R^3$ is each independently hydrogen, alkyl, or cyclopropyl. In certain embodiments, m is 1.

Certain compounds are directed to those wherein m is 1, $R^4$ is each independently hydrogen or $C_1$-$C_4$ alkyl, and $R^3$ is each independently hydrogen or alkyl.

Thus, included herein are compounds of formula (I) wherein $R^1$ is —C($R^3$)$_2$(C($R^4$)$_2$)$_m$OH, m is 1, $R^4$ is hydrogen, one of $R^3$ is hydrogen, and the other is $C_1$-$C_4$ alkyl, such as, but not limited to, those exemplified in formula (I-b)

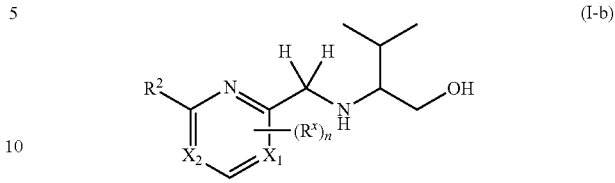

wherein $X_1$, $X_2$, $R^x$, $R^2$, and n, $R^y$ have values as described in the Summary and embodiments herein above and below.

$X_1$ and $X_2$ of formula (I), (I-i), (I-a), and (I-b) have values as described in the Summary and embodiments herein. One subset of compounds of formula (I), (I-i), (I-a), and (I-b) are those wherein one of $X_1$ and $X_2$ is CH, and the other is N. Within this subset of compounds, examples include those wherein $X_1$ is CH and $X_2$ is N; other examples include those wherein $X_1$ is N and $X_2$ is CH. Another subset of compounds of formula (I), (I-i), (I-a), and (I-b) are those wherein $X_1$ and $X_2$ are CH. Yet another subset of compounds of formula (I), (I-i), (I-a), and (I-b) are those wherein $X_1$ and $X_2$ are N.

$R^2$ has values as described in the Summary. For example, in certain compounds of formula (I), (I-i), (I-a), and (I-b), $R^2$ is —OR$^{2a}$, $G^{2a}$ (C$_1$-C$_6$ alkylenyl)-$G^{2a}$, $C_2$-$C_4$ alkenyl, or $C_2$-$C_4$ alkynyl wherein the $C_2$-$C_4$ alkenyl and $C_2$-$C_4$ alkynyl are independently unsubstituted or substituted with a $G^{2aa}$. In certain embodiments, $R^2$ is —OR$^{2a}$. In certain embodiments, $R^2$ is $G^{2a}$. In certain embodiments, $R^2$ is $C_2$-$C_4$ alkenyl, or $C_2$-$C_4$ alkynyl wherein the $C_2$-$C_4$ alkenyl and $C_2$-$C_4$ alkynyl are independently unsubstituted or substituted with a $G^{2aa}$. $R^{2a}$, $G^{2a}$, and $G^{2aa}$ are as disclosed in the Summary and embodiments herein.

In certain embodiments, $R^2$ is —OR$^{2a}$. In conjunction with any of the embodiments herein above or below, $R^{2a}$, for example, is alkyl (e.g. tert-butyl) or —(C$_1$-C$_6$ alkylenyl)-$G^{2b}$ (e.g. —CH$_2$-$G^{2b}$ wherein $G^{2b}$ is optionally substituted aryl such as, but not limited to, optionally substituted phenyl).

In conjunction with any of the embodiments herein above or below, $G^{2a}$ is, for example, aryl (e.g. phenyl, naphthyl, tetrahydronaphthalenyl, 3,4-dihydronaphthalenyl, 9H-fluoren-2-yl), heteroaryl (such as, but not limited to, pyridinyl, pyrimidinyl, thienyl, furanyl, pyrazolyl, 1,3-thiazolyl, 1,3,4-thiadiazolyl, quinolinyl, benzofuranyl, benzothienyl, benzothiazolyl, and indolyl), cycloalkyl (e.g. cyclopentyl, cyclohexyl, cycloheptyl, and bicyclo[2.2.1]heptyl), cycloalkenyl (e.g. cyclohexenyl), or heterocycle (such as, but not limited to, pyrrolidinyl, piperidinyl, piperazinyl, tetrahydrofuranyl, tetrahydropyranyl, morpholinyl, 3,4-dihydro-2H-1,5-benzodioxepin-7-yl, 3,4-dihydroisoquinolinyl, 2,3-dihydrobenzothienyl, 1,3-dihydroisoindolyl, 1,4-dioxaspiro[4.5]dec-7-yl, 1,4-dioxaspiro[4.5]dec-8-yl, 9H-carbazol-2-yl). In certain embodiments, $G^{2a}$ is phenyl.

Each $G^{2a}$ (including the exemplary rings) is optionally substituted as described in the Summary and embodiments herein. For example, each of the $G^{2a}$ is unsubstituted or substituted with 1, 2, 3, 4, or 5 substituents independently selected from the group consisting of alkyl such as, but not limited to, methyl, ethyl, isopropyl, n-propyl, sec-butyl, isobutyl, tert-butyl;

alkenyl such as, but not limited to $C_2$-$C_4$ alkenyl (e.g. ethenyl);

halogen such as, but not limited to, F, Cl, Br;

haloalkyl, e.g. trifluoromethyl, 2,2,2-trifluoromethyl;

$G^a$ such as, but not limited to, aryl (e.g. phenyl), heterocycle (e.g. pyrrolidinyl, morpholinyl, piperidinyl, piperazinyl), heteroaryl (e.g. pyrazolyl, 1,3,4-thiadiazolyl), or cycloalkyl (e.g. cyclopropyl); wherein each $G^a$ (including exemplary rings) is optionally substituted;

$NO_2$;

CN;

—$OR^f$ wherein $R^f$ is as described in the Summary, for example, $R^f$ is hydrogen, alkyl (e.g. methyl, ethyl, isopropyl, n-propyl, n-butyl, isobutyl, tert-butyl), haloalkyl (e.g. trifluoromethyl, 2,2,2-trifluoroethyl), or —($C_1$-$C_6$ alkylenyl)-$G^a$ wherein $G^a$ is aryl (e.g. phenyl, naphthyl) or cycloalkyl (e.g. cyclopropyl), and each $G^a$ (including the exemplary rings) is optionally substituted;

—Si(alkyl)$_3$ such as, but not limited to, —Si(methyl)$_3$, —Si(methyl)$_2$(tert-butyl);

—$SF_5$;

—$SR^f$ wherein $R^f$ is as described in the Summary, for example, $R^f$ is hydrogen, alkyl (e.g. methyl, ethyl, isopropyl), or —($C_1$-$C_6$ alkylenyl)-$G^a$ wherein $G^a$ is optionally substituted cycloalkyl (e.g. optionally substituted cyclopropyl);

—S(O)$_2$$R^e$ wherein $R^e$ is as described in the Summary, for example, $R^e$ is alkyl (e.g. methyl, ethyl), haloalkyl (e.g. trifluoromethyl), or $G^a$ (e.g. optionally substituted heterocycle such as, but not limited to, morpholinyl, thiomorpholinyl, pyrrolidinyl, piperidinyl, each of which is optionally substituted);

—S(O)$_2$N($R^f$)$_2$ wherein $R^f$ is as described in the Summary, for example, each $R^f$ is independently alkyl (e.g. methyl, ethyl, isopropyl, tert-butyl) or $G^a$ wherein $G^a$ is, for example, optionally substituted cycloalkyl (e.g. optionally substituted cyclopropyl);

—C(O)$R^f$ wherein $R^f$ is as described in the Summary, for example, $R^f$ is hydrogen, alkyl (e.g. methyl, ethyl, isopropyl), or $G^a$ such as, but not limited to, heterocycles (e.g. pyrrolidinyl, morpholinyl, piperidinyl, thiomorpholinyl) or aryl (e.g. phenyl) wherein each $G^a$ (including the exemplary rings) is optionally substituted;

—C(O)$OR^f$ wherein $R^f$ is as described in the Summary, for example, $R^f$ is alkyl (e.g. isopropyl, tert-butyl);

—N($R^f$)$_2$ wherein $R^f$ is as described in the Summary, for example, each $R^f$ is independently hydrogen or alkyl such as, but not limited to, methyl, ethyl, isopropyl;

—N($R^f$)C(O)$R^e$ wherein $R^e$ and $R^f$ are as described in the Summary, for example, $R^f$ is hydrogen or alkyl (e.g. methyl) and $R^e$ is alkyl (e.g. tert-butyl);

—C(O)N($R^f$)$_2$ wherein $R^f$ is as described in the Summary, for example, each $R^f$ is independently hydrogen, alkyl (methyl, ethyl, n-propyl, isopropyl, n-butyl, isobutyl), $G^a$ such as, but not limited to, cycloalkyl (e.g. cyclohexyl) or heteroaryl (e.g. thiazolyl) wherein each $G^a$ (including the exemplary rings) is optionally substituted, or —($C_1$-$C_6$ alkylenyl)-$G^a$ (e.g. benzyl), —($C_1$-$C_6$ alkylenyl)-$G^a$ wherein $G^a$ is as described in the Summary, for example, $G^a$ is heterocycle (e.g. 1,3-dioxolanyl) or aryl (e.g. phenyl); each $G^a$ (including exemplary rings) is optionally substituted;

—($C_1$-$C_6$ alkylenyl)-$OR^f$ wherein $R^f$ is as described in the Summary, for example, $R^f$ is alkyl (e.g. methyl, ethyl) or optionally substituted aryl (e.g. phenyl or naphthyl, each of which is optionally substituted; and —($C_1$-$C_6$ alkylenyl)-N($R^f$)$_2$ wherein $R^f$ is as described in the Summary, for example, each $R^f$ is independently hydrogen, alkyl (e.g. methyl, ethyl, isopropyl), or optionally substituted aryl (e.g. optionally substituted phenyl).

In certain embodiments, $R^2$ is $C_2$-$C_4$ alkenyl, or $C_2$-$C_4$ alkynyl wherein the $C_2$-$C_4$ alkenyl and $C_2$-$C_4$ alkynyl are independently unsubstituted or substituted with a $G^{2aa}$. $G^{2aa}$ is as disclosed in the Summary and embodiments herein. In conjunction with any of the embodiments herein above or below, $G^{2aa}$, for example, is aryl (e.g. phenyl) or cycloalkyl (e.g. cyclopentyl, cyclohexyl) wherein each $G^{2aa}$ (including the exemplary rings) is optionally substituted as disclosed in the Summary and herein. For example, each $G^{2aa}$ is independently unsubstituted or substituted with 1, 2, 3, or 4 substituents independently selected from the group consisting of alkyl (e.g. methyl, tert-butyl, ethyl, isopropyl), halogen (e.g. F, Cl), —$OR^f$ (e.g. —$OCH_3$), —$SF_5$, and haloalkyl (e.g. trifluoromethyl).

$R^x$ has values as disclosed in the Summary and herein. In conjunction with any of the embodiments herein above and below, $R^x$, for example, is alkyl (e.g. $C_1$-$C_4$ alkyl such as, but not limited to, methyl), halogen (e.g. F, Cl), haloalkyl (trifluoromethyl), or $O(R^{1a})$ (e.g. $OCH_3$).

It is appreciated that the present application contemplates compounds of formula (I), (I-i), (I-a), and (I-b) with combinations of the above embodiments, including particular, more particular and preferred embodiments.

Accordingly, one aspect is directed to a group of compounds of formula (I), wherein $X_1$ and $X_2$ are CH, and $R^1$ is monocyclic cycloalkyl, a monocyclic heterocycle, or —$CH_2$—(monocyclic cycloalkyl); wherein the monocyclic cycloalkyl and the monocyclic heterocycle moieties are substituted with one $R^y$ group, and optionally further substituted with 1, 2, 3, 4, or 5 $R^z$ group. In certain embodiments, $R^y$ is OH or —(CH$_2$)OH. In other embodiments, $R^y$ is OH. In yet other embodiments, $R^y$ is —(CH$_2$)OH.

Another aspect is directed to a group of compounds of formula (I), wherein $X_1$ and $X_2$ are CH, and $R^1$ is monocyclic cycloalkyl substituted with one $R^y$ group, and optionally further substituted with 1, 2, 3, 4, or 5 $R^z$ group. In certain embodiments, $R^y$ is OH or —(CH$_2$)OH. In other embodiments, $R^y$ is OH. In yet other embodiments, $R^y$ is —(CH$_2$)OH.

Another aspect is directed to a group of compounds of formula (I), wherein $X_1$ and $X_2$ are CH, and $R^1$ is cyclohexyl substituted with one $R^y$ group, and optionally further substituted with 1, 2, 3, 4, or 5 $R^z$ group. In certain embodiments, $R^y$ is OH or —(CH$_2$)OH. In other embodiments, $R^y$ is OH. In yet other embodiments, $R^y$ is —(CH$_2$)OH.

Another aspect is directed to a group of compounds of formula (I-a) and (I-i) wherein $X_1$ and $X_2$ are CH, $G^2$ is a $C_3$-$C_6$ cycloalkyl wherein two non-adjacent atoms are optionally linked by an alkylenyl bridge of 1 or 2 carbon atoms, and $R^y$ is OH or —(CH$_2$)—OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I-a) and (I-i) wherein $X_1$ and $X_2$ are CH, $G^2$ is a $C_3$-$C_6$ cycloalkyl wherein two non-adjacent atoms are optionally linked by an alkylenyl bridge of 1 or 2 carbon atoms, and $R^y$ is OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I-a) and (I-i) wherein $X_1$ and $X_2$ are CH, $G^2$ is a $C_3$-$C_6$ cycloalkyl wherein two non-adjacent atoms are optionally linked by an alkylenyl bridge of 1 or 2 carbon atoms, and $R^y$ is —(CH$_2$)—OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I), wherein $X_1$ and $X_2$ are CH, $R^1$ is

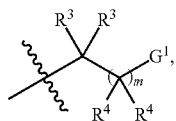

and
$G^1$ is OH.

Another aspect is directed to a group of compounds of formula (I), wherein $X_1$ and $X_2$ are CH, $R^1$ is

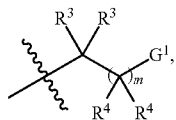

$G^1$ is OH, and each $R^4$ is independently hydrogen, alkyl, phenyl, or haloalkyl; two $R^4$ together with the carbon atom to which they are attached optionally form a $C_3$-$C_6$ cycloalkyl, oxtanyl, or tetrahydropyranyl, each of which is optionally substituted.

Another aspect is directed to a group of compounds of formula (I), wherein $X_1$ and $X_2$ are CH, $R^1$ is

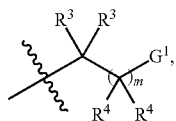

$G^1$ is OH, m is 1, and each $R^4$ is independently hydrogen or $C_1$-$C_4$ alkyl.

Another aspect is directed to a group of compounds of formula (I), wherein $X_1$ and $X_2$ are CH, $R^1$ is

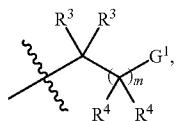

$G^1$ is OH, and one $R^3$ is hydrogen or alkyl and the other $R^3$ is hydrogen, alkyl, alkoxyalkyl, —C(O)N($R^{3a}$)($R^{3b}$), hydroxyalkyl, $G^{3a}$, or —($C_1$-$C_6$ alkylenyl)-$G^{3a}$; or two $R^3$ together with the carbon atom to which they are attached form a $C_3$-$C_6$ cycloalkyl.

Another aspect is directed to a group of compounds of formula (I), wherein $X_1$ and $X_2$ are CH, $R^1$ is

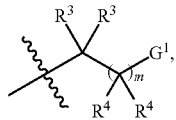

$G^1$ is OH, m is 1, each $R^4$ is independently hydrogen or $C_1$-$C_4$ alkyl, and each $R^3$ is independently hydrogen, alkyl, or cyclopropyl.

Another aspect is directed to a group of compounds of formula (I), wherein $X_1$ and $X_2$ are CH, $R^1$ is

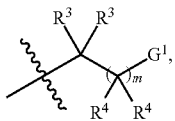

$G^1$ is —C(O)N($R^5$)$_2$, and m is 0.

Another aspect is directed to a group of compounds of formula (I), wherein $X_1$ and $X_2$ are CH, $R^1$ is

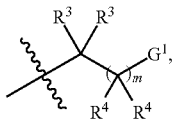

$G^1$ is —C(O)N($R^5$)$_2$, m is 0, and each $R^3$ is independently hydrogen or alkyl.

Another aspect is directed to a group of compounds of formula (I) and (I-a), wherein one of $X_1$ and $X_2$ is CH, and the other is N, and $R^1$ is monocyclic cycloalkyl, monocyclic heterocycle, or —CH$_2$—(monocyclic cycloalkyl); wherein the monocyclic cycloalkyl and the monocyclic heterocycle moieties are substituted with one $R^y$ group, and optionally further substituted with 1, 2, 3, 4, or 5 $R^z$ group. In certain embodiments, $R^y$ is OH or —(CH$_2$)OH. In other embodiments, $R^y$ is OH. In yet other embodiments, $R^y$ is —(CH$_2$)OH.

Another aspect is directed to a group of compounds of formula (I), wherein one of $X_1$ and $X_2$ is CH, and the other is N, and $R^1$ is monocyclic cycloalkyl substituted with one $R^y$ group, and optionally further substituted with 1, 2, 3, 4, or 5 $R^z$ group. In certain embodiments, $R^y$ is OH or —(CH$_2$)OH. In other embodiments, $R^y$ is OH. In yet other embodiments, $R^y$ is —(CH$_2$)OH.

Another aspect is directed to a group of compounds of formula (I), wherein one of $X_1$ and $X_2$ is CH, and the other is N, and $R^1$ is cyclohexyl substituted with one $R^y$ group, and optionally further substituted with 1, 2, 3, 4, or 5 $R^z$ group. In certain embodiments, $R^y$ is OH or —(CH$_2$)OH. In other embodiments, $R^y$ is OH. In yet other embodiments, $R^y$ is —(CH$_2$)OH.

Another aspect is directed to a group of compounds of formula (I-a) and (I-i) wherein one of $X_1$ and $X_2$ is CH, and the other is N, $G^2$ is a $C_3$-$C_6$ cycloalkyl wherein two non-adjacent atoms are optionally linked by an alkylenyl bridge of 1 or 2 carbon atoms, and $R^y$ is OH or —(CH$_2$)—OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I-a) and (I-i) wherein one of $X_1$ and $X_2$ is CH, and the other is N, $G^2$ is a $C_3$-$C_6$ cycloalkyl wherein two non-adjacent atoms are optionally linked by an alkylenyl bridge of 1 or 2 carbon atoms, and $R^y$ is OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I-a) and (I-i) wherein one of $X_1$ and $X_2$ is CH, and the other is N, $G^2$ is a $C_3$-$C_6$ cycloalkyl wherein two non-adjacent atoms are optionally linked by an alkylenyl bridge of 1 or 2 carbon atoms, and $R^y$ is —(CH$_2$)—OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I), wherein one of $X_1$ and $X_2$ is CH, and the other is N, $R^1$ is

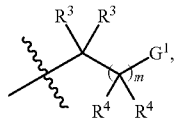

and $G^1$ is OH.

Another aspect is directed to a group of compounds of formula (I), wherein one of $X_1$ and $X_2$ is CH, and the other is N, $R^1$ is

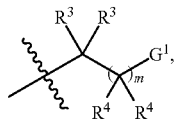

$G^1$ is OH, and each $R^4$ is independently hydrogen, alkyl, phenyl, or haloalkyl; two $R^4$ together with the carbon atom to which they are attached optionally form a $C_3$-$C_6$ cycloalkyl, oxtanyl, or tetrahydropyranyl, each of which is optionally substituted.

Another aspect is directed to a group of compounds of formula (I), wherein one of $X_1$ and $X_2$ is CH, and the other is N, $R^1$ is

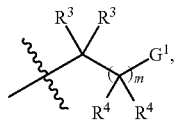

$G^1$ is OH, m is 1, and each $R^4$ is independently hydrogen or $C_1$-$C_4$ alkyl.

Another aspect is directed to a group of compounds of formula (I), wherein one of $X_1$ and $X_2$ is CH, and the other is N, $R^1$ is

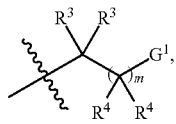

$G^1$ is OH, and one $R^3$ is hydrogen or alkyl and the other $R^3$ is hydrogen, alkyl, alkoxyalkyl, —C(O)N($R^{3a}$)($R^{3b}$), hydroxyalkyl, $G^{3a}$, or —($C_1$-$C_6$ alkylenyl)-$G^{3a}$; or two $R^3$ together with the carbon atom to which they are attached form a $C_3$-$C_6$ cycloalkyl.

Another aspect is directed to a group of compounds of formula (I), wherein one of $X_1$ and $X_2$ is CH, and the other is N, $R^1$ is

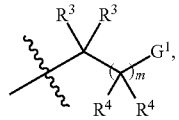

$G^1$ is OH, m is 1, each $R^4$ is independently hydrogen or $C_1$-$C_4$ alkyl, and each $R^3$ is independently hydrogen, alkyl, or cyclopropyl.

Another aspect is directed to a group of compounds of formula (I), wherein one of $X_1$ and $X_2$ is CH, and the other is N, $R^1$ is

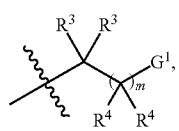

$G^1$ is —C(O)N($R^5$)$_2$, and m is 0.

Another aspect is directed to a group of compounds of formula (I), wherein one of $X_1$ and $X_2$ is CH, and the other is N, $R^1$ is

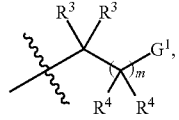

$G^1$ is —C(O)N($R^5$)$_2$, m is 0, and each $R^3$ is independently hydrogen or alkyl.

Another aspect is directed to a group of compounds of formula (I) and (I-a), wherein $X_1$ is N, $X_2$ is CH, and $R^1$ is monocyclic cycloalkyl, monocyclic heterocycle, or —CH$_2$—(monocyclic cycloalkyl); wherein the monocyclic cycloalkyl and the monocyclic heterocycle moieties are substituted with one $R^y$ group, and optionally further substituted with 1, 2, 3, 4, or 5 $R^z$ group. In certain embodiments, $R^y$ is OH or —(CH$_2$) OH. In other embodiments, $R^y$ is OH. In yet other embodiments, $R^y$ is —(CH$_2$)OH.

Another aspect is directed to a group of compounds of formula (I), wherein $X_1$ is N, $X_2$ is CH, and $R^1$ is monocyclic cycloalkyl substituted with one $R^y$ group, and optionally further substituted with 1, 2, 3, 4, or 5 $R^z$ group. In certain embodiments, $R^y$ is OH or —(CH$_2$)OH. In other embodiments, $R^y$ is OH. In yet other embodiments, $R^y$ is —(CH$_2$)OH.

Another aspect is directed to a group of compounds of formula (I), wherein $X_1$ is N, $X_2$ is CH, and $R^1$ is cyclohexyl substituted with one $R^y$ group, and optionally further substituted with 1, 2, 3, 4, or 5 $R^z$ group. In certain embodiments, $R^y$ is OH or —(CH$_2$)OH. In other embodiments, $R^y$ is OH. In yet other embodiments, $R^y$ is —(CH$_2$)OH.

Another aspect is directed to a group of compounds of formula (I-a) and (I-i) wherein $X_1$ is N, $X_2$ is CH, $G^2$ is a $C_3$-$C_6$ cycloalkyl wherein two non-adjacent atoms are optionally linked by an alkylenyl bridge of 1 or 2 carbon atoms, and $R^y$ is OH or —(CH$_2$)—OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I-a) and (I-i) wherein $X_1$ is N, $X_2$ is CH, $G^2$ is a $C_3$-$C_6$ cycloalkyl wherein two non-adjacent atoms are optionally linked by an alkylenyl bridge of 1 or 2 carbon atoms, and $R^y$ is OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I-a) and (I-i) wherein $X_1$ is N, $X_2$ is CH, $G^2$ is a $C_3$-$C_6$ cycloalkyl wherein two non-adjacent atoms are optionally linked by an alkylenyl bridge of 1 or 2 carbon atoms, and $R^y$ is —($CH_2$)—OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I), wherein $X_1$ is N, $X_2$ is CH, $R^1$ is

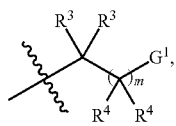

and
$G^1$ is OH.

Another aspect is directed to a group of compounds of formula (I), wherein $X_1$ is N, $X_2$ is CH, $R^1$ is

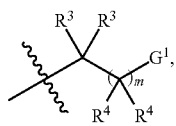

$G^1$ is OH, and each $R^4$ is independently hydrogen, alkyl, phenyl, or haloalkyl; two $R^4$ together with the carbon atom to which they are attached optionally form a $C_3$-$C_6$ cycloalkyl, oxtanyl, or tetrahydropyranyl, each of which is optionally substituted.

Another aspect is directed to a group of compounds of formula (I), wherein $X_1$ is N, $X_2$ is CH, $R^1$ is

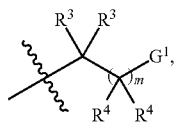

$G^1$ is OH, m is 1, and each $R^4$ is independently hydrogen or $C_1$-$C_4$ alkyl.

Another aspect is directed to a group of compounds of formula (I), wherein $X_1$ is N, $X_2$ is CH, $R^1$ is

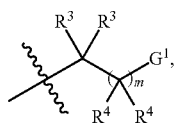

$G^1$ is OH, and one $R^3$ is hydrogen or alkyl and the other $R^3$ is hydrogen, alkyl, alkoxyalkyl, —C(O)N($R^{3a}$)($R^{3b}$), hydroxyalkyl, $G^{3a}$, or —($C_1$-$C_6$ alkylenyl)-$G^{3a}$; or two $R^3$ together with the carbon atom to which they are attached form a $C_3$-$C_6$ cycloalkyl.

Another aspect is directed to a group of compounds of formula (I), wherein $X_1$ is N, $X_2$ is CH, $R^1$ is

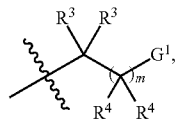

$G^1$ is OH, m is 1, each $R^4$ is independently hydrogen or $C_1$-$C_4$ alkyl, and each $R^3$ is independently hydrogen, alkyl, or cyclopropyl.

Another aspect is directed to a group of compounds of formula (I), wherein $X_1$ is N, $X_2$ is CH, $R^1$ is

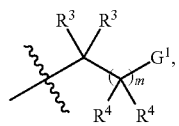

$G^1$ is —C(O)N($R^5$)$_2$, and m is 0.

Another aspect is directed to a group of compounds of formula (I), wherein $X_1$ is N, $X_2$ is CH, $R^1$ is

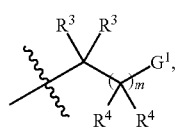

$G^1$ is —C(O)N($R^5$)$_2$, m is 0, and each $R^3$ is independently hydrogen or alkyl.

Another aspect is directed to a group of compounds of formula (I) and (I-a), wherein $X_1$ is CH, $X_2$ is N, and $R^1$ is monocyclic cycloalkyl, monocyclic heterocycle, or —$CH_2$—(monocyclic cycloalkyl); wherein the monocyclic cycloalkyl and the monocyclic heterocycle moieties are substituted with one $R^y$ group, and optionally further substituted with 1, 2, 3, 4, or 5 $R^z$ group. In certain embodiments, $R^y$ is OH or —($CH_2$)OH. In other embodiments, $R^y$ is OH. In yet other embodiments, $R^y$ is —($CH_2$)OH.

Another aspect is directed to a group of compounds of formula (I), wherein $X_1$ is CH, $X_2$ is N, and $R^1$ is monocyclic cycloalkyl substituted with one $R^y$ group, and optionally further substituted with 1, 2, 3, 4, or 5 $R^z$ group. In certain embodiments, $R^y$ is OH or —($CH_2$)OH. In other embodiments, $R^y$ is OH. In yet other embodiments, $R^y$ is —($CH_2$)OH.

Another aspect is directed to a group of compounds of formula (I), wherein $X_1$ is CH, $X_2$ is N, and $R^1$ is cyclohexyl substituted with one $R^y$ group, and optionally further substituted with 1, 2, 3, 4, or 5 $R^z$ group. In certain embodiments, $R^y$ is OH or —($CH_2$)OH. In other embodiments, $R^y$ is OH. In yet other embodiments, $R^y$ is —($CH_2$)OH.

Another aspect is directed to a group of compounds of formula (I-a) and (I-i) wherein $X_1$ is CH, $X_2$ is N, $G^2$ is a $C_3$-$C_6$ cycloalkyl wherein two non-adjacent atoms are optionally linked by an alkylenyl bridge of 1 or 2 carbon atoms, and $R^y$ is OH or —($CH_2$)—OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I-a) and (I-i) wherein $X_1$ is CH, and $X_2$ is N, $G^2$ is a $C_3$-$C_6$ cycloalkyl wherein two non-adjacent atoms are optionally linked by an alkylenyl bridge of 1 or 2 carbon atoms, and $R^y$ is OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I-a) and (I-i) wherein $X_1$ is CH, $X_2$ is N, $G^2$ is a $C_3$-$C_6$ cycloalkyl wherein two non-adjacent atoms are optionally linked by an alkylenyl bridge of 1 or 2 carbon atoms, and $R^y$ is —(CH$_2$)—OH. In certain embodiments, $G^2$ is cyclopentyl, cyclohexyl, or bicyclo[2.2.1]heptyl. In certain embodiments, $G^2$ is cyclohexyl.

Another aspect is directed to a group of compounds of formula (I), wherein $X_1$ is CH,

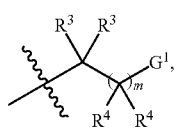

and
$G^1$ is OH.

Another aspect is directed to a group of compounds of formula (I), wherein $X_1$ is CH, $X_2$ is N, $R^1$ is

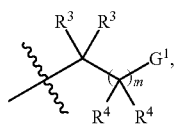

$G^1$ is OH, and each $R^4$ is independently hydrogen, alkyl, phenyl, or haloalkyl; two $R^4$ together with the carbon atom to which they are attached optionally form a $C_3$-$C_6$ cycloalkyl, oxtanyl, or tetrahydropyranyl, each of which is optionally substituted.

Another aspect is directed to a group of compounds of formula (I), wherein $X_1$ is CH, $X_2$ is N, $R^1$ is

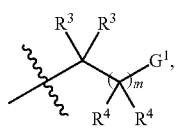

$G^1$ is OH, m is 1, and each $R^4$ is independently hydrogen or $C_1$-$C_4$ alkyl.

Another aspect is directed to a group of compounds of formula (I), wherein $X_1$ is CH, $X_2$ is N, $R^1$ is

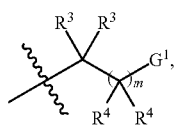

$G^1$ is OH, and one $R^3$ is hydrogen or alkyl and the other $R^3$ is hydrogen, alkyl, alkoxyalkyl, —C(O)N($R^{3a}$)($R^{3b}$), hydroxyalkyl, $G^{3a}$; or —($C_1$-$C_6$ alkylenyl)-$G^{3a}$; or two $R^3$ together with the carbon atom to which they are attached form a $C_3$-$C_6$ cycloalkyl.

Another aspect is directed to a group of compounds of formula (I), wherein $X_1$ is CH, $X_2$ is N, and the other is N, $R^1$ is

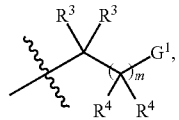

$G^1$ is OH, m is 1, each $R^4$ is independently hydrogen or $C_1$-$C_4$ alkyl, and each $R^3$ is independently hydrogen, alkyl, or cyclopropyl.

Another aspect is directed to a group of compounds of formula (I), wherein $X_1$ is CH, $X_2$ is N, $R^1$ is

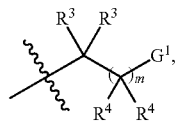

$G^1$ is —C(O)N($R^5$)$_2$, and m is 0.

Another aspect is directed to a group of compounds of formula (I), wherein $X_1$ is CH, $X_2$ is N, $R^1$ is

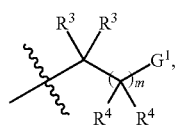

$G^1$ is —C(O)N($R^5$)$_2$, m is 0, and each $R^3$ is independently hydrogen or alkyl.

Within each group of the compounds of formula (I), (I-i), (I-a), and (I-b) described above, $R^z$, $R^2$, $R^5$, $R^x$, and n have values as described in the Summary and embodiments herein above.

Thus, within each group of the compounds described above, examples of a subgroup of compounds of formula (I), (I-i), (I-a), and (I-b) include, but not limited to, those wherein $R^2$ is —$OR^{2a}$, $G^{2a}$, —($C_1$-$C_6$ alkylenyl)-$G^{2a}$, $C_2$-$C_4$ alkenyl, or $C_2$-$C_4$ alkynyl, wherein the $C_2$-$C_4$ alkenyl and $C_2$-$C_4$ alkynyl are independently unsubstituted or substituted with a $G^{2aa}$.

Examples of another subgroup of compounds of formula (I), (I-i), (I-a), and (I-b) include, but not limited to, those wherein $R^2$ is —$OR^{2a}$ or $G^{2a}$.

Examples of another subgroup of compounds of formula (I), (I-i), (I-a), and (I-b) include, but not limited to, those wherein $R^2$ is —$OR^{2a}$.

Examples of another subgroup of compounds of formula (I), (I-i), (I-a), and (I-b) include, but not limited to, those wherein $R^2$ is —$OR^{2a}$, and $R^{2a}$ is alkyl or —($C_1$-$C_6$ alkylenyl)-$G^{2b}$.

Other examples of a subgroup of compounds of formula (I), (I-i), (I-a), and (I-b) include, but not limited to, those wherein $R^2$ is $G^{2a}$.

Yet other examples of a subgroup of compounds of formula (I), (I-i), (I-a), and (I-b) include, but not limited to, those wherein $R^2$ is $G^{2a}$, and $G^{2a}$ is aryl, heteroaryl, or heterocycle, each of which is optionally substituted as described in the Summary and embodiments herein above.

Yet other examples of a subgroup of compounds of formula (I), (I-i), (I-a), and (I-b) include, but not limited to, those wherein $R^2$ is $G^{2a}$, and $G^{2a}$ is aryl, optionally substituted as described in the Summary and embodiments herein above.

Yet other examples of a subgroup of compounds of formula (I), (I-i), (I-a), and (I-b) include, but not limited to, those wherein $R^2$ is $G^{2a}$, and $G^{2a}$ is phenyl, optionally substituted as described in the Summary and embodiments herein above.

Yet other examples of a subgroup of compounds of formula (I), (I-i), (I-a), and (I-b) include, but not limited to, those wherein $R^2$ is $G^{2a}$, and $G^{2a}$ is heteroaryl, optionally substituted as described in the Summary and embodiments herein above.

Yet other examples of a subgroup of compounds of formula (I), (I-i), (I-a), and (I-b) include, but not limited to, those wherein $R^2$ is $G^{2a}$, and $G^{2a}$ is heterocycle, optionally substituted as described in the Summary and embodiments herein above.

Yet other examples of a subgroup of compounds of formula (I), (I-i), (I-a), and (I-b) include, but not limited to, those wherein $R^2$ is $C_2$-$C_4$ alkenyl or $C_2$-$C_4$ alkynyl wherein the $C_2$-$C_4$ alkenyl and $C_2$-$C_4$ alkynyl are independently unsubstituted or substituted with a $G^{2aa}$.

Yet other examples of a subgroup of compounds of formula (I), (I-i), (I-a), and (I-b) include, but not limited to, those wherein $R^2$ is $C_2$-$C_4$ alkenyl or $C_2$-$C_4$ alkynyl wherein the $C_2$-$C_4$ alkenyl and $C_2$-$C_4$ alkynyl are independently unsubstituted or substituted with a $G^{2aa}$, and $G^{2aa}$ is optionally substituted aryl (e.g. phenyl) or optionally substituted cycloalkyl (e.g. cyclopentyl, cyclohexyl).

For example, included herein are compounds of formula (I-b) wherein $R^2$ is $G^{2a}$, $X_1$ and $X_2$ are CH. In certain embodiments, $G^{2a}$ is optionally substituted aryl. In certain embodiments, $G^{2a}$ is optionally substituted phenyl.

Other examples of compounds of formula (I-b) include those wherein $R^2$ is $G^{2a}$, $X_1$ and $X_2$ are CH, n is 1, and $R^x$ is alkyl, halogen, $O(R^{1a})$, or haloalkyl. In certain embodiments, $G^{2a}$ is optionally substituted aryl. In certain embodiments, $G^{2a}$ is optionally substituted phenyl.

For example, included herein are compounds of formula (I-b) wherein $R^2$ is $C_2$-$C_4$ alkenyl or $C_2$-$C_4$ alkynyl wherein the $C_2$-$C_4$ alkenyl and $C_2$-$C_4$ alkynyl are optionally substituted with a $G^{2aa}$ group, $X_1$ and $X_2$ are CH. In certain embodiments, $G^{2aa}$ is optionally substituted aryl (e.g. phenyl) or optionally substituted cycloalkyl (e.g. optionally substituted cyclopentyl, optionally substituted cyclohexyl).

Other examples of compounds of formula (I-b) include those wherein $R^2$ is $C_2$-$C_4$ alkenyl or $C_2$-$C_4$ alkynyl wherein the $C_2$-$C_4$ alkenyl and $C_2$-$C_4$ alkynyl are optionally substituted with a $G^{2aa}$ group wherein $G^{2aa}$ is phenyl, cyclopentyl, or cyclohexyl, each of which is optionally substituted, $X_1$ and $X_2$ are CH, n is 1, and $R^x$ is alkyl, halogen, $O(R^{1a})$, or haloalkyl.

For example, included herein are compounds of formula (I-b) wherein $R^2$ is $G^{2a}$, one of $X_1$ and $X_2$ is CH and the other is N. In certain embodiments, $G^{2a}$ is optionally substituted aryl. In certain embodiments, $G^{2a}$ is optionally substituted phenyl.

Other examples of compounds of formula (I-b) include those wherein $R^2$ is $G^{2a}$, one of $X_1$ and $X_2$ is CH and the other is N, n is 1, and $R^x$ is alkyl, halogen, $O(R^{1a})$, or haloalkyl. In certain embodiments, $G^{2a}$ is optionally substituted aryl. In certain embodiments, $G^{2a}$ is optionally substituted phenyl.

For example, included herein are compounds of formula (I-b) wherein $R^2$ is $C_2$-$C_4$ alkenyl or $C_2$-$C_4$ alkynyl wherein the $C_2$-$C_4$ alkenyl and $C_2$-$C_4$ alkynyl are optionally substituted with a $G^{2aa}$ group, one of $X_1$ and $X_2$ is CH and the other is N. In certain embodiments, $G^{2aa}$ is optionally substituted aryl (e.g. phenyl) or optionally substituted cycloalkyl (e.g. optionally substituted cyclopentyl, optionally substituted cyclohexyl).

Other examples of compounds of formula (I-b) include those wherein $R^2$ is $C_2$-$C_4$ alkenyl or $C_2$-$C_4$ alkynyl wherein the $C_2$-$C_4$ alkenyl and $C_2$-$C_4$ alkynyl are optionally substituted with a $G^{2aa}$ group wherein $G^{2aa}$ is phenyl, cyclopentyl, or cyclohexyl, each of which is optionally substituted, one of $X_1$ and $X_2$ is CH and the other is N, n is 1, and $R^x$ is alkyl, halogen, $O(R^{1a})$, or haloalkyl.

For example, included herein are compounds of formula (I-b) wherein $R^2$ is $G^{2a}$, $X_1$ is N, and $X_2$ is CH. In certain embodiments, $G^{2a}$ is optionally substituted aryl. In certain embodiments, $G^{2a}$ is optionally substituted phenyl.

Other examples of compounds of formula (I-b) include those wherein $R^2$ is $G^{2a}$, $X_1$ is N, $X_2$ is CH, n is 1, and $R^x$ is alkyl, halogen, $O(R^{1a})$, or haloalkyl. In certain embodiments, $G^{2a}$ is optionally substituted aryl. In certain embodiments, $G^{2a}$ is optionally substituted phenyl.

For example, included herein are compounds of formula (I-b) wherein $R^2$ is $C_2$-$C_4$ alkenyl or $C_2$-$C_4$ alkynyl wherein the $C_2$-$C_4$ alkenyl and $C_2$-$C_4$ alkynyl are optionally substituted with a $G^{2aa}$ group, $X_1$ is N, $X_2$ is CH. In certain embodiments, $G^{2aa}$ is optionally substituted aryl (e.g. phenyl) or optionally substituted cycloalkyl (e.g. optionally substituted cyclopentyl, optionally substituted cyclohexyl).

Other examples of compounds of formula (I-b) include those wherein $R^2$ is $C_2$-$C_4$ alkenyl or $C_2$-$C_4$ alkynyl wherein the $C_2$-$C_4$ alkenyl and $C_2$-$C_4$ alkynyl are optionally substituted with a $G^{2aa}$ group wherein $G^{2aa}$ is phenyl, cyclopentyl, or cyclohexyl, each of which is optionally substituted, $X_1$ is N, $X_2$ is CH, n is 1, and $R^x$ is alkyl, halogen, $O(R^{1a})$, or haloalkyl.

For example, included herein are compounds of formula (I-b) wherein $R^2$ is $G^{2a}$, $X_1$ is CH, and $X_2$ is N. In certain embodiments, $G^{2a}$ is optionally substituted aryl. In certain embodiments, $G^{2a}$ is optionally substituted phenyl.

Other examples of compounds of formula (I-b) include those wherein $R^2$ is $G^{2a}$, $X_1$ is CH, $X_2$ is N, and n is 1, $R^x$ is alkyl, halogen, $O(R^{1a})$, or haloalkyl. In certain embodiments, $G^{2a}$ is optionally substituted aryl. In certain embodiments, $G^{2a}$ is optionally substituted phenyl.

For example, included herein are compounds of formula (I-b) wherein $R^2$ is $C_2$-$C_4$ alkenyl or $C_2$-$C_4$ alkynyl wherein the $C_2$-$C_4$ alkenyl and $C_2$-$C_4$ alkynyl are optionally substituted with a $G^{2aa}$ group, $X_1$ is CH, and $X_2$ is N. In certain embodiments, $G^{2aa}$ is optionally substituted aryl (e.g. phenyl) or optionally substituted cycloalkyl (e.g. optionally substituted cyclopentyl, optionally substituted cyclohexyl).

Other examples of compounds of formula (I-b) include those wherein $R^2$ is $C_2$-$C_4$ alkenyl or $C_2$-$C_4$ alkynyl wherein the $C_2$-$C_4$ alkenyl and $C_2$-$C_4$ alkynyl are optionally substituted with a $G^{2aa}$ group wherein $G^{2aa}$ is phenyl, cyclopentyl, or cyclohexyl, each of which is optionally substituted, $X_1$ is CH, and $X_2$ is N, n is 1, and $R^x$ is alkyl, halogen, $O(R^{1a})$, or haloalkyl.

Exemplary compounds include, but are not limited to:
(1S,2S)-2-[({6-[4-(trifluoromethyl)phenyl]pyridin-2-yl}methyl)amino]cyclohexanol;
(2S,3S)-3-methyl-2-[({6-[4-(trifluoromethyl)phenyl]pyridin-2-yl}methyl)amino]pentan-1-ol;
(2S)-3-methyl-2-[({6-[4-(trifluoromethyl)phenyl]pyridin-2-yl}methyl)amino]butan-1-ol;
(1R,2S)-2-[({6-[4-(trifluoromethyl)phenyl]pyridin-2-yl}methyl)amino]cyclohexanol;
2-[({6-[4-(trifluoromethyl)phenyl]pyridin-2-yl}methyl) amino]cyclohexanol;
(1R,2R)-2-[({6-[4-(trifluoromethyl)phenyl]pyridin-2-yl}methyl)amino]cyclohexanol;

(1S,2R)-2-[({6-[4-(trifluoromethyl)phenyl]pyridin-2-yl}methyl)amino]cyclohexanol;
2,2-dimethyl-3-[({6-[4-(trifluoromethyl)phenyl]pyridin-2-yl}methyl)amino]propan-1-ol;
{(1R,2R,3S,4S)-3-[({6-[4-(trifluoromethyl)phenyl]pyridin-2-yl}methyl)amino]bicyclo[2.2.1]hept-2-yl}methanol;
(2R)-3-methyl-2-({[6-(pyrrolidin-1-yl)pyridin-2-yl]methyl}amino)butan-1-ol;
(2R)-3-methyl-2-({[6-(piperidin-1-yl)pyridin-2-yl]methyl}amino)butan-1-ol;
(2R)-2-({[6-(benzyloxy)pyridin-2-yl]methyl}amino)-3-methylbutan-1-ol;
(2R)-2-({[3-fluoro-6-(2-fluorophenyl)pyridin-2-yl]methyl}amino)-3-methylbutan-1-ol;
(2R)-2-({[3-fluoro-6-(3-fluorophenyl)pyridin-2-yl]methyl}amino)-3-methylbutan-1-ol;
(2R)-2-({[6-(3-chlorophenyl)-3-fluoropyridin-2-yl]methyl}amino)-3-methylbutan-1-ol;
(2R)-2-[({3-fluoro-6-[3-(trifluoromethyl)phenyl]pyridin-2-yl}methyl)amino]-3-methylbutan-1-ol;
(2R)-2-[({3-fluoro-6-[4-(trifluoromethyl)phenyl]pyridin-2-yl}methyl)amino]-3-methylbutan-1-ol;
(2R)-2-[({3-fluoro-6-[3-(trifluoromethoxy)phenyl]pyridin-2-yl}methyl)amino]-3-methylbutan-1-ol;
(2R)-2-[({3-fluoro-6-[4-(trifluoromethoxy)phenyl]pyridin-2-yl}methyl)amino]-3-methylbutan-1-ol;
(2R)-2-({[6-(3,4-dichlorophenyl)-3-fluoropyridin-2-yl]methyl}amino)-3-methylbutan-1-ol;
(2R)-2-({[6-(3,5-dichlorophenyl)-3-fluoropyridin-2-yl]methyl}amino)-3-methylbutan-1-ol;
(2R)-2-[({6-[3,5-bis(trifluoromethyl)phenyl]-3-fluoropyridin-2-yl}methyl)amino]-3-methylbutan-1-ol;
(2R)-2-[({3-fluoro-6-[2-fluoro-5-(propan-2-yloxy)phenyl]pyridin-2-yl}methyl)amino]-3-methylbutan-1-ol;
(2R)-2-[({3-fluoro-6-[3-(propan-2-yloxy)phenyl]pyridin-2-yl}methyl)amino]-3-methylbutan-1-ol;
(2R)-2-[({3-fluoro-6-[3-fluoro-4-(propan-2-yloxy)phenyl]pyridin-2-yl}methyl)amino]-3-methylbutan-1-ol;
(2R)-2-{[(6-tert-butoxypyridin-2-yl)methyl]amino}-3-methylbutan-1-ol;
(2R)-2-({[3-fluoro-6-(4-fluorophenyl)pyridin-2-yl]methyl}amino)-3-methylbutan-1-ol;
(2R)-2-({[5-fluoro-6'-(trifluoromethyl)-2,3'-bipyridin-6-yl]methyl}amino)-3-methylbutan-1-ol;
(2R)-2-cyclopropyl-2-[({3-fluoro-6-[4-(trifluoromethyl)phenyl]pyridin-2-yl}methyl)amino]ethanol;
(2R)-2-({[5-fluoro-2'-(trifluoromethyl)-2,4'-bipyridin-6-yl]methyl}amino)-3-methylbutan-1-ol;
(2R)-2-({[4-(4-fluorophenyl)pyrimidin-2-yl]methyl}amino)-3-methylbutan-1-ol;
(2R)-3-methyl-2-[({4-[4-(trifluoromethyl)phenyl]pyrimidin-2-yl}methyl)amino]butan-1-ol;
(2R)-2-({[2-(4-chlorophenyl)pyrimidin-4-yl]methyl}amino)-3-methylbutan-1-ol;
(2R)-2-{[(5,5'-difluoro-2,2'-bipyridin-6-yl)methyl]amino}-3-methylbutan-1-ol;
1-{2-fluoro-3-[5-fluoro-6-({[(2R)-1-hydroxy-3-methylbutan-2-yl]amino}methyl)pyridin-2-yl]phenyl}ethanone;
(2R)-2-{[(6'-chloro-5-fluoro-2,3'-bipyridin-6-yl)methyl]amino}-3-methylbutan-1-ol;
3-[5-fluoro-6-({[(2R)-1-hydroxy-3-methylbutan-2-yl]amino}methyl)pyridin-2-yl]-N,N-dimethylbenzenesulfonamide;
1-{3-[5-fluoro-6-({[(2R)-1-hydroxy-3-methylbutan-2-yl]amino}methyl)pyridin-2-yl]phenyl}ethanone;
N,N-diethyl-3-[5-fluoro-6-({[(2R)-1-hydroxy-3-methylbutan-2-yl]amino}methyl)pyridin-2-yl]benzamide;
(2R)-2-({[6-(4-chlorophenyl)-3-fluoropyridin-2-yl]methyl}amino)-3-methylbutan-1-ol;
(2R)-2-[({6-[3-(dimethylamino)phenyl]-3-fluoropyridin-2-yl}methyl)amino]-3-methylbutan-1-ol;
(2R)-2-[({3-fluoro-6-[3-(morpholin-4-yl)phenyl]pyridin-2-yl}methyl)amino]-3-methylbutan-1-ol;
{3-[5-fluoro-6-({[(2R)-1-hydroxy-3-methylbutan-2-yl]amino}methyl)pyridin-2-yl]phenyl}(piperidin-1-yl)methanone;
{3-[5-fluoro-6-({[(2R)-1-hydroxy-3-methylbutan-2-yl]amino}methyl)pyridin-2-yl]phenyl}(4-methylpiperidin-1-yl)methanone;
(2R)-2-[({6-[3-chloro-4-(trifluoromethyl)phenyl]-3-fluoropyridin-2-yl}methyl)amino]-3-methylbutan-1-ol;
(2R)-2-[({3-fluoro-6-[3-(piperidin-1-ylsulfonyl)phenyl]pyridin-2-yl}methyl)amino]-3-methylbutan-1-ol;
(2R)-2-[({3-fluoro-6-[3-(pyrrolidin-1-yl)phenyl]pyridin-2-yl}methyl)amino]-3-methylbutan-1-ol;
3-[5-fluoro-6-({[(2R)-1-hydroxy-3-methylbutan-2-yl]amino}methyl)pyridin-2-yl]-N,N,4-trimethylbenzenesulfonamide;
N,N-diethyl-3-[5-fluoro-6-({[(2R)-1-hydroxy-3-methylbutan-2-yl]amino}methyl)pyridin-2-yl]benzenesulfonamide;
N-cyclohexyl-3-[5-fluoro-6-({[(2R)-1-hydroxy-3-methylbutan-2-yl]amino}methyl)pyridin-2-yl]-N-methylbenzamide;
(2R)-2-[({3-fluoro-6-[4-(2,2,2-trifluoroethoxy)phenyl]pyridin-2-yl}methyl)amino]-3-methylbutan-1-ol;
(2R)-2-[({3-fluoro-6-[3-(morpholin-4-ylsulfonyl)phenyl]pyridin-2-yl}methyl)amino]-3-methylbutan-1-ol;
(2R)-2-({[5-fluoro-2'-(morpholin-4-yl)-2,4'-bipyridin-6-yl]methyl}amino)-3-methylbutan-1-ol;
3-[5-fluoro-6-({[(2R)-1-hydroxy-3-methylbutan-2-yl]amino}methyl)pyridin-2-yl]-N,N-di(propan-2-yl)benzamide;
(2R)-2-({[5-fluoro-6'-(propan-2-yloxy)-2,3'-bipyridin-6-yl]methyl}amino)-3-methylbutan-1-ol;
N-benzyl-3-[5-fluoro-6-({[(2R)-1-hydroxy-3-methylbutan-2-yl]amino}methyl)pyridin-2-yl]-N-methylbenzamide;
(2R)-2-{[(3-fluoro-6-{2-methyl-5-[(trifluoromethyl)sulfonyl]phenyl}pyridin-2-yl)methyl]amino}-3-methylbutan-1-ol;
(2R)-2-[({3-fluoro-6-[3-(pyrrolidin-1-ylsulfonyl)phenyl]pyridin-2-yl}methyl)amino]-3-methylbutan-1-ol;
N-tert-butyl-3-[5-fluoro-6-({[(2R)-1-hydroxy-3-methylbutan-2-yl]amino}methyl)pyridin-2-yl]-N-methylbenzenesulfonamide;
{3-[5-fluoro-6-({[(2R)-1-hydroxy-3-methylbutan-2-yl]amino}methyl)pyridin-2-yl]phenyl}(thiomorpholin-4-yl)methanone;
(2R)-2-({[3-fluoro-6-(1-methyl-1H-indol-4-yl)pyridin-2-yl]methyl}amino)-3-methylbutan-1-ol;
(2R)-2-({[3-fluoro-6-(1-methyl-1H-indol-6-yl)pyridin-2-yl]methyl}amino)-3-methylbutan-1-ol;
(2R)-2-[({3-fluoro-6-[3-(trifluoromethyl)piperidin-1-yl]pyridin-2-yl}methyl)amino]-3-methylbutan-1-ol;
(2R)-2-[({3-fluoro-6-[4-(trifluoromethyl)piperidin-1-yl]pyridin-2-yl}methyl)amino]-3-methylbutan-1-ol;
(2R)-2-[({3-fluoro-6-[3-(trifluoromethyl)pyrrolidin-1-yl]pyridin-2-yl}methyl)amino]-3-methylbutan-1-ol;
(2R)-2-({[5-fluoro-6'-(2,2,2-trifluoroethoxy)-2,3'-bipyridin-6-yl]methyl}amino)-3-methylbutan-1-ol;
(2R)-3-methyl-2-({[6'-(trifluoromethyl)-2,3'-bipyridin-6-yl]methyl}amino)butan-1-ol;
(2R)-2-({[6-(3,4-dihydroisoquinolin-2(1H)-yl)-3-fluoropyridin-2-yl]methyl}amino)-3-methylbutan-1-ol;

(2R)-2-({[6-(1,3-dihydro-2H-isoindol-2-yl)-3-fluoropyridin-2-yl]methyl}amino)-3-methylbutan-1-ol;
(2R)-2-({[3-fluoro-6-(quinolin-3-yl)pyridin-2-yl]methyl}amino)-3-methylbutan-1-ol;
(2R)-2-({[5-fluoro-5'-(trifluoromethyl)-2,2'-bipyridin-6-yl]methyl}amino)-3-methylbutan-1-ol;
2-[({3-fluoro-6-[4-(trifluoromethyl)phenyl]pyridin-2-yl}methyl)amino]-3-methoxypropan-1-ol;
(2R)-2-cyclopropyl-2-({[5-fluoro-6'-(trifluoromethyl)-2,3'-bipyridin-6-yl]methyl}amino)ethanol;
(2R)-2-cyclopropyl-2-({[5-fluoro-6'-(2,2,2-trifluoroethoxy)-2,3'-bipyridin-6-yl]methyl}amino)ethanol;
(2R)-2-[({3-fluoro-6-[4-(trifluoromethyl)phenyl]pyridin-2-yl}methyl)amino]butan-1-ol;
(2R)-2-({[5-fluoro-6'-(trifluoromethyl)-2,3'-bipyridin-6-yl]methyl}amino)butan-1-ol;
{1-[({3-fluoro-6-[4-(trifluoromethyl)phenyl]pyridin-2-yl}methyl)amino]cyclobutyl}methanol;
{1-[({3-fluoro-6-[4-(trifluoromethyl)phenyl]pyridin-2-yl}methyl)amino]cyclopentyl}methanol;
{1-[({3-fluoro-6-[4-(trifluoromethyl)phenyl]pyridin-2-yl}methyl)amino]cyclohexyl}methanol;
(2R)-2-[({3-fluoro-6-[4-(trifluoromethyl)phenyl]pyridin-2-yl}methyl)amino]propan-1-ol;
(2R)-2-[({3-fluoro-6-[4-(trifluoromethyl)phenyl]pyridin-2-yl}methyl)amino]pentan-1-ol;
(2R)-2-cyclohexyl-2-[({3-fluoro-6-[4-(trifluoromethyl)phenyl]pyridin-2-yl}methyl)amino]ethanol;
(2R)-2-[({3-fluoro-6-[4-(trifluoromethyl)phenyl]pyridin-2-yl}methyl)amino]-3,3-dimethylbutan-1-ol;
3-[({3-fluoro-6-[4-(trifluoromethyl)phenyl]pyridin-2-yl}methyl)amino]butan-2-ol;
(2R)-2-({[5-fluoro-6'-(trifluoromethyl)-2,3'-bipyridin-6-yl]methyl}amino)pentan-1-ol;
(2R)-2-cyclohexyl-2-({[5-fluoro-6'-(trifluoromethyl)-2,3'-bipyridin-6-yl]methyl}amino)ethanol;
(2R)-2-({[5-fluoro-6'-(trifluoromethyl)-2,3'-bipyridin-6-yl]methyl}amino)-3,3-dimethylbutan-1-ol;
3-({[5-fluoro-6'-(trifluoromethyl)-2,3'-bipyridin-6-yl]methyl}amino)butan-2-ol;
(2R)-2-({[6-(4,4-difluoropiperidin-1-yl)-3-fluoropyridin-2-yl]methyl}amino)-3-methylbutan-1-ol;
(2R)-2-({[3-fluoro-6-(5-fluoro-1,3-dihydro-2H-isoindol-2-yl)pyridin-2-yl]methyl}amino)-3-methylbutan-1-ol;
(2R)-2-({[3-fluoro-6-(4-fluoro-1,3-dihydro-2H-isoindol-2-yl)pyridin-2-yl]methyl}amino)-3-methylbutan-1-ol;
(2R)-2-({[6-(4-chloro-1,3-dihydro-2H-isoindol-2-yl)-3-fluoropyridin-2-yl]methyl}amino)-3-methylbutan-1-ol;
(2R)-2-[({3-fluoro-6-[5-(trifluoromethyl)-1,3-dihydro-2H-isoindol-2-yl]pyridin-2-yl}methyl)amino]-3-methylbutan-1-ol;
(2R)-2-({[3-fluoro-6-(5-fluoro-3,4-dihydroisoquinolin-2(1H)-yl)pyridin-2-yl]methyl}amino)-3-methylbutan-1-ol;
(2R)-2-({[3-fluoro-6-(7-fluoro-3,4-dihydroisoquinolin-2(1H)-yl)pyridin-2-yl]methyl}amino)-3-methylbutan-1-ol;
(2R)-2-({[3-fluoro-6-(8-fluoro-3,4-dihydroisoquinolin-2(1H)-yl)pyridin-2-yl]methyl}amino)-3-methylbutan-1-ol;
(2R)-2-({[6-(6-chloro-3,4-dihydroisoquinolin-2(1H)-yl)-3-fluoropyridin-2-yl]methyl}amino)-3-methylbutan-1-ol;
(2R)-2-[({3-fluoro-6-[5-(trifluoromethyl)-3,4-dihydroisoquinolin-2(1H)-yl]pyridin-2-yl}methyl)amino]-3-methylbutan-1-ol;
(2R)-2-[({3-fluoro-6-[7-(trifluoromethyl)-3,4-dihydroisoquinolin-2(1H)-yl]pyridin-2-yl}methyl)amino]-3-methylbutan-1-ol;
(3R)-3-[({3-fluoro-6-[4-(trifluoromethyl)phenyl]pyridin-2-yl}methyl)amino]-2,4-dimethylpentan-2-ol;
(3R)-3-({[5-fluoro-6'-(trifluoromethyl)-2,3'-bipyridin-6-yl]methyl}amino)-2,4-dimethylpentan-2-ol;
(3R)-3-[({3-fluoro-6-[4-(trifluoromethyl)phenyl]pyridin-2-yl}methyl)amino]-4-methylpentan-2-ol;
(3R)-3-({[5-fluoro-6'-(trifluoromethyl)-2,3'-bipyridin-6-yl]methyl}amino)-4-methylpentan-2-ol;
(2R)-2-({[3-fluoro-6'-(trifluoromethyl)-2,3'-bipyridin-6-yl]methyl}amino)-3-methylbutan-1-ol;
(2R)-2-({[5-chloro-6'-(trifluoromethyl)-2,3'-bipyridin-6-yl]methyl}amino)-3-methylbutan-1-ol;
(2R)-3-methyl-2-({[5-methyl-6'-(trifluoromethyl)-2,3'-bipyridin-6-yl]methyl}amino)butan-1-ol;
(2R)-2-({[5-methoxy-6'-(trifluoromethyl)-2,3'-bipyridin-6-yl]methyl}amino)-3-methylbutan-1-ol;
(2R)-2-[({3-fluoro-6-[2-(trifluoromethyl)pyrimidin-5-yl]pyridin-2-yl}methyl)amino]-3-methylbutan-1-ol;
(2R)-2-[({3-fluoro-6-[2-(2,2,2-trifluoroethoxy)pyrimidin-5-yl]pyridin-2-yl}methyl)amino]-3-methylbutan-1-ol;
(3R)-3-({[5-fluoro-6'-(trifluoromethyl)-2,3'-bipyridin-6-yl]methyl}amino)pentan-2-ol;
(2R,3R)-2-({[5-fluoro-6'-(trifluoromethyl)-2,3'-bipyridin-6-yl]methyl}amino)butane-1,3-diol;
(1S,2S)-2-({[5-fluoro-6'-(trifluoromethyl)-2,3'-bipyridin-6-yl]methyl}amino)cyclohexanol;
(1R,2S)-2-({[5-fluoro-6'-(trifluoromethyl)-2,3'-bipyridin-6-yl]methyl}amino)cyclohexanol;
(2R)-2-({[3-fluoro-6-(1-phenylethenyl)pyridin-2-yl]methyl}amino)-3-methylbutan-1-ol;
(2R)-2-[({3-fluoro-6-[1-(4-fluorophenyl)ethenyl]pyridin-2-yl}methyl)amino]-3-methylbutan-1-ol;
(2R)-2-({[6-(cyclohex-1-en-1-yl)-3-fluoropyridin-2-yl]methyl}amino)-3-methylbutan-1-ol;
(2R)-2-({[3-fluoro-6-(1-phenylethyl)pyridin-2-yl]methyl}amino)-3-methylbutan-1-ol;
(2R)-2-[({3-fluoro-6-[1-(4-fluorophenyl)ethyl]pyridin-2-yl}methyl)amino]-3-methylbutan-1-ol;
(2R)-2-{[(6-cyclohexyl-3-fluoropyridin-2-yl)methyl]amino}-3-methylbutan-1-ol;
$N^2$-{[5-fluoro-6'-(trifluoromethyl)-2,3'-bipyridin-6-yl]methyl}-N-naphthalen-2-yl-L-threoninamide;
(2R)-2-[({5-fluoro-2-[4-(trifluoromethyl)phenyl]pyrimidin-4-yl}methyl)amino]-3-methylbutan-1-ol;
{1-[({2-[4-(trifluoromethyl)phenyl]pyrimidin-4-yl}methyl)amino]cyclopentyl}methanol;
{1-[({2-[4-(trifluoromethyl)phenyl]pyrimidin-4-yl}methyl)amino]cyclohexyl}methanol;
(2R)-2-[({2-[4-(trifluoromethyl)phenyl]pyrimidin-4-yl}methyl)amino]propan-1-ol;
(2R)-2-[({2-[4-(trifluoromethyl)phenyl]pyrimidin-4-yl}methyl)amino]butan-1-ol;
(2R)-2-phenyl-2-[({2-[4-(trifluoromethyl)phenyl]pyrimidin-4-yl}methyl)amino]ethanol;
(2R)-2-[({2-[4-(trifluoromethyl)phenyl]pyrimidin-4-yl}methyl)amino]pentan-1-ol;
(2R)-4-methyl-2-[({2-[4-(trifluoromethyl)phenyl]pyrimidin-4-yl}methyl)amino]pentan-1-ol;
3-methyl-2-[({2-[4-(trifluoromethyl)phenyl]pyrimidin-4-yl}methyl)amino]pentan-1-ol;
3-methoxy-2-[({2-[4-(trifluoromethyl)phenyl]pyrimidin-4-yl}methyl)amino]propan-1-ol;
(2R)-2-cyclopropyl-2-[({2-[4-(trifluoromethyl)phenyl]pyrimidin-4-yl}methyl)amino]ethanol;
(2R)-2-cyclohexyl-2-[({2-[4-(trifluoromethyl)phenyl]pyrimidin-4-yl}methyl)amino]ethanol;
(2R)-3,3-dimethyl-2-[({2-[4-(trifluoromethyl)phenyl]pyrimidin-4-yl}methyl)amino]butan-1-ol;

3-[({2-[4-(trifluoromethyl)phenyl]pyrimidin-4-yl}methyl) amino]butan-2-ol;

(2R,3R)-2-[({2-[4-(trifluoromethyl)phenyl]pyrimidin-4-yl}methyl)amino]butane-1,3-diol;

(1S,2S)-1-phenyl-2-[({2-[4-(trifluoromethyl)phenyl]pyrimidin-4-yl}methyl)amino]propane-1,3-diol;

(1-{[({2-[4-(trifluoromethyl)phenyl]pyrimidin-4-yl}methyl)amino]methyl}cyclohexyl)methanol;

{(1S,2S,3R,4R)-3-[({2-[4-(trifluoromethyl)phenyl]pyrimidin-4-yl}methyl)amino]bicyclo[2.2.1]hept-2-yl}methanol;

(1S,2S)-2-[({2-[4-(trifluoromethyl)phenyl]pyrimidin-4-yl}methyl)amino]cyclohexanol;

(1R,2S)-2-[({2-[4-(trifluoromethyl)phenyl]pyrimidin-4-yl}methyl)amino]cyclohexanol;

3-[({2-[6-(trifluoromethyl)pyridin-3-yl]pyrimidin-4-yl}methyl)amino]butan-2-ol;

(2R)-2-({[6-(bicyclo[2.2.1]hept-2-yl)-3-fluoropyridin-2-yl]methyl}amino)-3-methylbutan-1-ol;

(2R)-2-({[3-fluoro-6-(4-methylcyclohexyl)pyridin-2-yl]methyl}amino)-3-methylbutan-1-ol;

(2R)-2-({[6-(4-ethylcyclohexyl)-3-fluoropyridin-2-yl]methyl}amino)-3-methylbutan-1-ol;

(2R)-2-({[6-(4,4-dimethylcyclohexyl)-3-fluoropyridin-2-yl]methyl}amino)-3-methylbutan-1-ol;

(2R)-2-({[6-(4,4-difluorocyclohexyl)-3-fluoropyridin-2-yl]methyl}amino)-3-methylbutan-1-ol;

tert-butyl 4-[5-fluoro-6-({[(2R)-1-hydroxy-3-methylbutan-2-yl]amino}methyl)pyridin-2-yl]piperidine-1-carboxylate;

(2R)-2-{[(6-cycloheptyl-3-fluoropyridin-2-yl)methyl]amino}-3-methylbutan-1-ol;

(2R)-3-methyl-2-{[(2-{4-[(trifluoromethyl)sulfonyl]phenyl}pyrimidin-4-yl)methyl]amino}butan-1-ol;

(1-{[(2-{4-[(trifluoromethyl)sulfonyl]phenyl}pyrimidin-4-yl)methyl]amino}cyclohexyl)methanol;

(2R)-2-{[(2-{4-[(trifluoromethyl)sulfonyl]phenyl}pyrimidin-4-yl)methyl]amino}butan-1-ol;

3-methoxy-2-{[(2-{4-[(trifluoromethyl)sulfonyl]phenyl}pyrimidin-4-yl)methyl]amino}propan-1-ol;

(2R,3R)-2-{[(2-{4-[(trifluoromethyl)sulfonyl]phenyl}pyrimidin-4-yl)methyl]amino 1 butane-1,3-diol;

(2R)-2-({[6-(4-tert-butylcyclohexyl)-3-fluoropyridin-2-yl]methyl}amino)-3-methylbutan-1-ol;

(2R)-2-({[6-(1,4-dioxaspiro[4.5]dec-8-yl)-3-fluoropyridin-2-yl]methyl}amino)-3-methylbutan-1-ol;

(2R)-2-({[6-(1,4-dioxaspiro[4.5]dec-7-yl)-3-fluoropyridin-2-yl]methyl}amino)-3-methylbutan-1-ol;

(2R)-2-[({3-fluoro-6-[4-(trifluoromethyl)cyclohexyl]pyridin-2-yl}methyl)amino]-3-methylbutan-1-ol;

(2R)-2-({[3-fluoro-6-(1,2,3,4-tetrahydronaphthalen-2-yl)pyridin-2-yl]methyl}amino)-3-methylbutan-1-ol;

tert-butyl 3-[5-fluoro-6-({[(2R)-1-hydroxy-3-methylbutan-2-yl]amino}methyl)pyridin-2-yl]piperidine-1-carboxylate;

(2R)-2-{[(6-cyclopentyl-3-fluoropyridin-2-yl)methyl]amino}-3-methylbutan-1-ol;

tert-butyl 3-[5-fluoro-6-({[(2R)-1-hydroxy-3-methylbutan-2-yl]amino}methyl)pyridin-2-yl]pyrrolidine-1-carboxylate;

(2R)-2-[({3-fluoro-6-[4-(trifluoromethyl)cyclohex-1-en-1-yl]pyridin-2-yl}methyl)amino]-3-methylbutan-1-ol;

(2R)-2-({[6-(4,4-difluorocyclohex-1-en-1-yl)-3-fluoropyridin-2-yl]methyl}amino)-3-methylbutan-1-ol;

(2R)-3-methyl-2-{[(6-phenylpyridin-2-yl)methyl]amino}butan-1-ol;

(2R)-3-methyl-2-[({6-[3-(trimethylsilyl)phenyl]pyridin-2-yl}methyl)amino]butan-1-ol;

(2R)-2-{[(6-{5-[tert-butyl(dimethyl)silyl]thiophen-2-yl}pyridin-2-yl)methyl]amino}-3-methylbutan-1-ol;

(2R)-2-({[6-(3,4-difluorophenyl)-3-fluoropyridin-2-yl]methyl}amino)-3-methylbutan-1-ol;

(2R)-2-({[6-(1-benzothiophen-2-yl)-3-fluoropyridin-2-yl]methyl}amino)-3-methylbutan-1-ol;

(2R)-2-({[2-(4,4-difluoropiperidin-1-yl)-5-fluoropyrimidin-4-yl]methyl}amino)-3-methylbutan-1-ol;

(2R)-2-[({3-fluoro-6-[(E)-2-(3-fluorophenyl)ethenyl]pyridin-2-yl}methyl)amino]-3-methylbutan-1-ol;

(2R)-2-({[6-(1,3-benzothiazol-5-yl)-3-fluoropyridin-2-yl]methyl}amino)-3-methylbutan-1-ol;

(2R)-2-[({3-fluoro-6-[(4-methoxyphenyl)ethynyl]pyridin-2-yl}methyl)amino]-3-methylbutan-1-ol;

(2R)-2-({[6-(3-cyclohexylprop-1-yn-1-yl)-3-fluoropyridin-2-yl]methyl}amino)-3-methylbutan-1-ol;

2-methyl-2-[({6-[3-(trimethylsilyl)phenyl]pyridin-2-yl}methyl)amino]propan-1-ol;

(2R)-2-[({3-fluoro-6-[(4-fluorophenyl)ethynyl]pyridin-2-yl}methyl)amino]-3-methylbutan-1-ol;

(2R)-2-[({6-[(3,4-difluorophenyl)ethynyl]-3-fluoropyridin-2-yl}methyl)amino]-3-methylbutan-1-ol;

(2R)-2-({[6-(cyclohexylethynyl)-3-fluoropyridin-2-yl]methyl}amino)-3-methylbutan-1-ol;

(2R)-2-[({6-[(4-tert-butylphenyl)ethynyl]-3-fluoropyridin-2-yl}methyl)amino]-3-methylbutan-1-ol;

(2R)-2-({[6-(5-chlorothiophen-2-yl)-3-fluoropyridin-2-yl]methyl}amino)-3-methylbutan-1-ol;

(2R)-2-({[3-fluoro-6-(5-methylthiophen-2-yl)pyridin-2-yl]methyl}amino)-3-methylbutan-1-ol;

(2R)-2-({[3-fluoro-6-(3,4,5-trifluorophenyl)pyridin-2-yl]methyl}amino)-3-methylbutan-1-ol;

(2R)-2-({[3-fluoro-6-(2,3,4-trifluorophenyl)pyridin-2-yl]methyl}amino)-3-methylbutan-1-ol;

(2R)-2-({[3-fluoro-6-(2,4,5-trifluorophenyl)pyridin-2-yl]methyl}amino)-3-methylbutan-1-ol;

(2R)-2-({[6-(3,5-difluorophenyl)-3-fluoropyridin-2-yl]methyl}amino)-3-methylbutan-1-ol;

(2R)-2-({[3-fluoro-6-(1-methyl-1H-indol-5-yl)pyridin-2-yl]methyl}amino)-3-methylbutan-1-ol;

(2R)-2-({[3-fluoro-6-(1-methyl-1H-indol-2-yl)pyridin-2-yl]methyl}amino)-3-methylbutan-1-ol;

(2R)-2-({[3-fluoro-6-(furan-3-yl)pyridin-2-yl]methyl}amino)-3-methylbutan-1-ol;

(2R)-2-({[5-fluoro-5'-methyl-6'-(morpholin-4-yl)-2,3'-bipyridin-6-yl]methyl}amino)-3-methylbutan-1-ol;

(2R)-2-({[6-(1-benzothiophen-5-yl)-3-fluoropyridin-2-yl]methyl}amino)-3-methylbutan-1-ol;

(2R)-2-({[6-(1-benzofuran-5-yl)-3-fluoropyridin-2-yl]methyl}amino)-3-methylbutan-1-ol;

(2R)-2-[({3-fluoro-6-[cis-4-(trifluoromethyl)cyclohexyl]pyridin-2-yl}methyl)amino]-3-methylbutan-1-ol;

(2R)-2-[({3-fluoro-6-[trans-4-(trifluoromethyl)cyclohexyl]pyridin-2-yl}methyl)amino]-3-methylbutan-1-ol;

tert-butyl 4-(benzyloxy)-2-[5-fluoro-6-({[(2R)-1-hydroxy-3-methylbutan-2-yl]amino}methyl)pyridin-2-yl]-1H-indole-1-carboxylate;

(2R)-2-[({3-fluoro-6-[3-(1H-pyrazol-1-yl)phenyl]pyridin-2-yl}methyl)amino]-3-methylbutan-1-ol;

(2R)-2-[({6-[2-(dimethylamino)pyrimidin-5-yl]-3-fluoropyridin-2-yl}methyl)amino]-3-methylbutan-1-ol;

(2R)-2-({[6-(4-butoxy-3-chlorophenyl)pyridin-2-yl]methyl}amino)-3-methylbutan-1-ol;

(2R)-3-methyl-2-{[(6-{[4-(pentafluoro-$\lambda^6$-sulfanyl)phenyl]ethynyl}pyridin-2-yl)methyl]amino}butan-1-ol;

(2R)-2-[({6-[(4-fluorophenyl)ethynyl]pyridin-2-yl}methyl)amino]-3-methylbutan-1-ol;
(2R)-2-[({6-[(3,4-difluorophenyl)ethynyl]pyridin-2-yl}methyl)amino]-3-methylbutan-1-01;
[1-({[6-(3-chloro-4-fluorophenyl)pyridin-2-yl]methyl}amino)cyclopentyl]methanol;
(2R)-2-[({6-[4-fluoro-3-(trifluoromethyl)phenyl]pyridin-2-yl}methyl)amino]-3-methylbutan-1-ol;
{1-[({6-[4-fluoro-3-(trifluoromethyl)phenyl]pyridin-2-yl}methyl)amino]cyclopentyl}methanol;
2-fluoro-5-[6-({[(2R)-1-hydroxy-3-methylbutan-2-yl]amino}methyl)pyridin-2-yl]benzonitrile;
(2R)-2-[({6-[2,4-bis(trifluoromethyl)phenyl]pyridin-2-yl}methyl)amino]-3-methylbutan-1-ol;
{1-[({6-[2,4-bis(trifluoromethyl)phenyl]pyridin-2-yl}methyl)amino]cyclopentyl}methanol;
{1-[({6-[3,5-bis(trifluoromethyl)phenyl]pyridin-2-yl}methyl)amino]cyclopentyl}methanol;
tert-butyl 2-[5-fluoro-6-({[(2R)-1-hydroxy-3-methylbutan-2-yl]amino}methyl)pyridin-2-yl]-1H-indole-1-carboxylate;
(2R)-2-({[3-fluoro-6-(1H-indol-2-yl)pyridin-2-yl]methyl}amino)-3-methylbutan-1-ol;
{4-[5-fluoro-6-({[(2R)-1-hydroxy-3-methylbutan-2-yl]amino}methyl)pyridin-2-yl]phenyl}(4-methylpiperidin-1-yl)methanone;
{4-[5-fluoro-6-({[(2R)-1-hydroxy-3-methylbutan-2-yl]amino}methyl)pyridin-2-yl]phenyl}(pyrrolidin-1-yl)methanone;
4-[5-fluoro-6-({[(2R)-1-hydroxy-3-methylbutan-2-yl]amino}methyl)pyridin-2-yl]-N,N-dipropylbenzamide;
(2R)-2-{[(5'-chloro-5-fluoro-2,3'-bipyridin-6-yl)methyl]amino}-3-methylbutan-1-ol;
2-fluoro-5-[5-fluoro-6-({[(2R)-1-hydroxy-3-methylbutan-2-yl]amino}methyl)pyridin-2-yl]benzonitrile;
(2R)-2-({[3-fluoro-6-(4-fluoro-3-methylphenyl)pyridin-2-yl]methyl}amino)-3-methylbutan-1-ol;
(2R)-2-[({3-fluoro-6-[4-fluoro-3-(trifluoromethyl)phenyl]pyridin-2-yl}methyl)amino]-3-methylbutan-1-ol;
(2R)-2-[({3-fluoro-6-[2-fluoro-5-(trifluoromethyl)phenyl]pyridin-2-yl}methyl)amino]-3-methylbutan-1-ol;
(2R)-2-({[6-(3,4-difluoro-5-methoxyphenyl)-3-fluoropyridin-2-yl]methyl}amino)-3-methylbutan-1-ol;
(2R)-2-[({6-[(2,4-difluorophenyl)ethynyl]pyridin-2-yl}methyl)amino]-3-methylbutan-1-ol;
(2R)-2-[({6-[(2-fluorophenyl)ethynyl]pyridin-2-yl}methyl)amino]-3-methylbutan-1-ol;
(2R)-2-[({6-[(4-chlorophenyl)ethynyl]pyridin-2-yl}methyl)amino]-3-methylbutan-1-ol;
(2R)-2-({[3-fluoro-6-(4-methyl-2-phenyl-1,3-thiazol-5-yl)pyridin-2-yl]methyl}amino)-3-methylbutan-1-ol;
(2R)-2-({[6-(4-cyclohexylbut-1-yn-1-yl)-3-fluoropyridin-2-yl]methyl}amino)-3-methylbutan-1-ol;
(2R)-2-({[3-fluoro-6-(phenylethynyl)pyridin-2-yl]methyl}amino)-3-methylbutan-1-ol;
(2R)-2-[({3-fluoro-6-[5-(trifluoromethyl)thiophen-2-yl]pyridin-2-yl}methyl)amino]-3-methylbutan-1-ol;
(2R)-2-[({3-fluoro-6-[1-methyl-3-(trifluoromethyl)-1H-pyrazol-5-yl]pyridin-2-yl}methyl)amino]-3-methylbutan-1-ol;
(2R)-2-({[5-fluoro-5'-(trifluoromethyl)-2,3'-bipyridin-6-yl]methyl}amino)-3-methylbutan-1-ol;
(2R)-2-[({6-[2,4-bis(trifluoromethyl)phenyl]-3-fluoropyridin-2-yl}methyl)amino]-3-methylbutan-1-ol; and
(2R)-2-({[6-(3-chloro-4-fluorophenyl)-3-fluoropyridin-2-yl]methyl}amino)-3-methylbutan-1-ol.
Exemplary compounds include, but are not limited to:
(2S)-2-[({3-fluoro-6-[4-(trifluoromethyl)phenyl]pyridin-2-yl}methyl)amino]-3-methylbutan-1-ol;
(2S)-2-({[5-fluoro-6'-(trifluoromethyl)-2,3'-bipyridin-6-yl]methyl}amino)-3-methylbutan-1-ol;
(2R)-3-methyl-2-[({2-[4-(trifluoromethyl)phenyl]pyrimidin-4-yl}methyl)amino]butan-1-ol;
(R)-2-((3-fluoro-6-(4-(trifluoromethyl)phenyl)pyridin-2-yl)methylamino)-3-methylbutanamide;
(R)-2-((5-fluoro-6'-(trifluoromethyl)-2,3'-bipyridin-6-yl)methylamino)-3-methylbutanamide;
(2R)-2-({[4,6'-bis(trifluoromethyl)-2,3'-bipyridin-6-yl]methyl}amino)-3-methylbutan-1-ol;
(S)-2-((5-fluoro-6'-(trifluoromethyl)-2,3'-bipyridin-6-yl)methylamino)-3-methylbutanamide;
(2S,3R)-2-((5-fluoro-6'-(trifluoromethyl)-2,3'-bipyridin-6-yl)methylamino)-3-hydroxybutanamide;
{1-[({2-[4-(trifluoromethyl)phenyl]pyrimidin-4-yl}methyl)amino]cyclobutyl}methanol;
{1-[({2-[4-(trifluoromethyl)phenyl]pyrimidin-4-yl}methyl)amino]cyclopropyl}methanol;
2-methyl-2-[({2-[4-(trifluoromethyl)phenyl]pyrimidin-4-yl}methyl)amino]propan-1-ol;
(2R)-3-phenyl-2-[({2-[4-(trifluoromethyl)phenyl]pyrimidin-4-yl}methyl)amino]propan-1-ol;
(2S,3S)-2-[({2-[4-(trifluoromethyl)phenyl]pyrimidin-4-yl}methyl)amino]butane-1,3-diol;
(2R,3S)-2-[({2-[4-(trifluoromethyl)phenyl]pyrimidin-4-yl}methyl)amino]butane-1,3-diol;
(2S,3R)-2-[({2-[4-(trifluoromethyl)phenyl]pyrimidin-4-yl}methyl)amino]butane-1,3-diol;
(1R,2R)-1-phenyl-2-[({2-[4-(trifluoromethyl)phenyl]pyrimidin-4-yl}methyl)amino]propane-1,3-diol;
(2S)-3-methyl-2-[({2-[4-(trifluoromethyl)phenyl]pyrimidin-4-yl}methyl)amino]butan-1-ol;
2,2-dimethyl-3-[({2-[4-(trifluoromethyl)phenyl]pyrimidin-4-yl}methyl)amino]propan-1-ol;
(1-{[({2-[4-(trifluoromethyl)phenyl]pyrimidin-4-yl}methyl)amino]methyl}cyclobutyl)methanol;
(1-{[({2-[4-(trifluoromethyl)phenyl]pyrimidin-4-yl}methyl)amino]methyl}cyclopentyl)methanol;
(3-{[({2-[4-(trifluoromethyl)phenyl]pyrimidin-4-yl}methyl)amino]methyl}oxetan-3-yl)methanol;
(4-{[({2-[4-(trifluoromethyl)phenyl]pyrimidin-4-yl}methyl)amino]methyl}tetrahydro-2H-pyran-4-yl)methanol;
(3R)-3-phenyl-3-[({2-[4-(trifluoromethyl)phenyl]pyrimidin-4-yl}methyl)amino]propan-1-ol;
(3S)-3-phenyl-3-[({2-[4-(trifluoromethyl)phenyl]pyrimidin-4-yl}methyl)amino]propan-1-ol;
1-phenyl-3-[({2-[4-(trifluoromethyl)phenyl]pyrimidin-4-yl}methyl)amino]propan-1-ol;
(1S,2R)-2-{[({2-[4-(trifluoromethyl)phenyl]pyrimidin-4-yl}methyl)amino]methyl}cyclohexanol;
(1R,2R)-2-{[({2-[4-(trifluoromethyl)phenyl]pyrimidin-4-yl}methyl)amino]methyl}cyclohexanol;
{(1S,2S)-2-[({2-[4-(trifluoromethyl)phenyl]pyrimidin-4-yl}methyl)amino]cyclohexyl}methanol;
{(1R,2S)-2-[({2-[4-(trifluoromethyl)phenyl]pyrimidin-4-yl}methyl)amino]cyclohexyl}methanol;
{(1S,2R,3S,4R)-3-[({2-[4-(trifluoromethyl)phenyl]pyrimidin-4-yl}methyl)amino]bicyclo[2.2.1]hept-2-yl}methanol;
(1R,2S)-2-[({2-[4-(trifluoromethyl)phenyl]pyrimidin-4-yl}methyl)amino]cyclopentanol;
(1S,2S)-2-[({2-[4-(trifluoromethyl)phenyl]pyrimidin-4-yl}methyl)amino]cyclopentanol;

2-methyl-1-[({2-[4-(trifluoromethyl)phenyl]pyrimidin-4-yl}methyl)amino]propan-2-ol;
1-{[({2-[4-(trifluoromethyl)phenyl]pyrimidin-4-yl}methyl)amino]methyl}cyclopropanol;
1-{[({2-[4-(trifluoromethyl)phenyl]pyrimidin-4-yl}methyl)amino]methyl}cyclopentanol;
1-{[({2-[4-(trifluoromethyl)phenyl]pyrimidin-4-yl}methyl)amino]methyl}cyclohexanol;
1,1,1-trifluoro-34({2-[4-(trifluoromethyl)phenyl]pyrimidin-4-yl}methyl)amino]propan-2-ol;
(2S)-1-[({2-[4-(trifluoromethyl)phenyl]pyrimidin-4-yl}methyl)amino]propan-2-ol;
1-[({2-[4-(trifluoromethyl)phenyl]pyrimidin-4-yl}methyl)amino]butan-2-ol;
1-phenyl-2-[({2-[4-(trifluoromethyl)phenyl]pyrimidin-4-yl}methyl)amino]ethanol;
(2R)-1-[({2-[4-(trifluoromethyl)phenyl]pyrimidin-4-yl}methyl)amino]propan-2-ol;
(2R)-3-methyl-2-[({2-[6-(trifluoromethyl)pyridin-3-yl]pyrimidin-4-yl}methyl)amino]butan-1-ol;
{1-[({2-[6-(trifluoromethyl)pyridin-3-yl]pyrimidin-4-yl}methyl)amino]cyclohexyl}methanol;
(2R)-2-[({2-[6-(trifluoromethyl)pyridin-3-yl]pyrimidin-4-yl}methyl)amino]butan-1-ol;
3-methoxy-2-[({2-[6-(trifluoromethyl)pyridin-3-yl]pyrimidin-4-yl}methyl)amino]propan-1-ol;
(2R)-2-cyclopropyl-2-[({2-[6-(trifluoromethyl)pyridin-3-yl]pyrimidin-4-yl}methyl)amino]ethanol;
(2S)-3-methyl-2-[({2-[6-(trifluoromethyl)pyridin-3-yl]pyrimidin-4-yl}methyl)amino]butane-1,3-diol;
(2R,3R)-2-[({2-[6-(trifluoromethyl)pyridin-3-yl]pyrimidin-4-yl}methyl)amino]butane-1,3-diol;
(2R)-3-methyl-2-[({2-[5-(trifluoromethyl)pyridin-2-yl]pyrimidin-4-yl}methyl)amino]butan-1-ol;
{1-[({2-[5-(trifluoromethyl)pyridin-2-yl]pyrimidin-4-yl}methyl)amino]cyclohexyl}methanol;
(2R)-2-[({2-[5-(trifluoromethyl)pyridin-2-yl]pyrimidin-4-yl}methyl)amino]butan-1-ol;
3-methoxy-2-[({2-[5-(trifluoromethyl)pyridin-2-yl]pyrimidin-4-yl}methyl)amino]propan-1-ol;
(2R)-2-cyclopropyl-2-[({2-[5-(trifluoromethyl)pyridin-2-yl]pyrimidin-4-yl}methyl)amino]ethanol;
(2S)-3-methyl-2-[({2-[5-(trifluoromethyl)pyridin-2-yl]pyrimidin-4-yl}methyl)amino]butane-1,3-diol;
(2R,3R)-2-[({2-[5-(trifluoromethyl)pyridin-2-yl]pyrimidin-4-yl}methyl)amino]butane-1,3-diol;
(2R)-2-({[3-fluoro-6-(tetrahydro-2H-pyran-4-yl)pyridin-2-yl]methyl}amino)-3-methylbutan-1-ol;
(2S)-3-methyl-2-{[(2-{4-[(trifluoromethyl)sulfonyl]phenyl}pyrimidin-4-yl)methyl]amino}butane-1,3-diol;
(2R)-2-({[3-fluoro-6-(tetrahydro-2H-pyran-3-yl)pyridin-2-yl]methyl}amino)-3-methylbutan-1-ol;
(2R)-2-({[3-fluoro-6-(tetrahydrofuran-3-yl)pyridin-2-yl]methyl}amino)-3-methylbutan-1-ol;
(2R)-2-[({6-[1-(1,3-dioxolan-2-ylmethyl)-1H-pyrazol-4-yl]-3-fluoropyridin-2-yl}methyl)amino]-3-methylbutan-1-ol;
(2R)-2-({[3-fluoro-6-(1-methyl-1H-pyrazol-5-yl)pyridin-2-yl]methyl}amino)-3-methylbutan-1-ol; and
(2R)-2-({[5-fluoro-6'-(4-methylpiperazin-1-yl)-2,3'-bipyridin-6-yl]methyl}amino)-3-methylbutan-1-ol.
Examplary compounds include, but are not limited to,
(1S,2S)-2-[({6-[4-(trifluoromethyl)phenyl]pyridin-2-yl}methyl)amino]cyclohexanol;
(2S,3S)-3-methyl-2-[({6-[4-(trifluoromethyl)phenyl]pyridin-2-yl}methyl)amino]pentan-1-ol;
(2S)-3-methyl-2-[({6-[4-(trifluoromethyl)phenyl]pyridin-2-yl}methyl)amino]butan-1-ol;
(1R,2S)-2-[({6-[4-(trifluoromethyl)phenyl]pyridin-2-yl}methyl)amino]cyclohexanol;
2-[({6-[4-(trifluoromethyl)phenyl]pyridin-2-yl}methyl)amino]cyclohexanol;
(1R,2R)-2-[({6-[4-(trifluoromethyl)phenyl]pyridin-2-yl}methyl)amino]cyclohexanol;
(1S,2R)-2-[({6-[4-(trifluoromethyl)phenyl]pyridin-2-yl}methyl)amino]cyclohexanol;
2,2-dimethyl-3-[({6-[4-(trifluoromethyl)phenyl]pyridin-2-yl}methyl)amino]propan-1-ol;
{(1R,2R,3S,4S)-3-[({6-[4-(trifluoromethyl)pyridin-2-yl}methyl)amino]bicyclo[2.2.1]hept-2-yl}methanol;
(2R)-3-methyl-2-({[6-(pyrrolidin-1-yl)pyridin-2-yl]methyl}amino)butan-1-ol;
(2R)-3-methyl-2-({[6-(piperidin-1-yl)pyridin-2-yl]methyl}amino)butan-1-ol;
(2R)-2-({[6-(benzyloxy)pyridin-2-yl]methyl}amino)-3-methylbutan-1-ol;
(2R)-2-({[3-fluoro-6-(2-fluorophenyl)pyridin-2-yl]methyl}amino)-3-methylbutan-1-ol;
(2R)-2-({[3-fluoro-6-(3-fluorophenyl)pyridin-2-yl]methyl}amino)-3-methylbutan-1-ol;
(2R)-2-({[6-(3-chlorophenyl)-3-fluoropyridin-2-yl]methyl}amino)-3-methylbutan-1-ol;
(2R)-2-[({3-fluoro-6-[3-(trifluoromethyl)phenyl]pyridin-2-yl}methyl)amino]-3-methylbutan-1-ol;
(2R)-2-[({3-fluoro-6-[4-(trifluoromethyl)phenyl]pyridin-2-yl}methyl)amino]-3-methylbutan-1-ol;
(2R)-2-[({3-fluoro-6-[3-(trifluoromethoxy)phenyl]pyridin-2-yl}methyl)amino]-3-methylbutan-1-ol;
(2R)-2-[({3-fluoro-6-[4-(trifluoromethoxy)phenyl]pyridin-2-yl}methyl)amino]-3-methylbutan-1-ol;
(2R)-2-({[6-(3,4-dichlorophenyl)-3-fluoropyridin-2-yl]methyl}amino)-3-methylbutan-1-ol;
(2R)-2-({[6-(3,5-dichlorophenyl)-3-fluoropyridin-2-yl]methyl}amino)-3-methylbutan-1-ol;
(2R)-2-[({6-[3,5-bis(trifluoromethyl)phenyl]-3-fluoropyridin-2-yl}methyl)amino]-3-methylbutan-1-ol;
(2R)-2-[({3-fluoro-6-[2-fluoro-5-(propan-2-yloxy)phenyl]pyridin-2-yl}methyl)amino]-3-methylbutan-1-ol;
(2R)-2-[({3-fluoro-6-[3-(propan-2-yloxy)phenyl]pyridin-2-yl}methyl)amino]-3-methylbutan-1-ol;
(2R)-2-[({3-fluoro-6-[3-fluoro-4-(propan-2-yloxy)phenyl]pyridin-2-yl}methyl)amino]-3-methylbutan-1-ol;
(2R)-2-{[(6-tert-butoxypyridin-2-yl)methyl]amino}-3-methylbutan-1-ol;
(2R)-2-({[3-fluoro-6-(4-fluorophenyl)pyridin-2-yl]methyl}amino)-3-methylbutan-1-ol;
(2R)-2-({[5-fluoro-6'-(trifluoromethyl)-2,3'-bipyridin-6-yl]methyl}amino)-3-methylbutan-1-ol;
(2R)-2-cyclopropyl-2-[({3-fluoro-6-[4-(trifluoromethyl)phenyl]pyridin-2-yl}methyl)amino]ethanol;
(2S)-2-[({3-fluoro-6-[4-(trifluoromethyl)phenyl]pyridin-2-yl}methyl)amino]-3-methylbutan-1-ol;
(2R)-2-({[5-fluoro-2'-(trifluoromethyl)-2,4'-bipyridin-6-yl]methyl}amino)-3-methylbutan-1-ol;
(2R)-2-({[4-(4-fluorophenyl)pyrimidin-2-yl]methyl}amino)-3-methylbutan-1-ol;
(2R)-3-methyl-2-[({4-[4-(trifluoromethyl)phenyl]pyrimidin-2-yl}methyl)amino]butan-1-ol;
(2R)-2-({[2-(4-chlorophenyl)pyrimidin-4-yl]methyl}amino)-3-methylbutan-1-ol;
(2S)-2-({[5-fluoro-6'-(trifluoromethyl)-2,3'-bipyridin-6-yl]methyl}amino)-3-methylbutan-1-ol;

(2R)-2-{[(5,5'-difluoro-2,2'-bipyridin-6-yl)methyl]amino}-3-methylbutan-1-ol;
1-{2-fluoro-3-[5-fluoro-6-({[(2R)-1-hydroxy-3-methylbutan-2-yl]amino}methyl)pyridin-2-yl]phenyl}ethanone;
(2R)-2-{[(6'-chloro-5-fluoro-2,3'-bipyridin-6-yl)methyl]amino}-3-methylbutan-1-ol;
3-[5-fluoro-6-({[(2R)-1-hydroxy-3-methylbutan-2-yl]amino}methyl)pyridin-2-yl]-N,N-dimethylbenzenesulfonamide;
1-{3-[5-fluoro-6-({[(2R)-1-hydroxy-3-methylbutan-2-yl]amino}methyl)pyridin-2-yl]phenyl}ethanone;
N,N-diethyl-3-[5-fluoro-6-({[(2R)-1-hydroxy-3-methylbutan-2-yl]amino}methyl)pyridin-2-yl]benzamide;
(2R)-2-({[6-(4-chlorophenyl)-3-fluoropyridin-2-yl]methyl}amino)-3-methylbutan-1-ol;
(2R)-2-[({6-[3-(dimethylamino)phenyl]-3-fluoropyridin-2-yl}methyl)amino]-3-methylbutan-1-ol;
(2R)-2-[({3-fluoro-6-[3-(morpholin-4-yl)phenyl]pyridin-2-yl}methyl)amino]-3-methylbutan-1-ol;
{3-[5-fluoro-6-({[(2R)-1-hydroxy-3-methylbutan-2-yl]amino}methyl)pyridin-2-yl]phenyl}(piperidin-1-yl)methanone;
{3-[5-fluoro-6-({[(2R)-1-hydroxy-3-methylbutan-2-yl]amino}methyl)pyridin-2-yl]phenyl}(4-methylpiperidin-1-yl)methanone;
(2R)-2-[({6-[3-chloro-4-(trifluoromethyl)phenyl]-3-fluoropyridin-2-yl}methyl)amino]-3-methylbutan-1-ol;
(2R)-2-[({3-fluoro-6-[3-(piperidin-1-ylsulfonyl)phenyl]pyridin-2-yl}methyl)amino]-3-methylbutan-1-ol;
(2R)-2-[({3-fluoro-6-[3-(pyrrolidin-1-yl)phenyl]pyridin-2-yl}methyl)amino]-3-methylbutan-1-ol;
3-[5-fluoro-6-({[(2R)-1-hydroxy-3-methylbutan-2-yl]amino}methyl)pyridin-2-yl]-N,N,4-trimethylbenzenesulfonamide;
N,N-diethyl-3-[5-fluoro-6-({[(2R)-1-hydroxy-3-methylbutan-2-yl]amino}methyl)pyridin-2-yl]benzenesulfonamide;
N-cyclohexyl-3-[5-fluoro-6-({[(2R)-1-hydroxy-3-methylbutan-2-yl]amino}methyl)pyridin-2-yl]-N-methylbenzamide;
(2R)-2-[({3-fluoro-6-[4-(2,2,2-trifluoro ethoxy)phenyl]pyridin-2-yl}methyl)amino]-3-methylbutan-1-ol;
(2R)-2-[({3-fluoro-6-[3-(morpholin-4-ylsulfonyl)phenyl]pyridin-2-yl}methyl)amino]-3-methylbutan-1-ol;
(2R)-2-({[5-fluoro-2'-(morpholin-4-yl)-2,4'-bipyridin-6-yl]methyl}amino)-3-methylbutan-1-ol;
3-[5-fluoro-6-({[(2R)-1-hydroxy-3-methylbutan-2-yl]amino}methyl)pyridin-2-yl]-N,N-di(propan-2-yl)benzamide;
(2R)-2-({[5-fluoro-6'-(propan-2-yloxy)-2,3'-bipyridin-6-yl]methyl}amino)-3-methylbutan-1-ol;
N-benzyl-3-[5-fluoro-64 {[(2R)-1-hydroxy-3-methylbutan-2-yl]amino}methyl)pyridin-2-yl]-N-methylbenzamide;
(2R)-2-{[(3-fluoro-6-{2-methyl-5-[(trifluoromethyl)sulfonyl]phenyl}pyridin-2-yl)methyl]amino}-3-methylbutan-1-ol;
(2R)-2-[({3-fluoro-6-[3-(pyrrolidin-1-ylsulfonyl)phenyl]pyridin-2-yl}methyl)amino]-3-methylbutan-1-ol;
N-tert-butyl-3-[5-fluoro-64 {[(2R)-1-hydroxy-3-methylbutan-2-yl]amino}methyl)pyridin-2-yl]-N-methylbenzenesulfonamide;
{3-[5-fluoro-6-({[(2R)-1-hydroxy-3-methylbutan-2-yl]amino}methyl)pyridin-2-yl]phenyl}(thiomorpholin-4-yl)methanone;
(2R)-2-({[3-fluoro-6-(1-methyl-1H-indol-4-yl)pyridin-2-yl]methyl}amino)-3-methylbutan-1-ol;
(2R)-2-({[3-fluoro-6-(1-methyl-1H-indol-6-yl)pyridin-2-yl]methyl}amino)-3-methylbutan-1-ol;
(2R)-2-[({3-fluoro-6-[3-(trifluoromethyl)piperidin-1-yl]pyridin-2-yl}methyl)amino]-3-methylbutan-1-ol;
(2R)-2-[({3-fluoro-6-[4-(trifluoromethyl)piperidin-1-yl]pyridin-2-yl}methyl)amino]-3-methylbutan-1-ol;
(2R)-2-[({3-fluoro-6-[3-(trifluoromethyl)pyrrolidin-1-yl]pyridin-2-yl}methyl)amino]-3-methylbutan-1-ol;
(2R)-2-({[5-fluoro-6'-(2,2,2-trifluoroethoxy)-2,3'-bipyridin-6-yl]methyl}amino)-3-methylbutan-1-ol;
(2R)-3-methyl-2-({[6'-(trifluoromethyl)-2,3'-bipyridin-6-yl]methyl}amino)butan-1-ol;
(2R)-2-({[6-(3,4-dihydroisoquinolin-2(1H)-yl)-3-fluoropyridin-2-yl]methyl}amino)-3-methylbutan-1-ol;
(2R)-2-({[6-(1,3-dihydro-2H-isoindol-2-yl)-3-fluoropyridin-2-yl]methyl}amino)-3-methylbutan-1-ol;
(2R)-2-({[3-fluoro-6-(quinolin-3-yl)pyridin-2-yl]methyl}amino)-3-methylbutan-1-ol;
(2R)-2-({[5-fluoro-5'-(trifluoromethyl)-2,2'-bipyridin-6-yl]methyl}amino)-3-methylbutan-1-ol;
2-[({3-fluoro-6-[4-(trifluoromethyl)phenyl]pyridin-2-yl}methyl)amino]-3-methoxypropan-1-ol;
(2R)-2-cyclopropyl-2-({[5-fluoro-6'-(trifluoromethyl)-2,3'-bipyridin-6-yl]methyl}amino)ethanol;
(2R)-2-cyclopropyl-2-({[5-fluoro-6'-(2,2,2-trifluoroethoxy)-2,3'-bipyridin-6-yl]methyl}amino)ethanol;
(2R)-2-[({3-fluoro-6-[4-(trifluoromethyl)phenyl]pyridin-2-yl}methyl)amino]butan-1-ol;
(2R)-2-({[5-fluoro-6'-(trifluoromethyl)-2,3'-bipyridin-6-yl]methyl}amino)butan-1-ol;
{1-[({3-fluoro-6-[4-(trifluoromethyl)phenyl]pyridin-2-yl}methyl)amino]cyclobutyl}methanol;
{1-[({3-fluoro-6-[4-(trifluoromethyl)phenyl]pyridin-2-yl}methyl)amino]cyclopentyl}methanol;
{1-[({3-fluoro-6-[4-(trifluoromethyl)phenyl]pyridin-2-yl}methyl)amino]cyclohexyl}methanol;
(2R)-2-[({3-fluoro-6-[4-(trifluoromethyl)phenyl]pyridin-2-yl}methyl)amino]propan-1-ol;
(2R)-2-[({3-fluoro-6-[4-(trifluoromethyl)phenyl]pyridin-2-yl}methyl)amino]pentan-1-ol;
(2R)-2-cyclohexyl-2-[({3-fluoro-6-[4-(trifluoromethyl)phenyl]pyridin-2-yl}methyl)amino]ethanol;
(2R)-2-[({3-fluoro-6-[4-(trifluoromethyl)phenyl]pyridin-2-yl}methyl)amino]-3,3-dimethylbutan-1-ol;
3-[({3-fluoro-6-[4-(trifluoromethyl)phenyl]pyridin-2-yl}methyl)amino]butan-2-ol;
(2R)-2-({[5-fluoro-6'-(trifluoromethyl)-2,3'-bipyridin-6-yl]methyl}amino)pentan-1-ol;
(2R)-2-cyclohexyl-2-({[5-fluoro-6'-(trifluoromethyl)-2,3'-bipyridin-6-yl]methyl}amino)ethanol;
(2R)-2-({[5-fluoro-6'-(trifluoromethyl)-2,3'-bipyridin-6-yl]methyl}amino)-3,3-dimethylbutan-1-ol;
3-({[5-fluoro-6'-(trifluoromethyl)-2,3'-bipyridin-6-yl]methyl}amino)butan-2-ol;
(2R)-3-methyl-2-[({2-[4-(trifluoromethyl)phenyl]pyrimidin-4-yl}methyl)amino]butan-1-ol;
(2R)-2-({[6-(4,4-difluoropiperidin-1-yl)-3-fluoropyridin-2-yl]methyl}amino)-3-methylbutan-1-ol;
(2R)-2-({[3-fluoro-6-(5-fluoro-1,3-dihydro-2H-isoindol-2-yl)pyridin-2-yl]methyl}amino)-3-methylbutan-1-ol;
(2R)-2-({[3-fluoro-6-(4-fluoro-1,3-dihydro-2H-isoindol-2-yl)pyridin-2-yl]methyl}amino)-3-methylbutan-1-ol;
(2R)-2-({[6-(4-chloro-1,3-dihydro-2H-isoindol-2-yl)-3-fluoropyridin-2-yl]methyl}amino)-3-methylbutan-1-ol;
(2R)-2-[({3-fluoro-6-[5-(trifluoromethyl)-1,3-dihydro-2H-isoindol-2-yl]pyridin-2-yl}methyl)amino]-3-methylbutan-1-ol;

(2R)-2-({[3-fluoro-6-(5-fluoro-3,4-dihydroisoquinolin-2 (1H)-yl)pyridin-2-yl]methyl}amino)-3-methylbutan-1-ol;
(2R)-2-({[3-fluoro-6-(7-fluoro-3,4-dihydroisoquinolin-2 (1H)-yl)pyridin-2-yl]methyl}amino)-3-methylbutan-1-ol;
(2R)-2-({[3-fluoro-6-(8-fluoro-3,4-dihydroisoquinolin-2 (1H)-yl)pyridin-2-yl]methyl}amino)-3-methylbutan-1-ol;
(2R)-2-({[6-(5-chloro-3,4-dihydroisoquinolin-2(1H)-yl)-3-fluoropyridin-2-yl]methyl}amino)-3-methylbutan-1-ol;
(2R)-2-({[6-(6-chloro-3,4-dihydroisoquinolin-2(1H)-yl)-3-fluoropyridin-2-yl]methyl}amino)-3-methylbutan-1-ol;
(2R)-2-[({3-fluoro-6-[5-(trifluoromethyl)-3,4-dihydroisoquinolin-2(1H)-yl]pyridin-2-yl}methyl)amino]-3-methylbutan-1-ol;
(2R)-2-[({3-fluoro-6-[7-(trifluoromethyl)-3,4-dihydroisoquinolin-2(1H)-yl]pyridin-2-yl}methyl)amino]-3-methylbutan-1-ol;
(2R)-2-({[6-(4,4-dimethyl-3,4-dihydroisoquinolin-2(1H)-yl)-3-fluoropyridin-2-yl]methyl}amino)-3-methylbutan-1-ol;
(3R)-3-[({3-fluoro-6-[4-(trifluoromethyl)phenyl]pyridin-2-yl}methyl)amino]-2,4-dimethylpentan-2-ol;
(3R)-3-({[5-fluoro-6'-(trifluoromethyl)-2,3'-bipyridin-6-yl]methyl}amino)-2,4-dimethylpentan-2-ol;
(3R)-3-[({3-fluoro-6-[4-(trifluoromethyl)phenyl]pyridin-2-yl}methyl)amino]-4-methylpentan-2-ol;
(3R)-3-({[5-fluoro-6'-(trifluoromethyl)-2,3'-bipyridin-6-yl]methyl}amino)-4-methylpentan-2-ol;
(2R)-2-({[3-fluoro-6'-(trifluoromethyl)-2,3'-bipyridin-6-yl]methyl}amino)-3-methylbutan-1-ol;
(2R)-2-({[5-chloro-6'-(trifluoromethyl)-2,3'-bipyridin-6-yl]methyl}amino)-3-methylbutan-1-ol;
(2R)-3-methyl-2-({[5-methyl-6'-(trifluoromethyl)-2,3'-bipyridin-6-yl]methyl}amino)butan-1-ol;
(2R)-2-({[5-methoxy-6'-(trifluoromethyl)-2,3'-bipyridin-6-yl]methyl}amino)-3-methylbutan-1-ol;
(2R)-2-[({3-fluoro-6-[2-(trifluoromethyl)pyrimidin-5-yl]pyridin-2-yl}methyl)amino]-3-methylbutan-1-ol;
(2R)-2-[({3-fluoro-6-[2-(2,2,2-trifluoroethoxy)pyrimidin-5-yl]pyridin-2-yl}methyl)amino]-3-methylbutan-1-ol;
(3R)-3-({[5-fluoro-6'-(trifluoromethyl)-2,3'-bipyridin-6-yl]methyl}amino)pentan-2-ol;
(R)-2-((3-fluoro-6-(4-(trifluoromethyl)phenyl)pyridin-2-yl)methylamino)-3-methylbutanamide;
(R)-2-((5-fluoro-6'-(trifluoromethyl)-2,3'-bipyridin-6-yl)methylamino)-3-methylbutanamide;
(2R)-2-({[4,6'-bis(trifluoromethyl)-2,3'-bipyridin-6-yl]methyl}amino)-3-methylbutan-1-ol;
(S)-2-((5-fluoro-6'-(trifluoromethyl)-2,3'-bipyridin-6-yl)methylamino)-3-methylbutanamide;
(2S,3R)-2-((5-fluoro-6'-(trifluoromethyl)-2,3'-bipyridin-6-yl)methylamino)-3-hydroxybutanamide;
(2R,3R)-2-({[5-fluoro-6'-(trifluoromethyl)-2,3'-bipyridin-6-yl]methyl}amino)butane-1,3-diol;
(2R)-2-({[3-fluoro-6-(1-phenylethenyl)pyridin-2-yl]methyl}amino)-3-methylbutan-1-ol;
(2R)-2-[({3-fluoro-6-[1-(4-fluorophenyl)ethenyl]pyridin-2-yl}methyl)amino]-3-methylbutan-1-ol;
(2R)-2-({[6-(cyclohex-1-en-1-yl)-3-fluoropyridin-2-yl]methyl}amino)-3-methylbutan-1-ol;
(2R)-2-({[3-fluoro-6-(1-phenylethyl)pyridin-2-yl]methyl}amino)-3-methylbutan-1-ol;
(2R)-2-[({3-fluoro-6-[1-(4-fluorophenyl)ethyl]pyridin-2-yl}methyl)amino]-3-methylbutan-1-ol;
(2R)-2-{[(6-cyclohexyl-3-fluoropyridin-2-yl)methyl]amino}-3-methylbutan-1-ol;
(2R)-2-[({5-fluoro-2-[4-(trifluoromethyl)phenyl]pyrimidin-4-yl}methyl)amino]-3-methylbutan-1-ol;
(2R)-2-[({3-fluoro-6-[4-(trifluoromethyl)cyclohex-1-en-1-yl]pyridin-2-yl}methyl)amino]-3-methylbutan-1-ol;
(2R)-2-({[6-(4,4-difluorocyclohex-1-en-1-yl)-3-fluoropyridin-2-yl]methyl}amino)-3-methylbutan-1-ol;
(2R)-3-methyl-2-{[(6-phenylpyridin-2-yl)methyl]amino}butan-1-ol;
(2R)-3-methyl-2-[({6-[3-(trimethylsilyl)phenyl]pyridin-2-yl}methyl)amino]butan-1-ol;
(2R)-2-{[(6-{5-[tert-butyl(dimethyl)silyl]thiophen-2-yl}pyridin-2-yl)methyl]amino}-3-methylbutan-1-ol;
(2R)-2-({[6-(3,4-difluorophenyl)-3-fluoropyridin-2-yl]methyl}amino)-3-methylbutan-1-ol;
(2R)-2-({[6-(1-benzothiophen-2-yl)-3-fluoropyridin-2-yl]methyl}amino)-3-methylbutan-1-ol;
(2R)-2-({[2-(4,4-difluoropiperidin-1-yl)-5-fluoropyrimidin-4-yl]methyl}amino)-3-methylbutan-1-ol;
(2R)-2-[({3-fluoro-6-[(E)-2-(3-fluorophenyl)ethenyl]pyridin-2-yl}methyl)amino]-3-methylbutan-1-ol;
(2R)-2-({[6-(1,3-benzothiazol-5-yl)-3-fluoropyridin-2-yl]methyl}amino)-3-methylbutan-1-ol;
(2R)-2-[({3-fluoro-6-[(4-methoxyphenyl)ethynyl]pyridin-2-yl}methyl)amino]-3-methylbutan-1-ol;
(2R)-2-({[6-(3-cyclohexylprop-1-yn-1-yl)-3-fluoropyridin-2-yl]methyl}amino)-3-methylbutan-1-ol;
2-methyl-2-[({6-[3-(trimethylsilyl)phenyl]pyridin-2-yl}methyl)amino]propan-1-ol;
(2R)-2-[({3-fluoro-6-[(4-fluorophenyl)ethynyl]pyridin-2-yl}methyl)amino]-3-methylbutan-1-ol;
(2R)-2-[({6-[(3,4-difluorophenyl)ethynyl]-3-fluoropyridin-2-yl}methyl)amino]-3-methylbutan-1-ol;
(2R)-2-({[6-(cyclohexylethynyl)-3-fluoropyridin-2-yl]methyl}amino)-3-methylbutan-1-ol;
(2R)-2-[({6-[(4-tert-butylphenyl)ethynyl]-3-fluoropyridin-2-yl}methyl)amino]-3-methylbutan-1-ol;
(2R)-2-({[6-(5-chlorothiophen-2-yl)-3-fluoropyridin-2-yl]methyl}amino)-3-methylbutan-1-ol;
(2R)-2-({[3-fluoro-6-(5-methylthiophen-2-yl)pyridin-2-yl]methyl}amino)-3-methylbutan-1-ol;
(2R)-2-({[3-fluoro-6-(1-methyl-1H-indol-2-yl)pyridin-2-yl]methyl}amino)-3-methylbutan-1-ol;
(2R)-2-[({6-[1-(1,3-dioxolan-2-ylmethyl)-1H-pyrazol-4-yl]-3-fluoropyridin-2-yl}methyl)amino]-3-methylbutan-1-ol;
(2R)-2-({[3-fluoro-6-(furan-3-yl)pyridin-2-yl]methyl}amino)-3-methylbutan-1-ol;
(2R)-2-({[3-fluoro-6-(1-methyl-1H-pyrazol-5-yl)pyridin-2-yl]methyl}amino)-3-methylbutan-1-ol;
(2R)-2-({[5-fluoro-5'-methyl-6'-(morpholin-4-yl)-2,3'-bipyridin-6-yl]methyl}amino)-3-methylbutan-1-ol;
(2R)-2-({[5-fluoro-6'-(4-methylpiperazin-1-yl)-2,3'-bipyridin-6-yl]methyl}amino)-3-methylbutan-1-ol;
(2R)-2-({[6-(1-benzothiophen-5-yl)-3-fluoropyridin-2-yl]methyl}amino)-3-methylbutan-1-ol;
(2R)-2-({[6-(1-benzofuran-5-yl)-3-fluoropyridin-2-yl]methyl}amino)-3-methylbutan-1-ol;
(2R)-2-[({3-fluoro-6-[cis-4-(trifluoromethyl)cyclohexyl]pyridin-2-yl}methyl)amino]-3-methylbutan-1-ol;
(2R)-2-[({3-fluoro-6-[trans-4-(trifluoromethyl)cyclohexyl]pyridin-2-yl}methyl)amino]-3-methylbutan-1-ol;
tert-butyl 4-(benzyloxy)-2-[5-fluoro-6-({[(2R)-1-hydroxy-3-methylbutan-2-yl]amino}methyl)pyridin-2-yl]-1H-indole-1-carboxylate;
(2R)-2-[({3-fluoro-6-[3-(1H-pyrazol-1-yl)phenyl]pyridin-2-yl}methyl)amino]-3-methylbutan-1-ol;
(2R)-2-[({6-[2-(dimethylamino)pyrimidin-5-yl]-3-fluoropyridin-2-yl}methyl)amino]-3-methylbutan-1-ol;

(2R)-2-({[6-(4-butoxy-3-chlorophenyl)pyridin-2-yl]methyl}amino)-3-methylbutan-1-ol;
(2R)-3-methyl-2-{[(6-{[4-(pentafluoro-λ⁶-sulfanyl)phenyl]ethynyl}pyridin-2-yl)methyl]amino}butan-1-ol;
(2R)-2-[({6-[(4-fluorophenyl)ethynyl]pyridin-2-yl}methyl)amino]-3-methylbutan-1-ol;
(2R)-2-[({6-[(3,4-difluorophenyl)ethynyl]pyridin-2-yl}methyl)amino]-3-methylbutan-1-ol;
[1-({[6-(3-chloro-4-fluorophenyl)pyridin-2-yl]methyl}amino)cyclopentyl]methanol;
(2R)-2-[({6-[4-fluoro-3-(trifluoromethyl)phenyl]pyridin-2-yl}methyl)amino]-3-methylbutan-1-ol;
{1-[({6-[4-fluoro-3-(trifluoromethyl)phenyl]pyridin-2-yl}methyl)amino]cyclopentyl}methanol;
2-fluoro-5-[6-({[(2R)-1-hydroxy-3-methylbutan-2-yl]amino}methyl)pyridin-2-yl]benzonitrile;
(2R)-2-[({6-[2,4-bis(trifluoromethyl)phenyl]pyridin-2-yl}methyl)amino]-3-methylbutan-1-ol;
{1-[({6-[2,4-bis(trifluoromethyl)phenyl]pyridin-2-yl}methyl)amino]cyclopentyl}methanol;
{1-[({6-[3,5-bis(trifluoromethyl)phenyl]pyridin-2-yl}methyl)amino]cyclopentyl}methanol;
tert-butyl 2-[5-fluoro-6-({[(2R)-1-hydroxy-3-methylbutan-2-yl]amino}methyl)pyridin-2-yl]-1H-indole-1-carboxylate;
(2R)-2-({[3-fluoro-6-(1H-indol-2-yl)pyridin-2-yl]methyl}amino)-3-methylbutan-1-ol;
{4-[5-fluoro-6-({[(2R)-1-hydroxy-3-methylbutan-2-yl]amino}methyl)pyridin-2-yl]phenyl}(4-methylpiperidin-1-yl)methanone;
{4-[5-fluoro-6-({[(2R)-1-hydroxy-3-methylbutan-2-yl]amino}methyl)pyridin-2-yl]phenyl}(pyrrolidin-1-yl)methanone;
4-[5-fluoro-6-({[(2R)-1-hydroxy-3-methylbutan-2-yl]amino}methyl)pyridin-2-yl]-N,N-dipropylbenzamide;
(2R)-2-{[(5'-chloro-5-fluoro-2,3'-bipyridin-6-yl)methyl]amino}-3-methylbutan-1-ol;
2-fluoro-5-[5-fluoro-6-({[(2R)-1-hydroxy-3-methylbutan-2-yl]amino}methyl)pyridin-2-yl]benzonitrile;
(2R)-2-({[3-fluoro-6-(4-fluoro-3-methylphenyl)pyridin-2-yl]methyl}amino)-3-methylbutan-1-ol;
(2R)-2-[({3-fluoro-6-[4-fluoro-3-(trifluoromethyl)phenyl]pyridin-2-yl}methyl)amino]-3-methylbutan-1-ol;
(2R)-2-[({3-fluoro-6-[2-fluoro-5-(trifluoromethyl)phenyl]pyridin-2-yl}methyl)amino]-3-methylbutan-1-ol;
(2R)-2-({[6-(3,4-difluoro-5-methoxyphenyl)-3-fluoropyridin-2-yl]methyl}amino)-3-methylbutan-1-ol;
(2R)-2-[({6-[(2,4-difluorophenyl)ethynyl]pyridin-2-yl}methyl)amino]-3-methylbutan-1-ol;
(2R)-2-[({6-[(2-fluorophenyl)ethynyl]pyridin-2-yl}methyl)amino]-3-methylbutan-1-ol;
(2R)-2-[({6-[(4-chlorophenyl)ethynyl]pyridin-2-yl}methyl)amino]-3-methylbutan-1-ol;
(2R)-2-({[3-fluoro-6-(4-methyl-2-phenyl-1,3-thiazol-5-yl)pyridin-2-yl]methyl}amino)-3-methylbutan-1-ol;
(2R)-2-({[6-(4-cyclohexylbut-1-yn-1-yl)-3-fluoropyridin-2-yl]methyl}amino)-3-methylbutan-1-ol;
(2R)-2-({[3-fluoro-6-(phenylethynyl)pyridin-2-yl]methyl}amino)-3-methylbutan-1-ol;
(2R)-2-[({3-fluoro-6-[5-(trifluoromethyl)thiophen-2-yl]pyridin-2-yl}methyl)amino]-3-methylbutan-1-ol;
(2R)-2-[({3-fluoro-6-[1-methyl-3-(trifluoromethyl)-1H-pyrazol-5-yl]pyridin-2-yl}methyl)amino]-3-methylbutan-1-ol;
(2R)-2-({[5-fluoro-5'-(trifluoromethyl)-2,3'-bipyridin-6-yl]methyl}amino)-3-methylbutan-1-ol;
(2R)-2-[({6-[2,4-bis(trifluoromethyl)phenyl]-3-fluoropyridin-2-yl}methyl)amino]-3-methylbutan-1-ol;
(2R)-2-({[6-(3-chloro-4-fluorophenyl)-3-fluoropyridin-2-yl]methyl}amino)-3-methylbutan-1-ol;
(2R)-2-({[6-(3,4-dihydronaphthalen-2-yl)-3-fluoropyridin-2-yl]methyl}amino)-3-methylbutan-1-ol;
(2R)-2-({[3-fluoro-6-(prop-1-en-2-yl)pyridin-2-yl]methyl}amino)-3-methylbutan-1-ol;
(2R)-2-({[6-(1-benzyl-1H-pyrazol-4-yl)-3-fluoropyridin-2-yl]methyl}amino)-3-methylbutan-1-ol;
(2R)-2-[({6-[(1E)-3-cyclopentylprop-1-en-1-yl]-3-fluoropyridin-2-yl}methyl)amino]-3-methylbutan-1-ol;
(2R)-2-({[6-(3,4-dihydro-2H-1,5-benzodioxepin-7-yl)-3-fluoropyridin-2-yl]methyl}amino)-3-methylbutan-1-ol;
(2R)-2-({[6'-(dimethylamino)-5-fluoro-2,3'-bipyridin-6-yl]methyl}amino)-3-methylbutan-1-ol;
(2R)-2-[({3-fluoro-6-[4-(1H-pyrazol-1-yl)phenyl]pyridin-2-yl}methyl)amino]-3-methylbutan-1-ol;
(2R)-2-({[6'-(cyclopropylmethoxy)-5-fluoro-2,3'-bipyridin-6-yl]methyl}amino)-3-methylbutan-1-ol;
N-butyl-3-[5-fluoro-6-{[(2R)-1-hydroxy-3-methylbutan-2-yl]amino}methyl)pyridin-2-yl]benzamide;
(2R)-2-{[(3-fluoro-6-{4-[5-(methylamino)-1,3,4-thiadiazol-2-yl]phenyl}pyridin-2-yl)methyl]amino}-3-methylbutan-1-ol;
(2R)-2-({[3-fluoro-6-(3-methylthiophen-2-yl)pyridin-2-yl]methyl}amino)-3-methylbutan-1-ol;
(2R)-2-{[(6-{3-chloro-4-[(3-chlorobenzyl)oxy]phenyl}-3-fluoropyridin-2-yl)methyl]amino}-3-methylbutan-1-ol;
(2R)-2-{[(6-{4-[(3-chlorobenzyl)oxy]phenyl}-3-fluoropyridin-2-yl)methyl]amino 1-3-methylbutan-1-ol;
(2R)-2-{[(6-{4-[(4-chlorobenzyl)oxy]phenyl}-3-fluoropyridin-2-yl)methyl]amino 1-3-methylbutan-1-ol;
(2R)-2-({[6-(4-{[(4-chloronaphthalen-1-yl)oxy]methyl}phenyl)-3-fluoropyridin-2-yl]methyl}amino)-3-methylbutan-1-ol;
(2R)-2-{[(3-fluoro-6-{4-[(naphthalen-1-yloxy)methyl]phenyl}pyridin-2-yl)methyl]amino}-3-methylbutan-1-ol;
(2R)-2-{[(6-{3-[(3-chlorobenzyl)oxy]phenyl}-3-fluoropyridin-2-yl)methyl]amino 1-3-methylbutan-1-ol;
N-cyclopropyl-3-[5-fluoro-6-{ {[(2R)-1-hydroxy-3-methylbutan-2-yl]amino}methyl)pyridin-2-yl]benzenesulfonamide;
3-[5-fluoro-6-({[(2R)-1-hydroxy-3-methylbutan-2-yl]amino}methyl)pyridin-2-yl]-N-(1,3-thiazol-2-yl)benzamide; and
(2R)-2-[({6-[4-(benzyloxy)-3-chlorophenyl]-3-fluoropyridin-2-yl}methyl)amino]-3-methylbutan-1-ol.

Exemplary compounds include, but are not limited to,
(1S,2S)-2-({[5-fluoro-6'-(trifluoromethyl)-2,3'-bipyridin-6-yl]methyl}amino)cyclohexanol;
(1R,2S)-2-({[5-fluoro-6'-(trifluoromethyl)-2,3'-bipyridin-6-yl]methyl}amino)cyclohexanol;
$N^2$-{[5-fluoro-6'-(trifluoromethyl)-2,3'-bipyridin-6-yl]methyl}-N-naphthalen-2-yl-L-threoninamide;
{1-[({2-[4-(trifluoromethyl)phenyl]pyrimidin-4-yl}methyl)amino]cyclobutyl}methanol;
{1-[({2-[4-(trifluoromethyl)phenyl]pyrimidin-4-yl}methyl)amino]cyclopentyl}methanol;
{1-[({2-[4-(trifluoromethyl)phenyl]pyrimidin-4-yl}methyl)amino]cyclohexyl}methanol;
{1-[({2-[4-(trifluoromethyl)phenyl]pyrimidin-4-yl}methyl)amino]cyclopropyl}methanol;
2-methyl-2-[({2-[4-(trifluoromethyl)phenyl]pyrimidin-4-yl}methyl)amino]propan-1-ol;
(2R)-2-[({2-[4-(trifluoromethyl)phenyl]pyrimidin-4-yl}methyl)amino]propan-1-ol;

(2R)-2-[({2-[4-(trifluoromethyl)phenyl]pyrimidin-4-yl}methyl)amino]butan-1-ol;
(2R)-2-phenyl-2-[({2-[4-(trifluoromethyl)phenyl]pyrimidin-4-yl}methyl)amino]ethanol;
(2R)-3-phenyl-2-[({2-[4-(trifluoromethyl)phenyl]pyrimidin-4-yl}methyl)amino]propan-1-ol;
(2R)-2-[({2-[4-(trifluoromethyl)phenyl]pyrimidin-4-yl}methyl)amino]pentan-1-ol;
(2R)-4-methyl-2-R {2-[4-(trifluoromethyl)phenyl]pyrimidin-4-yl}methyl)amino]pentan-1-ol;
3-methyl-2-[({2-[4-(trifluoromethyl)phenyl]pyrimidin-4-yl}methyl)amino]pentan-1-ol;
3-methoxy-2-[({2-[4-(trifluoromethyl)phenyl]pyrimidin-4-yl}methyl)amino]propan-1-01;
(2R)-2-cyclopropyl-2-[({2-[4-(trifluoromethyl)phenyl]pyrimidin-4-yl}methyl)amino]ethanol;
(2R)-2-cyclohexyl-2-[({2-[4-(trifluoromethyl)phenyl]pyrimidin-4-yl}methyl)amino]ethanol;
(2R)-3,3-dimethyl-2-[({2-[4-(trifluoromethyl)phenyl]pyrimidin-4-yl}methyl)amino]butan-1-ol;
3-[({2-[4-(trifluoromethyl)phenyl]pyrimidin-4-yl}methyl)amino]butan-2-ol;
(2S,3S)-2-[({2-[4-(trifluoromethyl)phenyl]pyrimidin-4-yl}methyl)amino]butane-1,3-diol;
(2R,3R)-2-[({2-[4-(trifluoromethyl)phenyl]pyrimidin-4-yl}methyl)amino]butane-1,3-diol;
(2R,3S)-2-[({2-[4-(trifluoromethyl)phenyl]pyrimidin-4-yl}methyl)amino]butane-1,3-diol;
(2S,3R)-2-[({2-[4-(trifluoromethyl)phenyl]pyrimidin-4-yl}methyl)amino]butane-1,3-diol;
(1S,2S)-1-phenyl-2-[({2-[4-(trifluoromethyl)phenyl]pyrimidin-4-yl}methyl)amino]propane-1,3-diol;
(1R,2R)-1-phenyl-2-[({2-[4-(trifluoromethyl)phenyl]pyrimidin-4-yl}methyl)amino]propane-1,3-diol;
(2S)-3-methyl-2-[({2-[4-(trifluoromethyl)phenyl]pyrimidin-4-yl}methyl)amino]butan-1-ol;
2,2-dimethyl-3-[({2-[4-(trifluoromethyl)phenyl]pyrimidin-4-yl}methyl)amino]propan-1-ol;
(1-{[({2-[4-(trifluoromethyl)phenyl]pyrimidin-4-yl}methyl)amino]methyl}cyclobutyl)methanol;
(1-{[({2-[4-(trifluoromethyl)phenyl]pyrimidin-4-yl}methyl)amino]methyl}cyclopentyl)methanol;
(1-{[({2-[4-(trifluoromethyl)phenyl]pyrimidin-4-yl}methyl)amino]methyl}cyclohexyl)methanol;
(3-{[({2-[4-(trifluoromethyl)phenyl]pyrimidin-4-yl}methyl)amino]methyl}oxetan-3-yl)methanol;
(4-{[({2-[4-(trifluoromethyl)phenyl]pyrimidin-4-yl}methyl)amino]methyl}tetrahydro-2H-pyran-4-yl)methanol;
(3R)-3-phenyl-3-[({2-[4-(trifluoromethyl)phenyl]pyrimidin-4-yl}methyl)amino]propan-1-ol;
(3S)-3-phenyl-3-[({2-[4-(trifluoromethyl)phenyl]pyrimidin-4-yl}methyl)amino]propan-1-ol;
1-phenyl-3-[({2-[4-(trifluoromethyl)phenyl]pyrimidin-4-yl}methyl)amino]propan-1-ol;
(1S,2R)-2-{[({2-[4-(trifluoromethyl)phenyl]pyrimidin-4-yl}methyl)amino]methyl}cyclohexanol;
(1R,2R)-2-{[({2-[4-(trifluoromethyl)phenyl]pyrimidin-4-yl}methyl)amino]methyl}cyclohexanol;
{(1S,2S)-2-[({2-[4-(trifluoromethyl)phenyl]pyrimidin-4-yl}methyl)amino]cyclohexyl}methanol;
{(1R,2S)-2-[({2-[4-(trifluoromethyl)phenyl]pyrimidin-4-yl}methyl)amino]cyclohexyl}methanol;
{(1S,2R,3S,4R)-3-[({2-[4-(trifluoromethyl)phenyl]pyrimidin-4-yl}methyl)amino]bicyclo[2.2.1]hept-2-yl}methanol;
{(1S,2S,3R,4R)-3-[({2-[4-(trifluoromethyl)phenyl]pyrimidin-4-yl}methyl)amino]bicyclo[2.2.1]hept-2-yl}methanol;
(1S,2S)-2-[({2-[4-(trifluoromethyl)phenyl]pyrimidin-4-yl}methyl)amino]cyclohexanol;
(1R,2S)-2-[({2-[4-(trifluoromethyl)phenyl]pyrimidin-4-yl}methyl)amino]cyclohexanol;
(1R,2S)-2-[({2-[4-(trifluoromethyl)phenyl]pyrimidin-4-yl}methyl)amino]cyclopentanol;
(1S,2S)-2-[({2-[4-(trifluoromethyl)phenyl]pyrimidin-4-yl}methyl)amino]cyclopentanol;
2-methyl-1-[({2-[4-(trifluoromethyl)phenyl]pyrimidin-4-yl}methyl)amino]propan-2-ol;
1-{[({2-[4-(trifluoromethyl)phenyl]pyrimidin-4-yl}methyl)amino]methyl}cyclopropanol;
1-{[({2-[4-(trifluoromethyl)phenyl]pyrimidin-4-yl}methyl)amino]methyl}cyclopentanol;
1-{[({2-[4-(trifluoromethyl)phenyl]pyrimidin-4-yl}methyl)amino]methyl}cyclohexanol;
1,1,1-trifluoro-3-[({2-[4-(trifluoromethyl)phenyl]pyrimidin-4-yl}methyl)amino]propan-2-ol;
(2S)-1-[({2-[4-(trifluoromethyl)phenyl]pyrimidin-4-yl}methyl)amino]propan-2-ol;
1-[({2-[4-(trifluoromethyl)phenyl]pyrimidin-4-yl}methyl)amino]butan-2-ol;
1-phenyl-2-[({2-[4-(trifluoromethyl)phenyl]pyrimidin-4-yl}methyl)amino]ethanol;
(2R)-1-[({2-[4-(trifluoromethyl)phenyl]pyrimidin-4-yl}methyl)amino]propan-2-ol;
(2R)-3-methyl-2-[({2-[6-(trifluoromethyl)pyridin-3-yl]pyrimidin-4-yl}methyl)amino]butan-1-ol;
{1-[({2-[6-(trifluoromethyl)pyridin-3-yl]pyrimidin-4-yl}methyl)amino]cyclohexyl}methanol;
(2R)-2-[({2-[6-(trifluoromethyl)pyridin-3-yl]pyrimidin-4-yl}methyl)amino]butan-1-ol;
3-methoxy-2-[({2-[6-(trifluoromethyl)pyridin-3-yl]pyrimidin-4-yl}methyl)amino]propan-1-ol;
(2R)-2-cyclopropyl-2-[({2-[6-(trifluoromethyl)pyridin-3-yl]pyrimidin-4-yl}methyl)amino]ethano 1;
(2S)-3-methyl-2-[({2-[6-(trifluoromethyl)pyridin-3-yl]pyrimidin-4-yl}methyl)amino]butane-1,3-diol;
3-[({2-[6-(trifluoromethyl)pyridin-3-yl]pyrimidin-4-yl}methyl)amino]butan-2-ol;
(2R,3R)-2-[({2-[6-(trifluoromethyl)pyridin-3-yl]pyrimidin-4-yl}methyl)amino]butane-1,3-diol;
(2R)-3-methyl-2-[({2-[5-(trifluoromethyl)pyridin-2-yl]pyrimidin-4-yl}methyl)amino]butan-1-ol;
{1-[({2-[5-(trifluoromethyl)pyridin-2-yl]pyrimidin-4-yl}methyl)amino]cyclohexyl}methanol;
(2R)-2-[({2-[5-(trifluoromethyl)pyridin-2-yl]pyrimidin-4-yl}methyl)amino]butan-1-ol;
3-methoxy-2-[({2-[5-(trifluoromethyl)pyridin-2-yl]pyrimidin-4-yl}methyl)amino]propan-1-ol;
(2R)-2-cyclopropyl-2-[({2-[5-(trifluoromethyl)pyridin-2-yl]pyrimidin-4-yl}methyl)amino]ethano 1;
(2S)-3-methyl-2-[({2-[5-(trifluoromethyl)pyridin-2-yl]pyrimidin-4-yl}methyl)amino]butane-1,3-diol;
(2R,3R)-2-[({2-[5-(trifluoromethyl)pyridin-2-yl]pyrimidin-4-yl}methyl)amino]butane-1,3-diol;
(2R)-2-({[6-(bicyclo[2.2.1]hept-2-yl)-3-fluoropyridin-2-yl]methyl}amino)-3-methylbutan-1-ol;
(2R)-2-({[3-fluoro-6-(4-methylcyclohexyl)pyridin-2-yl]methyl}amino)-3-methylbutan-1-ol;
(2R)-2-({[6-(4-ethylcyclohexyl)-3-fluoropyridin-2-yl]methyl}amino)-3-methylbutan-1-ol;
(2R)-2-({[6-(4,4-dimethylcyclohexyl)-3-fluoropyridin-2-yl]methyl}amino)-3-methylbutan-1-ol;

(2R)-2-({[6-(4,4-difluorocyclohexyl)-3-fluoropyridin-2-yl]methyl}amino)-3-methylbutan-1-ol;
(2R)-2-({[3-fluoro-6-(tetrahydro-2H-pyran-4-yl)pyridin-2-yl]methyl}amino)-3-methylbutan-1-ol;
tert-butyl 4-[5-fluoro-6-({[(2R)-1-hydroxy-3-methylbutan-2-yl]amino}methyl)pyridin-2-yl]piperidine-1-carboxylate;
(2R)-2-{[(6-cycloheptyl-3-fluoropyridin-2-yl)methyl]amino}-3-methylbutan-1-ol;
(2R)-3-methyl-2-{[(2-{4-[(trifluoromethyl)sulfonyl]phenyl}pyrimidin-4-yl)methyl]amino}butan-1-ol;
(1-{[(2-{4-[(trifluoromethyl)sulfonyl]phenyl}pyrimidin-4-yl)methyl]amino}cyclohexyl)methanol;
(2R)-2-{[(2-{4-[(trifluoromethyl)sulfonyl]phenyl}pyrimidin-4-yl)methyl]amino}butan-1-ol;
3-methoxy-2-{[(2-{4-[(trifluoromethyl)sulfonyl]phenyl}pyrimidin-4-yl)methyl]amino}propan-1-ol;
(2S)-3-methyl-2-{[(2-{4-[(trifluoromethyl)sulfonyl]phenyl}pyrimidin-4-yl)methyl]amino 1 butane-1,3-diol;
(2R,3R)-2-{[(2-{4-[(trifluoromethyl)sulfonyl]phenyl}pyrimidin-4-yl)methyl]amino 1 butane-1,3-diol;
(2R)-2-({[6-(4-tert-butylcyclohexyl)-3-fluoropyridin-2-yl]methyl}amino)-3-methylbutan-1-ol;
(2R)-2-({[6-(1,4-dioxaspiro[4.5]dec-8-yl)-3-fluoropyridin-2-yl]methyl}amino)-3-methylbutan-1-ol;
(2R)-2-({[6-(1,4-dioxaspiro[4.5]dec-7-yl)-3-fluoropyridin-2-yl]methyl}amino)-3-methylbutan-1-ol;
(2R)-2-[({3-fluoro-6-[4-(trifluoromethyl)cyclohexyl]pyridin-2-yl}methyl)amino]-3-methylbutan-1-ol;
(2R)-2-({[3-fluoro-6-(1,2,3,4-tetrahydronaphthalen-2-yl)pyridin-2-yl]methyl}amino)-3-methylbutan-1-ol;
(2R)-2-({[3-fluoro-6-(tetrahydro-2H-pyran-3-yl)pyridin-2-yl]methyl}amino)-3-methylbutan-1-ol;
tert-butyl 3-[5-fluoro-6-({[(2R)-1-hydroxy-3-methylbutan-2-yl]amino}methyl)pyridin-2-yl]piperidine-1-carboxylate;
(2R)-2-{[(6-cyclopentyl-3-fluoropyridin-2-yl)methyl]amino}-3-methylbutan-1-ol;
(2R)-2-({[3-fluoro-6-(tetrahydrofuran-3-yl)pyridin-2-yl]methyl}amino)-3-methylbutan-1-ol;
tert-butyl 3-[5-fluoro-6-({[(2R)-1-hydroxy-3-methylbutan-2-yl]amino}methyl)pyridin-2-yl]pyrrolidine-1-carboxylate;
(2R)-2-({[3-fluoro-6-(3,4,5-trifluorophenyl)pyridin-2-yl]methyl}amino)-3-methylbutan-1-ol;
(2R)-2-({[3-fluoro-6-(2,3,4-trifluorophenyl)pyridin-2-yl]methyl}amino)-3-methylbutan-1-ol;
(2R)-2-({[3-fluoro-6-(2,4,5-trifluorophenyl)pyridin-2-yl]methyl}amino)-3-methylbutan-1-ol;
(2R)-2-({[6-(3,5-difluorophenyl)-3-fluoropyridin-2-yl]methyl}amino)-3-methylbutan-1-ol;
(2R)-2-({[3-fluoro-6-(1-methyl-1H-indol-5-yl)pyridin-2-yl]methyl}amino)-3-methylbutan-1-ol;
(2R)-2-({[3-fluoro-6-(6-methoxynaphthalen-2-yl)pyridin-2-yl]methyl}amino)-3-methylbutan-1-ol;
(2R)-2-({[3-fluoro-6-(4-methylnaphthalen-1-yl)pyridin-2-yl]methyl}amino)-3-methylbutan-1-ol;
(2R)-2-({[6-(9H-carbazol-2-yl)-3-fluoropyridin-2-yl]methyl}amino)-3-methylbutan-1-ol;
(2R)-2-({[3-fluoro-6-(naphthalen-2-yl)pyridin-2-yl]methyl}amino)-3-methylbutan-1-ol;
{4-[5-fluoro-6-({[(2R)-1-hydroxy-3-methylbutan-2-yl]amino}methyl)pyridin-2-yl]phenyl}(phenyl)methanone;
(2R)-2-({[3-fluoro-6-(3-fluoro-4-methoxyphenyl)pyridin-2-yl]methyl}amino)-3-methylbutan-1-ol;
(2R)-2-[({6-[4-(ethylsulfanyl)phenyl]-3-fluoropyridin-2-yl}methyl)amino]-3-methylbutan-1-ol;
(2R)-2-({[3-fluoro-6-(3-fluoro-4-methylphenyl)pyridin-2-yl]methyl}amino)-3-methylbutan-1-ol;
(2R)-2-[({3-fluoro-6-[2-(propan-2-yl)phenyl]pyridin-2-yl}methyl)amino]-3-methylbutan-1-ol;
(2R)-2-({[6-(4-cyclopropylphenyl)-3-fluoropyridin-2-yl]methyl}amino)-3-methylbutan-1-ol;
(2R)-2-[({6-[4-(butan-2-yl)phenyl]-3-fluoropyridin-2-yl}methyl)amino]-3-methylbutan-1-ol;
(2R)-2-({[3-fluoro-6-(2,3,5-trifluorophenyl)pyridin-2-yl]methyl}amino)-3-methylbutan-1-ol;
(2R)-2-[({3-fluoro-6-[4-(propan-2-yl)phenyl]pyridin-2-yl}methyl)amino]-3-methylbutan-1-ol;
(2R)-2-({[3-fluoro-6-(4-propylphenyl)pyridin-2-yl]methyl}amino)-3-methylbutan-1-ol;
(2R)-2-[({6-[3-(ethylsulfanyl)phenyl]-3-fluoropyridin-2-yl}methyl)amino]-3-methylbutan-1-ol;
(2R)-2-[({6-[2-(ethylsulfanyl)phenyl]-3-fluoropyridin-2-yl}methyl)amino]-3-methylbutan-1-ol;
(2R)-2-({[6-(4-chloro-3-methylphenyl)-3-fluoropyridin-2-yl]methyl}amino)-3-methylbutan-1-ol;
(2R)-2-({[6-(biphenyl-4-yl)-3-fluoropyridin-2-yl]methyl}amino)-3-methylbutan-1-ol;
(2R)-2-[({6-[2-(benzyloxy)phenyl]-3-fluoropyridin-2-yl}methyl)amino]-3-methylbutan-1-ol;
(2R)-2-({[6-(2-ethenylphenyl)-3-fluoropyridin-2-yl]methyl}amino)-3-methylbutan-1-ol;
(2R)-2-({[3-fluoro-6-(4-methyl-3-nitrophenyl)pyridin-2-yl]methyl}amino)-3-methylbutan-1-ol;
(2R)-2-[({6-[2-chloro-4-(trifluoromethyl)phenyl]-3-fluoropyridin-2-yl}methyl)amino]-3-methylbutan-1-ol;
(2R)-2-[({3-fluoro-6-[2-(trifluoromethoxy)phenyl]pyridin-2-yl}methyl)amino]-3-methylbutan-1-ol;
(2R)-2-({[6-(5-chloro-2-methylphenyl)-3-fluoropyridin-2-yl]methyl}amino)-3-methylbutan-1-ol;
4-[5-fluoro-6-({[(2R)-1-hydroxy-3-methylbutan-2-yl]amino}methyl)pyridin-2-yl]-N-(2-methylpropyl)benzamide;
(2R)-2-({[6-(4-bromo-3-fluorophenyl)-3-fluoropyridin-2-yl]methyl}amino)-3-methylbutan-1-ol;
(2R)-2-[({3-fluoro-6-[3-(propan-2-yl)phenyl]pyridin-2-yl}methyl)amino]-3-methylbutan-1-ol;
(2R)-2-({[6-(2,4-difluorophenyl)-3-fluoropyridin-2-yl]methyl}amino)-3-methylbutan-1-ol;
(2R)-2-({[6-(biphenyl-3-yl)-3-fluoropyridin-2-yl]methyl}amino)-3-methylbutan-1-ol;
(2R)-2-({[3-fluoro-6-(2,4,5-trimethylphenyl)pyridin-2-yl]methyl}amino)-3-methylbutan-1-ol;
(2R)-2-[({3-fluoro-6-[4-(propan-2-ylsulfanyl)phenyl]pyridin-2-yl}methyl)amino]-3-methylbutan-1-ol;
(2R)-2-({[6-(4-chloro-3-fluorophenyl)-3-fluoropyridin-2-yl]methyl}amino)-3-methylbutan-1-ol;
(2R)-2-({[3-fluoro-6-(4-sulfanylphenyl)pyridin-2-yl]methyl}amino)-3-methylbutan-1-ol;
(2R)-2-({[6-(2-chloro-4-fluorophenyl)-3-fluoropyridin-2-yl]methyl}amino)-3-methylbutan-1-ol;
(2R)-2-[({3-fluoro-6-[2-(methylsulfanyl)phenyl]pyridin-2-yl}methyl)amino]-3-methylbutan-1-ol;
(2R)-2-({[3-fluoro-6-(2,3,5,6-tetramethylphenyl)pyridin-2-yl]methyl}amino)-3-methylbutan-1-ol;
(2R)-2-({[6-(2-ethylphenyl)-3-fluoropyridin-2-yl]methyl}amino)-3-methylbutan-1-ol;
(2R)-2-({[3-fluoro-6-(4-fluoro-2-methylphenyl)pyridin-2-yl]methyl}amino)-3-methylbutan-1-ol;
(2R)-2-({[3-fluoro-6-(5-fluoro-2-methylphenyl)pyridin-2-yl]methyl}amino)-3-methylbutan-1-ol;
(2R)-2-({[6-(2,6-dimethylphenyl)-3-fluoropyridin-2-yl]methyl}amino)-3-methylbutan-1-ol;

(2R)-2-({[6-(2,3-difluorophenyl)-3-fluoropyridin-2-yl]
methyl}amino)-3-methylbutan-1-ol;
(2R)-2-[({3-fluoro-6-[2-fluoro-4-(trifluoromethyl)phenyl]
pyridin-2-yl}methyl)amino]-3-methylbutan-1-ol;
(2R)-2-({[6-(2,5-difluorophenyl)-3-fluoropyridin-2-yl]
methyl}amino)-3-methylbutan-1-ol;
(2R)-2-({[6-(4-ethylphenyl)-3-fluoropyridin-2-yl]
methyl}amino)-3-methylbutan-1-ol;
(2R)-2-({[6-(4-tert-butylphenyl)-3-fluoropyridin-2-yl]
methyl}amino)-3-methylbutan-1-ol;
(2R)-2-({[3-fluoro-6-(2,4,6-trimethylphenyl)pyridin-2-yl]
methyl}amino)-3-methylbutan-1-ol;
N-{2-[5-fluoro-6-({[(2R)-1-hydroxy-3-methylbutan-2-yl]
amino}methyl)pyridin-2-yl]phenyl}-2,2-dimethylpropanamide;
(2R)-2-[({3-fluoro-6-[4-(2-methylpropyl)phenyl]pyridin-2-
yl}methyl)amino]-3-methylbutan-1-ol;
(2R)-2-({[3-fluoro-6-(4-methylphenyl)pyridin-2-yl]
methyl}amino)-3-methylbutan-1-ol;
(2R)-2-[({6-[4-(benzyloxy)phenyl]-3-fluoropyridin-2-
yl}methyl)amino]-3-methylbutan-1-ol;
(2R)-2-({[3-fluoro-6-(3-methylphenyl)pyridin-2-yl]
methyl}amino)-3-methylbutan-1-ol;
(2R)-2-({[6-(2-chlorophenyl)-3-fluoropyridin-2-yl]
methyl}amino)-3-methylbutan-1-ol;
(2R)-2-({[6-(3-bromo-5-methylphenyl)-3-fluoropyridin-2-
yl]methyl}amino)-3-methylbutan-1-ol;
(2R)-2-({[6-(3-chloro-2-methylphenyl)-3-fluoropyridin-2-
yl]methyl}amino)-3-methylbutan-1-ol;
(2R)-2-({[6-(4-bromo-2,5-dimethylphenyl)-3-fluoropyridin-2-yl]methyl}amino)-3-methylbutan-1-ol;
(2R)-2-({[6-(3-chloro-2-fluorophenyl)-3-fluoropyridin-2-
yl]methyl}amino)-3-methylbutan-1-ol;
N-butyl-4-[5-fluoro-6-({[(2R)-1-hydroxy-3-methylbutan-2-
yl]amino}methyl)pyridin-2-yl]benzamide;
(2R)-2-({[6-(3-bromo-5-fluorophenyl)-3-fluoropyridin-2-
yl]methyl}amino)-3-methylbutan-1-ol;
(2R)-2-[({6-[4-(dimethylamino)phenyl]-3-fluoropyridin-2-
yl}methyl)amino]-3-methylbutan-1-ol;
(2R)-2-({[6-(5-bromo-2-fluorophenyl)-3-fluoropyridin-2-
yl]methyl}amino)-3-methylbutan-1-ol;
(2R)-2-({[6-(3-bromo-2-fluorophenyl)-3-fluoropyridin-2-
yl]methyl}amino)-3-methylbutan-1-ol;
(2R)-2-({[6-(5-chloro-2-fluorophenyl)-3-fluoropyridin-2-
yl]methyl}amino)-3-methylbutan-1-ol;
(2R)-2-({[3-fluoro-6-(2-fluoro-4-methylphenyl)pyridin-2-
yl]methyl}amino)-3-methylbutan-1-ol;
(2R)-2-[({6-[2-(dimethylamino)phenyl]-3-fluoropyridin-2-
yl}methyl)amino]-3-methylbutan-1-ol;
(2R)-2-({[3-fluoro-6-(4-fluoro-2-methoxyphenyl)pyridin-2-
yl]methyl}amino)-3-methylbutan-1-ol;
(2R)-2-[({3-fluoro-6-[3-fluoro-5-(trifluoromethyl)phenyl]
pyridin-2-yl}methyl)amino]-3-methylbutan-1-ol;
(2R)-2-({[6-(9H-fluoren-2-yl)-3-fluoropyridin-2-yl]
methyl}amino)-3-methylbutan-1-ol;
(2R)-2-[({3-fluoro-6-[2-fluoro-3-(trifluoromethyl)phenyl]
pyridin-2-yl}methyl)amino]-3-methylbutan-1-ol;
(2R)-2-[({3-fluoro-6-[2-fluoro-5-(trifluoromethoxy)phenyl]
pyridin-2-yl}methyl)amino]-3-methylbutan-1-ol;
(2R)-2-({[6-(2-chloro-5-methylphenyl)-3-fluoropyridin-2-
yl]methyl}amino)-3-methylbutan-1-ol;
(2R)-2-({[3-fluoro-6-(2-methylphenyl)pyridin-2-yl]
methyl}amino)-3-methylbutan-1-ol;
(2R)-2-({[3-fluoro-6-(3-fluoro-5-methylphenyl)pyridin-2-
yl]methyl}amino)-3-methylbutan-1-ol;
(2R)-2-[({6-[2-(ethoxymethyl)phenyl]-3-fluoropyridin-2-
yl}methyl)amino]-3-methylbutan-1-ol;
(2R)-2-[({3-fluoro-6-[2-(trifluoromethyl)phenyl]pyridin-2-
yl}methyl)amino]-3-methylbutan-1-ol;
(2R)-2-({[6-(3-chloro-5-fluorophenyl)-3-fluoropyridin-2-
yl]methyl}amino)-3-methylbutan-1-ol;
(2R)-2-{[(3-fluoro-6-{4-[(phenylamino)methyl]
phenyl}pyridin-2-yl)methyl]amino}-3-methylbutan-1-ol;
(2R)-2-[({3-fluoro-6-[3-(1-methoxyethyl)phenyl]pyridin-2-
yl}methyl)amino]-3-methylbutan-1-ol;
(2R)-2-[({3-fluoro-6-[4-(1-methoxyethyl)phenyl]pyridin-2-
yl}methyl)amino]-3-methylbutan-1-ol;
(2R)-2-{[(6-{4-[1-(dimethylamino)ethyl]phenyl}-3-fluoropyridin-2-yl)methyl]amino}-3-methylbutan-1-ol;
(2R)-2-[({3-fluoro-6-[3-fluoro-4-(trifluoromethoxy)phenyl]
pyridin-2-yl}methyl)amino]-3-methylbutan-1-ol;
(2R)-2-({[3-fluoro-6-(2-methoxynaphthalen-1-yl)pyridin-2-
yl]methyl}amino)-3-methylbutan-1-ol;
(2R)-2-({[5-fluoro-6'-(trifluoromethyl)-2,3'-bipyridin-6-yl]
methyl}amino)-2-phenylethanol;
$N^2$-{[5-fluoro-6'-(trifluoromethyl)-2,3'-bipyridin-6-yl]methyl}-L-leucinamide;
(2S)-2-({[5-fluoro-6'-(trifluoromethyl)-2,3'-bipyridin-6-yl]
methyl}amino)-4-methylpentan-1-ol;
(2S)-2-({[5-fluoro-6'-(trifluoromethyl)-2,3'-bipyridin-6-yl]
methyl}amino)-2-phenylethanol;
(2R)-2-({[3-fluoro-6-(4-methoxy-3-methylphenyl)pyridin-
2-yl]methyl}amino)-3-methylbutan-1-ol;
(2R)-2-({[6-(4-ethoxyphenyl)-3-fluoropyridin-2-yl]
methyl}amino)-3-methylbutan-1-ol;
(2R)-2-[({6-[3-(benzyloxy)phenyl]-3-fluoropyridin-2-
yl}methyl)amino]-3-methylbutan-1-ol;
(2R)-2-({[6-(2-butoxyphenyl)-3-fluoropyridin-2-yl]
methyl}amino)-3-methylbutan-1-ol;
(2R)-2-({[6-(4-ethoxy-3,5-dimethylphenyl)-3-fluoropyridin-2-yl]methyl}amino)-3-methylbutan-1-ol;
(2R)-2-({[6-(3-butoxyphenyl)-3-fluoropyridin-2-yl]
methyl}amino)-3-methylbutan-1-ol;
propan-2-yl]-[5-fluoro-6-({[(2R)-1-hydroxy-3-methylbutan-2-yl]amino}methyl)pyridin-2-yl]benzoate;
4-[5-fluoro-6-({[(2R)-1-hydroxy-3-methylbutan-2-yl]
amino}methyl)pyridin-2-yl]-2,6-dimethylphenol;
(2R)-2-({[6-(4-butoxyphenyl)-3-fluoropyridin-2-yl]
methyl}amino)-3-methylbutan-1-ol;
(2R)-2-({[6-(3,5-dimethoxyphenyl)-3-fluoropyridin-2-yl]
methyl}amino)-3-methylbutan-1-ol;
(2R)-2-[({3-fluoro-6-[4-methoxy-2-(trifluoromethyl)phenyl]pyridin-2-yl}methyl)amino]-3-methylbutan-1-ol;
(2R)-2-({[6-(3,5-difluoro-2-methoxyphenyl)-3-fluoropyridin-2-yl]methyl}amino)-3-methylbutan-1-ol;
(2R)-2-({[6-(6-ethoxynaphthalen-2-yl)-3-fluoropyridin-2-
yl]methyl}amino)-3-methylbutan-1-ol;
(2R)-2-({[6-(2,3-dimethoxyphenyl)-3-fluoropyridin-2-yl]
methyl}amino)-3-methylbutan-1-ol;
(2R)-2-({[3-fluoro-6-(2-methoxy-5-methylphenyl)pyridin-
2-yl]methyl}amino)-3-methylbutan-1-ol;
(2R)-2-({[6-(2-ethoxy-5-methylphenyl)-3-fluoropyridin-2-
yl]methyl}amino)-3-methylbutan-1-ol;
(2R)-2-({[3-fluoro-6-(4-methoxy-2-methylphenyl)pyridin-
2-yl]methyl}amino)-3-methylbutan-1-ol;
(2R)-2-({[6-(2-ethoxyphenyl)-3-fluoropyridin-2-yl]
methyl}amino)-3-methylbutan-1-ol;
(2R)-2-[({3-fluoro-6-[2-(propan-2-yloxy)phenyl]pyridin-2-
yl}methyl)amino]-3-methylbutan-1-ol;
(2R)-2-({[3-fluoro-6-(5-fluoro-2-methoxyphenyl)pyridin-2-
yl]methyl}amino)-3-methylbutan-1-ol;
(2R)-2-({[3-fluoro-6-(2-fluoro-3-methoxyphenyl)pyridin-2-
yl]methyl}amino)-3-methylbutan-1-ol;

(2R)-2-({[6-(2-ethoxy-4-fluorophenyl)-3-fluoropyridin-2-yl]methyl}amino)-3-methylbutan-1-ol;
(2R)-2-({[6-(2,6-dimethoxyphenyl)-3-fluoropyridin-2-yl]methyl}amino)-3-methylbutan-1-ol;
(2R)-2-({[6-(3-chloro-4-propoxyphenyl)-3-fluoropyridin-2-yl]methyl}amino)-3-methylbutan-1-ol;
(2R)-2-({[6-(4-ethoxy-3-fluorophenyl)-3-fluoropyridin-2-yl]methyl}amino)-3-methylbutan-1-ol;
(2R)-2-({[3-fluoro-6-(3-propoxyphenyl)pyridin-2-yl]methyl}amino)-3-methylbutan-1-ol;
(2R)-2-({[3-fluoro-6-(5-fluoro-2-propoxyphenyl)pyridin-2-yl]methyl}amino)-3-methylbutan-1-ol;
(2R)-2-({[3-fluoro-6-(3-fluoro-4-propoxyphenyl)pyridin-2-yl]methyl}amino)-3-methylbutan-1-ol;
(2R)-2-[({3-fluoro-6-[3-(2-methylpropoxy)phenyl]pyridin-2-yl}methyl)amino]-3-methylbutan-1-ol;
(2R)-2-({[3-fluoro-6-(2-fluoro-6-propoxyphenyl)pyridin-2-yl]methyl}amino)-3-methylbutan-1-ol;
(2R)-2-({[3-fluoro-6-(2-methyl-4-propoxyphenyl)pyridin-2-yl]methyl}amino)-3-methylbutan-1-ol;
(2R)-2-({[6-(5-chloro-2-propoxyphenyl)-3-fluoropyridin-2-yl]methyl}amino)-3-methylbutan-1-ol;
(2R)-2-[({6-[5-chloro-2-(propan-2-yloxy)phenyl]-3-fluoropyridin-2-yl}methyl)amino]-3-methylbutan-1-ol;
(2R)-2-({[6-(2-ethoxynaphthalen-1-yl)-3-fluoropyridin-2-yl]methyl}amino)-3-methylbutan-1-ol;
(2R)-2-[({3-fluoro-6-[4-(methylsulfanyl)phenyl]pyridin-2-yl}methyl)amino]-3-methylbutan-1-ol;
(2R)-2-({[6-(3,4-dimethoxyphenyl)-3-fluoropyridin-2-yl]methyl}amino)-3-methylbutan-1-ol;
(2R)-2-({[6-(5-butoxy-2-fluorophenyl)-3-fluoropyridin-2-yl]methyl}amino)-3-methylbutan-1-ol;
(2R)-2-({[3-fluoro-6-(4-methoxyphenyl)pyridin-2-yl]methyl}amino)-3-methylbutan-1-ol;
(2R)-2-({[3-fluoro-6-(2-propoxyphenyl)pyridin-2-yl]methyl}amino)-3-methylbutan-1-ol;
(2R)-2-({[3-fluoro-6-(3-methoxyphenyl)pyridin-2-yl]methyl}amino)-3-methylbutan-1-ol;
(2R)-2-({[3-fluoro-6-(4-propoxyphenyl)pyridin-2-yl]methyl}amino)-3-methylbutan-1-ol;
(2R)-2-[({3-fluoro-6-[2-(2-methylpropoxy)phenyl]pyridin-2-yl}methyl)amino]-3-methylbutan-1-ol;
(2R)-2-[({3-fluoro-6-[5-fluoro-2-(propan-2-yloxy)phenyl]pyridin-2-yl}methyl)amino]-3-methylbutan-1-ol;
(2R)-2-({[3-fluoro-6-(5-methyl-2-propoxyphenyl)pyridin-2-yl]methyl}amino)-3-methylbutan-1-ol;
(2R)-2-({[6-(2-butoxy-5-fluorophenyl)-3-fluoropyridin-2-yl]methyl}amino)-3-methylbutan-1-ol;
(2R)-2-({[6-(4-butoxy-3-fluorophenyl)-3-fluoropyridin-2-yl]methyl}amino)-3-methylbutan-1-ol;
(2R)-2-({[3-fluoro-6-(2-methoxyphenyl)pyridin-2-yl]methyl}amino)-3-methylbutan-1-ol;
(2R)-2-[({3-fluoro-6-[5-methyl-2-(propan-2-yloxy)phenyl]pyridin-2-yl}methyl)amino]-3-methylbutan-1-ol;
(2R)-2-({[6-(4-ethoxy-2-methylphenyl)-3-fluoropyridin-2-yl]methyl}amino)-3-methylbutan-1-ol;
(2R)-2-({[6-(5-chloro-2-ethoxyphenyl)-3-fluoropyridin-2-yl]methyl}amino)-3-methylbutan-1-ol;
(2R)-2-({[6-(2-ethoxy-5-fluorophenyl)-3-fluoropyridin-2-yl]methyl}amino)-3-methylbutan-1-ol;
(2R)-2-({[6-(2-ethoxy-6-fluorophenyl)-3-fluoropyridin-2-yl]methyl}amino)-3-methylbutan-1-ol;
(2R)-2-({[6-(5-ethoxy-2-fluorophenyl)-3-fluoropyridin-2-yl]methyl}amino)-3-methylbutan-1-ol;
(2R)-2-({[3-fluoro-6-(2-fluoro-5-methoxyphenyl)pyridin-2-yl]methyl}amino)-3-methylbutan-1-ol;
(2R)-2-({[6-(2-chloro-6-methoxyphenyl)-3-fluoropyridin-2-yl]methyl}amino)-3-methylbutan-1-ol;
(2R)-2-({[6-(2,5-difluoro-4-methoxyphenyl)-3-fluoropyridin-2-yl]methyl}amino)-3-methylbutan-1-ol;
(2R)-2-({[3-fluoro-6-(2-fluoro-5-propoxyphenyl)pyridin-2-yl]methyl}amino)-3-methylbutan-1-ol;
(2R)-2-({[6-(3-chloro-4-ethoxyphenyl)-3-fluoropyridin-2-yl]methyl}amino)-3-methylbutan-1-ol;
(2R)-2-({[6-(3-ethoxy-2-fluorophenyl)-3-fluoropyridin-2-yl]methyl}amino)-3-methylbutan-1-ol;
(2R)-2-[({3-fluoro-6-[3-methoxy-5-(trifluoromethyl)phenyl]pyridin-2-yl}methyl)amino]-3-methylbutan-1-ol;
(2R)-2-({[6-(4-ethoxy-3-methylphenyl)-3-fluoropyridin-2-yl]methyl}amino)-3-methylbutan-1-ol;
(2R)-2-[({3-fluoro-6-[4-methoxy-3-(trifluoromethyl)phenyl]pyridin-2-yl}methyl)amino]-3-methylbutan-1-ol;
(2R)-2-{[(6-{3-[(cyclopropylmethyl)sulfanyl]phenyl}-3-fluoropyridin-2-yl)methyl]amino}-3-methylbutan-1-ol;
(2R)-2-[({3-fluoro-6-[4-(2-methylpropoxy)phenyl]pyridin-2-yl}methyl)amino]-3-methylbutan-1-ol;
(2R)-2-[({6-[3,5-dimethyl-4-(propan-2-yloxy)phenyl]-3-fluoropyridin-2-yl}methyl)amino]-3-methylbutan-1-ol;
(2R)-2-({[6-(2-ethoxy-4,5-difluorophenyl)-3-fluoropyridin-2-yl]methyl}amino)-3-methylbutan-1-ol;
(2R)-2-({[6-(2,4-diethoxyphenyl)-3-fluoropyridin-2-yl]methyl}amino)-3-methylbutan-1-ol;
(2R)-2-({[6-(2-butoxy-6-fluorophenyl)-3-fluoropyridin-2-yl]methyl}amino)-3-methylbutan-1-ol;
(2R)-2-({[6-(3-ethoxy-5-fluorophenyl)-3-fluoropyridin-2-yl]methyl}amino)-3-methylbutan-1-ol;
(2R)-2-[({3-fluoro-6-[2-methoxy-6-(propan-2-yloxy)phenyl]pyridin-2-yl}methyl)amino]-3-methylbutan-1-ol;
(2R)-2-[({3-fluoro-6-[2-fluoro-6-(propan-2-yloxy)phenyl]pyridin-2-yl}methyl)amino]-3-methylbutan-1-ol;
(2R)-2-[({3-fluoro-6-[2-methoxy-6-(2-methylpropoxy)phenyl]pyridin-2-yl}methyl)amino]-3-methylbutan-1-ol;
(2R)-2-({[3-fluoro-6-(4-fluoro-3-methoxyphenyl)pyridin-2-yl]methyl}amino)-3-methylbutan-1-ol;
(2R)-2-[({3-fluoro-6-[3-fluoro-5-(propan-2-yloxy)phenyl]pyridin-2-yl}methyl)amino]-3-methylbutan-1-ol;
(2R)-2-[({3-fluoro-6-[5-methyl-2-(2-methylpropoxy)phenyl]pyridin-2-yl}methyl)amino]-3-methylbutan-1-ol;
(2R)-2-({[6-(4,5-difluoro-2-methoxyphenyl)-3-fluoropyridin-2-yl]methyl}amino)-3-methylbutan-1-ol; and
2-ethoxy-3-[5-fluoro-6-({[(2R)-1-hydroxy-3-methylbutan-2-yl]amino}methyl)pyridin-2-yl]-5-methylbenzaldehyde.

The present compounds may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

Various stereoisomers of the present compounds and mixtures thereof are included within the scope of this application. Stereoisomers include enantiomers and diastereomers, and mixtures of enantiomers or diastereomers. Individual stereoisomers may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. Various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

Compounds disclosed herein may exhibit the phenomenon of tautomerism.

Thus, the formula drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formula drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of TRPV3 modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to TRPV3 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N. Y. Acad. Sci. 1960 84: 770; Thomson J F, Ann. New York Acad. Sci. 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling 0 Eds. 1994. Advanced Medical Publishing, Madison Wis. pp. 125-134; Diabetes Metab. 23: 251 (1997)).

Stable isotope labeling of a drug may alter its physicochemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-isotopic compound.

c. Biological Data (i) In Vitro Methods-Calcium Flux Assays:

Experiments were conducted using the FLIPR$^{TETRA®}$. On the day prior to the experiment, recombinant HEK293 cells that stably express human and mouse TRPV3 were removed from tissue culture flasks and plated in growth medium at 20,000 cells/well into black-walled clear-bottom 384-well Biocoat™ poly-D-lysine assay plates (BD Biosciences, Bedford, Mass.) using a Multidrop® dispenser (ThermoScientific, Waltham, Mass.). On the day of the experiment, growth medium was removed, and the no-wash FLIPR® Calcium-4 dye ($\lambda_{EX}$=470-495 nm, $\lambda_{EM}$=515-575 nm; Molecular Devices, Sunnyvale, Calif.) was added to each well using the Multidrop® dispenser. Cells were incubated for 90-120 minutes in the dark. Compounds were dissolved in DMSO to prepare a 10 mM stock solution. The intensity of the fluorescence was captured and digitally transferred to an interfaced PC. The peak increase in fluorescence over baseline (relative fluorescence units) was calculated and expressed as the percentage of the maximal 2-APB (2-aminoethoxyldiphenyl borate) response (in the absence of compound). The concentration of 2-APB corresponds to its $EC_{80}$. $IC_{50}$ values of the compounds at human TRPV3 receptors are shown in Table 1.

TABLE 1

| Example | IC$_{50}$ (μM) |
|---|---|
| 1 | 4.02 |
| 2 | 3.81 |
| 3 | 9.38 |
| 4 | 3.00 |
| 5 | 3.71 |
| 6 | 3.70 |
| 7 | 3.25 |
| 8 | 2.60 |
| 9 | 3.65 |
| 10 | 3.79 |
| 11 | 1.94 |
| 12 | 0.91 |
| 13 | 1.12 |
| 14 | 0.81 |
| 15 | 1.84 |
| 16 | 1.11 |
| 17 | 0.20 |
| 18 | 1.12 |
| 19 | 0.23 |
| 20 | 1.39 |
| 21 | 3.30 |
| 22 | 1.28 |
| 23 | 0.70 |
| 24 | 0.75 |
| 25 | 0.65 |
| 26 | 4.06 |
| 27 | 0.32 |
| 28 | 0.95 |
| 29 | 0.41 |
| 30 | >20 |
| 31 | 2.19 |
| 32 | 12.00 |
| 33 | 2.36 |
| 34 | 1.39 |
| 35 | >20 |
| 36 | 0.95 |
| 37 | 1.19 |
| 38 | 2.85 |
| 39 | 1.70 |
| 40 | 1.40 |
| 41 | 2.97 |
| 42 | 0.39 |
| 43 | 0.46 |
| 44 | 0.83 |
| 45 | 3.47 |
| 46 | 2.02 |
| 47 | 0.29 |
| 48 | 0.33 |
| 49 | 0.48 |
| 50 | 1.77 |
| 51 | 0.50 |
| 52 | 1.42 |
| 53 | 0.46 |
| 54 | 0.76 |
| 55 | 2.16 |
| 56 | 1.78 |
| 57 | 0.50 |
| 58 | 1.49 |
| 59 | 0.63 |
| 60 | 1.08 |
| 61 | 0.19 |
| 62 | 4.00 |
| 63 | 1.74 |
| 64 | 0.48 |
| 65 | 0.32 |
| 66 | 0.22 |
| 67 | 0.42 |
| 68 | 0.59 |
| 69 | 3.72 |
| 70 | 0.18 |
| 71 | 0.16 |
| 72 | 2.39 |
| 73 | 0.14 |
| 74 | 3.68 |
| 75 | 3.02 |
| 76 | 1.60 |
| 77 | 0.54 |
| 78 | 10.20 |
| 79 | 0.70 |
| 80 | 0.29 |
| 81 | 0.68 |
| 82 | 1.64 |
| 83 | 0.46 |
| 84 | 0.70 |
| 85 | 0.52 |
| 86 | 0.30 |
| 87 | 3.10 |
| 88 | 0.57 |
| 89 | 0.51 |
| 90 | 2.59 |
| 91 | >20 |
| 92 | 0.96 |
| 93 | 0.27 |
| 94 | 0.12 |
| 95 | 0.34 |
| 96 | 0.33 |
| 97 | 0.11 |
| 98 | 0.32 |
| 99 | 0.14 |
| 101 | 0.50 |
| 102 | 0.35 |
| 103 | 0.26 |
| 105 | 2.76 |
| 106 | 1.26 |
| 107 | 0.70 |
| 108 | 0.54 |
| 109 | 3.59 |
| 110 | 0.63 |
| 111 | 1.07 |
| 112 | 15.30 |
| 113 | 2.65 |
| 114 | 2.33 |
| 115 | 0.51 |
| 116 | >20 |
| 117 | >20 |
| 118 | >20 |
| 119 | >20 |
| 120 | >20 |
| 121 | 6.18 |
| 122 | 3.94 |
| 123 | 8.55 |
| 124 | 0.92 |
| 125 | 1.63 |
| 126 | 0.74 |
| 127 | 1.44 |
| 128 | 0.48 |
| 129 | 0.36 |
| 130 | 2.55 |
| 131 | 0.46 |
| 132 | >20 |
| 133 | 9.32 |
| 134 | 11.00 |
| 135 | >20 |
| 136 | >20 |
| 137 | 7.83 |
| 138 | 3.05 |
| 139 | 8.08 |
| 140 | >20 |
| 141 | 4.90 |
| 142 | 7.30 |
| 143 | 12.40 |
| 144 | 15.60 |
| 145 | 3.05 |
| 146 | 8.65 |
| 147 | 6.43 |
| 148 | 1.87 |
| 149 | >20 |
| 150 | 3.82 |
| 151 | >20 |
| 152 | >20 |
| 153 | 9.31 |
| 154 | >20 |
| 155 | >20 |
| 156 | >20 |
| 157 | >20 |
| 158 | >20 |

TABLE 1-continued

| Example | IC$_{50}$ (μM) |
|---|---|
| 159 | 17.60 |
| 160 | >20 |
| 161 | >20 |
| 162 | >20 |
| 163 | >20 |
| 164 | >20 |
| 165 | >20 |
| 166 | >20 |
| 167 | >20 |
| 168 | >20 |
| 169 | >20 |
| 170 | 6.16 |
| 171 | 5.51 |
| 172 | 4.93 |
| 173 | >20 |
| 174 | >20 |
| 175 | >20 |
| 176 | >20 |
| 177 | >20 |
| 178 | >20 |
| 179 | >20 |
| 180 | >20 |
| 181 | >20 |
| 182 | >20 |
| 183 | >20 |
| 184 | 2.94 |
| 185 | >20 |
| 186 | >20 |
| 187 | >20 |
| 188 | >20 |
| 189 | >20 |
| 190 | 8.15 |
| 191 | >20 |
| 192 | >20 |
| 193 | >20 |
| 194 | >20 |
| 195 | >20 |
| 196 | >20 |
| 197 | >20 |
| 198 | >20 |
| 199 | 1.59 |
| 200 | 1.03 |
| 201 | 0.77 |
| 202 | 0.79 |
| 203 | 0.53 |
| 204 | >20 |
| 205 | 2.46 |
| 206 | 1.23 |
| 207 | 0.68 |
| 208 | 13.50 |
| 209 | 1.47 |
| 210 | 18.50 |
| 211 | >20 |
| 212 | 2.53 |
| 213 | 0.79 |
| 214 | 8.28 |
| 215 | 5.67 |
| 216 | 0.31 |
| 217 | 0.35 |
| 218 | >20 |
| 219 | 0.66 |
| 220 | 0.48 |
| 221 | >20 |
| 222 | 0.71 |
| 223 | 0.08 |
| 224 | 0.14 |
| 225 | 2.92 |
| 226 | 0.60 |
| 227 | 1.80 |
| 228 | 0.14 |
| 229 | 0.37 |
| 231 | 1.53 |
| 233 | 0.38 |
| 234 | 1.52 |
| 235 | 1.11 |
| 236 | 0.98 |
| 237 | 5.75 |
| 238 | 0.29 |

TABLE 1-continued

| Example | IC$_{50}$ (μM) |
|---|---|
| 239 | 0.37 |
| 240 | 0.51 |
| 241 | 1.86 |
| 242 | 0.41 |
| 243 | 0.38 |
| 244 | 0.16 |
| 245 | 0.16 |
| 246 | 0.16 |
| 247 | 0.08 |
| 248 | 1.44 |
| 249 | 0.35 |
| 250 | >20 |
| 251 | 0.58 |
| 252 | >20 |
| 253 | 0.70 |
| 254 | >20 |
| 255 | 0.23 |
| 256 | 0.42 |
| 257 | 0.34 |
| 258 | 0.29 |
| 259 | 0.52 |
| 260 | 0.30 |
| 261 | 0.75 |
| 262 | 0.81 |
| 263 | 0.23 |
| 264 | 0.17 |
| 265 | 0.19 |
| 266 | 0.39 |
| 267 | 0.18 |
| 268 | 0.42 |
| 269 | 0.44 |
| 270 | 0.55 |
| 271 | 0.58 |
| 272 | 0.22 |
| 273 | 0.12 |
| 274 | 0.26 |
| 275 | 1.33 |
| 276 | 10.90 |
| 277 | 0.65 |
| 278 | 2.69 |
| 279 | 0.94 |
| 280 | 0.25 |
| 281 | 0.39 |
| 282 | 0.37 |
| 283 | 0.26 |
| 284 | 0.52 |
| 285 | 0.99 |
| 286 | 0.52 |
| 287 | 0.73 |
| 288 | 0.17 |
| 289 | 0.13 |
| 290 | 0.17 |
| 291 | 0.79 |
| 292 | 0.28 |
| 293 | 0.55 |
| 294 | 0.12 |

(ii) In Vivo Data There are many animal models for studying pain. Generally, the pain models mimic one of the mechanisms of pain (e.g. nociceptive, inflammatory, or neuropathic), rather than the pain associated with any one disease or injury. Such model provides evidence of whether a drug or therapy would be effective in treating any of a number of injuries, diseases, or conditions that generate pain via a particular mechanism.

Exemplary animal models of pain include, but are not limited to, the Chung model (spinal nerve ligation), the carageenan induced hyperalgesia model, the Freund's complete adjuvant (CFA) induced hyperalgesia model, and the Bennett Model (Chronic Constriction Injury Model, CCI).

Chronic Constriction Injury (CCI) Model of Neuropathic Pain:

CD1 mice (Charles River) were used for these studies. Prior to testing (2-4 weeks) animals underwent a surgical procedure consisting of approximately 3 loose ligatures around the sciatic nerve. Briefly, following sterilization procedures, under isofluorane anesthetic, a 1.5 cm incision was made dorsal to the pelvis. The biceps femoris and gluteous superficialis (right side) were separated and the sciatic nerve exposed, isolated, and 2-4 loose ligatures (5-0 chromic gut) with <1 mm spacing were placed around it. Following hemostasis, the wound was sutured (layer of muscle closed with 5-0 nylon suture, and the wound closed with surgical staples) and coated with iodine. The mice were allowed to recover on a warming plate and are returned to their home cages (soft bedding) when able to walk on their own. Two to four weeks after the surgery, TRPV3 antagonsists were tested in these mice following P.O. (1 hour pretreatment) or I.P. (30 minutes pretreatment) dosing, and mechanical allodynia evaluated where the threshold to response was assessed using calibrated von Frey monofilaments. The von Frey monofilaments were applied to the hind paw at increasing forces until the animal responded by lifting its paw. Normally, the force of the von Frey monofilament was innocuous; only in the altered state (allodynia or hyperalgesia) did the animals respond to this stimulation. Compounds were examined to determine the degree to which they showed analgesic activity by prolonging the latency to respond to thermal stimulation or increasing the grams of force needed to elicit a withdrawal response. Example 28 and Example 129 demonstrated statistically significant effects vs. vehicle in the mouse Chronic Constriction Injury Model of neuropathic pain after a acute oral administration of a 100 mg/kg oral dose.

d. Methods of Using the Compounds

Data in Table 1 demonstrates that present compounds are modulators of TRPV3 receptors, and thus are useful in the treatment of diseases, conditions, and/or disorders modulated by TRPV3. The relationship between therapeutic effect and inhibition of TRPV3 has been shown in WO2007/056124; Wissenbach, U. et al., Biology of the cell (2004), 96, 47-54; Nilius, B. et al., Physiol Rev (2007), 87, 165-217; Okuhara, D. Y. et al., Expert Opinion on Therapeutic Targets (2007), 11, 391-401; Hu, H. Z. et al., Journal of Cellular Physiology (2006), 208, 201-212.

One embodiment is therefore directed to a method for treating a disease, condition, and/or disorder modulated by TRPV3 in a subject in need thereof, said method comprises administering to the subject a therapeutically effective amount of a compound, or pharmaceutically acceptable salt, solvate, salt of a solvate or solvate of a salt thereof, with or without a pharmaceutically acceptable carrier.

Diseases, conditions, and/or disorders that are modulated by TRPV3 include, but are not limited to, migraine, arthralgia, cardiac pain arising from an ischemic myocardium, acute pain, chronic pain, nociceptive pain, neuropathic pain, post-operative pain, pain due to neuralgia (e.g., post-herpetic neuralgia, traumatic neuralgia, fibromyalgia, trigeminal neuralgia), pain due to diabetic neuropathy, dental pain, cancer pain, inflammatory pain conditions (e.g. arthritis and osteoarthritis).

Diseases, conditions, and/or disorders that are modulated by TRPV3 also include, but are not limited to, pain such as neuropathic pain, nociceptive pain, dental pain, HIV pain, cardiac pain arising from an ischemic myocardium, pain due to migraine, arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratocanthoma, alopecia, Meniere's disease, tinnitus, hyperacusis, anxiety disorders and benign prostate hyperplasia.

One embodiment provides methods for treating pain (for example, migraine, inflammatory pain, acute pain, chronic pain, neuropathic pain, nociceptive pain, rheumatoid arthritic pain, osteoarthritic pain, post-operative pain, post stroke pain, post hepatic neuralgia, cancer pain, dental pain, eye pain, lower back pain, eye pain) in a subject (including human) in need of such treatment. The methods comprise administering to the subject therapeutically effective amount of a compound as described herein, or a pharmaceutically acceptable salt, solvate, salt of a solvate, or solvate of a salt thereof, alone or in combination with a pharmaceutically acceptable carrier. The method further comprises administration of the present compound as a single dose. The method also comprises repeated or chronic administration of the present compound over a period of days, weeks, months, or longer. In certain embodiments, the method comprises administering to the subject a therapeutically effective amount of any of the compounds as described herein, or a pharmaceutically acceptable salt, solvate, salt of a solvate, or solvate of a salt thereof, in combination with a nonsteroidal anti-inflammatory drugs (NSAIDs), or other analgesic (for example, acetaminophen, opioids such as morphine or other related opioids), or combinations thereof.

Another embodiment provides method for increasing the therapeutic effectiveness or potency of compounds described herein by repeated or chronic administration over a period of days, weeks, or months.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the compounds may be required to achieve the desired therapeutic response. "Repeated or chronic administration" refers to the administration of the compounds daily (i.e., every day) or intermittently (i.e., not every day) over a period of days, weeks, months, or longer. In particular, the treatment of chronic painful conditions is anticipated to require such repeated or chronic administration of compounds described herein. The compounds may become more effective upon repeated or chronic administration such that the therapeutically effective doses on repeated or chronic administration may be lower than the therapeutically effective dose from a single administration.

Compounds can also be administered as a pharmaceutical composition comprising the compounds of interest, or pharmaceutically acceptable salts, solvates, or salts of solvates thereof, in combination with one or more pharmaceutically acceptable carriers. The phrase "therapeutically effective amount" of a compound means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The compounds may be administered alone, or in combination with one or more other compounds described herein, or in combination (i.e. co-administered) with one or more additional pharmaceutical agents. For example, one or more compounds, or pharmaceutically acceptable salts, solvates, salts of solvates, or solvates of salts thereof, may be administered in combination with one or more analgesic (e.g. acetaminophen, opioid such as morphine), or with one or more nonsteroidal anti-inflammatory drugs (NSAIDs), or combinations thereof. Non-limiting examples of NSAIDs include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent, in its own separate pharmaceutical dosage formulation. For example, one or more compounds described herein and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, the compounds and one or more additional pharmaceutical agents may be administered at essentially the same time (e.g., concurrently) or at separately staggered times (e.g., sequentially).

The total daily dose of the compounds administered to a human or other animal range from about 0.01 mg/kg body weight to about 100 mg/kg body weight, for example, in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

e. Pharmaceutical Compositions

Further provided herein is a pharmaceutical composition that comprises a compound or a pharmaceutically acceptable salt, solvate, salt of a solvate, or solvate of a salt thereof, formulated together with a pharmaceutically acceptable carrier.

Another aspect provides pharmaceutical composition comprising a compound or a pharmaceutically acceptable salt, solvate, salt of a solvate, or solvate of a salt thereof, in combination with an analgesic (e.g. acetaminophen or opioid such as morphine or other related opioids), or in combination with a nonsteroidal anti-inflammatory drugs (NSAIDs), or a combination thereof, formulated together with a pharmaceutically acceptable carrier.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N. Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of the compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds can be prepared by a variety of processes well known for the preparation of compounds of this class. For example, the compounds described herein wherein the groups $X_1$, $X_2$, $R^1$, $R^2$, $R^x$, and n have the meanings as set forth in the summary section unless otherwise noted, may be synthesized as shown in Schemes 1 and 2.

Abbreviations which have been used in the descriptions of the Schemes and the Examples that follow are: BINAP for 2,2'-bis(diphenylphosphino)-1,1'-binaphthyl, dba for dibenzylideneacetone, DIBAL-H for diisobutylaluminum hydride, dppf for 1,1'-bis(diphenylphosphino)ferrocene, DME for dimethoxy ethane, DMF for N,N-dimethylformamide, DMSO for dimethyl sulfoxide, EtOAc for ethyl acetate, EtOH for ethanol, MeOH for methanol, MTBE for methyl tert-butyl ether, NMP for 1-methyl-2-pyrrolidinone, $Pd_2(dba)_3$ for tris(dibenzylideneacetone)dipalladium(0), $Pd(dppf)_2Cl_2$ for [1,1'-bis(diphenylphosphino)ferrocene] dichloropalladium(II), $PdCl_2(PPh_3)_2$ for bis(triphenylphosphine)palladium(II) dichloride, $Pd(PPh_3)_4$ for tetrakis(triphenylphosphine)palladium(0), TFA for trifluoroacetic acid, and THF for tetrahydrofuran.

Compounds of general formula (I) can be prepared using general procedures as illustrated in Scheme 1.

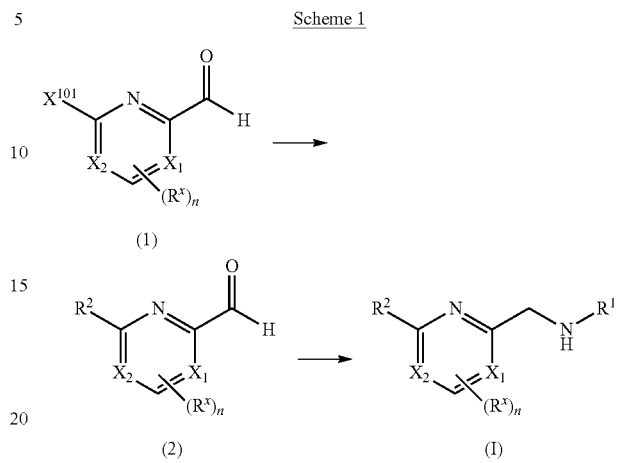

Scheme 1

Treatment of aldehydes of formula (1) wherein $X^{101}$ is Cl, Br, or I with a boronic acid of formula $R^2B(OH)_2$ or its corresponding pinacol ester in the presence of a base, a palladium catalyst, and optionally a ligand, in a solvent such as, but not limited to, dimethoxy ethane (DME), DMF, DMSO, dioxane, water, ethanol, toluene, or a mixture thereof, and at a temperature ranging from about 60° C. to about 150° C., and optionally with microwave irradiation, provide aldehydes of formula (2). Examples of suitable base for the reaction include, but not limited to, sodium carbonate, potassium carbonate, cesium carbonate, triethylamine, and cesium fluoride. Examples of suitable palladium catalyst include, but are not limited to, $Pd(PPh_3)_4$, $Pd_2(dba)_3$, palladium (II) acetate, $PdCl_2(dppf)$, and bis(triphenylphosphine)palladium (II) chloride. An example of a suitable ligand includes, but is not limited to, dppf.

Compounds of formula (1) wherein $X^{101}$ is Cl, Br, or I can also be treated with nitrogen containing heterocycles in the presence of a palladium catalyst such as, but not limited to, $Pd_2(dba)_3$, a ligand such as, but not limited to, BINAP, and a base such as, but not limited to, sodium tert-butoxide, at a temperature from about 60° C. to about 150° C., and optionally with microwave irradiation, provide aldehydes of formula (2).

Reductive amination of (1) with amines of formula $R^1NH_2$ using reaction conditions known to one skilled in the art produces compounds of general formula (I). For example, aldehydes of formula (2) can be treated with $R^1NH_2$ in the presence of a reducing agent such as, but not limited to, sodium borohydride, in a solvent such as, but not limited to, methanol, and at ambient temperature, to provide amines of formula (I) or the corresponding imines. The imines can be further reduced by hydrogenation in the presence of a catalyst such as, but not limited to, $R^a/Ni$, at about room temperature to provide the amines of formula (I).

Alternatively, compounds of general formula (I) can also be prepared by alternating the sequence of the reactions outlines above. For example, aldehydes of formula (1) can undergo reductive amination before coupling with the appropriate boronic acids or the corresponding pinacol esters.

Scheme 2 illustrates synthetic methods for the preparation of the intermediate aldehydes used in Scheme1.

Scheme 2

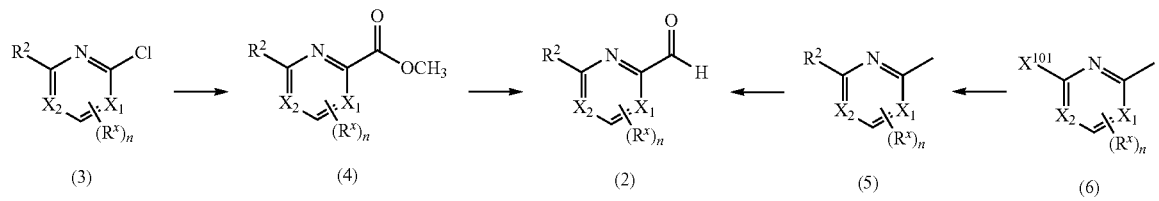

Chloro compounds of formula (3) when pressurized with carbon monoxide in the presence of a palladium catalyst such as, but not limited to, PdCl$_2$(dppf) and a base such as, but not limited to, triethylamine, in methanol, at a temperature from about 80° C. to about 120° C., provide esters of formula (4). Reduction of the esters (4) using reaction conditions known to one skilled in the art provides the aldehydes (2).

Coupling of compounds of formula (6) wherein $X^{101}$ is Cl, Br, or I with boronic acids of formula R$^2$B(OH)$_2$ or the corresponding pinacol esters using reaction conditions as described in Scheme 1 provide compounds of formula (5). Treatment of (5) with selenium oxide in dioxane at a temperature of about 100° C. to about 170° C. with microwave irradiation provides aldehydes of formula (2)

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. Examples $^1$H NMR spectra were recorded on Bruker AVIII 500. Generally, LCMS measurement were run on Agilent 1200 HPLC/6100 SQ System using the following condition: Mobile Phase: A: Water(0.05% TFA) B: Acetonitirle (0.05% TFA); Gradient Phase: 5%-95% in 1.3 min; Flow rate: 1.6 mL/min; Column: XBridge, 2.5 min; Oven temp: 50° C. Conditions for reverse phase chromatography: Samples were purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). Samples were injected in 1.5 mL DMSO:MeOH (1:1). A custom purification system was used, consisting of the following modules: Waters LC4000 preparative pump; Waters 996 diode-array detector; Waters 717+autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking Fractions were collected based upon UV signal threshold and selected fractions subsequently analyzed by flow injection analysis mass spectrometry using positive APCI ionization on a Finnigan LCQ using 70:30 MeOH:10 mM NH$_4$OH(aq) at a flow rate of 0.8 mL/min. Loop-injection mass spectra were acquired using a Finnigan LCQ running LCQ Navigator 1.2 software and a Gilson 215 liquid handler for fraction injection controlled by an Abbott developed Visual Basic application.

Example 1

(1S,2S)-2-[({6-[4-(trifluoromethyl)phenyl]pyridin-2-yl}methyl)amino]cyclohexanol The title compound was prepared using procedure similar to that described for Example 28B, substituting Example 3A for Example 28A and (1S,2S)-2-aminocyclohexanol for (R)-2-amino-3-methylbutan-1-ol. MS (ESI$^+$) m/z 351.1 (M+H); $^1$H NMR (400 MHz, DMSO-d$_6$/D$_2$O) δ 8.44 (d, J=8.2, 2H), 8.11 (d, J=7.4, 1H), 8.05 (t, J=7.7, 1H), 7.89 (d, J=8.3, 2H), 7.55 (d, J=7.4, 1H), 4.50 (s, 2H), 3.61 (td, J=10.0, 4.7, 1H), 2.97 (ddd, J=12.2, 10.0, 4.0, 1H), 2.22-2.13 (m, 1H), 2.02-1.91 (m, 1H), 1.73 (d, J=11.8, 1H), 1.67 (d, J=4.8, 1H), 1.50-1.36 (m, 1H), 1.33-1.13 (m, 3H).

Example 2

(2S,3S)-3-methyl-2-[({6-[4-(trifluoromethyl)phenyl]pyridin-2-yl}methyl)amino]pentan-1-ol The title compound was prepared using procedure similar to that described for Example 28B, substituting Example 3A for Example 28A and (2S,3S)-2-amino-3-methylpentan-1-ol for (R)-2-amino-3-methylbutan-1-ol. MS (ESI$^+$) m/z 353 (M+H); $^1$H NMR (500 MHz, pyridine-d$_5$) δ 8.34 (d, J=8.2, 2H), 7.83 (d, J=7.8, 1H), 7.77 (t, J=7.6, 1H), 7.77 (d, J=8.2, 2H), 7.60 (d, J=8.0, 1H), 5.09 (d, J=14.8, 1H), 4.93 (d, J=14.8, 1H), 4.32 (dd, J=11.9, 7.8, 1H), 4.23 (dd, J=11.9, 3.6, 1H), 3.66 (dt, J=7.8, 4.0, 1H), 2.33-2.24 (m, 1H), 1.58-1.48 (m, 1H), 1.38-1.25 (m, 1H), 1.17 (d, J=6.9, 3H), 0.79 (t, J=7.4, 3H).

Example 3

(2S)-3-methyl-2-[({6-[4-(trifluoromethyl)phenyl]pyridin-2-yl}methyl)amino]butan-1-ol

Example 3A

6-[4-(trifluoromethyl)phenyl]picolinaldehyde

The title compound was prepared using procedure similar to that described for Example 28A, substituting 4-(trifluoromethyl)phenylboronic acid for 6-(trifluoromethyl)pyridin-3-ylboronic acid and 6-bromopicolinaldehyde for 6-bromo-3-fluoropicolinaldehyde. MS (ESI$^+$) m/z 283.9 (M+H+MeOH); $^1$H NMR (300 MHz, DMSO-d$_6$) δ 10.09 (s, 1H), 8.46-8.38 (m, 3H), 8.21 (t, J=7.7, 1H), 8.00-7.89 (m, 3H).

Example 3B

(2S)-3-methyl-2-[({6-[4-(trifluoromethyl)phenyl]pyridin-2-yl}methyl)amino]butan-1-ol The title compound was prepared using procedure similar to that described for Example 28B, substituting Example 3A for Example 28A and (S)-2-amino-3-methylbutan-1-ol for (R)-2-amino-3-methylbutan-1-ol. MS (DCI+) m/z 339.0 (M+H); $^1$H NMR (300 MHz, DMSO-d$_6$) δ 8.31 (d, J=8.1, 2H), 7.96-7.88 (m, 2H), 7.85 (d, J=8.3, 2H), 7.51 (dd, J=6.2, 2.4, 1H), 4.44 (t, J=5.1, 1H), 3.99-3.86 (m, 2H), 3.48 (dt, J=9.7, 4.7, 1H), 3.36 (dd, J=11.2, 5.7, 1H), 2.40-2.23 (m, 2H), 1.93-1.76 (m, 1H), 0.89 (t, J=7.0, 6H).

Example 4

(1R,2S)-2-[({6-[4-(trifluoromethyl)phenyl]pyridin-2-yl}methyl)amino]cyclohexanol The title compound was prepared using procedure similar to that described for Example 28B, substituting Example 3A for Example 28A and (1R,2S)-2-aminocyclohexanol for (R)-2-amino-3-methylbutan-1-ol. MS (ESI$^+$) m/z 351.1 (M+H); $^1$H NMR (400 MHz, DMSO-d$_6$/D$_2$O) δ 8.41 (d, J=8.2, 2H), 8.09 (d, J=7.4, 1H), 8.04 (t, J=7.7, 1H), 7.90 (d, J=8.3, 2H), 7.55 (d, J=7.3, 1H), 4.43 (s, 2H), 4.21 (s, 1H), 3.28-3.19 (m, 1H), 1.90-1.67 (m, 4H), 1.62-1.33 (m, 3H), 1.31-1.15 (m, 1H).

Example 5

2-[({6-[4-(trifluoromethyl)phenyl]pyridin-2-yl}methyl)amino]cyclohexanol

The title compound was prepared using procedure similar to that described for Example 28B, substituting Example 3A for Example 28A and 2-aminocyclohexanol for (R)-2-amino-3-methylbutan-1-ol. MS (ESI$^+$) m/z 351.1 (M+H); $^1$H NMR (400 MHz, DMSO-d$_6$/D$_2$O) δ 8.41 (d, J=8.2, 2H), 8.10 (d, J=7.3, 1H), 8.04 (t, J=7.7, 1H), 7.90 (d, J=8.3, 2H), 7.55 (d, J=7.3, 1H), 4.43 (s, 2H), 4.21 (s, 1H), 3.28-3.19 (m, 1H), 1.89-1.67 (m, 4H), 1.61-1.34 (m, 3H), 1.32-1.17 (m, 1H).

Example 6

(1R,2R)-2-[({6-[4-(trifluoromethyl)phenyl]pyridin-2-yl}methyl)amino]cyclohexanol The title compound was prepared using procedure similar to that described for Example 28B, substituting Example 3A for Example 28A and (1R,2R)-2-aminocyclohexanol for (R)-2-amino-3-methylbutan-1-ol. MS (ESI$^+$) m/z 351.1 (M+H); $^1$H NMR (400 MHz, DMSO-d$_6$/D$_2$O) δ 8.44 (d, J=8.2, 2H), 8.11 (d, J=7.4, 1H), 8.05 (t, J=7.7, 1H), 7.89 (d, J=8.3, 2H), 7.55 (d, J=7.4, 1H), 4.50 (s, 2H), 3.61 (td, J=9.9, 4.6, 1H), 2.97 (ddd, J=12.2, 10.0, 4.0, 1H), 2.23-2.12 (m, 1H), 2.01-1.91 (m, 1H), 1.73 (d, J=11.7, 1H), 1.67 (d, J=4.6, 1H), 1.50-1.35 (m, 1H), 1.33-1.12 (m, 3H).

Example 7

(1S,2R)-2-[({6-[4-(trifluoromethyl)phenyl]pyridin-2-yl}methyl)amino]cyclohexanol The title compound was prepared using procedure similar to that described for Example 28B, substituting Example 3A for Example 28A and (1S,2R)-2-aminocyclohexanol for (R)-2-amino-3-methylbutan-1-ol. MS (ESI$^+$) m/z 351.2 (M+H); $^1$H NMR (400 MHz, DMSO-d$_6$/D$_2$O) δ 8.41 (d, J=8.2, 2H), 8.10 (d, J=7.3, 1H), 8.04 (t, J=7.7, 1H), 7.90 (d, J=8.3, 2H), 7.55 (d, J=7.3, 1H), 4.43 (s, 2H), 4.21 (s, 1H), 3.28-3.19 (m, 1H), 1.89-1.67 (m, 4H), 1.61-1.34 (m, 3H), 1.31-1.17 (m, 1H).

Example 8

2,2-dimethyl-3-[({6-[4-(trifluoromethyl)phenyl]pyridin-2-yl}methyl)amino]propan-1-ol The title compound was prepared using procedure similar to that described for Example 28B, substituting Example 3A for Example 28A and 3-amino-2,2-dimethylpropan-1-ol for (R)-2-amino-3-methylbutan-1-ol. MS (ESI⁺) m/z 339.5 (M+H); ¹H NMR (400 MHz, DMSO-d₆/D₂O) δ 8.42 (d, J=8.3, 2H), 8.12 (d, J=7.9, 1H), 8.05 (t, J=7.7, 1H), 7.89 (d, J=8.4, 2H), 7.52 (d, J=7.5, 1H), 4.44 (s, 2H), 3.40 (s, 2H), 3.05 (s, 2H), 0.99 (s, 6H).

Example 9

{(1R,2R,3S,4S)-3-[({6-[4-(trifluoromethyl)phenyl] pyridin-2-yl}methyl)amino]bicyclo[2.2.1]heptan-2-yl}methanol The title compound was prepared using procedure similar to that described for Example 28B, substituting Example 3A for Example 28A and ((1R,2R,3S,4S)-3-aminobicyclo[2.2.1] heptan-2-yl)methanol for (R)-2-amino-3-methylbutan-1-ol. MS (ESI⁺) m/z 377.5 (M+H); ¹H NMR (400 MHz, DMSO-d₆/D₂O) δ 8.43 (d, J=8.1, 2H), 8.14 (d, J=7.5, 1H), 8.07 (t, J=7.8, 1H), 7.88 (d, J=8.3, 2H), 7.55 (d, J=7.3, 1H), 4.46 (dd, J=46.3, 15.3, 2H), 3.81-3.73 (m, 3H), 2.67 (s, 1H), 2.38-2.30 (m, 1H), 2.29 (d, J=3.5, 1H), 1.75-1.66 (m, 1H), 1.59-1.47 (m, 3H), 1.47-1.35 (m, 2H).

Example 10

(2R)-3-methyl-2-({[6-(pyrrolidin-1-yl)pyridin-2-yl] methyl}amino)butan-1-ol

The title compound was prepared using procedure similar to that described for Example 28B, substituting 6-(pyrrolidin-1-yl)picolinaldehyde for Example 28A. MS (ESI⁺) m/z 264.1 (M+H); ¹H NMR (500 MHz, DMSO-d₆/D₂O) δ 7.59 (dd, J=8.5, 7.2, 1H), 6.66 (d, J=7.2, 1H), 6.53 (d, J=8.6, 1H), 4.25 (q, J=14.8, 2H), 3.65 (dd, J=12.2, 6.8, 1H), 3.49-3.38 (m, 4H), 3.10 (td, J=6.5, 3.7, 1H), 2.18-2.07 (m, 1H), 2.00-1.93 (m, 4H), 1.02 (d, J=6.9, 3H), 0.96 (d, J=6.9, 3H).

Example 11

(2R)-3-methyl-2-({[6-(piperidin-1-yl)pyridin-2-yl] methyl}amino)butan-1-ol

The title compound was prepared using procedure similar to that described for Example 28B, substituting 6-(piperidin-1-yl)picolinaldehyde for Example 28A. MS (ESI⁺) m/z 278.5 (M+H); ¹H NMR (500 MHz, DMSO-d₆/D₂O) δ 7.56 (dd, J=8.6, 7.2, 1H), 6.81 (d, J=8.6, 1H), 6.65 (d, J=7.2, 1H), 4.22 (dd, J=31.4, 14.8, 2H), 3.75 (dd, J=12.2, 3.8, 1H), 3.64 (dd, J=12.2, 6.7, 1H), 3.60-3.52 (m, 4H), 3.04 (td, J=6.4, 3.8, 1H), 2.16-2.06 (m, 1H), 1.66-1.58 (m, 2H), 1.58-1.48 (m, 4H), 1.00 (d, J=6.9, 3H), 0.95 (d, J=6.9, 3H).

Example 12

(2R)-2-({[6-(benzyloxy)pyridin-2-yl] methyl}amino)-3-methylbutan-1-ol

The title compound was prepared using procedure similar to that described for Example 28B, substituting 6-(benzyloxy)picolinaldehyde for Example 28A. MS (ESI⁺) m/z 301.1 (M+H); ¹H NMR (500 MHz, DMSO-d₆/D₂O) δ 7.82 (dd, J=8.3, 7.3, 1H), 7.48-7.38 (m, 4H), 7.38-7.33 (m, 1H), 7.14 (d, J=7.3, 1H), 6.92 (d, J=8.3, 1H), 5.44 (s, 2H), 4.37-4.30 (m, 2H), 3.77 (dd, J=12.3, 3.7, 1H), 3.66 (dd, J=12.3, 6.5, 1H), 3.03 (td, J=6.1, 3.8, 1H), 2.16-2.05 (m, 1H), 0.97 (d, J=6.9, 3H), 0.94 (d, J=6.9, 3H).

Example 13

(2R)-2-({[3-fluoro-6-(2-fluorophenyl)pyridin-2-yl] methyl}amino)-3-methylbutan-1-ol 3-Fluoro-6-(2-fluorophenyl)picolinaldehyde was prepared using procedure similar to that described for Example 28A, substituting 2-fluorophenylboronic acid for 6-(trifluoromethyl)pyridin-3-ylboronic acid. The title compound was prepared using procedure similar to that described for Example 28B, substituting 3-fluoro-6-(2-fluorophenyl)picolinaldehyde for Example 28A. MS (ESI⁺) m/z 307.0 (M+H); ¹H NMR (500 MHz, DMSO-d₆/D₂O) δ 8.07-7.91 (m, 3H), 7.58-7.51 (m, 1H), 7.41-7.35 (m, 2H), 4.59 (dd, J=37.0, 15.6, 2H), 3.81 (dd, J=12.4, 3.6, 1H), 3.75-3.72 (m, 1H), 3.22 (td, J=6.3, 3.5, 1H), 2.18 (td, J=13.6, 6.8, 1H), 1.03 (d, J=6.9, 3H), 0.97 (d, J=6.9, 3H).

Example 14

(2R)-2-({[3-fluoro-6-(3-fluorophenyl)pyridin-2-yl] methyl}amino)-3-methylbutan-1-ol 3-Fluoro-6-(3-fluorophenyl)picolinaldehyde was prepared using procedure similar to that described for Example 28A, substituting 3-fluorophenylboronic acid for 6-(trifluoromethyl)pyridin-3-ylboronic acid. The title compound was prepared using procedure similar to that described for Example 28B, substituting 3-fluoro-6-(3-fluorophenyl)picolinaldehyde for Example 28A. MS (ESI⁺) m/z 307.3 (M+H); ¹H NMR (500 MHz, DMSO-d₆/D₂O) δ 8.15 (dd, J=8.8, 3.6, 1H), 8.09-7.96 (m, 2H), 7.93 (t, J=9.0, 1H), 7.63-7.53 (m, 1H), 7.36-7.27 (m, 1H), 4.59 (dd, J=37.5, 15.1, 2H), 3.82 (dd, J=12.3, 3.6, 1H), 3.74 (dd, J=12.4, 6.7, 1H), 3.20 (td, J=6.3, 3.6, 1H), 2.20 (dq, J=13.7, 6.9, 1H), 1.04 (d, J=6.9, 3H), 0.99 (d, J=6.9, 3H).

Example 15

(2R)-2-({[6-(3-chlorophenyl)-3-fluoropyridin-2-yl] methyl}amino)-3-methylbutan-1-ol 6-(3-Chlorophenyl)-3-fluoropicolinaldehyde was prepared using procedure similar to that described for Example 28A, substituting 3-chlorophenylboronic acid for 6-(trifluoromethyl)pyridin-3-ylboronic acid. The title compound was prepared using procedure similar to that described for Example 28B, substituting 6-(3-chlorophenyl)-3-fluoropicolinaldehyde for Example 28A. MS (ESI⁺) m/z 323.0 (M+H); ¹H NMR (500 MHz, DMSO-d₆/D₂O) δ 8.29-8.04 (m, 3H), 7.93 (t, J=9.0, 1H), 7.60-7.49 (m, 2H), 4.58 (dd, J=39.9, 16.0, 2H), 3.84-3.77 (m, 1H), 3.23-3.15 (m, 1H), 2.25-2.15 (m, 1H), 1.05 (d, J=6.9, 3H), 0.99 (d, J=6.8, 3H).

Example 16

(2R)-2-[({3-fluoro-6-[3-(trifluoromethyl)phenyl] pyridin-2-yl}methyl)amino]-3-methylbutan-1-ol 3-Fluoro-6-[3-(trifluoromethyl)phenyl]picolinaldehyde was prepared using procedure similar to that described for Example 28A, substituting 3-(trifluoromethyl)phenylboronic acid for 6-(trifluoromethyl)pyridin-3-ylboronic acid. The title compound was prepared using procedure similar to that described for Example 28B, substituting 3-fluoro-6-[3-(trifluoromethyl)phenyl]picolinaldehyde for Example 28A. MS (ESI$^+$) m/z 357.3 (M+H); $^1$H NMR (500 MHz, DMSO-d$_6$/D$_2$O) δ 8.55 (s, 1H), 8.42 (d, J=7.9, 1H), 8.23 (dd, J=8.7, 3.6, 1H), 7.96 (t, J=9.0, 1H), 7.85 (d, J=7.5, 1H), 7.78 (t, J=7.8, 1H), 4.61 (dd, J=43.4, 15.7, 2H), 3.80 (dd, J=12.4, 3.5, 1H), 3.74 (dd, J=12.5, 6.5, 1H), 3.20 (td, J=6.1, 3.6, 1H), 2.22 (td, J=13.6, 6.8, 1H), 1.04 (d, J=6.9, 3H), 0.99 (d, J=6.9, 3H).

Example 17

(2R)-2-[({3-fluoro-6-[4-(trifluoromethyl)phenyl]pyridin-2-yl}methyl)amino]-3-methylbutan-1-ol Example 17A 3-fluoro-6-[4-(trifluoromethyl)phenyl]picolinaldehyde The title compound was prepared using procedure similar to that described for Example 28A, substituting 4-(trifluoromethyl)phenylboronic acid for 6-(trifluoromethyl)pyridin-3-ylboronic acid. MS (ESI$^+$) m/z 301.8 (M+H+MeOH); $^1$H NMR (300 MHz, DMSO-d$_6$) δ 10.14 (s, 1H), 8.48 (dd, J=8.8, 3.6, 1H), 8.37 (d, J=8.2, 2H), 8.11 (dd, J=10.1, 9.1, 1H), 7.92 (d, J=8.4, 2H).

Example 17B (2R)-2-[({3-fluoro-6-[4-(trifluoromethyl)phenyl]pyridin-2-yl}methyl)amino]-3-methylbutan-1-ol The title compound was prepared using procedure similar to that described for Example 28B, substituting Example 17A for Example 28A. MS (ESI$^L$m/z 357.1 (M+H); $^1$H NMR (300 MHz, DMSO-d$_6$) δ 8.29 (d, J=8.1, 2H), 8.05 (dd, J=8.7, 3.7, 1H), 7.90-7.75 (m, 3H), 4.46 (t, J=5.2, 1H), 4.00-3.91 (m, 2H), 3.47 (dt, J=9.5, 4.7, 1H), 2.39-2.33 (m, 2H), 1.92-1.78 (m, 1H), 0.86 (dd, J=8.4, 7.0, 6H).

Example 18

(2R)-2-[({3-fluoro-6-[3-(trifluoromethoxy)phenyl]pyridin-2-yl}methyl)amino]-3-methylbutan-1-ol 3-Fluoro-6-[3-(trifluoromethoxy)phenyl]picolinaldehyde was prepared using procedure similar to that described for Example 28A, substituting 3-(trifluoromethoxy)phenylboronic acid for 6-(trifluoromethyl)pyridin-3-ylboronic acid. The title compound was prepared using procedure similar to that described for Example 28B, substituting 3-fluoro-6-[3-(trifluoromethoxy)phenyl]picolinaldehyde for Example 28A. MS (ESI$^+$) m/z 373.2 (M+H); $^1$H NMR (500 MHz, DMSO-d$_6$/D$_2$O) δ 8.21-8.13 (m, 3H), 7.95 (t, J=9.0, 1H), 7.68 (t, J=8.0, 1H), 7.52-7.44 (m, 1H), 4.60 (dd, J=38.1, 15.1, 2H), 3.81 (dd, J=12.4, 3.6, 1H), 3.74 (dd, J=12.6, 6.4, 1H), 3.19 (td, J=6.2, 3.6, 1H), 2.20 (dq, J=13.8, 6.9, 1H), 1.04 (d, J=6.9, 3H), 0.99 (d, J=6.9, 3H).

Example 19

(2R)-2-[({3-fluoro-6-[4-(trifluoromethoxy)phenyl]pyridin-2-yl}methyl)amino]-3-methylbutan-1-ol Example 19A 3-fluoro-6-[4-(trifluoromethoxy)phenyl]picolinaldehyde The title compound was prepared using procedure similar to that described for Example 28A, substituting 4-(trifluoromethoxy)phenylboronic acid for 6-(trifluoromethyl)pyridin-3-ylboronic acid. MS (ESI$^+$) m/z 317.9 (M+H+MeOH); $^1$H NMR (300 MHz, DMSO-d$_6$) δ 10.13 (s, 1H), 8.39 (dd, J=8.8, 3.7, 1H), 8.30-8.24 (m, 2H), 8.11-8.03 (m, 1H), 7.54 (dd, J=8.9, 0.9, 2H).

Example 19B (2R)-2-[({3-fluoro-6-[4-(trifluoromethoxy)phenyl]pyridin-2-yl}methyl)amino]-3-methylbutan-1-ol The title compound was prepared using procedure similar to that described for Example 28B, substituting Example 19A for Example 28A. MS (ESI$^+$) m/z 373.1 (M+H); $^1$H NMR (300 MHz, DMSO-d$_6$) δ 8.19 (d, J=8.9, 2H), 7.96 (dd, J=8.7, 3.7, 1H), 7.83-7.73 (m, 1H), 7.48 (dd, J=8.9, 0.9, 2H), 4.44 (t, J=5.2, 1H), 4.03-3.87 (m, 2H), 3.46 (dt, J=9.5, 4.7, 1H), 2.41-2.27 (m, 2H), 1.92-1.77 (m, 1H), 0.86 (dd, J=8.2, 6.9, 6H).

Example 20

(2R)-2-({[6-(3,4-dichlorophenyl)-3-fluoropyridin-2-yl]methyl}amino)-3-methylbutan-1-ol 6-(3,4-Dichlorophenyl)-3-fluoropicolinaldehyde was prepared using procedure similar to that described for Example 28A, substituting 3,4-dichlorophenylboronic acid for 6-(trifluoromethyl)pyridin-3-ylboronic acid. The title compound was prepared using procedure similar to that described for Example 28B, substituting 6-(3,4-dichlorophenyl)-3-fluoropicolinaldehyde for Example 28A. MS (ESI$^+$) m/z 357.0 (M+H); $^1$H NMR (500 MHz, DMSO-d$_6$/D$_2$O) δ 8.48 (d, J=2.1, 1H), 8.17 (dd, J=8.8, 3.6, 1H), 8.13 (dd, J=8.5, 2.2, 1H), 7.94 (t, J=8.9, 1H), 7.79 (d, J=8.5, 1H), 4.59 (dd, J=39.0, 15.1, 2H), 3.83-3.76 (m, 1H), 3.76-3.71 (m, 1H), 3.21-3.15 (m, 1H), 2.20 (dq, J=13.6, 6.8, 1H), 1.05 (d, J=6.9, 3H), 0.99 (d, J=6.8, 3H).

Example 21

(2R)-2-({[6-(3,5-dichlorophenyl)-3-fluoropyridin-2-yl]methyl}amino)-3-methylbutan-1-ol 6-(3,5-Dichlorophenyl)-3-fluoropicolinaldehyde was prepared using procedure similar to that described for Example 28A, substituting 3,5-dichlorophenylboronic acid for 6-(trifluoromethyl)pyridin-3-ylboronic acid. The title compound was prepared using procedure similar to that described for Example 28B, substituting 6-(3,5-dichlorophenyl)-3-fluoropicolinaldehyde for Example 28A. MS (ESI$^+$) m/z 356.9 (M+H); $^1$H NMR (500 MHz, DMSO-d$_6$/D$_2$O) δ 8.16 (d, J=1.9, 2H), 7.99 (d, J=8.6, 1H), 7.60 (t, J=1.9, 1H), 7.40 (d, J=8.6, 1H), 4.44 (dd, J=54.6, 16.0, 2H), 3.83-3.77 (m, 1H), 3.76-3.71 (m, 1H), 3.21-3.15 (m, 1H), 2.21 (dq, J=13.4, 6.9, 1H), 1.06 (d, J=6.9, 3H), 1.00 (d, J=6.9, 3H).

Example 22

(2R)-2-[({6-[3,5-bis(trifluoromethyl)phenyl]-3-fluoropyridin-2-yl}methyl)amino]-3-methylbutan-1-ol 6-[3,5-Bis(trifluoromethyl)phenyl]-3-fluoropicolinaldehyde was prepared using procedure similar to that described for Example 28A, substituting 3,5-bis(trifluoromethyl)phenylboronic acid for 6-(trifluoromethyl)pyridin-3-ylboronic acid. The title compound was prepared using procedure similar to that described for Example 28B, substituting 6-[3,5-bis(trifluoromethyl)phenyl]-3-fluoropicolinaldehyde for Example 28A. MS (ESI$^+$) m/z 425.3 (M+H); $^1$H NMR (500 MHz, DMSO-d$_6$/D$_2$O) δ 8.84 (s, 1H), 8.75 (s, 1H), 8.41 (dd, J=8.7, 3.5, 1H), 8.22 (d, J=6.2, 1H), 8.01 (t, J=9.0, 1H), 4.64 (dd, J=46.1, 15.2, 2H), 3.81-3.72 (m, 2H), 3.20-3.13 (m, 1H), 2.28-2.16 (m, 1H), 1.04 (d, J=6.9, 3H), 1.00 (d, J=6.9, 3H).

Example 23

(2R)-2-[({3-fluoro-6-[2-fluoro-5-(propan-2-yloxy)phenyl]pyridin-2-yl}methyl)amino]-3-methylbutan-1-ol 3-Fluoro-6-(2-fluoro-5-isopropoxyphenyl)picolinaldehyde was prepared using procedure similar to that described for Example 28A, substituting 2-fluoro-5-isopropoxyphenylboronic acid for 6-(trifluoromethyl)pyridin-3-ylboronic acid. The title compound was prepared using procedure similar to that described for Example 28B, substituting 3-fluoro-6-(2-fluoro-5-isopropoxyphenyl)picolinaldehyde for Example 28A. MS (ESI$^+$) m/z 365.1 (M+H); $^1$H NMR (500 MHz, DMSO-d$_6$/D$_2$O) δ 7.93 (d, J=6.9, 2H), 7.59 (dd, J=6.5, 3.2, 1H), 7.28 (dd, J=10.9, 9.0, 1H), 7.06 (dt, J=9.0, 3.6, 1H), 4.67-4.54 (m, 3H), 3.81 (dd, J=12.4, 3.5, 1H), 3.73 (dd, J=12.4, 6.5, 1H), 3.21 (td, J=6.1, 3.5, 1H), 2.24-2.15 (m, 1H), 1.28 (d, J=6.0, 6H), 1.03 (d, J=6.9, 3H), 0.98 (d, J=6.9, 3H).

Example 24

(2R)-2-[({3-fluoro-6-[3-(propan-2-yloxy)phenyl]pyridin-2-yl}methyl)amino]-3-methylbutan-1-ol 3-Fluoro-6-(3-isopropoxyphenyl)picolinaldehyde was prepared using procedure similar to that described for Example 28A, substituting 3-isopropoxyphenylboronic acid for 6-(trifluoromethyl)pyridin-3-ylboronic acid. The title compound was prepared using procedure similar to that described for Example 28B, substituting 3-fluoro-6-(3-isopropoxyphenyl)picolinaldehyde for Example 28A. MS (ESI$^+$) m/z 347.3 (M+H); $^1$H NMR (500 MHz, DMSO-d$_6$/D$_2$O) δ 8.08 (dd, J=8.8, 3.6, 1H), 7.89 (t, J=9.0, 1H), 7.73-7.69 (m, 1H), 7.66 (d, J=7.7, 1H), 7.42 (t, J=8.0, 1H), 7.03 (dd, J=7.8, 2.4, 1H), 4.78-4.69 (m, 1H), 4.58 (dd, J=34.7, 14.9, 2H), 3.82 (dd, J=12.3, 3.5, 1H), 3.74 (dd, J=12.4, 6.7, 1H), 3.21 (td, J=6.3, 3.6, 1H), 2.26-2.17 (m, 1H), 1.30 (d, J=6.0, 6H), 1.05 (d, J=6.9, 3H), 0.99 (d, J=6.9, 3H).

Example 25

(2R)-2-[({3-fluoro-6-[3-fluoro-4-(propan-2-yloxy)phenyl]pyridin-2-yl}methyl)amino]-3-methylbutan-1-ol 3-Fluoro-6-(3-fluoro-4-isopropoxyphenyl)picolinaldehyde was prepared using procedure similar to that described for Example 28A, substituting 3-fluoro-4-isopropoxyphenylboronic acid for 6-(trifluoromethyl)pyridin-3-ylboronic acid. The title compound was prepared using procedure similar to that described for Example 28B, substituting 3-fluoro-6-(3-fluoro-4-isopropoxyphenyl)picolinaldehyde for Example 28A. MS (ESI$^+$) m/z 365.4 (M+H); $^1$H NMR (500 MHz, DMSO-d$_6$/D$_2$O) δ 8.09 (dd, J=13.1, 2.2, 1H), 8.05 (dd, J=8.8, 3.6, 1H), 7.94-7.84 (m, 2H), 7.29 (t, J=8.8, 1H), 4.79-4.70 (m, 1H), 4.56 (dd, J=38.1, 15.1, 2H), 3.81 (dd, J=12.3, 3.5, 1H), 3.74 (dd, J=12.4, 6.8, 1H), 3.18 (td, J=6.3, 3.6, 1H), 2.24-2.16 (m, 1H), 1.33 (d, J=6.0, 6H), 1.04 (d, J=6.9, 3H), 0.99 (d, J=6.9, 3H).

Example 26

(2R)-2-{[(6-tert-butoxypyridin-2-yl)methyl]amino 1-3-methylbutan-1-ol

The title compound was prepared using procedure similar to that described for Example 28B, substituting 6-tert-butoxypicolinaldehyde for Example 28A. MS (ESI$^+$) m/z 266.9 (M+H); $^1$H NMR (300 MHz, DMSO-d$_6$) δ 7.56 (dd, J=8.1, 7.4, 1H), 6.91 (d, J=7.2, 1H), 6.49 (d, J=8.1, 1H), 4.37 (t, J=5.2, 1H), 3.79-3.62 (m, 2H), 3.49-3.39 (m, 1H), 2.33 (dd, J=10.4, 5.4, 1H), 2.06 (br s, 1H), 1.90-1.73 (m, 1H), 1.54 (s, 9H), 0.87 (dd, J=6.9, 2.3, 6H).

Example 27

(2R)-2-({[3-fluoro-6-(4-fluorophenyl)pyridin-2-yl]methyl}amino)-3-methylbutan-1-ol Example 27A 3-fluoro-6-(4-fluorophenyl)picolinaldehyde The title compound was prepared using procedure similar to that described for Example 28A, substituting 4-fluorophenylboronic acid for 6-(trifluoromethyl)pyridin-3-ylboronic acid. MS (DCI$^+$) m/z 220.0 (M+H); $^1$H NMR (300 MHz, DMSO-d$_6$) δ 10.12 (d, J=0.6, 1H), 8.36 (dd, J=8.9, 3.7, 1H), 8.21 (dd, J=9.0, 5.5, 2H), 8.04 (ddd, J=10.4, 8.9, 0.6, 1H), 7.38 (t, J=8.9, 2H).

Example 27B (2R)-2-({[3-fluoro-6-(4-fluorophenyl)pyridin-2-yl]methyl}amino)-3-methylbutan-1-ol The title compound was prepared using procedure similar to that described for Example 28B, substituting Example 27A for Example 28A. MS (ESI$^+$) m/z 307.1 (M+H); $^1$H NMR (300 MHz, DMSO-d$_6$) δ 8.12 (dd, J=8.9, 5.5, 2H), 7.91 (dd, J=8.6, 3.7, 1H), 7.74 (dd, J=9.4, 8.8, 1H), 7.31 (t, J=8.9, 2H), 4.44 (t, J=5.2, 1H), 4.03-3.86 (m, 2H), 3.52-3.41 (m, 1H), 2.41-2.29 (m, 2H), 1.92-1.75 (m, 1H), 0.86 (dd, J=8.2, 7.0, 6H).

Example 28

(2R)-2-({[5-fluoro-6'-(trifluoromethyl)-2,3'-bipyridin-6-yl]methyl}amino)-3-methylbutan-1-ol Example 28A 5-fluoro-6'-(trifluoromethyl)-2,3'-bipyridine-6-carbaldehyde Nitrogen was bubbled through a mixture of 6-(trifluoromethyl)pyridin-3-ylboronic acid (3.74 g, 19.61 mmol), 6-bromo-3-fluoropicolinaldehyde (4.0 g, 19.61 mmol), Pd(Ph$_3$P)$_4$ (0.340 g, 0.294 mmol) was added and nitrogen was bubbled for 10 minutes, and the reaction mixture was heated overnight at 80° C. EtOAc (300 mL) was added and the mixture was washed with water (300 mL) and brine (300 mL), dried over Na$_2$SO$_4$, filtered, and concentrated. The residue was chromatographed on a Grace Reveleris 80 g column, eluted with 0-40% EtOAc in Heptane (30 mL/min) to provide the title compound (3.681 g, 13.62 mmol, 69.5% yield). MS (ESI$^+$) m/z 303.0 (M+H+MeOH); $^1$H NMR (300 MHz, DMSO-d$_6$) δ 10.15 (s, 1H), 9.50 (d, J=2.0, 1H), 8.82-8.75 (m, 1H), 8.58 (dd, J=8.9, 3.7, 1H), 8.23-8.13 (m, 1H), 8.10 (d, J=8.3, 1H).

Example 28B (2R)-2-({[5-fluoro-6'-(trifluoromethyl)-2,3'-bipyridin-6-yl]methyl}amino)-3-methylbutan-1-ol Example 28A (3.681 g, 13.62 mmol) and (R)-2-amino-3-methylbutan-1-ol (1.585 mL, 14.31 mmol) were dissolved in methanol (50 mL), stirred at ambient temperature for 1 hour, then added sodium borohydride (0.515 g, 13.62 mmol). The reaction mixture was quenched with 200 mL 1.0 N NaOH, extracted with 200 mL dichloromethane (2×), and concentrated. The residue was dissolved in 200 mL EtOAc, extracted with 1.0 N HCl, and partitioned. The aqueous layer was neutralized with 3.0 N NaOH, extracted with EtOAc, and partitioned. The resulting organic phase was washed with brine, dried over Na$_2$SO$_4$, filtered, and concentrated to provide the title compound as a light yellow solid. MS (ESI$^+$) m/z 358.0 (M+H); $^1$H NMR (300 MHz, DMSO-d$_6$) δ 9.45 (d, J=1.8, 1H), 8.71 (dd, J=8.2, 2.0, 1H), 8.16 (dd, J=8.6, 3.7, 1H), 8.04 (d, J=8.2, 1H), 7.93-7.84 (m, 1H), 4.47 (t, J=5.2, 1H), 4.08-3.89 (m, 2H), 3.52-3.42 (m, 1H), 2.46-2.32 (m, 2H), 1.97-1.78 (m, 1H), 0.92-0.80 (m, 6H).

Example 29

(2R)-2-cyclopropyl-2-[({3-fluoro-6-[4-(trifluoromethyl)phenyl]pyridin-2-yl}methyl)amino]ethano 1

The title compound was prepared using procedure similar to that described for Example 75, substituting Example 17A for Example 28A. MS (ESI$^+$) m/z 355.0 (M+H); 1H NMR (300 MHz, DMSO-d$_6$) δ 8.30 (d, J=8.1, 2H), 8.04 (dd, J=8.7, 3.7, 1H), 7.89-7.77 (m, 3H), 4.61 (dd, J=5.8, 4.9, 1H), 4.17 (d, J=14.4, 1H), 3.99 (d, J=14.0, 1H), 3.55 (ddd, J=10.5, 4.7, 3.9, 1H), 3.39-3.34 (m, 1H), 2.79-2.65 (m, 1H), 1.84 (td, J=8.3, 3.8, 1H), 0.66-0.46 (m, 2H), 0.39-0.18 (m, 2H), 0.09-0.01 (m, 1H).

Example 30

(2S)-2-[({3-fluoro-6-[4-(trifluoromethyl)phenyl]pyridin-2-yl}methyl)amino]-3-methylbutan-1-ol The title compound was prepared using procedure similar to that described for Example 28B, substituting Example 17A for Example 28A and (S)-2-amino-3-methylbutan-1-ol for (R)-2-amino-3-methylbutan-1-ol. MS (ESI$^+$) m/z 357.1 (M+H); $^1$H NMR (300 MHz, DMSO-d$_6$) δ 8.29 (d, J=8.1, 2H), 8.04 (dd, J=8.7, 3.7, 1H), 7.89-7.77 (m, 3H), 4.44 (t, J=5.2, 1H), 4.05-3.89 (m, 2H), 3.47 (dt, J=9.5, 4.7, 1H), 2.42-2.29 (m, 2H), 1.92-1.78 (m, 1H), 0.86 (dd, J=8.2, 6.9, 6H).

Example 31

(2R)-2-({[5-fluoro-2'-(trifluoromethyl)-2,4'-bipyridin-6-yl]methyl}amino)-3-methylbutan-1-ol The title compound was prepared using procedure similar to that described for Example 113, substituting 2-(trifluoromethyl)pyridin-4-ylboronic acid for 2-(trifluoromethyl)pyrimidin-5-ylboronic acid. MS (ESI$^+$) m/z 358.1 (M+H); $^1$H NMR (500 MHz, DMSO-d$_6$/D$_2$O) δ 8.92 (d, J=5.1, 1H), 8.66 (s, 1H), 8.42 (dd, J=5.1, 1.3, 1H), 8.37 (dd, J=8.7, 3.6, 1H), 8.02 (t, J=8.9, 1H), 4.64 (dd, J=41.5, 15.5, 2H), 3.82 (dd, J=12.4, 3.5, 1H), 3.75 (dd, J=12.4, 6.5, 1H), 3.19 (td, J=6.2, 3.7, 1H), 2.27-2.18 (m, 1H), 1.05 (d, J=6.9, 3H), 1.00 (d, J=6.9, 3H).

Example 32

(2R)-2-({[4-(4-fluorophenyl)pyrimidin-2-yl]methyl}amino)-3-methylbutan-1-ol

Example 32A methyl 4-(4-fluorophenyl)pyrimidine-2-carboxylate

2-Chloro-4-(4-fluorophenyl)pyrimidine (1 g, 4.79 mmol) in methanol (20 mL) was added to PdCl$_2$(dppf) (0.070 g, 0.096 mmol) and triethylamine (1.336 mL, 9.59 mmol) in a 50 ml, pressure bottle. The mixture was pressurized with carbon monoxide (60 psi), and stirred for 15 hours at 100° C. The mixture was partitioned between 300 mL EtOAc and 300 mL water, washed with brine, dried over Na$_2$SO$_4$, filtered, and concentrated. The residue was chromatographed on a Grace Reveleris 40 g column, eluted with 0-100% EtOAc in Hexanes (30 mL/min) to provide the title compound (1.428 g, 6.15 mmol, 64.1% yield) as a tan solid. MS (ESI$^+$) m/z 233.0 (M+H); $^1$H NMR (300 MHz, DMSO-d$_6$) δ 9.02 (d, J=5.4, 1H), 8.34 (dd, J=9.1, 5.5, 2H), 8.29 (d, J=5.4, 1H), 7.43 (t, J=8.9, 2H), 3.95 (s, 3H).

Example 32B 4-(4-fluorophenyl)pyrimidine-2-carbaldehyde

DIBAL-H (3.62 mL, 3.62 mmol, 1.0 M in toluene) was slowly added to a suspension of Example 32A (700 mg, 3.01 mmol) in toluene (30 mL) at −75° C. After 2 hours, DIBAL-H (1.507 mL, 1.507 mmol, 1.0 M in toluene) was added to the reaction mixture and warmed slowly to ambient temperature overnight. The reaction was a clear orange-red solution and the methyl ester was consumed, yielding a mixture of aldehyde and alcohol. Additional DIBAL-H (1.507 mL, 1.507 mmol, 1.0 M in toluene) was added at ambient temperature. After 4 hours, the reaction was quenched with 5% acetic acid in water (200 mL), extracted twice with EtOAc (200 mL), washed with brine, dried over Na$_2$SO$_4$, filtered, and concentrated. The residue was chromatographed on a Grace Reveleris 12 g column, eluted with 0-60% EtOAc in dichloromethane (25 mL/min) to provide the title compound (62 mg, 0.307 mmol, 10.17% yield) as an off-white solid. MS (ESI$^+$) m/z 234.8 (M+H-MeOH); $^1$H NMR (300 MHz, DMSO-d$_6$) δ 10.04 (s, 1H), 9.12 (d, J=5.3, 1H), 8.38 (dd, J=9.0, 5.5, 2H), 8.32 (d, J=5.4, 1H), 7.45 (t, J=8.9, 2H).

Example 32C (2R)-2-({[4-(4-fluorophenyl)pyrimidin-2-yl]methyl}amino)-3-methylbutan-1-ol The title compound was prepared using procedure similar to that described for Example 28B, substituting Example 32B for Example 28A. MS (ESI$^+$) m/z 289.9 (M+H); $^1$H NMR (300 MHz, DMSO-d$_6$) δ 8.81 (d, J=5.3, 1H), 8.30 (dd, J=9.0, 5.5, 2H), 7.94 (d, J=5.4, 1H), 7.39 (t, J=8.9, 2H), 4.48 (t, J=5.2, 1H), 4.05-3.91 (m, 2H), 3.53-3.42 (m, 1H), 3.39-3.32 (m, 1H), 2.40 (dt, J=6.9, 4.8, 1H), 1.93-1.78 (m, 1H), 0.89 (t, J=7.1, 6H).

Example 33

(2R)-3-methyl-2-[({4-[4-(trifluoromethyl)phenyl] pyrimidin-2-yl}methyl)amino]butan-1-ol

Example 33A methyl 4-[4-(trifluoromethyl)phenyl]pyrimidine-2-carboxylate

2-Chloro-4[4-(trifluoromethyl)phenyl]pyrimidine (2.0 g, 7.73 mmol) in methanol (25 mL) was added to $PdCl_2$(dppf) (0.113 g, 0.155 mmol) and triethylamine (2.156 mL, 15.47 mmol) in a 50 mL pressure bottle. The mixture was pressurized with carbon monoxide (60 psi), and stirred for 15 hours at 100° C. The mixture was partitioned between 200 mL EtOAc and 200 mL water, washed with brine, dried over $Na_2SO_4$, filtered, and concentrated. The residue was chromatographed on a Grace Reveleris 40 g column, eluted with 0-60% EtOAc in dichloromethane (30 mL/min) to provide the title compound (0.560 g, 1.984 mmol, 25.7% yield) as a tan solid. MS (ESI$^+$) m/z 283.0 (M+H); $^1$H NMR (300 MHz, DMSO-$d_6$) δ 9.12 (d, J=5.3, 1H), 8.47 (d, J=8.2, 2H), 8.41 (d, J=5.3, 1H), 7.97 (d, J=8.4, 2H), 3.96 (s, 3H).

Example 33B

4-[4-(trifluoromethyl)phenyl]pyrimidine-2-carbaldehyde

DIBAL-H (2.3 mL, 2.300 mmol, 1.0 M in toluene) was slowly added to an orange solution of Example 33A (550 mg, 1.949 mmol) in dichloromethane (10 mL) at −75° C. The reaction was warmed to ambient temperature overnight. Quenched with methanol (10 mL), concentrated to an orange residue, and supported on silica gel. Chromatographed on a Grace Reveleris 12 g column, eluted with 0-60% EtOAc in dichloromethane (25 mL/min) to provide the title compound (135 mg, 0.418 mmol, 21.42% yield) as a beige solid, a mixture of 78% aldehyde and 22% methyl ester by proton NMR. MS (ESI$^+$) m/z 253.1 (M+H).

Example 33C (2R)-3-methyl-2-[({4-[4-(trifluoromethyl)phenyl] pyrimidin-2-yl}methyl)amino]butan-1-ol The title compound was prepared using procedure similar to that described for Example 28B, substituting Example 33B for Example 28A. MS (ESI$^+$) m/z 340.0 (M+H); $^1$H NMR (300 MHz, DMSO-$d_6$) δ 8.91 (d, J=5.4, 1H), 8.43 (d, J=8.1, 2H), 8.05 (d, J=5.4, 1H), 7.93 (d, J=8.2, 2H), 4.48 (t, J=5.2, 1H), 4.10-3.95 (m, 2H), 3.53-3.43 (m, 1H), 3.39-3.31 (m, 1H), 2.41 (dt, J=6.7, 4.7, 1H), 1.93-1.79 (m, 1H), 0.89 (t, J=7.1, 6H).

Example 34

(2R)-2-({[2-(4-chlorophenyl)pyrimidin-4-yl] methyl}amino)-3-methylbutan-1-ol

The title compound was prepared using procedure similar to that described for Example 28B, substituting 2-(4-chlorophenyl)pyrimidine-4-carbaldehyde for Example 28A. MS (ESI$^+$) m/z 305.9 (M+H); $^1$H NMR (300 MHz, DMSO-$d_6$) δ 8.83 (d, J=5.1, 1H), 8.40 (d, J=8.6, 2H), 7.59 (d, J=8.6, 2H), 7.55 (d, J=5.2, 1H), 4.45 (t, J=5.3, 1H), 4.03-3.84 (m, 2H), 3.48 (dt, J=9.6, 4.6, 1H), 3.41-3.33 (m, 1H), 2.32 (d, J=3.1, 2H), 1.91-1.73 (m, 1H), 0.89 (t, J=6.6, 6H).

Example 35

(2S)-2-({[5-fluoro-6'-(trifluoromethyl)-2,3'-bipyridin-6-yl]methyl}amino)-3-methylbutan-1-ol The title compound was prepared using procedure similar to that described for Example 28B, substituting (S)-2-amino-3-methylbutan-1-ol for (R)-2-amino-3-methylbutan-1-ol. LC-MS: m/z 358.3 (M+H); $^1$H NMR (300 MHz, DMSO-$d_6$) δ 9.45 (d, J=1.9, 1H), 8.71 (dd, J=8.2, 1.9, 1H), 8.16 (dd, J=8.6, 3.7, 1H), 8.04 (d, J=8.3, 1H), 7.93-7.83 (m, 1H), 4.47 (t, J=5.2, 1H), 3.98 (q, J=14.0, 2H), 3.47 (dt, J=9.3, 4.5, 1H), 2.45-2.33 (m, 2H), 1.93-1.78 (m, 1H), 0.86 (dd, J=7.7, 7.2, 6H).

Example 36

(2R)-2-{[(5,5'-difluoro-2,2'-bipyridin-6-yl)methyl] amino}-3-methylbutan-1-ol

The title compound was prepared using procedure similar to that described for Example 73B, substituting 5-fluoropyridin-2-ylboronic acid pinacol ester for 5-(trifluoromethyl)pyridin-2-ylboronic acid pinacol ester. MS (ESI$^+$) m/z 308.1 (M+H); $^1$H NMR (300 MHz, DMSO-$d_6$) δ 8.67 (d, J=2.9, 1H), 8.42 (dd, J=8.9, 4.6, 1H), 8.26 (dd, J=8.6, 3.8, 1H), 7.89 (td, J=8.8, 3.0, 1H), 7.80 (dd, J=9.5, 8.8, 1H), 4.45 (t, J=5.2, 1H), 4.06-3.87 (m, 2H), 3.47 (dt, J=9.4, 4.6, 1H), 3.37-3.32 (m, 1H), 2.42-2.33 (m, 2H), 1.92-1.78 (m, 1H), 0.86 (dd, J=8.1, 6.9, 6H).

Example 37

1-{2-fluoro-3-[5-fluoro-6-({[(2R)-1-hydroxy-3-methylbutan-2-yl]amino}methyl)pyridin-2-yl] phenyl}ethanone The title compound was prepared using procedure similar to that described for Example 113, substituting 3-acetyl-2-fluorophenylboronic acid for 2-(trifluoromethyl)pyrimidin-5-ylboronic acid. MS (ESI$^+$) m/z 349.0 (M+H); $^1$H NMR (400 MHz, DMSO-$d_6$/$D_2O$) δ 8.20 (td, J=7.5, 1.9, 1H), 7.97 (d, J=7.2, 2H), 7.94-7.88 (m, 1H), 7.49 (t, J=7.7, 1H), 4.60 (qd, J=15.7, 1.5, 2H), 3.81 (dd, J=12.3, 3.6, 1H), 3.22 (td, J=6.2, 3.6, 1H), 2.65 (d, J=4.2, 3H), 2.23-2.12 (m, 1H), 1.02 (d, J=6.9, 3H), 0.97 (d, J=6.9, 3H).

Example 38

(2R)-2-{[(6'-chloro-5-fluoro-2,3'-bipyridin-6-yl) methyl]amino}-3-methylbutan-1-ol The title compound was prepared using procedure similar to that described for Example 113, substituting 6-chloropyridin-3-ylboronic acid for 2-(trifluoromethyl)pyrimidin-5-ylboronic acid. MS (ESI$^+$) m/z 323.9 (M+H); $^1$H NMR (400 MHz, DMSO-$d_6$/$D_2O$) δ 9.21 (d, J=2.5, 1H), 8.57 (dd, J=8.4, 2.6, 1H), 8.19 (dd, J=8.7, 3.7, 1H), 7.97 (t, J=9.0, 1H), 7.69 (d, J=8.4, 1H), 4.67-4.52 (m, 2H), 3.81 (dd, J=12.4, 3.6, 1H), 3.18 (td, J=6.2, 3.6, 1H), 2.25-2.13 (m, 1H), 1.03 (d, J=6.9, 3H), 0.98 (d, J=6.8, 3H).

Example 39

3-[5-fluoro-6-({[(2R)-1-hydroxy-3-methylbutan-2-yl]amino}methyl)pyridin-2-yl]-N,N-dimethylbenzenesulfonamide The title compound was prepared using procedure similar to that described for Example 113, substituting 3-(N,N-dimethylsulfamoyl)phenylboronic acid for 2-(trifluoromethyl)pyrimidin-5-ylboronic acid. MS (ESI$^+$) m/z 396.0 (M+H); $^1$H NMR (400 MHz, DMSO-d$_6$/D$_2$O) δ 8.48-8.41 (m, 2H), 8.21 (dd, J=8.8, 3.7, 1H), 7.97 (t, J=9.0, 1H), 7.86 (dt, J=7.9, 1.7, 1H), 7.82 (t, J=7.6, 1H), 4.61 (q, J=14.8, 2H), 3.82 (dd, J=12.3, 3.4, 1H), 3.21 (td, J=6.1, 3.6, 1H), 2.67 (s, 6H), 2.29-2.14 (m, 1H), 1.04 (d, J=6.9, 3H), 0.99 (d, J=6.9, 3H).

Example 40

1-{3-[5-fluoro-6-({[(2R)-1-hydroxy-3-methylbutan-2-yl]amino}methyl)pyridin-2-yl]phenyl}ethanone The title compound was prepared using procedure similar to that described for Example 113, substituting 3-acetylphenylboronic acid for 2-(trifluoromethyl)pyrimidin-5-ylboronic acid. MS (ESI$^+$) m/z 331.0 (M+H); $^1$H NMR (400 MHz, DMSO-d$_6$/D$_2$O) δ 8.68 (t, J=1.7, 1H), 8.43-8.37 (m, 1H), 8.20 (dd, J=8.8, 3.7, 1H), 8.09-8.03 (m, 1H), 7.95 (t, J=9.0, 1H), 7.70 (t, J=7.8, 1H), 4.61 (q, J=14.6, 2H), 3.82 (dd, J=12.4, 3.6, 1H), 3.23 (td, J=6.2, 3.6, 1H), 2.68 (s, 3H), 2.29-2.17 (m, 1H), 1.06 (d, J=6.9, 3H), 1.00 (d, J=6.9, 3H).

Example 41

N,N-diethyl-3-[5-fluoro-6-({[(2R)-1-hydroxy-3-methylbutan-2-yl]amino}methyl)pyridin-2-yl]benzamide The title compound was prepared using procedure similar to that described for Example 113, substituting 3-(diethylcarbamoyl)phenylboronic acid for 2-(trifluoromethyl)pyrimidin-5-ylboronic acid. MS (ESI$^+$) m/z 388.1 (M+H); $^1$H NMR (400 MHz, DMSO-d$_6$/D$_2$O) δ 8.21-8.09 (m, 3H), 7.92 (t, J=9.0, 1H), 7.60 (t, J=7.8, 1H), 7.47-7.40 (m, 1H), 4.59 (q, J=14.7, 2H), 3.81 (dd, J=12.4, 3.5, 1H), 3.47 (d, J=5.8, 2H), 3.27-3.13 (m, 3H), 2.27-2.13 (m, 1H), 1.28-1.12 (m, 3H), 1.11-1.01 (m, 6H), 0.98 (d, J=6.9, 3H).

Example 42

(2R)-2-({[6-(4-chlorophenyl)-3-fluoropyridin-2-yl]methyl}amino)-3-methylbutan-1-ol The title compound was prepared using procedure similar to that described for Example 113, substituting 4-chlorophenylboronic acid for 2-(trifluoromethyl)pyrimidin-5-ylboronic acid. MS (ESI$^+$) m/z 322.9 (M+H); $^1$H NMR (400 MHz, DMSO-d$_6$/D$_2$O) δ 8.19 (d, J=8.7, 2H), 8.10 (dd, J=8.8, 3.7, 1H), 7.92 (t, J=9.0, 1H), 7.59 (d, J=8.7, 2H), 4.58 (qd, J=15.7, 1.3, 2H), 3.82 (dd, J=12.4, 3.6, 1H), 3.19 (td, J=6.4, 3.6, 1H), 2.26-2.14 (m, 1H), 1.04 (d, J=6.9, 3H), 0.98 (d, J=6.9, 3H).

Example 43

(2R)-2-[({6-[3-(dimethylamino)phenyl]-3-fluoropyridin-2-yl}methyl)amino]-3-methylbutan-1-ol The title compound was prepared using procedure similar to that described for Example 113, substituting 3-(dimethylamino)phenylboronic acid for 2-(trifluoromethyl)pyrimidin-5-ylboronic acid. MS (ESI$^+$) m/z 332.0 (M+H); $^1$H NMR (400 MHz, DMSO-d$_6$/D$_2$O) δ 8.07 (dd, J=8.8, 3.7, 1H), 7.89 (t, J=9.0, 1H), 7.62-7.57 (m, 1H), 7.49 (d, J=8.0, 1H), 7.38 (t, J=7.9, 1H), 6.95 (dd, J=8.1, 2.2, 1H), 4.59 (q, J=14.6, 2H), 3.82 (dd, J=12.4, 3.6, 1H), 3.21 (td, J=6.3, 3.6, 1H), 3.01 (s, 6H), 2.28-2.16 (m, 1H), 1.05 (d, J=6.9, 3H), 0.99 (d, J=6.9, 3H).

Example 44

(2R)-2-[({3-fluoro-6-[3-(morpholin-4-yl)phenyl]pyridin-2-yl}methyl)amino]-3-methylbutan-1-ol The title compound was prepared using procedure similar to that described for Example 113, substituting 3-morpholinophenylboronic acid pinacol ester for 2-(trifluoromethyl)pyrimidin-5-ylboronic acid. MS (ESI$^+$) m/z 374.1 (M+H); $^1$H NMR (400 MHz, DMSO-d$_6$/D$_2$O) δ 8.09 (dd, J=8.8, 3.7, 1H), 7.89 (t, J=9.0, 1H), 7.77-7.72 (m, 1H), 7.56 (d, J=8.1, 1H), 7.39 (t, J=8.0, 1H), 7.07 (dd, J=8.1, 2.3, 1H), 4.59 (q, J=14.8, 2H), 3.84-3.77 (m, 5H), 3.26-3.13 (m, 5H), 2.29-2.15 (m, 1H), 1.04 (d, J=6.9, 3H), 0.99 (d, J=6.9, 3H).

Example 45

{3-[5-fluoro-6-({[(2R)-1-hydroxy-3-methylbutan-2-yl]amino}methyl)pyridin-2-yl]phenyl}(piperidin-1-yl)methanone The title compound was prepared using procedure similar to that described for Example 113, substituting 3-(piperidine-1-carbonyl)phenylboronic acid for 2-(trifluoromethyl)pyrimidin-5-ylboronic acid. MS (ESI$^+$) m/z 400.1 (M+H); $^1$H NMR (400 MHz, DMSO-d$_6$/D$_2$O) δ 8.21-8.16 (m, 1H), 8.16-8.10 (m, 2H), 7.92 (t, J=9.0, 1H), 7.60 (t, J=7.7, 1H), 7.48-7.42 (m, 1H), 4.59 (q, J=14.8, 2H), 3.81 (dd, J=12.4, 3.6, 1H), 3.62 (br s, 2H), 3.30 (br s, 2H), 3.21 (td, J=6.2, 3.6, 1H), 2.27-2.15 (m, 1H), 1.66-1.52 (m, 4H), 1.46 (br s, 2H), 1.04 (d, J=6.9, 3H), 0.99 (d, J=6.9, 3H).

Example 46

{3-[5-fluoro-6-({[(2R)-1-hydroxy-3-methylbutan-2-yl]amino}methyl)pyridin-2-yl]phenyl}(4-methylpiperidin-1-yl)methanone The title compound was prepared using procedure similar to that described for Example 113, substituting 3-(4-methylpiperidine-1-carbonyl)phenylboronic acid for 2-(trifluoromethyl)pyrimidin-5-ylboronic acid. MS (ESI$^+$) m/z 414.1 (M+H); $^1$H NMR (400 MHz, DMSO-d$_6$/D$_2$O) δ 8.22-8.16 (m, 1H), 8.16-8.10 (m, 2H), 7.93 (t, J=9.0, 1H), 7.60 (t, J=7.7, 1H), 7.48-7.41 (m, 1H), 4.59 (q, J=14.7, 2H), 4.47 (d, J=11.2, 1H), 3.81 (dd, J=12.4, 3.5, 1H), 3.55 (d, J=12.7, 1H), 3.21 (d, J=2.8, 1H), 3.07 (t, J=12.3, 1H), 2.79 (t, J=12.3, 1H), 2.27-

2.14 (m, 1H), 1.80-1.50 (m, 3H), 1.19-1.01 (m, 5H), 0.98 (d, J=6.8, 3H), 0.93 (d, J=6.5, 3H).

Example 47

(2R)-2-[({6-[3-chloro-4-(trifluoromethyl)phenyl]-3-fluoropyridin-2-yl}methyl)amino]-3-methylbutan-1-ol The title compound was prepared using procedure similar to that described for Example 113, substituting 3-chloro-4-(trifluoromethyl)phenylboronic acid for 2-(trifluoromethyl)pyrimidin-5-ylboronic acid. MS (ESI$^+$) m/z 391.0 (M+H); $^1$H NMR (400 MHz, DMSO-d$_6$/D$_2$O) δ 8.55 (s, 1H), 8.32-8.24 (m, 2H), 8.03-7.94 (m, 2H), 4.61 (q, J=15.7, 2H), 3.81 (dd, J=12.3, 3.6, 1H), 3.77-3.72 (m, 1H), 3.25-3.15 (m, 1H), 2.26-2.15 (m, 1H), 1.05 (d, J=6.9, 3H), 1.00 (d, J=6.9, 3H).

Example 48

(2R)-2-[({3-fluoro-6-[3-(piperidin-1-ylsulfonyl)phenyl]pyridin-2-yl}methyl)amino]-3-methylbutan-1-ol The title compound was prepared using procedure similar to that described for Example 113, substituting 3-(piperidin-1-ylsulfonyl)phenylboronic acid for 2-(trifluoromethyl)pyrimidin-5-ylboronic acid. MS (ESI$^+$) m/z 436.0 (M+H); $^1$H NMR (400 MHz, DMSO-d$_6$/D$_2$O) δ 8.46-8.39 (m, 2H), 8.20 (dd, J=8.8, 3.7, 1H), 7.97 (t, J=9.0, 1H), 7.86-7.77 (m, 2H), 4.61 (q, J=14.8, 2H), 3.82 (dd, J=12.4, 3.6, 1H), 3.78-3.73 (m, 1H), 3.21 (td, J=6.1, 3.6, 1H), 2.99-2.90 (m, 4H), 2.27-2.14 (m, 1H), 1.62-1.51 (m, 4H), 1.41-1.32 (m, 2H), 1.05 (d, J=6.9, 3H), 0.99 (d, J=6.9, 3H).

Example 49

(2R)-2-[({3-fluoro-6-[3-(pyrrolidin-1-yl)phenyl]pyridin-2-yl}methyl)amino]-3-methylbutan-1-ol The title compound was prepared using procedure similar to that described for Example 113, substituting 3-(pyrrolidin-1-yl)phenylboronic acid for 2-(trifluoromethyl)pyrimidin-5-ylboronic acid. MS (ESI$^+$) m/z 358.1 (M+H); $^1$H NMR (400 MHz, DMSO-d$_6$/D$_2$O) δ 8.05 (dd, J=8.8, 3.7, 1H), 7.87 (t, J=9.0, 1H), 7.35-7.27 (m, 3H), 6.70-6.62 (m, 1H), 4.58 (q, J=14.6, 2H), 3.82 (dd, J=12.3, 3.6, 1H), 3.37-3.25 (m, 4H), 3.22 (td, J=6.3, 3.6, 1H), 2.28-2.17 (m, 1H), 2.04-1.92 (m, 4H), 1.05 (d, J=6.9, 3H), 1.00 (d, J=6.8, 3H).

Example 50

3-[5-fluoro-6-({[(2R)-1-hydroxy-3-methylbutan-2-yl]amino}methyl)pyridin-2-yl]-N,N,4-trimethylbenzenesulfonamide The title compound was prepared using procedure similar to that described for Example 113, substituting 5-(N,N-dimethylsulfamoyl)-2-methylphenylboronic acid for 2-(trifluoromethyl)pyrimidin-5-ylboronic acid. MS (ESI$^+$) m/z 410.0 (M+H); $^1$H NMR (400 MHz, DMSO-d$_6$/D$_2$O) δ 7.99-7.92 (m, 1H), 7.81-7.72 (m, 3H), 7.65 (d, J=8.2, 1H), 4.58 (q, J=14.5, 2H), 3.79 (dd, J=12.3, 3.6, 1H), 3.18 (td, J=6.2, 3.6, 1H), 2.63 (s, 6H), 2.44 (s, 3H), 2.20-2.07 (m, 1H), 0.99 (d, J=6.9, 3H), 0.93 (d, J=6.9, 3H).

Example 51

N,N-diethyl-3-[5-fluoro-6-({[(2R)-1-hydroxy-3-methylbutan-2-yl]amino}methyl)pyridin-2-yl]benzenesulfonamide The title compound was prepared using procedure similar to that described for Example 113, substituting 3-(N,N-diethylsulfamoyl)phenylboronic acid for 2-(trifluoromethyl)pyrimidin-5-ylboronic acid. MS (ESI$^+$) m/z 424.0 (M+H); $^1$H NMR (400 MHz, DMSO-d$_6$/D$_2$O) δ 8.50 (t, J=1.7, 1H), 8.40-8.36 (m, 1H), 8.19 (dd, J=8.8, 3.6, 1H), 7.96 (t, J=9.0, 1H), 7.92-7.87 (m, 1H), 7.78 (t, J=7.8, 1H), 4.61 (q, J=14.8, 2H), 3.82 (dd, J=12.4, 3.5, 1H), 3.78-3.74 (m, 1H), 3.28-3.16 (m, 5H), 2.29-2.15 (m, 1H), 1.10-1.02 (m, 9H), 1.00 (d, J=6.8, 3H).

Example 52

N-cyclohexyl-3-[5-fluoro-6-({[(2R)-1-hydroxy-3-methylbutan-2-yl]amino}methyl)pyridin-2-yl]-N-methylbenzamide The title compound was prepared using procedure similar to that described for Example 113, substituting 3-[cyclohexyl(methyl)carbamoyl]phenylboronic acid for 2-(trifluoromethyl)pyrimidin-5-ylboronic acid. MS (ESI$^+$) m/z 428.1 (M+H); $^1$H NMR (400 MHz, DMSO-d$_6$/D$_2$O) δ 8.23-8.09 (m, 3H), 7.92 (t, J=9.0, 1H), 7.60 (t, J=7.7, 1H), 7.43 (dd, J=13.2, 7.6, 1H), 4.59 (q, J=15.6, 2H), 4.32 (br s, 0.5H), 3.81 (dd, J=12.4, 3.6, 1H), 3.33 (br s, 0.5H), 3.20 (d, J=2.7, 1H), 2.90 (s, 1.5H), 2.77 (s, 1.5H), 2.20 (br s, 1H), 1.82 (d, J=10.9, 1H), 1.75-1.29 (m, 7H), 1.21-1.07 (m, 1H), 1.03 (d, J=6.9, 3H), 0.98 (d, J=6.8, 3H), 0.94-0.79 (m, 1H).

Example 53

(2R)-2-[({3-fluoro-6-[4-(2,2,2-trifluoroethoxy)phenyl]pyridin-2-yl}methyl)amino]-3-methylbutan-1-ol The title compound was prepared using procedure similar to that described for Example 113, substituting 4-(2,2,2-trifluoroethoxy)phenylboronic acid for 2-(trifluoromethyl)pyrimidin-5-ylboronic acid. MS (ESI$^+$) m/z 387.1 (M+H); $^1$H NMR (400 MHz, DMSO-d$_6$/D$_2$O) δ 8.15 (d, J=8.9, 2H), 8.04 (dd, J=8.8, 3.7, 1H), 7.88 (t, J=9.1, 1H), 7.20 (d, J=9.0, 2H), 4.82 (q, J=8.8, 2H), 4.56 (q, J=14.5, 2H), 3.82 (dd, J=12.3, 3.6, 1H), 3.77-3.73 (m, 1H), 3.20 (td, J=6.4, 3.6, 1H), 2.26-2.14 (m, 1H), 1.04 (d, J=6.9, 3H), 0.99 (d, J=6.9, 3H).

Example 54

(2R)-2-[({3-fluoro-6-[3-(morpholin-4-ylsulfonyl)phenyl]pyridin-2-yl}methyl)amino]-3-methylbutan-1-ol The title compound was prepared using procedure similar to that described for Example 113, substituting 3-(morpholinosulfonyl)phenylboronic acid for 2-(trifluoromethyl)pyrimidin-5-ylboronic acid. MS (ESI$^+$) m/z 438.0 (M+H); $^1$H NMR (400 MHz, DMSO-d$_6$/D$_2$O) δ 8.49-8.42 (m, 2H), 8.21 (dd, J=8.8, 3.6, 1H), 7.98 (t, J=9.0, 1H), 7.88-7.82 (m, 2H), 4.61 (q, J=14.8, 2H), 3.82 (dd, J=12.4, 3.5, 1H), 3.69-3.63 (m, 4H), 3.21 (td, J=6.1, 3.6, 1H), 2.97-2.90 (m, 4H), 2.28-2.15 (m, 1H), 1.05 (d, J=6.9, 3H), 0.99 (d, J=6.9, 3H).

Example 55

(2R)-2-({[5-fluoro-2'-(morpholin-4-yl)-2,4'-bipyridin-6-yl]methyl}amino)-3-methylbutan-1-ol The title compound was prepared using procedure similar to that described for Example 113, substituting 2-morpholinopyridin-4-ylboronic acid pinacol ester for 2-(trifluoromethyl)pyrimidin-5-ylboronic acid. MS (ESI$^+$) m/z 375.1 (M+H); $^1$H NMR (400 MHz, DMSO-d$_6$/D$_2$O) δ 8.32 (dd, J=8.8, 3.6, 1H), 8.21 (d, J=6.0, 1H), 8.01 (t, J=9.0, 1H), 7.82 (s, 1H), 7.59 (dd, J=6.0, 1.3, 1H), 4.63 (q, J=15.2, 2H), 3.85-3.76 (m, 6H), 3.68-3.61 (m, 4H), 3.17 (td, J=6.4, 3.6, 1H), 2.26-2.14 (m, 1H), 1.03 (d, J=6.9, 3H), 0.99 (d, J=6.9, 3H).

Example 56

3-[5-fluoro-6-({[(2R)-1-hydroxy-3-methylbutan-2-yl]amino}methyl)pyridin-2-yl]-N,N-diisopropylbenzamide The title compound was prepared using procedure similar to that described for Example 113, substituting 3-(diisopropylcarbamoyl)phenylboronic acid for 2-(trifluoromethyl)pyrimidin-5-ylboronic acid. MS (ESI$^+$) m/z 416.1 (M+H); $^1$H NMR (400 MHz, DMSO-d$_6$/D$_2$O) δ 8.18-8.11 (m, 2H), 8.04 (t, J=1.6, 1H), 7.92 (t, J=9.0, 1H), 7.59 (t, J=7.7, 1H), 7.40-7.33 (m, 1H), 4.59 (q, J=14.7, 2H), 3.81 (dd, J=12.4, 3.5, 1H), 3.70-3.51 (m, 2H), 3.22 (td, J=6.1, 3.6, 1H), 2.27-2.15 (m, 1H), 1.46 (br s, 6H), 1.12 (br s, 6H), 1.05 (d, J=6.9, 3H), 0.98 (d, J=6.9, 3H).

Example 57

(2R)-2-({[5-fluoro-6'-(propan-2-yloxy)-2,3'-bipyridin-6-yl]methyl}amino)-3-methylbutan-1-ol The title compound was prepared using procedure similar to that described for Example 113, substituting 6-isopropoxypyridin-3-ylboronic acid for 2-(trifluoromethyl)pyrimidin-5-ylboronic acid. MS (ESI$^+$) m/z 348.1 (M+H); $^1$H NMR (400 MHz, DMSO-d$_6$/D$_2$O) δ 8.96 (d, J=2.3, 1H), 8.43 (dd, J=8.7, 2.6, 1H), 8.06 (dd, J=8.8, 3.7, 1H), 7.89 (t, J=9.0, 1H), 6.89 (d, J=8.6, 1H), 5.37-5.25 (m, 1H), 4.56 (q, J=15.7, 2H), 3.82 (dd, J=12.3, 3.6, 1H), 3.18 (td, J=6.3, 3.6, 1H), 2.25-2.13 (m, 1H), 1.33 (d, J=6.2, 6H), 1.04 (d, J=6.9, 3H), 0.98 (d, J=6.8, 3H).

Example 58

N-benzyl-3-[5-fluoro-6-({[(2R)-1-hydroxy-3-methylbutan-2-yl]amino}methyl)pyridin-2-yl]-N-methylbenzamide The title compound was prepared using procedure similar to that described for Example 113, substituting 3-[benzyl(methyl)carbamoyl]phenylboronic acid for 2-(trifluoromethyl)pyrimidin-5-ylboronic acid. MS (ESI$^+$) m/z 436.1 (M+H); $^1$H NMR (400 MHz, DMSO-d$_6$/D$_2$O) δ 8.29-7.86 (m, 4H), 7.68-7.47 (m, 2H), 7.47-7.27 (m, 4H), 7.19 (d, J=7.1, 1H), 4.81-4.46 (m, 4H), 3.81 (dd, J=12.3, 3.3, 1H), 3.20 (td, J=6.2, 3.6, 1H), 2.91 (d, J=30.5, 3H), 2.27-2.13 (m, 1H), 1.09-0.92 (m, 6H).

Example 59

(2R)-2-{[(3-fluoro-6-{2-methyl-5-[(trifluoromethyl)sulfonyl]phenyl}pyridin-2-yl)methyl]amino}-3-methylbutan-1-ol The title compound was prepared using procedure similar to that described for Example 113, substituting 2-methyl-5-(trifluoromethylsulfonyl)phenylboronic acid for 2-(trifluoromethyl)pyrimidin-5-ylboronic acid. MS (ESI$^+$) m/z 434.9 (M+H); $^1$H NMR (400 MHz, DMSO-d$_6$/D$_2$O) δ 8.16 (d, J=2.1, 1H), 8.12 (dd, J=8.1, 2.1, 1H), 8.03-7.93 (m, 1H), 7.89-7.80 (m, 2H), 4.59 (q, J=14.7, 2H), 3.79 (dd, J=12.4, 3.5, 1H), 3.18 (td, J=6.1, 3.6, 1H), 2.20-2.08 (m, 1H), 0.98 (d, J=6.9, 3H), 0.93 (d, J=6.9, 3H).

Example 60

(2R)-2-[({3-fluoro-6-[3-(pyrrolidin-1-ylsulfonyl)phenyl]pyridin-2-yl}methyl)amino]-3-methylbutan-1-ol The title compound was prepared using procedure similar to that described for Example 113, substituting 3-(pyrrolidin-1-ylsulfonyl)phenylboronic acid for 2-(trifluoromethyl)pyrimidin-5-ylboronic acid. MS (ESI$^+$) m/z 422.1 (M+H); $^1$H NMR (400 MHz, DMSO-d$_6$/D$_2$O) δ 8.50 (t, J=1.7, 1H), 8.45-8.38 (m, 1H), 8.20 (dd, J=8.8, 3.7, 1H), 7.97 (t, J=9.0, 1H), 7.93-7.88 (m, 1H), 7.81 (t, J=7.8, 1H), 4.61 (q, J=14.7, 2H), 3.82 (dd, J=12.4, 3.5, 1H), 3.78-3.73 (m, 1H), 3.25-3.15 (m, 5H), 2.28-2.15 (m, 1H), 1.73-1.60 (m, 4H), 1.05 (d, J=6.9, 3H), 0.99 (d, J=6.8, 3H).

Example 61

N-tert-butyl-3-[5-fluoro-6-({[(2R)-1-hydroxy-3-methylbutan-2-yl]amino}methyl)pyridin-2-yl]-N-methylbenzenesulfonamide The title compound was prepared using procedure similar to that described for Example 113, substituting 3-(N-tert-butyl-N-methylsulfamoyl)phenylboronic acid for 2-(trifluoromethyl)pyrimidin-5-ylboronic acid. MS (ESI$^+$) m/z 438.1 (M+H); $^1$H NMR (400 MHz, DMSO-d$_6$/D$_2$O) δ 8.49 (t, J=1.7, 1H), 8.38-8.33 (m, 1H), 8.18 (dd, J=8.8, 3.7, 1H), 7.96 (t, J=9.0, 1H), 7.89 (ddd, J=7.8, 1.8, 1.0, 1H), 7.76 (t, J=7.8, 1H), 4.67-4.54 (m, 2H), 3.82 (dd, J=12.4, 3.5, 1H), 3.78-3.73 (m, 1H), 3.22 (td, J=6.1, 3.5, 1H), 2.98 (s, 3H), 2.29-2.14 (m, 1H), 1.28 (s, 9H), 1.05 (d, J=6.9, 3H), 0.99 (d, J=6.9, 3H).

Example 62

{3-[5-fluoro-6-({[(2R)-1-hydroxy-3-methylbutan-2-yl]amino}methyl)pyridin-2-yl]phenyl}(thiomorpholin-4-yl)methanone The title compound was prepared using procedure similar to that described for Example 113, substituting 3-(thiomorpholine-4-carbonyl)phenylboronic acid for 2-(trifluoromethyl)pyrimidin-5-ylboronic acid. MS (ESI$^+$) m/z 418.1 (M+H); $^1$H NMR (400 MHz, DMSO-d$_6$/D$_2$O) δ 8.24-8.19 (m, 1H), 8.18-8.12 (m, 2H), 7.93 (t, J=9.0, 1H), 7.62 (t, J=7.7, 1H), 7.52-7.45 (m, 1H), 4.59 (q, J=14.7, 2H), 3.91 (br s, 2H), 3.81 (dd, J=12.4, 3.5, 1H), 3.58 (br s, 2H), 3.21 (td, J=6.2, 3.6, 1H), 2.71 (br s, 2H), 2.60 (br s, 2H), 2.27-2.15 (m, 1H), 1.04 (d, J=6.9, 3H), 0.99 (d, J=6.9, 3H).

Example 63

(2R)-2-({[3-fluoro-6-(1-methyl-1H-indol-4-yl)pyridin-2-yl]methyl}amino)-3-methylbutan-1-ol The title compound was prepared using procedure similar to that described for Example 113, substituting 1-methyl-1H-indol-4-ylboronic acid pinacol ester for 2-(trifluoromethyl)pyrimidin-5-ylboronic acid. MS (ESI$^+$) m/z 342.0 (M+H); $^1$H NMR (400 MHz, DMSO-d$_6$/D$_2$O) δ 8.02 (dd, J=8.7, 3.9, 1H), 7.93 (t, J=9.0, 1H), 7.61 (dd, J=7.4, 0.7, 1H), 7.58 (d, J=8.2, 1H), 7.46 (d, J=3.2, 1H), 7.35-7.28 (m, 1H), 6.90 (dd, J=3.2, 0.7, 1H), 4.67-4.54 (m, 2H), 3.85 (s, 3H), 3.82 (dd, J=9.4, 3.0, 1H), 3.28 (td, J=6.3, 3.7, 1H), 2.25-2.14 (m, 1H), 1.03 (d, J=6.9, 3H), 0.97 (d, J=6.9, 3H).

Example 64

(2R)-2-({[3-fluoro-6-(1-methyl-1H-indol-6-yl)pyridin-2-yl]methyl}amino)-3-methylbutan-1-ol The title compound was prepared using procedure similar to that described for Example 113, substituting 1-methyl-1H-indol-6-ylboronic acid pinacol ester for 2-(trifluoromethyl)pyrimidin-5-ylboronic acid. MS (ESI$^+$) m/z 342.0 (M+H); $^1$H NMR (400 MHz, DMSO-d$_6$/D$_2$O) δ 8.28 (s, 1H), 8.16 (dd, J=8.8, 3.7, 1H), 7.88 (t, J=9.1, 1H), 7.86 (dd, J=8.3, 1.5, 1H), 7.67 (d, J=8.3, 1H), 7.43 (d, J=3.0, 1H), 6.49 (dd, J=3.0, 0.7, 1H), 4.60 (dd, J=36.2, 14.6, 2H), 3.87 (s, 3H), 3.84 (dd, J=12.3, 3.6, 1H), 3.75 (dd, J=12.5, 6.8, 1H), 3.25 (td, J=6.3, 3.6, 1H), 2.29-2.19 (m, 1H), 1.08 (d, J=6.9, 3H), 1.02 (d, J=6.9, 3H).

Example 65

(2R)-2-[({3-fluoro-6-[3-(trifluoromethyl)piperidin-1-yl]pyridin-2-yl}methyl)amino]-3-methylbutan-1-ol The title compound was prepared using procedure similar to that described for Example 70, substituting 3-(trifluoromethyl)piperidine for 1,2,3,4-tetrahydroisoquinoline. MS (ESI$^+$) m/z 364.1 (M+H); $^1$H NMR (300 MHz, DMSO-d$_6$) δ 7.44 (t, J=9.1, 1H), 6.79 (dd, J=9.1, 2.8, 1H), 4.52 (d, J=12.8, 1H), 4.33 (td, J=5.3, 1.3, 1H), 4.07 (d, J=12.8, 1H), 3.73 (d, J=4.9, 2H), 3.46-3.35 (m, 1H), 2.90-2.74 (m, 2H), 2.36-2.28 (m, 1H), 2.21-2.09 (m, 1H), 2.01-1.91 (m, 1H), 1.89-1.78 (m, 1H), 1.77-1.67 (m, 1H), 1.60-1.43 (m, 2H), 0.85 (dd, J=6.9, 1.0, 6H).

Example 66

(2R)-2-[({3-fluoro-6-[4-(trifluoromethyl)piperidin-1-yl]pyridin-2-yl}methyl)amino]-3-methylbutan-1-ol The title compound was prepared using procedure similar to that described for Example 70, substituting 4-(trifluoromethyl)piperidine hydrochloride for 1,2,3,4-tetrahydroisoquinoline. MS (ESI$^+$) m/z 364.1 (M+H); $^1$H NMR (300 MHz, DMSO-d$_6$) δ 7.43 (t, J=9.1, 1H), 6.76 (dd, J=9.1, 2.8, 1H), 4.40-4.27 (m, 3H), 3.81-3.62 (m, 2H), 3.42 (dt, J=10.6, 4.8, 1H), 3.28-3.21 (m, 1H), 2.81 (td, J=12.9, 2.2, 2H), 2.64-2.53 (m, 1H), 2.35-2.24 (m, 1H), 2.23-2.13 (m, 1H), 1.88-1.76 (m, 3H), 1.42 (qd, J=12.5, 4.1, 2H), 0.84 (dd, J=6.9, 5.5, 6H).

Example 67

(2R)-2-[({3-fluoro-6-[3-(trifluoromethyl)pyrrolidin-1-yl]pyridin-2-yl}methyl)amino]-3-methylbutan-1-ol The title compound was prepared using procedure similar to that described for Example 70, substituting 3-(trifluoromethyl)pyrrolidine hydrochloride for 1,2,3,4-tetrahydroisoquinoline. MS (ESI$^+$) m/z 350.1 (M+H); $^1$H NMR (300 MHz, DMSO-d$_6$) δ 7.43 (t, J=9.1, 1H), 6.41 (dd, J=9.0, 2.8, 1H), 4.41-4.34 (m, 1H), 3.80-3.62 (m, 3H), 3.56-3.34 (m, 5H), 3.29-3.23 (m, 1H), 2.38-2.20 (m, 3H), 2.17-2.01 (m, 1H), 1.89-1.76 (m, 1H), 0.85 (dd, J=6.9, 4.3, 6H).

Example 68

(2R)-2-({[5-fluoro-6'-(2,2,2-trifluoro ethoxy)-2,3'-bipyridin-6-yl]methyl}amino)-3-methylbutan-1-ol

Example 68A

5-fluoro-6'-(2,2,2-trifluoroethoxy)-2,3'-bipyridine-6-carbaldehyde

The title compound was prepared using procedure similar to that described for Example 28A, substituting 6-(2,2,2-trifluoroethoxy)pyridin-3-ylboronic acid pinacol ester for 6-(trifluoromethyl)pyridin-3-ylboronic acid. MS (ESI$^+$) m/z 332.8 (M+H+MeOH); $^1$H NMR (300 MHz, DMSO-d$_6$) δ 10.12 (s, 1H), 8.97 (d, J=2.3, 1H), 8.54 (dd, J=8.7, 2.5, 1H), 8.40 (dd, J=8.8, 3.6, 1H), 8.07 (dd, J=10.2, 9.0, 1H), 7.17 (d, J=8.7, 1H), 5.09 (q, J=9.1, 2H).

Example 68B

(2R)-2-({[5-fluoro-6'-(2,2,2-trifluoro ethoxy)-2,3'-bipyridin-6-yl]methyl}amino)-3-methylbutan-1-ol The title compound was prepared using procedure similar to that described for Example 28B, substituting Example 68A for Example 28A. MS (ESI$^+$) m/z 388.1 (M+H); $^1$H NMR (300 MHz, DMSO-d$_6$) δ 8.93-8.85 (m, 1H), 8.46 (dd, J=8.7, 2.5, 1H), 7.96 (dd, J=8.6, 3.7, 1H), 7.84-7.70 (m, 1H), 7.11 (dd, J=8.5, 0.5, 1H), 5.06 (q, J=9.1, 2H), 4.46 (t, J=5.2, 1H), 4.06-3.82 (m, 2H), 3.52-3.39 (m, 1H), 2.44-2.30 (m, 2H), 1.92-1.78 (m, 1H), 0.86 (dd, J=8.1, 7.0, 6H).

Example 69

(2R)-3-methyl-2-({[6'-(trifluoromethyl)-2,3'-bipyridin-6-yl]methyl}amino)butan-1-ol

Example 69A

6'-(trifluoromethyl)-2,3'-bipyridine-6-carbaldehyde

The title compound was prepared using procedure similar to that described for Example 28A, substituting 6-bromopicolinaldehyde for 6-bromo-3-fluoropicolinaldehyde. MS (ESI$^+$) m/z 284.9 (M+H+MeOH); $^1$H NMR (300 MHz, DMSO-d$_6$) δ 10.10 (d, J=0.6, 1H), 9.54 (d, J=2.1, 1H), 8.87-

8.78 (m, 1H), 8.50 (dd, J=7.9, 0.9, 1H), 8.26 (td, J=7.8, 0.6, 1H), 8.16-8.07 (m, 1H), 8.02 (dd, J=7.6, 0.9, 1H).

Example 69B (2R)-3-methyl-2-({[6'-(trifluoromethyl)-2,3'-bipyridin-6-yl]methyl}amino)butan-1-ol The title compound was prepared using procedure similar to that described for Example 28B, substituting Example 69A for Example 28A. MS (ESI$^+$) m/z 340.1 (M+H); $^1$H NMR (300 MHz, DMSO-d$_6$) δ 9.45 (d, J=1.9, 1H), 8.72 (dd, J=8.2, 1.9, 1H), 8.03 (d, J=8.2, 2H), 7.95 (t, J=7.7, 1H), 7.56 (d, J=7.4, 1H), 4.45 (t, J=5.3, 1H), 4.00-3.87 (m, 2H), 3.48 (dt, J=9.9, 4.8, 1H), 3.36 (dd, J=11.2, 5.6, 1H), 2.40-2.24 (m, 2H), 1.92-1.77 (m, 1H), 0.89 (t, J=6.9, 6H).

Example 70

(2R)-2-({[6-(3,4-dihydroisoquinolin-2(1H)-yl)-3-fluoropyridin-2-yl]methyl}amino)-3-methylbutan-1-ol A 5 mL microwave vial was charged with Example 73A (250 mg, 0.859 mmol), Pd$_2$(dba)$_3$ (23.59 mg, 0.026 mmol), BINAP (48.1 mg, 0.077 mmol), and sodium tert-butoxide (124 mg, 1.288 mmol), flushed with nitrogen, followed by addition of 1,2,3,4-tetrahydroisoquinoline (137 mg, 1.030 mmol) in dioxane (5 mL). The brown mixture was heated in the microwave for 15 minutes at 120° C. To the reaction mixtures was added 70 mL EtOAc, and extracted twice with 70 mL 1.0 N HCl. The pH of the combined aqueous phase was adjusted to about 10 with the addition of 100 mL 3.0 N NaOH, and extracted with 200 mL EtOAc. The organic phase was washed with brine, dried over Na$_2$SO$_4$, filtered, and concentrated to obtain the title compound as a yellow oil. MS (ESI$^+$) m/z 344.1 (M+H); $^1$H NMR (300 MHz, DMSO-d$_6$) δ 7.45 (t, J=9.1, 1H), 7.24-7.14 (m, 4H), 6.77 (dd, J=9.1, 2.7, 1H), 4.64 (s, 2H), 4.40 (t, J=5.2, 1H), 3.82-3.66 (m, 4H), 3.44 (dt, J=9.7, 4.7, 1H), 2.88 (t, J=5.9, 2H), 2.39-2.22 (m, 2H), 1.93-1.75 (m, 1H), 0.86 (dd, J=6.9, 5.1, 6H).

Example 71

(2R)-2-({[6-[1,3-dihydro-2H-isoindol-2-yl)-3-fluoropyridin-2-yl]methyl}amino)-3-methylbutan-1-ol The title compound was prepared using procedure similar to that described for Example 70, substituting isoindoline for 1,2,3,4-tetrahydroisoquinoline. MS (ESI$^+$) m/z 330.1 (M+H); $^1$H NMR (300 MHz, DMSO-d$_6$) δ 7.49 (t, J=9.1, 1H), 7.44-7.36 (m, 2H), 7.36-7.28 (m, 2H), 6.48 (dd, J=9.0, 2.7, 1H), 4.73 (s, 4H), 4.40 (t, J=5.2, 1H), 3.83-3.69 (m, 2H), 3.44 (dt, J=9.8, 4.9, 1H), 2.39-2.31 (m, 1H), 2.31-2.19 (m, 1H), 1.93-1.78 (m, 1H), 0.87 (dd, J=6.8, 5.7, 6H).

Example 72

(2R)-2-({[3-fluoro-6-(quinolin-3-yl)pyridin-2-yl]methyl}amino)-3-methylbutan-1-ol Example 72A 3-fluoro-6-(quinolin-3-yl)picolinaldehyde The title compound was prepared using procedure similar to that described for Example 28A, substituting quinolin-3-ylboronic acid for 6-(trifluoromethyl)pyridin-3-ylboronic acid. MS (ESI$^+$) m/z 285.0 (M+H+MeOH); $^1$H NMR (300 MHz, DMSO-d$_6$) δ 9.73 (d, J=2.3, 1H), 9.15 (d, J=2.2, 1H), 8.27 (dd, J=8.6, 3.6, 1H), 8.13-8.05 (m, 2H), 7.89 (dd, J=9.8, 8.7, 1H), 7.81 (ddd, J=8.5, 6.9, 1.5, 1H), 7.67 (ddd, J=8.0, 6.9, 1.2, 1H), 6.61 (s, 1H), 6.58 (s, 1H), 6.11-6.02 (m, 1H).

Example 72B (2R)-2-({[3-fluoro-6-(quinolin-3-yl)pyridin-2-yl]methyl}amino)-3-methylbutan-1-ol The title compound was prepared using procedure similar to that described for Example 28B, substituting Example 72A for Example 28A. MS (ESI$^+$) m/z 340.1 (M+H); $^1$H NMR (300 MHz, DMSO-d$_6$) δ 9.63 (d, J=2.3, 1H), 9.00 (d, J=2.1, 1H), 8.18 (dd, J=8.6, 3.7, 1H), 8.12-8.04 (m, 2H), 7.92-7.76 (m, 2H), 7.67 (ddd, J=8.1, 6.9, 1.2, 1H), 4.49 (t, J=5.2, 1H), 4.09-3.93 (m, 2H), 3.49 (dt, J=10.5, 4.7, 1H), 3.41-3.32 (m, 1H), 2.47-2.38 (m, 2H), 1.95-1.81 (m, 1H), 0.89 (dd, J=7.5, 7.1, 6H).

Example 73

(2R)-2-({[5-fluoro-5'-(trifluoromethyl)-2,2'-bipyridin-6-yl]methyl}amino)-3-methylbutan-1-ol Example 73A (2R)-2-{[(6-bromo-3-fluoropyridin-2-yl)methyl]amino}-3-methylbutan-1-ol 6-bromo-3-fluoropicolinaldehyde (4.0 g, 19.61 mmol) and (R)-2-amino-3-methylbutan-1-ol (2.281 mL, 20.59 mmol) were dissolved in methanol (100 mL) and stirred at ambient temperature for 1 hour and 15 minutes. Sodium borohydride (0.742 g, 19.61 mmol) was added and the mixture was stirred for another 1 hour and 30 minutes. The volume of the reaction mixture was reduced, and the mixture was quenched with 200 mL 1.0 N NaOH, and extracted with 200 mL dichloromethane (2×). The organic phase was extracted with 1.0 N HCl and partitioned. The aqueous phase was separated, neutralized with 3.0 N NaOH, extracted with EtOAc, organic phase separated and washed with brine. The organic phase was dried over Na$_2$SO$_4$, filtered, and concentrated to obtain the title compound as an orange solid. MS (ESI$^+$) m/z 291.0 (M+H); $^1$H NMR (300 MHz, DMSO-d$_6$) δ 7.69 (t, J=8.8, 1H), 7.60 (dd, J=8.6, 3.7, 1H), 4.42 (t, J=5.2, 1H), 3.92-3.75 (m, 2H), 3.43 (dt, J=10.7, 4.8, 1H), 2.34-2.24 (m, 1H), 2.08 (s, 1H), 1.87-1.71 (m, 1H), 0.83 (dd, J=8.5, 6.9, 6H).

Example 73B (2R)-2-({[5-fluoro-5'-(trifluoromethyl)-2,2'-bipyridin-6-yl]methyl}amino)-3-methylbutan-1-ol A 20 mL microwave vial was charged with 5-(trifluoromethyl)pyridin-2-ylboronic acid pinacol ester (1125 mg, 4.12 mmol), Example 73A (600 mg, 2.061 mmol), palladium(II) acetate (23.13 mg, 0.103 mmol), DPPF (114 mg, 0.206 mmol), cesium carbonate (1343 mg, 4.12 mmol), copper(I) chloride (204 mg, 2.061 mmol), and DMF (15 mL). Nitrogen was bubbled through the green mixture for 5 minutes, and microwaved for 4 hours at 100° C. The reaction mixtures was partitioned between 200 mL dichloromethane and 200 mL water, and filtered through a celite pad. The organic layer was dark brown, the aqueous layer was green, and the desired product was found in both phases. The aqueous phase was treated with 3.0 N NaOH to adjust the pH from 8 to 12, extracted with dichloromethane, partitioned, and the dichloromethane solution was dried over $Na_2SO_4$. The organic phase from the first partition was extracted with 1.0 N HCl, and partitioned. The resulting aqueous phase was neutralized with 3.0 N NaOH, extracted with dichloromethane, partitioned, and the dichloromethane solution was dried over $Na_2SO_4$. The combined dichloromethane solutions were dried over $Na_2SO_4$, filtered and concentrated. The residue was chromatographed on a Grace Reveleris 40 g column, eluted with 0-2% $NH_4OH$ in acetonitrile (30 mL/min) to obtain the title compound as an amber oil. MS (ESI$^+$) m/z 358.1 (M+H); $^1$H NMR (300 MHz, DMSO-$d_6$) δ 9.07 (s, 1H), 8.56 (d, J=8.4, 1H), 8.43-8.36 (m, 2H), 7.92-7.82 (m, 1H), 4.46 (t, J=5.2, 1H), 4.08-3.89 (m, 2H), 3.47 (dt, J=9.2, 4.5, 1H), 2.42-2.30 (m, 2H), 1.93-1.78 (m, 1H), 0.86 (dd, J=8.2, 7.0, 6H).

Example 74

2-[({3-fluoro-6-[4-(trifluoromethyl)phenyl]pyridin-2-yl}methyl)amino]-3-methoxypropan-1-ol The title compound was prepared using procedure similar to that described for Example 28B, substituting Example 17A for Example 28A and 2-amino-3-methoxypropan-1-ol for (R)-2-amino-3-methylbutan-1-ol. MS (ESI$^+$) m/z 359.1 (M+H); $^1$H NMR (300 MHz, DMSO-$d_6$) δ 8.30 (d, J=8.2, 2H), 8.05 (dd, J=8.6, 3.7, 1H), 7.89-7.78 (m, 3H), 4.56 (t, J=5.4, 1H), 4.01 (s, 2H), 3.47-3.32 (m, 4H), 3.23 (s, 3H), 2.84-2.73 (m, 1H).

Example 75

(2R)-2-cyclopropyl-2-({[5-fluoro-6'-(trifluoromethyl)-2,3'-bipyridin-6-yl]methyl}amino)ethanol Example 28A (800 mg, 2.96 mmol) and (R)-2-amino-2-cyclopropylethanol hydrochloride (448 mg, 3.26 mmol) were dissolved in methanol (20 mL) and triethylamine (0.451 mL, 3.26 mmol), stirred at ambient temperature for 1 hour, followed by the addition of sodium borohydride (246 mg, 6.51 mmol). Reaction was completed within 1 hour. The reaction mixture was quenched with 100 mL of 1.0 N NaOH, extracted with 100 mL dichloromethane (2×). The organic phase was treated with 1.0 N HCl (2×), partitioned, and the aqueous phase was neutralized with 3.0 N NaOH and extracted with EtOAc. The EtOAc layer was washed with brine, dried over $Na_2SO_4$, filtered, and concentrated to provide the title compound as a white solid. MS (ESI$^+$) m/z 356.0 (M+H); $^1$H NMR (300 MHz, DMSO-$d_6$) δ 9.46 (d, J=1.5, 1H), 8.71 (dd, J=8.2, 1.7, 1H), 8.16 (dd, J=8.6, 3.7, 1H), 8.04 (d, J=8.3, 1H), 7.88 (t, J=9.1, 1H), 4.65 (t, J=5.3, 1H), 4.18 (d, J=14.5, 1H), 4.02 (d, J=15.0, 1H), 3.55 (dt, J=10.3, 4.3, 1H), 3.40-3.34 (m, 1H), 2.78 (s, 1H), 1.83 (td, J=8.2, 3.6, 1H), 0.66-0.47 (m, 2H), 0.39-0.27 (m, 1H), 0.27-0.16 (m, 1H), 0.09-0.02 (m, 1H).

Example 76

(2R)-2-cyclopropyl-2-({[5-fluoro-6'-(2,2,2-trifluoroethoxy)-2,3'-bipyridin-6-yl]methyl}amino)ethanol The title compound was prepared using procedure similar to that described for Example 75, substituting Example 68A for Example 28A. MS (ESI$^+$) m/z 386.0 (M+H); $^1$H NMR (300 MHz, DMSO-$d_6$) δ 8.90 (d, J=2.0, 1H), 8.47 (dd, J=8.7, 2.5, 1H), 7.96 (dd, J=8.6, 3.7, 1H), 7.77 (dd, J=9.5, 8.7, 1H), 7.11 (dd, J=8.7, 0.6, 1H), 5.06 (q, J=9.1, 2H), 4.62 (dd, J=5.7, 5.0, 1H), 4.15 (d, J=14.0, 1H), 3.97 (d, J=13.7, 1H), 3.60-3.49 (m, 1H), 3.40-3.33 (m, 1H), 2.76 (s, 1H), 1.82 (td, J=8.2, 3.7, 1H), 0.65-0.46 (m, 2H), 0.38-0.27 (m, 1H), 0.27-0.18 (m, 1H), 0.08-0.01 (m, 1H).

Example 77

(2R)-2-[({3-fluoro-6-[4-(trifluoromethyl)phenyl]pyridin-2-yl}methyl)amino]butan-1-ol The title compound was prepared using procedure similar to that described for Example 28B, substituting Example 17A for Example 28A and (R)-2-aminobutan-1-ol for (R)-2-amino-3-methylbutan-1-ol. MS (ESI$^+$) m/z 343.1 (M+H); $^1$H NMR (300 MHz, DMSO-$d_6$) δ 8.30 (d, J=8.1, 2H), 8.05 (dd, J=8.6, 3.7, 1H), 7.89-7.77 (m, 3H), 4.50 (t, J=5.3, 1H), 4.06-3.86 (m, 2H), 3.42 (dt, J=10.0, 4.9, 1H), 2.38 (s, 1H), 1.49-1.36 (m, 2H), 0.84 (t, J=7.5, 3H).

Example 78

(2R)-2-({[5-fluoro-6'-(trifluoromethyl)-2,3'-bipyridin-6-yl]methyl}amino)butan-1-ol The title compound was prepared using procedure similar to that described for Example 28B, substituting (R)-2-aminobutan-1-ol for (R)-2-amino-3-methylbutan-1-ol. MS (ESI$^+$) m/z 344.1 (M+H); $^1$H NMR (300 MHz, DMSO-$d_6$) δ 9.45 (d, J=1.8, 1H), 8.71 (dd, J=8.2, 1.8, 1H), 8.16 (dd, J=8.6, 3.7, 1H), 8.04 (d, J=8.3, 1H), 7.93-7.84 (m, 1H), 4.52 (t, J=5.3, 1H), 4.08-3.88 (m, 2H), 3.42 (dt, J=9.9, 4.8, 1H), 2.47-2.40 (m, 1H), 1.49-1.35 (m, 2H), 0.84 (t, J=7.5, 3H).

Example 79

{1-[({3-fluoro-6-[4-(trifluoromethyl)phenyl]pyridin-2-yl}methyl)amino]cyclobutyl}methanol The title compound was prepared using procedure similar to that described for Example 28B, substituting Example 17A for Example 28A and (1-aminocyclobutyl)methanol for (R)-2-amino-3-methylbutan-1-ol. MS (ESI$^+$) m/z 355.0 (M+H); $^1$H NMR (500 MHz, DMSO-$d_6$/$D_2O$) δ 8.41 (d, J=8.2, 2H), 8.20 (dd, J=8.7, 3.6, 1H), 7.96 (t, J=9.0, 1H), 7.90 (d, J=8.3, 2H), 4.39 (s, 2H), 3.85 (s, 2H), 2.41-2.31 (m, 2H), 2.11-2.02 (m, 2H), 1.94-1.80 (m, 2H).

Example 80

{1-[({3-fluoro-6-[4-(trifluoromethyl)phenyl]pyridin-2-yl}methyl)amino]cyclopentyl}methanol The title compound was prepared using procedure similar to that described for Example 28B, substituting Example 17A for Example 28A and (1-aminocyclopentyl)methanol for (R)-2-amino-3-methylbutan-1-ol. MS (ESI$^+$) m/z 369.0 (M+H); $^1$H NMR (500 MHz, DMSO-$d_6$/$D_2O$) δ 8.39 (d, J=8.2, 2H), 8.19 (dd, J=8.7, 3.6, 1H), 7.96 (t, J=9.0, 1H), 7.90 (d, J=8.3, 2H), 4.46 (s, 2H), 3.63 (s, 2H), 1.93-1.82 (m, 4H), 1.82-1.71 (m, 2H), 1.68-1.57 (m, 2H).

Example 81

{1-[({3-fluoro-6-[4-(trifluoromethyl)phenyl]pyridin-2-yl}methyl)amino]cyclohexyl}methanol The title compound was prepared using procedure similar to that described for Example 28B, substituting Example 17A for Example 28A and (1-aminocyclohexyl)methanol for (R)-2-amino-3-methylbutan-1-ol. MS (ESI$^+$) m/z 383.1 (M+H); $^1$H NMR (500 MHz, DMSO-d$_6$/D$_2$O) δ 8.38 (d, J=8.2, 2H), 8.19 (dd, J=8.7, 3.6, 1H), 7.96 (t, J=8.9, 1H), 7.90 (d, J=8.3, 2H), 4.47 (s, 2H), 3.79 (s, 2H), 1.99 (d, J=13.5, 2H), 1.71-1.59 (m, 5H), 1.46-1.34 (m, 2H), 1.27-1.16 (m, 1H).

Example 82

(2R)-2-[({3-fluoro-6-[4-(trifluoromethyl)phenyl]pyridin-2-yl}methyl)amino]propan-1-ol The title compound was prepared using procedure similar to that described for Example 28B, substituting Example 17A for Example 28A and (R)-2-aminopropan-1-ol for (R)-2-amino-3-methylbutan-1-ol. MS (ESI$^+$) m/z 329.0 (M+H); $^1$H NMR (500 MHz, DMSO-d$_6$/D$_2$O) δ 8.39 (d, J=8.2, 2H), 8.19 (dd, J=8.7, 3.6, 1H), 7.96 (t, J=9.0, 1H), 7.89 (d, J=8.4, 2H), 4.54 (s, 2H), 3.62 (dd, J=11.9, 6.2, 1H), 3.54-3.45 (m, 1H), 1.32 (d, J=6.7, 3H).

Example 83

(2R)-2-[({3-fluoro-6-[4-(trifluoromethyl)phenyl]pyridin-2-yl}methyl)amino]pentan-1-ol The title compound was prepared using procedure similar to that described for Example 28B, substituting Example 17A for Example 28A and (R)-2-aminopentan-1-ol for (R)-2-amino-3-methylbutan-1-ol. MS (ESI$^+$) m/z 357.0 (M+H); $^1$H NMR (500 MHz, DMSO-d$_6$/D$_2$O) δ 8.39 (d, J=8.2, 2H), 8.19 (dd, J=8.7, 3.6, 1H), 7.96 (t, J=9.0, 1H), 7.89 (d, J=8.4, 2H), 4.59-4.51 (m, 2H), 3.83 (dd, J=12.3, 3.3, 1H), 3.66 (dd, J=12.4, 5.7, 1H), 3.37-3.30 (m, 1H), 1.75-1.66 (m, 2H), 1.48-1.38 (m, 1H), 1.38-1.27 (m, 1H), 0.89 (t, J=7.3, 3H).

Example 84

(2R)-2-cyclohexyl-2-[({3-fluoro-6-[4-(trifluoromethyl)phenyl]pyridin-2-yl}methyl)amino]ethanol The title compound was prepared using procedure similar to that described for Example 28B, substituting Example 17A for Example 28A and (R)-2-amino-2-cyclohexylethanol for (R)-2-amino-3-methylbutan-1-ol. MS (ESI$^+$) m/z 397.1 (M+H); $^1$H NMR (500 MHz, DMSO-d$_6$/D$_2$O) δ 8.37 (d, J=8.2, 2H), 8.19 (dd, J=8.7, 3.6, 1H), 7.97 (t, J=9.0, 1H), 7.89 (d, J=8.4, 2H), 4.60 (dd, J=36.8, 15.4, 2H), 3.82 (dd, J=12.3, 3.6, 1H), 3.24-3.16 (m, 1H), 1.92-1.83 (m, 1H), 1.80-1.66 (m, 4H), 1.63 (d, J=11.9, 1H), 1.26-1.02 (m, 5H).

Example 85

(2R)-2-((3-fluoro-6-(4-(trifluoromethyl)phenyl)pyridin-2-yl)methylamino)-3,3-dimethylbutan-1-ol The title compound was prepared using procedure similar to that described for Example 28B, substituting Example 17A for Example 28A and (R)-2-amino-3,3-dimethylbutan-1-ol for (R)-2-amino-3-methylbutan-1-ol. MS (ESI$^+$) m/z 371.1 (M+H); $^1$H NMR (500 MHz, DMSO-d$_6$/D$_2$O) δ 8.35 (d, J=8.2, 2H), 8.20 (dd, J=8.7, 3.6, 1H), 7.98 (t, J=9.0, 1H), 7.89 (d, J=8.4, 2H), 4.80 (d, J=15.2, 1H), 4.55 (d, J=15.4, 1H), 3.86 (dd, J=12.3, 3.4, 1H), 3.05 (dd, J=6.5, 3.0, 1H), 1.02 (s, 9H).

Example 86

3-[({3-fluoro-6-[4-(trifluoromethyl)phenyl]pyridin-2-yl}methyl)amino]butan-2-ol

The title compound was prepared using procedure similar to that described for Example 28B, substituting Example 17A for Example 28A and 3-aminobutan-2-ol for (R)-2-amino-3-methylbutan-1-ol. MS (ESI$^+$) m/z 343.0 (M+H); $^1$H NMR (500 MHz, DMSO-d$_6$/D$_2$O) syn:anti=3:2 or 2:3 δ 8.42-8.35 (m, 2H), 8.23-8.16 (m, 1H), 7.99-7.93 (m, 1H), 7.92-7.86 (m, 2H), 4.60-4.46 (m, 2H), 4.17 (qd, J=6.4, 2.7, 0.4H), 3.38 (qd, J=6.7, 2.8, 0.4H), 3.27-3.18 (m, 0.6H), 1.30 (d, J=6.7, 1.8H), 1.27 (d, J=6.8, 1.2H), 1.21 (d, J=6.2, 1.8H), 1.15 (d, J=6.5, 1.2H).

Example 87

(2R)-2-({[5-fluoro-6'-(trifluoromethyl)-2,3'-bipyridin-6-yl]methyl}amino)pentan-1-ol The title compound was prepared using procedure similar to that described for Example 28B, substituting (R)-2-aminopentan-1-ol for (R)-2-amino-3-methylbutan-1-ol. MS (ESI$^+$) m/z 358.0 (M+H); $^1$H NMR (500 MHz, DMSO-d$_6$/D$_2$O) δ 9.57 (d, J=1.9, 1H), 8.79 (dd, J=8.2, 2.0, 1H), 8.28 (dd, J=8.7, 3.6, 1H), 8.07 (d, J=8.3, 1H), 8.01 (t, J=9.0, 1H), 4.61-4.52 (m, 2H), 3.83 (dd, J=12.3, 3.3, 1H), 3.66 (dd, J=12.4, 5.6, 1H), 3.37-3.30 (m, 1H), 1.77-1.65 (m, 2H), 1.49-1.38 (m, 1H), 1.38-1.27 (m, 1H), 0.90 (t, J=7.3, 3H).

Example 88

(2R)-2-cyclohexyl-2-({[5-fluoro-6'-(trifluoromethyl)-2,3'-bipyridin-6-yl]methyl}amino)ethanol The title compound was prepared using procedure similar to that described for Example 28B, substituting (R)-2-amino-2-cyclohexylethanol for (R)-2-amino-3-methylbutan-1-ol. MS (ESI$^+$) m/z 398.0 (M+H); $^1$H NMR (500 MHz, DMSO-d$_6$/D$_2$O) δ 9.55 (d, J=1.9, 1H), 8.78 (dd, J=8.2, 2.0, 1H), 8.28 (dd, J=8.7, 3.6, 1H), 8.08 (d, J=8.3, 1H), 8.01 (t, J=9.0, 1H), 4.62 (q, J=15.5, 2H), 3.82 (dd, J=12.3, 3.6, 1H), 3.23-3.16 (m, 1H), 1.92-1.82 (m, 1H), 1.80-1.68 (m, 4H), 1.63 (d, J=11.6, 1H), 1.27-1.01 (m, 5H).

Example 89

(2R)-2-({[5-fluoro-6'-(trifluoromethyl)-2,3'-bipyridin-6-yl]methyl}amino)-3,3-dimethylbutan-1-ol The title compound was prepared using procedure similar to that described for Example 28B, substituting (R)-2-amino-3,3-dimethylbutan-1-ol for (R)-2-amino-3-methylbutan-1-ol. MS (ESI$^+$) m/z 372.0 (M+H); $^1$H NMR (500 MHz, DMSO-d$_6$/D$_2$O) δ 9.52 (d, J=1.8, 1H), 8.76 (dd, J=8.2, 2.0, 1H), 8.29 (dd, J=8.7, 3.6, 1H), 8.08 (d, J=8.3, 1H), 8.03 (t, J=9.0, 1H), 4.82 (d, J=15.1, 1H), 4.56 (d, J=15.4, 1H), 3.86 (dd, J=12.4, 3.4, 1H), 3.04 (dd, J=6.7, 3.3, 1H), 1.02 (s, 9H).

Example 90

3-({[5-fluoro-6'-(trifluoromethyl)-2,3'-bipyridin-6-yl]methyl}amino)butan-2-ol

The title compound was prepared using procedure similar to that described for Example 28B, substituting 3-aminobutan-2-ol for (R)-2-amino-3-methylbutan-1-ol. MS (ESI$^+$) m/z 344.0 (M+H); $^1$H NMR (500 MHz, DMSO-d$_6$/D$_2$O) syn:anti=3:2 or 2:3 δ 9.60-9.54 (m, 1H), 8.83-8.76 (m, 1H), 8.31-8.25 (m, 1H), 8.10-8.04 (m, 1H), 8.04-7.97 (m, 1H), 4.61-4.48 (m, 2H), 4.16 (qd, J=6.2, 2.5, 0.4H), 3.38 (qd, J=6.7, 2.8, 0.4H), 3.26-3.18 (m, 0.6H), 1.30 (d, J=6.7, 1.8H), 1.27 (d, J=6.8, 1.2H), 1.21 (d, J=6.2, 1.8H), 1.15 (d, J=6.5, 1.2H).

Example 91

(2R)-3-methyl-2-[({2-[4-(trifluoromethyl)phenyl]pyrimidin-4-yl}methyl)amino]butan-1-ol Example 91A 4-methyl-2-[4-(trifluoromethyl)phenyl]pyrimidine A 20 mL microwave vial was charged with 4-(trifluoromethyl)phenylboronic acid (813 mg, 4.28 mmol), 2-chloro-4-methylpyrimidine (500 mg, 3.89 mmol), bis(triphenylphosphine)palladium(II) chloride (136 mg, 0.194 mmol), and K$_2$CO$_3$ (1075 mg, 7.78 mmol), followed by the addition of DME (9.0 mL), water (3.86 mL) and ethanol (2.57 mL). The mixture was microwaved at 120° C. for 10 minutes. The reaction was repeated for three more batches. To the combined reaction mixtures was added 300 mL EtOAc, washed with 300 mL water and 300 mL brine, dried over Na$_2$SO$_4$, filtered, and concentrated. The residue was chromatographed on a Grace Reveleris 80 g column, eluted with 0-40% EtOAc in Hexanes (35 mL/min) to obtain the title compound (3.385 g, 14.21 mmol, 91% yield) as a light yellow solid. MS (ESI$^+$) m/z 239.2 (M+H); $^1$H NMR (300 MHz, DMSO-d$_6$) δ 8.81 (d, J=5.1, 1H), 8.59 (d, J=8.1, 2H), 7.89 (d, J=8.3, 2H), 7.42 (d, J=5.1, 1H), 2.58 (s, 3H).

Example 91B

2-[4-(trifluoromethyl)phenyl]pyrimidine-4-carbaldehyde

A 5 mL microwave vial was charged with Example 91A (500 mg, 2.099 mmol), selenium dioxide (470 mg, 4.24 mmol), and dioxane (5.0 mL). The white mixture was microwaved at 160° C. for 30 minutes. The reaction mixture was filtered and concentrated to obtain the title compound as a yellow solid. MS (DCI$^+$) m/z 252.1 (M+NH$_4$—H$_2$O); $^1$H NMR (300 MHz, DMSO-d$_6$) δ 10.07 (d, J=0.6, 1H), 9.29 (dd, J=4.8, 0.6, 1H), 8.68 (d, J=8.1, 2H), 7.97 (d, J=8.2, 2H), 7.90 (d, J=4.8, 1H).

Example 91C (2R)-3-methyl-2-[({2-[4-(trifluoromethyl)phenyl]pyrimidin-4-yl}methyl)amino]butan-1-ol The title compound was prepared using procedure similar to that described for Example 28B, substituting Example 91B for Example 28A. MS (ESI$^+$) m/z 340.1 (M+H); $^1$H NMR (300 MHz, DMSO-d$_6$) δ 8.89 (d, J=5.1, 1H), 8.60 (d, J=8.1, 2H), 7.90 (d, J=8.2, 2H), 7.63 (d, J=5.1, 1H), 4.45 (t, J=5.3, 1H), 4.03-3.90 (m, 2H), 3.54-3.42 (m, 1H), 3.41-3.33 (m, 1H), 2.38-2.28 (m, 2H), 1.90-1.76 (m, 1H), 0.90 (t, J=6.6, 6H).

Example 92

(2R)-2-({[6-(4,4-difluoropiperidin-1-yl)-3-fluoropyridin-2-yl]methyl}amino)-3-methylbutan-1-ol The title compound was prepared using procedure similar to that described for Example 70, substituting 4,4-difluoropiperidine for 1,2,3,4-tetrahydroisoquinoline. MS (ESI$^+$) m/z 332.0 (M+H); $^1$H NMR (400 MHz, pyridine-d$_5$) δ 7.37 (t, J=9.0, 1H), 6.69 (dd, J=9.1, 2.7, 1H), 4.15 (ddd, J=34.7, 14.0, 2.2, 2H), 3.99 (dd, J=10.7, 4.4, 1H), 3.85 (dd, J=10.7, 7.0, 1H), 3.74-3.67 (m, 4H), 2.78 (dt, J=7.0, 4.7, 1H), 2.17-2.07 (m, 1H), 2.05-1.92 (m, 4H), 1.05 (d, J=6.9, 6H).

Example 93

(2R)-2-({[3-fluoro-6-(5-fluoro-1,3-dihydro-2H-isoindol-2-yl)pyridin-2-yl]methyl}amino)-3-methylbutan-1-ol The title compound was prepared using procedure similar to that described for Example 70, substituting 5-fluoroisoindoline for 1,2,3,4-tetrahydroisoquinoline. MS (ESI$^+$) m/z 348.1 (M+H); $^1$H NMR (400 MHz, pyridine-d$_5$) δ 7.40 (t, J=9.0, 1H), 7.10-6.99 (m, 2H), 6.30 (dd, J=8.9, 2.7, 1H), 4.73-4.56 (m, 4H), 4.21 (qd, J=13.9, 2.2, 2H), 4.02 (dd, J=10.7, 4.5, 1H), 3.89 (dd, J=10.7, 6.9, 1H), 2.82 (dt, J=6.8, 4.7, 1H), 2.23-2.12 (m, 1H), 1.09 (dd, J=6.9, 2.3, 6H).

Example 94

(2R)-2-({[3-fluoro-6-(4-fluoro-1,3-dihydro-2H-isoindol-2-yl)pyridin-2-yl]methyl}amino)-3-methylbutan-1-ol The title compound was prepared using procedure similar to that described for Example 70, substituting 4-fluoroisoindoline for 1,2,3,4-tetrahydroisoquinoline. MS (ESI$^+$) m/z 348.1 (M+H); $^1$H NMR (400 MHz, pyridine-d$_5$) δ 7.41 (t, J=9.0, 1H), 7.29-7.23 (m, 1H), 7.08-6.99 (m, 2H), 6.33 (dd, J=8.9, 2.7, 1H), 4.83-4.65 (m, 4H), 4.20 (qd, J=13.9, 2.2, 2H), 4.01 (dd, J=10.7, 4.5, 1H), 3.88 (dd, J=10.7, 6.9, 1H), 2.81 (dt, J=6.8, 4.7, 1H), 2.22-2.10 (m, 1H), 1.08 (dd, J=6.9, 2.0, 6H).

Example 95

(2R)-2-({[6-(4-chloro-1,3-dihydro-2H-isoindol-2-yl)-3-fluoropyridin-2-yl]methyl}amino)-3-methylbutan-1-ol The title compound was prepared using procedure similar to that described for Example 70, substituting 4-chloroisoindoline for 1,2,3,4-tetrahydroisoquinoline. MS (ESI$^+$) m/z 364.0 (M+H); $^1$H NMR (400 MHz, pyridine-d$_5$) δ 7.42 (t, J=9.0, 1H), 7.29 (dd, J=7.8, 0.7, 1H), 7.13 (dd, J=7.5, 0.6, 1H), 6.33 (dd, J=8.9, 2.7, 1H), 4.80-4.68 (m, 4H), 4.22 (qd, J=14.0, 2.3, 2H), 4.01 (dd, J=10.8, 4.5, 1H), 3.89 (dd, J=10.7, 6.9, 1H), 2.83 (dt, J=6.7, 4.8, 1H), 2.22-2.12 (m, 1H), 1.09 (dd, J=6.9, 2.6, 6H).

Example 96

(2R)-2-[({3-fluoro-6-[5-(trifluoromethyl)-1,3-dihydro-2H-isoindol-2-yl]pyridin-2-yl}methyl)amino]-3-methylbutan-1-ol The title compound was prepared using procedure similar to that described for Example 70, substituting 5-(trifluoromethyl)isoindoline for 1,2,3,4-tetrahydroisoquinoline. MS (ESI⁺) m/z 398.0 (M+H); ¹H NMR (400 MHz, pyridine-d₅) δ 7.42 (t, J=9.0, 1H), 7.34 (d, J=7.7, 1H), 6.35 (dd, J=8.9, 2.7, 1H), 4.81-4.66 (m, 4H), 4.21 (qd, J=14.0, 2.2, 2H), 4.03 (dd, J=10.7, 4.4, 1H), 3.90 (dd, J=10.7, 7.0, 1H), 2.83 (dt, J=6.9, 4.7, 1H), 2.22-2.12 (m, 1H), 1.10 (dd, J=6.9, 2.4, 6H).

Example 97

(2R)-2-({[3-fluoro-6-(5-fluoro-3,4-dihydroisoquinolin-2(1H)-yl)pyridin-2-yl]methyl}amino)-3-methylbutan-1-ol The title compound was prepared using procedure similar to that described for Example 70, substituting 5-fluoro-1,2,3,4-tetrahydroisoquinoline for 1,2,3,4-tetrahydroisoquinoline. MS (ESI⁺) m/z 362.1 (M+H); ¹H NMR (400 MHz, pyridine-d₅) δ 7.37 (t, J=9.0, 1H), 7.18-7.10 (m, 1H), 7.03-6.94 (m, 2H), 6.65 (dd, J=9.1, 2.7, 1H), 4.77-4.67 (m, 2H), 4.15 (ddd, J=33.3, 14.0, 2.2, 2H), 3.99 (dd, J=10.7, 4.4, 1H), 3.86 (dd, J=10.7, 6.9, 1H), 3.80 (t, J=6.0, 2H), 2.83 (t, J=5.9, 2H), 2.78 (dt, J=6.9, 4.7, 1H), 2.18-2.08 (m, 1H), 1.06 (d, J=6.9, 6H).

Example 98

(2R)-2-({[3-fluoro-6-(7-fluoro-3,4-dihydroisoquinolin-2(1H)-yl)pyridin-2-yl]methyl}amino)-3-methylbutan-1-ol The title compound was prepared using procedure similar to that described for Example 70, substituting 7-fluoro-1,2,3,4-tetrahydroisoquinoline for 1,2,3,4-tetrahydroisoquinoline. MS (ESI⁺) m/z 362.1 (M+H); ¹H NMR (400 MHz, pyridine-d₅) δ 7.37 (t, J=9.0, 1H), 7.09-7.00 (m, 1H), 6.97 (d, J=9.1, 1H), 6.61 (dd, J=9.1, 2.7, 1H), 4.77-4.64 (m, 2H), 4.16 (ddd, J=34.2, 14.0, 2.3, 2H), 4.00 (dd, J=10.7, 4.4, 1H), 3.87 (dd, J=10.7, 7.0, 1H), 3.75 (t, J=5.9, 2H), 2.83-2.72 (m, 3H), 2.19-2.07 (m, 1H), 1.06 (d, J=6.9, 6H).

Example 99

(2R)-2-({[3-fluoro-6-(8-fluoro-3,4-dihydroisoquinolin-2(1H)-yl)pyridin-2-yl]methyl}amino)-3-methylbutan-1-ol The title compound was prepared using procedure similar to that described for Example 70, substituting 8-fluoro-1,2,3,4-tetrahydroisoquinoline for 1,2,3,4-tetrahydroisoquinoline. MS (ESI⁺) m/z 362.1 (M+H); ¹H NMR (400 MHz, pyridine-d₅) δ 7.37 (t, J=9.0, 1H), 7.14 (dd, J=13.8, 7.8, 1H), 7.02-6.94 (m, 1H), 6.90 (d, J=7.6, 1H), 6.63 (dd, J=9.1, 2.7, 1H), 4.72 (s, 2H), 4.23-4.10 (m, 2H), 3.99 (dd, J=10.7, 4.5, 1H), 3.87 (dd, J=10.7, 6.7, 1H), 3.79 (t, J=5.8, 2H), 2.87-2.74 (m, 3H), 2.21-2.09 (m, 1H), 1.07 (dd, J=6.9, 1.9, 6H).

Example 100

(2R)-2-({[6-(5-chloro-3,4-dihydroisoquinolin-2(1H)-yl)-3-fluoropyridin-2-yl]methyl}amino)-3-methylbutan-1-ol The title compound was prepared using procedure similar to that described for Example 70, substituting 5-chloro-1,2,3,4-tetrahydroisoquinoline for 1,2,3,4-tetrahydroisoquinoline. MS (ESI⁺) m/z 378.1 (M+H); ¹H NMR (400 MHz, pyridine-d₅) δ 7.36 (t, J=9.0, 1H), 7.32-7.25 (m, 1H), 7.17-7.07 (m, 2H), 6.66 (dd, J=9.1, 2.7, 1H), 4.71 (s, 2H), 4.15 (ddd, J=34.8, 14.0, 2.2, 2H), 4.00 (dd, J=10.7, 4.4, 1H), 3.87 (dd, J=10.7, 6.9, 1H), 3.80 (t, J=6.0, 2H), 2.85 (t, J=5.9, 2H), 2.78 (dt, J=6.9, 4.7, 1H), 2.19-2.08 (m, 1H), 1.06 (d, J=6.9, 6H).

Example 101

(2R)-2-({[6-(6-chloro-3,4-dihydroisoquinolin-2(1H)-yl)-3-fluoropyridin-2-yl]methyl}amino)-3-methylbutan-1-ol The title compound was prepared using procedure similar to that described for Example 70, substituting 6-chloro-1,2,3,4-tetrahydroisoquinoline for 1,2,3,4-tetrahydroisoquinoline. MS (ESI⁺) m/z 378.0 (M+H); ¹H NMR (400 MHz, pyridine-d₅) δ 7.47-7.34 (m, 3H), 7.13-7.06 (m, 1H), 6.60 (dd, J=9.0, 2.7, 1H), 4.70-4.59 (m, 2H), 4.16 (ddd, J=33.8, 14.0, 2.2, 2H), 4.00 (dd, J=10.7, 4.4, 1H), 3.87 (dd, J=10.7, 6.9, 1H), 3.75 (t, J=5.9, 2H), 2.82-2.72 (m, 3H), 2.19-2.08 (m, 1H), 1.06 (d, J=6.9, 6H).

Example 102

(2R)-2-[({3-fluoro-6-[5-(trifluoromethyl)-3,4-dihydroisoquinolin-2(1H)-yl]-pyridin-2-yl}methyl)amino]-3-methylbutan-1-ol The title compound was prepared using procedure similar to that described for Example 70, substituting 5-(trifluoromethyl)-1,2,3,4-tetrahydroisoquinoline for 1,2,3,4-tetrahydroisoquinoline. MS (ESI⁺) m/z 412.0 (M+H); ¹H NMR (400 MHz, pyridine-d₅) δ 7.53 (d, J=7.6, 1H), 7.39 (t, J=9.0, 1H), 7.35 (d, J=7.6, 1H), 7.25 (d, J=7.5, 1H), 6.64 (dd, J=9.0, 2.7, 1H), 4.81-4.70 (m, 2H), 4.17 (ddd, J=36.5, 14.0, 2.2, 2H), 4.01 (dd, J=10.7, 4.4, 1H), 3.87 (dd, J=10.7, 7.0, 1H), 3.76 (t, J=5.9, 2H), 3.02 (t, J=5.9, 2H), 2.79 (dt, J=7.0, 4.7, 1H), 2.19-2.08 (m, 1H), 1.07 (d, J=6.9, 6H).

Example 103

(2R)-2-[({3-fluoro-6-[7-(trifluoromethyl)-3,4-dihydroisoquinolin-2(1H)-yl]-pyridin-2-yl}methyl)amino]-3-methylbutan-1-ol The title compound was prepared using procedure similar to that described for Example 70, substituting 7-(trifluoromethyl)-1,2,3,4-tetrahydroisoquinoline for 1,2,3,4-tetrahydroisoquinoline. MS (ESI⁺) m/z 412.1 (M+H); ¹H NMR (400 MHz, pyridine-d₅) δ 7.49 (s, 1H), 7.45 (d, J=7.9, 1H), 7.39 (t, J=9.0, 1H), 7.17 (d, J=7.9, 1H), 6.67 (dd, J=9.0, 2.7, 1H), 4.75 (s, 2H), 4.17 (ddd, J=33.2, 14.0, 2.2, 2H), 4.00 (dd, J=10.7, 4.4, 1H), 3.86 (dd, J=10.7, 7.0, 1H), 3.79 (t, J=6.0, 2H), 2.83 (t, J=5.8, 2H), 2.79 (dt, J=7.0, 4.7, 1H), 2.19-2.07 (m, 1H), 1.06 (d, J=6.9, 6H).

Example 104

(2R)-2-({[6-(4,4-dimethyl-3,4-dihydroisoquinolin-2(1H)-yl)-3-fluoropyridin-2-yl]methyl}amino)-3-methylbutan-1-ol The title compound was prepared using procedure similar to that described for Example 70, substituting 4,4-dimethyl-1,2,3,4-tetrahydroisoquinoline for 1,2,3,4-tetrahydroisoquinoline. MS (ESI⁺) m/z 372.1 (M+H); ¹H NMR (400 MHz, pyridine-d₅) δ 7.39 (t, J=9.0, 1H), 7.34-7.24 (m, 4H), 6.64 (dd, J=9.0, 2.6, 1H), 4.75 (s, 2H), 4.18 (ddd, J=29.2, 14.1, 2.3, 2H), 4.00 (dd, J=10.6, 4.5, 1H), 3.88 (dd, J=10.7, 6.9, 1H), 3.65 (s, 2H), 2.81 (dt, J=6.8, 4.8, 1H), 2.19-2.10 (m, 1H), 1.31 (s, 6H), 1.08 (d, J=6.9, 6H).

Example 105

(3R)-3-[({3-fluoro-6-[4-(trifluoromethyl)phenyl]pyridin-2-yl}methyl)amino]-2,4-dimethylpentan-2-ol Example 105A (R)-methyl 2-(tert-butoxycarbonylamino)-3-methylbutanoate (R)-methyl 2-amino-3-methylbutanoate hydrochloride (4.0 g, 23.86 mmol) was dissolved in THF (60 mL) and methanol (15 mL). The colorless solution was chilled to 0° C., followed by the addition of sodium bicarbonate (6.01 g, 71.6 mmol) in one portion, immediately followed by addition of solid BOC-anhydride (7.81 g, 35.8 mmol). The reaction mixture was allowed to warm to ambient temperature and left stirring overnight, quenched with 200 mL water, and extracted twice with 200 mL MTBE. The organic phase was washed with 200 mL saturated NaHCO₃ solution and 200 mL brine, dried over Na₂SO₄, filtered, and concentrated. The residue was chromatographed on a Grace Reveleris 120 g column, eluted with 0-30% EtOAc in Hexanes (35 mL/min) to obtain the title compound (5.265 g, 22.76 mmol, 95% yield) as a colorless oil. MS (DCI⁺) m/z 249.2 (M+NH₄); ¹H NMR (300 MHz, DMSO-d₆) δ 7.15 (d, J=8.1, 1H), 3.83 (dd, J=8.0, 6.8, 1H), 3.62 (s, 3H), 2.06-1.91 (m, 1H), 1.38 (s, 9H), 0.86 (dd, J=6.8, 3.2, 6H).

Example 105B (R)-tert-butyl 2-hydroxy-2,4-dimethylpentan-3-ylcarbamate

Example 105A (3.0 g, 12.97 mmol) was dissolved in THF (50 mL) and cooled to 0° C. Methyl magnesium bromide (18.0 mL, 54.0 mmol, 3.0 M in diethyl ether) was carefully added via syringe. The reaction was allowed to warm to ambient temperature and left stirring overnight. The cloudy mixture was chilled to 0° C., quenched cautiously with methanol (3.0 mL, 74.0 mmol), followed by the addition of 200 mL saturated NH₄Cl solution, and extracted twice with 200 mL MTBE. The organic phase was washed with 200 mL brine, dried over Na₂SO₄, filtered, and concentrated to obtain the title compound (3.070 g, 13.27 mmol, 102% yield) as a colorless oil. MS (DCI⁺) m/z 232.2 (M+H); ¹H NMR (300 MHz, DMSO-d₆) δ 6.00 (d, J=10.4, 1H), 4.16 (s, 1H), 3.20 (dd, J=10.4, 3.3, 1H), 2.08-1.97 (m, 1H), 1.39 (s, 9H), 1.10 (s, 3H), 1.03 (s, 3H), 0.83 (dd, J=6.7, 5.4, 6H).

Example 105C (R)-3-amino-2,4-dimethylpentan-2-ol hydrochloride

To Example 105B (3.070 g, 13.27 mmol) was added hydrogen chloride (33 mL, 132 mmol, 4.0 M in dioxane). The reaction mixture was stirred for 90 minutes at ambient temperature, concentrated to an orange oil, and triturated with diethyl ether to give the title compound (1.988 g, 11.86 mmol, 89% yield) as a tan solid. MS (DCI⁺) m/z 132.0 (M+H); ¹H NMR (300 MHz, MeOH-D₄) δ 2.86 (d, J=3.3, 1H), 2.19-2.07 (m, 1H), 1.33 (s, 3H), 1.26 (s, 3H), 1.10 (d, J=7.1, 3H), 1.05 (d, J=7.0, 3H).

Example 105D (3R)-3-[({3-fluoro-6-[4-(trifluoromethyl)phenyl]pyridin-2-yl}methyl)amino]-2,4-dimethylpentan-2-ol Example 17A (800 mg, 2.97 mmol) and Example 105C (498 mg, 2.97 mmol) were dissolved in methanol (20 mL) and triethylamine (0.453 mL, 3.27 mmol). The yellow solution was stirred at ambient temperature for 90 minutes, followed by the addition of sodium borohydride (247 mg, 6.54 mmol). The reaction mixture was stirred over the weekend at ambient temperature, quenched with 100 mL 1.0 N NaOH, and extracted twice with 100 mL dichloromethane, dried over Na₂SO₄, filtered, and concentrated to obtain (R)-3-[({3-fluoro-6-[4-(trifluoromethyl)phenyl]pyridin-2-yl}methylene)amino]-2,4-dimethylpentan-2-ol (1.147 g, 3.00 mmol) as an orange oil. The imine (1.147 g, 3.00 mmol) in methanol (20 mL) was added to Raney Nickel (1.147 g) in a 50 mL pressure bottle. The mixture was pressurized with hydrogen (30 psi), and stirred for 48 hours at ambient temperature. The mixture was filtered through a nylon membrane, concentrated, and chromatographed on a Grace Reveleris 40 g column, eluted with 0-20% EtOAc in dichloromethane (30 mL/min) to provide the title compound (0.629 g, 1.636 mmol, 54.6% yield) as a colorless oil. MS (ESI⁺) m/z 385.0 (M+H); ¹H NMR (300 MHz, DMSO-d₆) δ 8.29 (d, J=8.2, 2H), 8.06 (dd, J=8.7, 3.7, 1H), 7.92-7.78 (m, 3H), 4.25 (s, 1H), 4.16-3.99 (m, 2H), 2.36 (q, J=6.2, 1H), 2.26 (dd, J=5.9, 2.4, 1H), 2.03-1.89 (m, 1H), 1.11 (d, J=9.2, 6H), 0.93 (dd, J=6.8, 5.8, 6H).

Example 106

(3R)-3-({[5-fluoro-6'-(trifluoromethyl)-2,3'-bipyridin-6-yl]methyl}amino)-2,4-dimethylpentan-2-ol Example 28A (640 mg, 2.369 mmol) and Example 105C (397 mg, 2.369 mmol) were dissolved in methanol (20 mL) and triethylamine (0.361 mL, 2.61 mmol). The yellow solution was stirred at ambient temperature for 1 hour, followed by the addition of sodium borohydride (197 mg, 5.21 mmol). The reaction mixture was stirred over the weekend at ambient temperature, quenched with 100 mL 1.0 N NaOH, extracted twice with 100 mL dichloromethane, dried over Na₂SO₄, filtered, and concentrated to obtain (R)-3-0Ξ-fluoro-6'-(trifluoromethyl)-2,3'-bipyridin-6-yl]methylene}amino)-2,4-dimethylpentan-2-ol (705 mg, 1.839 mmol) as a yellow oil. The imine (705 mg, 1.839 mmol) in methanol (20 mL) was added to Raney Nickel (1.410 g) in a 50 mL pressure bottle. The mixture was pressurized with hydrogen (30 psi), and stirred for 32 hours at ambient temperature. The mixture was filtered through a nylon membrane, concentrated, and chromatographed on a Grace Reveleris 40 g column, eluted with 0-25% EtOAc in dichloromethane (30 mL/min) to provide the title compound (352 mg, 0.913 mmol, 49.7% yield) as a colorless oil. MS (MTBE) m/z 386.0 (M+H); ¹H NMR (300 MHz, DMSO-d₆) δ 9.45 (d, J=2.0, 1H), 8.70 (dd, J=8.2, 1.9, 1H), 8.17 (dd, J=8.6, 3.7, 1H), 8.05 (d, J=8.3, 1H), 7.94-7.84 (m, 1H), 4.29 (s, 1H), 4.18-3.97 (m, 2H), 2.40 (dd, J=12.6, 6.4, 1H), 2.26 (dd, J=5.7, 2.4, 1H), 2.01-1.89 (m, 1H), 1.11 (d, J=9.4, 6H), 0.93 (t, J=6.7, 6H).

Example 107

(3R)-3-[({3-fluoro-6-[4-(trifluoromethyl)phenyl]pyridin-2-yl}methyl)amino]-4-methylpentan-2-ol

Example 107A tert-butyl (3R)-2-hydroxy-4-methylpentan-3-ylcarbamate (R)-tert-butyl 3-methyl-1-oxobutan-2-ylcarbamate (2.5 g, 12.42 mmol) was dissolved in THF (50 mL) and cooled to 0° C. Methyl magnesium bromide (17.0 mL, 51.0 mmol, 3.0 M in diethyl ether) was carefully added via syringe. The reaction was allowed to warm to ambient temperature and left stirring overnight. The cloudy mixture was chilled to 0° C., quenched with methanol (3.0 mL, 74.0 mmol), followed by the addition of 200 mL saturated $NH_4Cl$ solution, and extracted twice with 200 mL MTBE. The organic phase was washed with 200 mL brine, dried over $Na_2SO_4$, filtered, and concentrated to provide the title compound (2.484 g, 11.43 mmol, 92% yield) as a yellow oil. MS (DCI+) m/z 218.1 (M+H).

Example 107B (3R)-3-amino-4-methylpentan-2-ol hydrochloride

To Example 107A (2.484 g, 11.43 mmol) was added hydrogen chloride (29 mL, 116 mmol, 4.0 M in dioxane) and stirred for 90 minutes at ambient temperature. The reaction mixture was concentrated to an orange oil, and triturated with diethyl ether to provide the title compound (1.783 g, 11.60 mmol, 102% yield) as a sticky, tan solid. MS ($DCI^+$) m/z 118.1 (M+H).

Example 107C (3R)-3-[({3-fluoro-6-[4-(trifluoromethyl)phenyl]pyridin-2-yl}methyl)amino]-4-methylpentan-2-ol Example 17A (767 mg, 2.85 mmol) and Example 107B (460 mg, 2.99 mmol) were dissolve in methanol (20 mL) and triethylamine (0.434 mL, 3.13 mmol). The orange solution was stirred at ambient temperature for 2 hours and 20 minutes, followed by the addition of sodium borohydride (237 mg, 6.27 mmol). After 4 hours, additional sodium borohydride (237 mg, 6.27 mmol) was added. The reaction was stirred overnight at ambient temperature, quenched with 100 mL 1.0 N NaOH, and extracted twice with 100 mL dichloromethane. The combined organic phase was dried over $Na_2SO_4$, filtered, and concentrated to provide (3R)-3-[({3-fluoro-6-[4-(trifluoromethyl)phenyl]pyridin-2-yl}methylene)amino]-4-methylpentan-2-ol (1.009 g, 2.74 mmol) as an orange oil. The imine (1.009 g, 2.74 mmol) in THF (40 mL) was added to Raney Nickel (1.009 g) in a 250 mL stainless steel pressure bottle. The mixture was pressurized with hydrogen (30 psi), and stirred for 20 hours at ambient temperature. The mixture was filtered through a nylon membrane, concentrated, and chromatographed on a Grace Reveleris 40 g column, eluted with 0-30% EtOAc in dichloromethane (30 mL/min) to provide the title compound (0.533 g, 1.439 mmol, 52.5% yield) as a yellow oil, a 3:1 mix of diastereomers by proton NMR. MS ($ESI^+$) m/z 371.1 (M+H); $^1H$ NMR (300 MHz, DMSO-$d_6$) δ 8.29 (d, J=8.3, 2H), 8.05 (dd, J=8.6, 3.7, 1H), 7.89-7.77 (m, 3H), 4.43 (d, J=4.8, 0.75H), 4.38 (d, J=5.2, 0.25H), 4.14-3.95 (m, 2H), 3.71-3.58 (m, 1H), 2.40-2.29 (m, 0.75H), 2.25-2.17 (m, 0.25H), 2.15-2.06 (m, 1H), 1.93-1.73 (m, 1H), 1.11-1.04 (m, 3H), 0.96-0.79 (m, 6H).

Example 108

(3R)-3-({[5-fluoro-6'-(trifluoromethyl)-2,3'-bipyridin-6-yl]methyl}amino)-4-methylpentan-2-ol Example 28A (399 mg, 1.477 mmol) and Example 107B (238 mg, 1.551 mmol) were dissolved in methanol (20 mL) and triethylamine (0.225 mL, 1.624 mmol). The orange solution was stirred at ambient temperature for 1 hour and 55 minutes, followed by the addition of sodium borohydride (123 mg, 3.25 mmol). After 4 hours, additional sodium borohydride (123 mg, 3.25 mmol) was added, and the reaction was stirred overnight at ambient temperature, quenched with 100 mL 1.0 N NaOH, and extracted twice with 100 mL dichloromethane. The combined organic phase was dried over $Na_2SO_4$, filtered, and concentrated to provide (3R)-3-({[5-fluoro-6'-(trifluoromethyl)-2,3'-bipyridin-6-yl]methylene}amino)-4-methylpentan-2-ol (500 mg, 1.354 mmol) as an orange oil. The imine (500 mg, 1.354 mmol) in methanol (20 mL) was added to 5% palladium on carbon (100 mg) in a 250 mL stainless steel pressure bottle. The mixture was pressurized with hydrogen (30 psi), and stirred for 18 hours at ambient temperature. The mixture was filtered through a nylon membrane, concentrated to a yellow oil, and chromatographed on a Grace Reveleris 40 g column, eluted with 0-50% EtOAc in dichloromethane (30 mL/min) to provide the title compound (250 mg, 0.673 mmol, 49.7% yield) as a yellow oil, a 3:1 mix of diastereomers by proton NMR. MS ($ESI^+$) m/z 372.0 (M+H); $^1H$ NMR (300 MHz, MeOH-$D_4$) δ 9.39 (d, J=1.8, 1H), 8.71-8.64 (m, 1H), 8.02 (dd, J=8.6, 3.6, 1H), 7.92 (d, J=8.3, 1H), 7.76-7.66 (m, 1H), 4.27-4.04 (m, 2H), 3.95-3.86 (m, 0.25H), 3.83-3.73 (m, 0.75H), 2.37 (t, J=5.6, 0.25H), 2.27 (dd, J=6.1, 4.6, 0.75H), 2.00-1.88 (m, 1H), 1.25-1.18 (m, 3H), 1.08-1.01 (m, 3H), 1.00-0.93 (m, 3H).

Example 109

(2R)-2-({[3-fluoro-6'-(trifluoromethyl)-2,3'-bipyridin-6-yl]methyl}amino)-3-methylbutan-1-ol

Example 109A 3-fluoro-6-methyl-6'-(trifluoromethyl)-2,3'-bipyridine

A 20 mL microwave vial was charged with 6-(trifluoromethyl)pyridin-3-ylboronic acid (553 mg, 2.89 mmol), 2-bromo-3-fluoro-6-methylpyridine (500 mg, 2.63 mmol), bis(triphenylphosphine)palladium(II) chloride (92 mg, 0.132 mmol), and $K_2CO_3$ (727 mg, 5.26 mmol), followed by the addition of DME (9.0 mL), water (3.86 mL) and ethanol (2.57 mL). The reaction mixture was heated in the microwave at 120° C. for 10 minutes. To the reaction mixture was added 200 mL EtOAc, and washed with 200 mL water and 200 mL brine. The organic phase was separated, dried over $Na_2SO_4$, filtered, and concentrated. The residue was chromatographed on a Grace Reveleris 40 g column, eluted with 0-40% EtOAc in Hexanes (25 mL/min) to provide the title compound (7.47 mmol, 95% yield) as a white solid. MS ($ESI^+$) m/z 257.1 (M+H); $^1H$ NMR (300 MHz, DMSO-$d_6$) δ 9.24 (s, 1H), 8.59-8.52 (m, 1H), 8.07 (d, J=8.2, 1H), 7.84 (dd, J=11.1, 8.5, 1H), 7.46 (dd, J=8.5, 3.5, 1H), 2.57 (s, 3H).

Example 109B 3-fluoro-6'-(trifluoromethyl)-2,3'-bipyridine-6-carbaldehyde

A 5 mL microwave vial was charged with Example 109A (480 mg, 1.874 mmol), selenium dioxide (430 mg, 3.88 mmol), and dioxane (5.0 mL) and water (0.5 mL). The white mixture was heated in the microwave at 210° C. for 3 hours. The reaction mixture was filtered and concentrated. The residue was chromatographed on a Grace Reveleris 40 g column, eluted with 0-40% EtOAc in Hexanes (25 mL/min) to provide the title compound (1.194 g, 4.42 mmol, 79% yield) as a white solid. MS (ESI$^+$) m/z 302.9 (M+H+MeOH); $^1$H NMR (300 MHz, DMSO-$d_6$) δ 10.06 (s, 1H), 9.34 (s, 1H), 8.66 (d, J=8.3, 1H), 8.26-8.06 (m, 3H).

Example 109C (2R)-2-({[3-fluoro-6'-(trifluoromethyl)-2,3'-bipyridin-6-yl]methyl}amino)-3-methylbutan-1-ol The title compound was prepared using procedure similar to that described for Example 28B, substituting Example 109B for Example 28A. MS (ESI$^+$) m/z 358.0 (M+H);
$^1$H NMR (300 MHz, DMSO-$d_6$) δ 9.27 (s, 1H), 8.57 (dd, J=8.3, 0.8, 1H), 8.08 (d, J=8.3, 1H), 7.91 (dd, J=11.1, 8.5, 1H), 7.67 (dd, J=8.6, 3.7, 1H), 4.44 (t, J=5.3, 1H), 3.93 (s, 2H), 3.47 (dt, J=9.9, 4.9, 1H), 3.39-3.33 (m, 1H), 2.37-2.21 (m, 2H), 1.92-1.74 (m, 1H), 0.88 (t, J=6.9, 6H).

Example 110

(2R)-2-({[5-chloro-6'-(trifluoromethyl)-2,3'-bipyridin-6-yl]methyl}amino)-3-methylbutan-1-ol Example 110A 5-chloro-6'-(trifluoromethyl)-2,3'-bipyridine-6-carbaldehyde Nitrogen was bubbled through a mixture of 6-(trifluoromethyl)pyridin-3-ylboronic acid (828 mg, 4.34 mmol), 6-bromo-3-chloropicolinaldehyde (956 mg, 4.34 mmol), Na$_2$CO$_3$ (919 mg, 8.67 mmol), DME (20 mL) and water (10 mL) for 35 minutes, followed by the addition of Pd(Ph$_3$P)$_4$ (75 mg, 0.065 mmol). Nitrogen for bubbled through the mixture for 10 minutes. The reaction mixture was heated overnight at 75° C., after which it was cooled to room temperature, followed by the addition of 200 mL EtOAc and washing with 200 mL water and 200 mL brine. The organic phase was separated, dried over Na$_2$SO$_4$, filtered, and concentrated. The residue was chromatographed on a Grace Reveleris 40 g column, eluted with 0-50% EtOAc in Heptane (25 mL/min) to provide the title compound (715 mg, 2.494 mmol, 57.5% yield) as a yellow solid. MS (ESI$^+$) m/z 319.0 (M+H+MeOH); $^1$H NMR (300 MHz, DMSO-$d_6$) δ 10.21 (s, 1H), 9.52 (d, J=1.9, 1H), 8.82 (dd, J=8.3, 1.8, 1H), 8.48 (d, J=8.5, 1H), 8.34 (d, J=8.6, 1H), 8.11 (d, J=8.3, 1H).

Example 110B (2R)-2-({[5-chloro-6'-(trifluoromethyl)-2,3'-bipyridin-6-yl]methyl}amino)-3-methylbutan-1-ol The title compound was prepared using procedure similar to that described for Example 28B, substituting Example 110A for Example 28A. MS (ESI$^+$) m/z 374.0 (M+H); $^1$H NMR (300 MHz, DMSO-$d_6$) δ 9.49 (d, J=2.0, 1H), 8.75 (dd, J=8.1, 1.9, 1H), 8.16-8.07 (m, 2H), 8.06 (d, J=8.3, 1H), 4.48 (t, J=5.2, 1H), 4.04 (q, J=14.9, 2H), 3.48 (dt, J=10.3, 4.7, 1H), 3.39-3.33 (m, 1H), 2.45-2.36 (m, 1H), 1.95-1.80 (m, 1H), 0.88 (t, J=6.9, 6H).

Example 111

(2R)-3-methyl-2-({[5-methyl-6'-(trifluoromethyl)-2,3'-bipyridin-6-yl]methyl}amino)butan-1-ol Example 111A 5,6-dimethyl-6'-(trifluoromethyl)-2,3'-bipyridine A 20 mL microwave vial was charged with 6-(trifluoromethyl)pyridin-3-ylboronic acid (564 mg, 2.96 mmol), 6-bromo-2,3-dimethylpyridine (500 mg, 2.69 mmol), bis (triphenylphosphine)palladium(II) chloride (94 mg, 0.134 mmol), and K$_2$CO$_3$ (743 mg, 5.37 mmol), followed by the addition of DME (9.0 mL), water (3.86 mL) and ethanol (2.57 mL). The reaction mixture was heated in a microwave at 120° C. for 10 minutes. To the reaction mixture was added 200 mL EtOAc, and washed with 200 mL water and 200 mL brine. The organic phase was dried over Na$_2$SO$_4$, filtered, and concentrated. The residue was chromatographed on a Grace Reveleris 40 g column, eluted with 0-40% EtOAc in Hexanes (25 mL/min) to provide the title compound (1.997 g, 7.92 mmol, 98% yield) as a white solid. MS (ESI$^+$) m/z 253.2 (M+H); $^1$H NMR (300 MHz, DMSO-$d_6$) δ 9.40 (d, J=1.9, 1H), 8.68 (dd, J=8.3, 1.7, 1H), 8.00 (d, J=8.3, 1H), 7.92 (d, J=7.9, 1H), 7.71 (d, J=7.9, 1H), 2.54 (s, 3H), 2.33 (s, 3H).

Example 111B 5-methyl-6'-(trifluoromethyl)-2,3'-bipyridine-6-carbaldehyde

A 5 mL microwave vial was charged with Example 111A (480 mg, 1.903 mmol), selenium dioxide (430 mg, 3.88 mmol), dioxane (5.0 mL) and water (0.5 mL). The white mixture was heated in the microwave at 210° C. for 30 minutes. The reaction was filtered and concentrated. The residue was chromatographed on a Grace Reveleris 40 g column, eluted with 0-40% EtOAc in Hexanes (25 mL/min) to provide the title compound (606 mg, 2.276 mmol, 39.9% yield) as a white solid. MS (ESI$^+$) m/z 298.9 (M+H+MeOH); $^1$H NMR (300 MHz, DMSO-$d_6$) δ 10.19 (d, J=0.5, 1H), 9.53 (d, J=2.0, 1H), 8.81 (dd, J=8.1, 1.9, 1H), 8.37 (d, J=8.1, 1H), 8.09 (d, J=8.2, 1H), 8.04 (d, J=8.1, 1H), 2.65 (s, 3H).

Example 111C (2R)-3-methyl-2-({[5-methyl-6'-(trifluoromethyl)-2,3'-bipyridin-6-yl]methyl}amino)butan-1-ol The title compound was prepared using procedure similar to that described for Example 28B, substituting Example 111B for Example 28A. MS (ESI$^+$) m/z 354.1 (M+H); $^1$H NMR (300 MHz, DMSO-$d_6$) δ 9.46 (d, J=1.8, 1H), 8.71 (dd, J=8.2, 1.8, 1H), 8.02 (d, J=8.3, 1H), 7.98 (d, J=7.9, 1H), 7.75 (d, J=8.0, 1H), 4.48 (t, J=5.2, 1H), 3.92 (qd, J=14.4, 5.2, 2H), 3.50 (dt, J=9.6, 4.7, 1H), 3.41-3.33 (m, 1H), 2.46-2.34 (m, 4H), 1.95-1.80 (m, 1H), 0.89 (t, J=7.2, 6H).

Example 112

(2R)-2-({[5-methoxy-6'-(trifluoromethyl)-2,3'-bipyridin-6-yl]methyl}amino)-3-methylbutan-1-ol

Example 112A 5-methoxy-6-methyl-6'-(trifluoromethyl)-2,3'-bipyridine

A 20 mL microwave vial was charged with 6-(trifluoromethyl)pyridin-3-ylboronic acid (666 mg, 3.49 mmol), 6-chloro-3-methoxy-2-methylpyridine (500 mg, 3.17 mmol), bis(triphenylphosphine)palladium(II) chloride (111 mg, 0.159 mmol), and $K_2CO_3$ (877 mg, 6.35 mmol), followed by the addition of DME (9.0 mL), water (3.86 mL) and ethanol (2.57 mL). The mixture was heated on the microwave at 120° C. for 10 minutes. To the reaction mixture was added 200 mL EtOAc, and washed with 200 mL water and 200 mL brine. The organic phase was dried over $Na_2SO_4$, filtered, and concentrated. The residue was chromatographed on a Grace Reveleris 40 g column, eluted with 0-40% EtOAc in Hexanes (25 mL/min) to provide the title compound (1.583 g, 5.90 mmol, 62.0% yield) as a white solid. MS (ESI$^+$) m/z 269.1 (M+H); $^1$H NMR (300 MHz, DMSO-$d_6$) δ 9.37 (d, J=1.8, 1H), 8.64 (dd, J=8.3, 1.9, 1H), 8.03 (d, J=8.6, 1H), 7.97 (d, J=8.3, 1H), 7.50 (d, J=8.6, 1H), 3.90 (s, 3H), 2.47 (s, 3H).

Example 112B 5-methoxy-6'-(trifluoromethyl)-2,3'-bipyridine-6-carbaldehyde

A 5 mL microwave vial was charged with Example 112A (500 mg, 1.864 mmol), selenium dioxide (430 mg, 3.88 mmol), dioxane (5.0 mL) and water (0.5 mL). The white mixture was heated in the microwave at 200° C. for 30 minutes. The reaction mixture was filtered and concentrated. The residue was partitioned between 200 mL EtOAc and 200 mL water. The organic phase was washed with brine, dried over $Na_2SO_4$, filtered, and concentrated to provide the title compound (1.405 g, 4.98 mmol, 89% yield) as a yellow solid. MS (ESI$^+$) m/z 314.8 (M+H+MeOH); $^1$H NMR (300 MHz, DMSO-$d_6$) δ 10.26 (s, 1H), 9.46 (d, J=2.0, 1H), 8.77-8.70 (m, 1H), 8.47 (d, J=8.9, 1H), 8.05 (d, J=8.2, 1H), 7.94 (d, J=9.0, 1H), 4.01 (s, 3H).

Example 112C (2R)-2-({[5-methoxy-6'-(trifluoromethyl)-2,3'-bipyridin-6-yl]methyl}amino)-3-methylbutan-1-ol The title compound was prepared using procedure similar to that described for Example 28B, substituting Example 112B for Example 28A. MS (ESI$^+$) m/z 370.1 (M+H); $^1$H NMR (300 MHz, DMSO-$d_6$) δ 9.43 (d, J=2.0, 1H), 8.67 (dd, J=8.3, 1.7, 1H), 8.08 (d, J=8.6, 1H), 7.99 (d, J=8.3, 1H), 7.56 (d, J=8.7, 1H), 4.44 (t, J=5.2, 1H), 4.02-3.81 (m, 5H), 3.46 (dt, J=9.6, 4.8, 1H), 2.38 (dd, J=11.5, 4.7, 1H), 1.97-1.80 (m, 1H), 0.88 (t, J=6.9, 6H).

Example 113

(2R)-2-[({3-fluoro-6-[2-(trifluoromethyl)pyrimidin-5-yl]pyridin-2-yl}methyl)amino]-3-methylbutan-1-ol A 20 mL microwave vial was charged with 2-(trifluoromethyl)pyrimidin-5-ylboronic acid (363 mg, 1.889 mmol), Example 73A (500 mg, 1.717 mmol), bis(triphenylphosphine)palladium(II) chloride (60.3 mg, 0.086 mmol), and potassium carbonate (475 mg, 3.43 mmol), followed by the addition of DME (9.0 mL), water (3.86 mL) and ethanol (2.57 mL). The mixture was heated in the microwave at 120° C. for 10 minutes. To the reaction mixture was added 100 mL 1.0 N NaOH, and extracted with 100 mL dichloromethane (2×). The combined dichloromethane layers were washed with 1.0 N HCl and partitioned. The resulting aqueous phase was neutralized with 3.0 N NaOH, extracted with EtOAc, and partitioned. The EtOAc layer was washed with brine, separated, dried over $Na_2SO_4$, filtered, and concentrated. The residue was purified by reverse phase chromatography. The combined fractions were concentrated. To the resulting residue was added EtOAc, and the solution was washed with 1.0 N NaOH and brine sequentially, and partitioned. The organic phase was dried over $Na_2SO_4$, filtered, and concentrated to provide the title compound as a white solid. MS (ESI$^+$) m/z 359.0 (M+H); $^1$H NMR (300 MHz, DMSO-$d_6$) δ 9.69 (s, 2H), 8.24 (dd, J=8.6, 3.7, 1H), 7.94 (dd, J=9.4, 8.7, 1H), 4.49 (t, J=5.2, 1H), 4.00 (q, J=15.0, 2H), 3.47 (dt, J=10.5, 4.7, 1H), 3.39-3.32 (m, 1H), 2.38 (dt, J=6.9, 4.7, 1H), 1.95-1.74 (m, 1H), 0.86 (t, J=7.1, 6H).

Example 114

(2R)-2-[({3-fluoro-6-[2-(2,2,2-trifluoroethoxy)pyrimidin-5-yl]pyridin-2-yl}methyl)amino]-3-methylbutan-1-ol The title compound was prepared using procedure similar to that described for Example 113, substituting 2-(2,2,2-trifluoroethoxy)pyrimidin-5-ylboronic acid for 2-(trifluoromethyl)pyrimidin-5-ylboronic acid. MS (ESI$^+$) m/z 389.1 (M+H); $^1$H NMR (300 MHz, DMSO-$d_6$) δ 9.32 (s, 2H), 8.05 (dd, J=8.6, 3.7, 1H), 7.84 (dd, J=9.5, 8.6, 1H), 5.12 (q, J=9.0, 2H), 4.47 (t, J=5.2, 1H), 3.96 (q, J=14.0, 2H), 3.52-3.41 (m, 1H), 2.36 (dt, J=6.7, 4.8, 1H), 1.92-1.77 (m, 1H), 0.92-0.80 (m, 6H).

Example 115

(3R)-3-({[5-fluoro-6'-(trifluoromethyl)-2,3'-bipyridin-6-yl]methyl}amino)pentan-2-ol

Example 115A (R)-tert-butyl 1-oxobutan-2-ylcarbamate

A solution of (R)-tert-butyl 1-hydroxybutan-2-ylcarbamate (5.0 g, 26.4 mmol) in DMSO (50 mL) was chilled to 15° C., followed by the addition of triethylamine (10.99 mL, 79 mmol) and a solution of sulfur trioxide-pyridine complex (12.62 g, 79 mmol) in DMSO (50 mL) in succession. The mixture was stirred at 15° C. for 30 minutes, then allowed to warm to ambient temperature overnight. The reaction was quenched with 200 mL 1.0 M citric acid, and extracted twice with 250 mL MTBE. The organic phase was washed with 200 mL water and 200 mL brine, separated, dried over $Na_2SO_4$, filtered, and concentrated. The residue was chromatographed on a Grace Reveleris 80 g column, eluted with 0-35% EtOAc in Hexanes (40 mL/min) to provide the title compound (4.561 g, 24.36 mmol, 92.2% yield) as a light yellow solid. $^1$H NMR (300 MHz, DMSO-$d_6$) δ 9.42 (d, J=0.7, 1H), 7.27 (d, J=6.8, 1H), 3.73 (dd, J=13.3, 7.8, 1H), 1.78-1.58 (m, 1H), 1.54-1.28 (m, 10H), 0.87 (t, J=7.4, 3H).

Example 115B tert-butyl (3R)-2-hydroxypentan-3-ylcarbamate

Example 115A (2.753 g, 14.70 mmol) was dissolved in THF (60 mL) and cooled to 0° C. Methyl magnesium bromide (20.0 mL, 60.0 mmol, 3.0 M in diethyl ether) was carefully added via syringe. The reaction mixture was allowed to warm to ambient temperature and left stirring overnight. The cloudy mixture was chilled to 0° C., cautiously quenched with methanol (4.0 mL, 99 mmol), added 200 mL saturated NH$_4$Cl solution, and extracted twice with 200 mL MTBE. The combined organic phase was washed with 200 mL brine, separated, dried over Na$_2$SO$_4$, filtered, and concentrated. The residue was chromatographed on a Grace Reveleris 80 g column, eluted with 0-40% EtOAc in Hexanes (50 mL/min) to provide the title compound (2.020 g, 9.94 mmol, 67.6% yield) as a colorless oil. MS (DCI$^+$) m/z 204.1 (M+H).

Example 115C (3R)-3-aminopentan-2-ol hydrochloride

To Example 115B (2.020 g, 9.94 mmol) was added hydrogen chloride (25 mL, 100 mmol, 4.0 M in dioxane), stirred for 90 minutes at ambient temperature, and concentrated to provide the title compound (1.556 g, 11.14 mmol, 112% yield) as a viscous orange oil. MS (DCI+) m/z 104.0 (M+H).

Example 115D (3R)-3-({[5-fluoro-6'-(trifluoromethyl)-2,3'-bipyridin-6-yl]methyl}amino)pentan-2-ol Example 28A (1.25 g, 4.63 mmol) and Example 115C (0.775 g, 5.55 mmol) were dissolved in methanol (30 mL) and triethylamine (0.770 mL, 5.55 mmol), and the orange-red solution was stirred at ambient temperature for 1 hour, followed by the addition of sodium borohydride (0.420 g, 11.10 mmol). The reaction mixture was stirred overnight at ambient temperature, quenched with 150 mL 1.0 N NaOH, and extracted with 150 mL dichloromethane (2×). The combined organic phase was extracted with 1.0 N HCl, and partitioned. The resulting aqueous layer was neutralized with 3.0 N NaOH, and extracted with EtOAc. The EtOAc layer was washed with brine, separated, dried over Na$_2$SO$_4$, filtered, and concentrated. The residue was purified on a reverse phase chromatography. The collected fractions were concentrated. The residue was taken into EtOAc, and washed with 1.0 N NaOH and brine. The organic phase was dried over Na$_2$SO$_4$, filtered, and concentrated to obtain the title compound as a yellow solid, a 4:1 mix of diastereomers by proton NMR. MS (ESI$^+$) m/z 358.1 (M+H); $^1$H NMR (300 MHz, DMSO-d$_6$) δ 9.45 (d, J=1.8, 1H), 8.71 (dd, J=8.3, 1.5, 1H), 8.16 (dd, J=8.7, 3.7, 1H), 8.04 (d, J=8.3, 1H), 7.93-7.83 (m, 1H), 4.51 (d, J=4.8, 0.8H), 4.41 (d, J=4.6, 0.2H), 3.96 (dd, J=38.1, 14.6, 2H), 3.73-3.63 (m, 0.2H), 3.63-3.50 (m, 0.8H), 2.41-2.21 (m, 1H), 1.65-1.48 (m, 1H), 1.47-1.23 (m, 1H), 1.08-1.01 (m, 3H), 0.85 (t, J=7.4, 3H).

Example 116

(R)-2-((3-fluoro-6-(4-(trifluoromethyl)phenyl)pyridin-2-yl)methylamino)-3-methylbutanamide The title compound was prepared using procedure similar to that described for Example 75, substituting Example 17A for Example 28A and (R)-2-amino-3-methylbutanamide hydrochloride for (R)-2-amino-2-cyclopropylethanol hydrochloride. MS (ESI$^+$) m/z 370.0 (M+H); $^1$H NMR (300 MHz, DMSO-d$_6$) δ 8.29 (d, J=8.1, 2H), 8.05 (dd, J=8.6, 3.7, 1H), 7.89-7.77 (m, 3H), 7.37 (s, 1H), 7.04 (s, 1H), 3.96-3.77 (m, 2H), 2.83 (dd, J=7.8, 6.0, 1H), 2.61-2.53 (m, 1H), 1.83 (dq, J=13.4, 6.7, 1H), 0.87 (dd, J=6.8, 1.5, 6H).

Example 117

(R)-2-((5-fluoro-6'-(trifluoromethyl)-2,3'-bipyridin-6-yl)methylamino)-3-methylbutanamide The title compound was prepared using procedure similar to that described for Example 75, substituting (R)-2-amino-3-methylbutanamide hydrochloride for (R)-2-amino-2-cyclopropylethanol hydrochloride. MS (ESI$^+$) m/z 371.0 (M+H); $^1$H NMR (300 MHz, DMSO-d$_6$) δ 9.45 (d, J=1.8, 1H), 8.71 (dd, J=8.2, 1.7, 1H), 8.16 (dd, J=8.6, 3.6, 1H), 8.04 (d, J=8.3, 1H), 7.93-7.83 (m, 1H), 7.36 (s, 1H), 7.02 (s, 1H), 3.97-3.79 (m, 2H), 2.83 (dd, J=7.9, 6.0, 1H), 2.59 (dd, J=14.2, 7.3, 1H), 1.82 (dq, J=13.2, 6.6, 1H), 0.87 (dd, J=6.8, 1.5, 6H).

Example 118

(2R)-2-({[4,6'-bis(trifluoromethyl)-2,3'-bipyridin-6-yl]methyl}amino)-3-methylbutan-1-ol

Example 118A 6-methyl-4,6'-bis(trifluoromethyl)-2,3'-bipyridine

A 20 mL microwave vial was charged with 6-(trifluoromethyl)pyridin-3-ylboronic acid (644 mg, 3.37 mmol), 2-chloro-6-methyl-4-(trifluoromethyl)pyridine (600 mg, 3.07 mmol), bis(triphenylphosphine)palladium(II) chloride (108 mg, 0.153 mmol), and K$_2$CO$_3$ (848 mg, 6.14 mmol), followed by the addition of DME (9.0 mL), water (3.86 mL) and ethanol (2.57 mL). The mixture was heated in the microwave at 120° C. for 10 minutes. The combined reaction mixtures were added 200 mL EtOAc, and filtered through a celite pad. The filtrate was washed with 200 mL water and 200 mL brine. The organic phase was dried over Na$_2$SO$_4$, filtered, and concentrated. The residue was chromatographed on a Grace Reveleris 80 g column, eluted with 0-40% EtOAc in Hexanes (35 mL/min) to provide the title compound (2.858 g, 9.33 mmol, 101% yield) as a yellow solid. MS (ESI$^+$) m/z 307.1 (M+H); $^1$H NMR (300 MHz, DMSO-d$_6$) δ 9.51 (d, J=2.1, 1H), 8.82 (ddd, J=8.4, 2.2, 0.5, 1H), 8.36 (s, 1H), 8.06 (dd, J=8.4, 0.5, 1H), 7.78 (s, 1H), 2.70 (s, 3H).

Example 118B 4,6'-bis(trifluoromethyl)-2,3'-bipyridine-6-carbaldehyde

A 20 mL microwave vial was charged with Example 118A (1.4 g, 4.57 mmol), selenium dioxide (1.015 g, 9.14 mmol), and dioxane (15 mL) and water (3 mL). The yellow mixture was heated in the microwave at 170° C. for 6 hours. The reaction mixture was filtered, and concentrated. The residue was chromatographed on a Grace Reveleris 80 g column, eluted with 0-40% EtOAc in Hexanes (35 mL/min) to obtain the title compound (2.256 g, 7.05 mmol, 77% yield) as a white solid. MS (ESI m/z 352.9 (M+H+MeOH); $^1$H NMR (300

Example 118C (2R)-2-({[4,6'-bis(trifluoromethyl)-2,3'-bipyridin-6-yl]methyl}amino)-3-methylbutan-1-ol The title compound was prepared using procedure similar to that described for Example 28B, substituting Example 118B for Example 28A. MS (ESI$^+$) m/z 408.1 (M+H); $^1$H NMR (300 MHz, DMSO-d$_6$) δ 9.54 (d, J=2.0, 1H), 8.84 (dd, J=8.3, 1.7, 1H), 8.41 (s, 1H), 8.07 (d, J=8.3, 1H), 7.97 (s, 1H), 4.46 (t, J=5.3, 1H), 4.17-3.98 (m, 2H), 3.53-3.43 (m, 1H), 3.42-3.34 (m, 1H), 2.37-2.28 (m, 1H), 1.90-1.76 (m, 1H), 0.89 (t, J=7.0, 6H).

Example 119

(S)-2-((5-fluoro-6'-(trifluoromethyl)-2,3'-bipyridin-6-yl)methylamino)-3-methylbutanamide The title compound was prepared using procedure similar to that described for Example 75, substituting (S)-2-amino-3-methylbutanamide hydrochloride for (R)-2-amino-2-cyclopropylethanol hydrochloride. MS (ESI$^+$) m/z 371.0 (M+H); $^1$H NMR (500 MHz, DMSO-d$_6$/D$_2$O) δ 9.52 (s, 1H), 8.76 (d, J=7.9, 1H), 8.30-8.24 (m, 1H), 8.08 (d, J=8.3, 1H), 8.03-7.95 (m, 1H), 4.43 (dd, J=50.7, 15.4, 2H), 3.86 (d, J=5.1, 1H), 2.34-2.24 (m, 1H), 1.06 (d, J=6.9, 3H), 1.02 (d, J=6.9, 3H).

Example 120

(2S,3R)-2-((5-fluoro-6'-(trifluoromethyl)-2,3'-bipyridin-6-yl)methylamino)-3-hydroxybutanamide Example 28A (30 mg, 0.111 mmol), L-threonine amide hydrochloride (20.6 mg, 0.133 mmol), and acetic acid (33.3 mg, 0.555 mmol) were dissolved in 1:1 MeOH:dichloromethane. The mixture was stirred at 50° C. for 15 minutes, then MP-BH$_3$CN (Macroporous triethylammonium methylpolystyrene cyanoborohydride) (148 mg, 0.333 mmol, 2.25 mmol/g loading) was added. After stirring overnight at 50° C., the reaction was filtered and washed with MeOH. The residue was purified by reverse phase chromatography to yield the title compound as the trifluoroacetic acid salt. MS (ESI$^+$) m/z 372.9 (M+H); $^1$H NMR (500 MHz, DMSO-d$_6$/D$_2$O) δ 9.57 (d, J=2.1, 1H), 8.80 (dd, J=8.2, 2.0, 1H), 8.29 (dd, J=8.7, 3.6, 1H), 8.06 (d, J=8.2, 1H), 8.00 (t, J=9.0, 1H), 4.55-4.43 (m, 2H), 4.14-4.05 (m, 1H), 3.86 (d, J=7.1, 1H), 1.24 (d, J=6.4, 3H).

Example 121

(2R,3R)-2-({[5-fluoro-6'-(trifluoromethyl)-2,3'-bipyridin-6-yl]methyl}amino)butane-1,3-diol The title compound was prepared according to Example 75, substituting (2R,3R)-2-aminobutane-1,3-diol for (R)-2-amino-2-cyclopropylethanol hydrochloride. MS (ESI$^+$) m/z 360.0 (M+H); $^1$H NMR (300 MHz, DMSO-d$_6$) δ 9.46 (d, J=1.8, 1H), 8.72 (dd, J=8.3, 1.7, 1H), 8.16 (dd, J=8.6, 3.7, 1H), 8.03 (d, J=8.2, 1H), 7.88 (dd, J=9.4, 8.8, 1H), 4.50 (d, J=4.7, 1H), 4.43 (t, J=5.3, 1H), 4.13-3.96 (m, 2H), 3.75-3.61 (m, 1H), 3.55 (dt, J=10.6, 4.8, 1H), 3.37 (dt, J=11.1, 5.7, 1H), 2.65 (br s, 1H), 2.42 (q, J=5.4, 1H), 1.06 (d, J=6.4, 3H).

Example 122

(1S,2S)-2-({[5-fluoro-6'-(trifluoromethyl)-2,3'-bipyridin-6-yl]methyl}amino)cyclohexanol To a solution of Example 28A (25 mg, 0.09 mmol) 1:1 methanol:dichloromethane (1 mL) was added a solution of (1S,2S)-2-aminocyclohexanol (13 mg, 1.2 equivalents, 0.11 mmol) in 1:1 methanol:dichloromethane (1 mL) followed by acetic acid (27 μL, 5.0 equivalents, 0.46 mmol). The mixture was stirred for 15 minutes at 50° C. then sodium cyanoborohydride (124 mg, 3 eq, 2.25 mmol) was added. The mixture was stirred overnight at 50° C. then filtered and concentrated. Purification by reverse phase HPLC (C18, 0-100% CH$_3$CN/water (0.1% TFA)) afforded the title compound. MS (ESI$^+$) m/z 370 (M+H).

Example 123

(1R,2S)-2-({[5-fluoro-6'-(trifluoromethyl)-2,3'-bipyridin-6-yl]methyl}amino)cyclohexanol The title compound was prepared according to Example 122, substituting (1R,2S)-2-aminocyclohexanol for (1S,2S)-2-aminocyclohexanol. MS (ESI$^+$) m/z 370 (M+H).

Example 124

(2R)-2-({[3-fluoro-6-(1-phenylethenyl)pyridin-2-yl]methyl}amino)-3-methylbutan-1-ol The title compound was prepared as described for Example 113, substituting 1-phenylvinylboronic acid for 2-(trifluoromethyl)pyrimidin-5-ylboronic acid. MS (ESI$^+$) m/z 315.1 (M+H); $^1$H NMR (300 MHz, DMSO-d$_6$) δ 7.64 (dd, J=9.5, 8.7, 1H), 7.42-7.30 (m, 5H), 7.26 (dd, J=8.5, 3.8, 1H), 5.93 (d, J=1.4, 1H), 5.59 (d, J=1.3, 1H), 4.39 (t, J=5.2, 1H), 3.88 (d, J=4.1, 2H), 3.42 (dt, J=9.7, 4.8, 1H), 3.29-3.22 (m, 1H), 2.37-2.28 (m, 1H), 2.25-2.14 (m, 1H), 1.88-1.73 (m, 1H), 0.81 (dd, J=6.9, 4.4, 6H).

Example 125

(2R)-2-[({3-fluoro-6-[1-(4-fluorophenyl)ethenyl]pyridin-2-yl}methyl)amino]-3-methylbutan-1-ol The title compound was prepared as described for Example 113, substituting 2-(1-(4-fluorophenyl)vinyl)-4,4,5,5-tetramethyl-1,3,2-dioxaborolane for 2-(trifluoromethyl)pyrimidin-5-ylboronic acid. MS (ESI$^+$) m/z 333.1 (M+H); $^1$H NMR (300 MHz, DMSO-d$_6$) δ 7.65 (dd, J=9.6, 8.6, 1H), 7.37 (dd, J=8.9, 5.6, 2H), 7.31 (dd, J=8.6, 3.8, 1H), 7.20 (t, J=9.0, 2H), 5.91 (d, J=1.1, 1H), 5.60 (d, J=1.1, 1H), 4.37 (t, J=5.2, 1H), 3.87 (s, 2H), 3.41 (dt, J=10.5, 4.8, 1H), 3.28-3.22 (m, 1H), 2.31 (dd, J=9.9, 4.8, 1H), 2.18 (br s, 1H), 1.87-1.73 (m, 1H), 0.81 (dd, J=6.9, 3.9, 6H).

Example 126

(2R)-2-({[6-(cyclohex-1-en-1-yl)-3-fluoropyridin-2-yl]methyl}amino)-3-methylbutan-1-ol The title compound was prepared as described for Example 113, substituting 2-cyclohexenyl-4,4,5,5-tetramethyl-1,3,2- dioxaborolane for 2-(trifluoromethyl)pyrimidin-5-ylboronic acid. MS (ESI+) m/z 293.1 (M+H); ¹H NMR (300 MHz, DMSO-d₆) δ 7.62-7.53 (m, 1H), 7.43 (dd, J=8.7, 3.7, 1H), 6.71-6.62 (m, 1H), 4.41 (t, J=5.2, 1H), 3.91-3.76 (m, 2H), 3.49-3.39 (m, 1H), 2.48-2.40 (m, 2H), 2.39-2.29 (m, 1H), 2.25-2.15 (m, 2H), 1.91-1.76 (m, 1H), 1.76-1.66 (m, 2H), 1.66-1.55 (m, 2H), 0.85 (t, J=7.0, 6H).

Example 127

(2R)-2-({[3-fluoro-6-(1-phenylethyl)pyridin-2-yl]methyl}amino)-3-methylbutan-1-ol The title compound was prepared as described for Example 128, substituting Example 124 for Example 125. MS (ESI+) m/z 317.1 (M+H); ¹H NMR (300 MHz, DMSO-d₆) δ 7.53 (dd, J=9.8, 8.5, 1H), 7.35-7.12 (m, 6H), 4.40 (td, J=5.2, 2.3, 1H), 4.27 (q, J=7.2, 1H), 3.93-3.77 (m, 2H), 3.43 (dt, J=9.6, 4.7, 1H), 2.35-2.21 (m, 2H), 1.89-1.75 (m, 1H), 1.60 (d, J=7.2, 3H), 0.91-0.77 (m, 6H).

Example 128

(2R)-2-[({3-fluoro-6-[1-(4-fluorophenyl)ethyl]pyridin-2-yl}methyl)amino]-3-methylbutan-1-ol Example 125 (950 mg, 2.86 mmol) in MeOH (20 mL) was added to Raney Nickel (950 mg) in a 50 mL pressure bottle and stirred for 1 hour under 30 psi of hydrogen at ambient temperature. The mixture was filtered through a nylon membrane and concentrated to yield the title compound (902 mg, 2.70 mmol, 94% yield). MS (ESI+) m/z 335.1 (M+H); ¹H NMR (300 MHz, DMSO-d₆) δ 7.54 (dd, J=9.8, 8.5, 1H), 7.39-7.30 (m, 2H), 7.21 (dd, J=8.5, 3.8, 1H), 7.08 (td, J=9.0, 1.0, 2H), 4.40 (td, J=5.2, 2.8, 1H), 4.30 (q, J=7.1, 1H), 3.93-3.76 (m, 2H), 3.42 (dt, J=9.7, 4.8, 1H), 2.34-2.19 (m, 2H), 1.88-1.75 (m, 1H), 1.58 (d, J=7.2, 3H), 0.87-0.75 (m, 6H).

Example 129

(2R)-2-{[(6-cyclohexyl-3-fluoropyridin-2-yl)methyl]amino 1-3-methylbutan-1-ol

The title compound was prepared as described for Example 128, substituting Example 126 for Example 125. MS (ESI+) m/z 295.1 (M+H); ¹H NMR (300 MHz, DMSO-d₆) δ 7.53 (dd, J=9.8, 8.5, 1H), 7.18 (dd, J=8.5, 3.8, 1H), 4.41 (t, J=5.2, 1H), 3.93-3.73 (m, 2H), 3.42 (dt, J=9.7, 4.8, 1H), 2.66 (tt, J=11.7, 3.3, 1H), 2.35-2.25 (m, 1H), 2.20 (dd, J=10.8, 6.9, 1H), 1.90-1.63 (m, 6H), 1.57-1.14 (m, 5H), 0.83 (dd, J=7.6, 7.1, 6H).

Example 130

N²-{[5-fluoro-6'-(trifluoromethyl)-2,3'-bipyridin-6-yl]methyl}-N-naphthalen-2-yl-L-threoninamide The title compound was prepared according to Example 122, substituting (2S,3R)-2-amino-3-hydroxy-N-(naphthalen-2-yl)butanamide for (1S,2S)-2-amino cyclohexanol. MS (ESI+) m/z 499 (M+H).

Example 131

(2R)-2-[({5-fluoro-2-[4-(trifluoromethyl)phenyl]pyrimidin-4-yl}methyl)amino]-3-methylbutan-1-ol Example 131A 2-chloro-5-fluoro-4-methylpyrimidine A solution of 2,4-dichloro-5-fluoropyrimidine (2.5 g, 14.97 mmol) and iron(III) acetylacetonate (1.058 g, 2.99 mmol) in THF (100 mL) and NMP (10 mL) was chilled below 0° C. and methyl magnesium chloride (5.99 mL, 18.0 mmol, 3.0 M solution in THF) was added dropwise over 10 minutes. After stirring for 2 hours at 0° C., the mixture was quenched with 200 mL saturated NH₄Cl and extracted twice with 200 mL EtOAc. The combined organic extracts were washed with 200 mL saturated NH₄Cl and 200 mL brine, dried over Na₂SO₄ and concentrated. Purification by chromatography (Grace Reveleris 80 g column, eluted with 0-20% EtOAc/heptane, 35 mL/min) provided the title compound (1.13 g, 7.70 mmol, 51% yield). GC/MS (EI+) m/z 146.0 (M+); ¹H NMR (400 MHz, CDCl₃) δ 8.36 (s, 1H), 2.55 (d, J=2.5, 3H); ¹³C NMR (101 MHz, CDCl₃) δ 158.78, 158.61, 157.34, 154.92, 154.89, 154.74, 145.86, 145.63, 17.74, 17.73.

Example 131B 5-fluoro-4-methyl-2-(4-(trifluoromethyl)phenyl)pyrimidine

A 20 mL microwave vial was charged with Example 131A (560 mg, 3.82 mmol), 4-(trifluoromethyl)phenylboronic acid (871 mg, 4.59 mmol), bis(triphenylphosphine)palladium(II) chloride (134 mg, 0.191 mmol), and potassium carbonate (1056 mg, 7.64 mmol). DME (9.0 mL), water (3.86 mL), and EtOH (2.57 mL) were added and the mixture was heated by microwave at 120° C. for 10 minutes. The mixture was 200 mL EtOAc and washed with 200 mL water and 200 mL brine. The organic extract was dried over Na₂SO₄ and concentrated. Purification by chromatography (Grace Reveleris 40 g column, eluted with 0-40% EtOAc/heptane gradient, 30 mL/min) provided the title compound (892 mg, 3.48 mmol, 91% yield). LC/MS (APCI+) m/z 257.1 (M+H); ¹H NMR (300 MHz, DMSO-d₆) δ 8.88 (d, J=1.8, 1H), 8.53 (d, J=8.1, 2H), 7.90 (d, J=8.3, 2H), 2.58 (d, J=2.5, 3H).

Example 131C 5-fluoro-2-(4-(trifluoromethyl)phenyl)pyrimidine-4-carbaldehyde

A 20 mL microwave vial was charged with Example 131B (892 mg, 3.48 mmol), selenium dioxide (760 mg, 6.85 mmol), dioxane (10 mL) and water (0.4 mL). The white mixture was heated by microwave at 170° C. for 30 minutes. The mixture was diluted with 200 mL EtOAc, washed with 200 mL water and 200 mL brine. The organic extract was dried over Na₂SO₄ and concentrated. Purification by chromatography (Grace Reveleris 40 g column, eluted with 0-40% EtOAc/heptane gradient, 30 mL/min) provided the title compound (733 mg, 2.71 mmol, 78% yield). MS (DCI+) m/z 303.1 (M+H+MeOH); ¹H NMR (300 MHz, DMSO-d₆) δ 10.11 (s, 1H), 9.32 (d, J=2.2, 1H), 8.59 (d, J=8.1, 2H), 7.96 (d, J=8.2, 2H).

Example 131D (2R)-2-[({5-fluoro-2-[4-(trifluoromethyl)phenyl]pyrimidin-4-yl}methyl)amino]-3-methylbutan-1-ol The title compound was prepared as described for Example 28B, substituting Example 131C for Example 28A. MS (ESI+) m/z 358.1 (M+H); ¹H NMR (300 MHz, DMSO-d₆) δ 8.93 (d, J=1.8, 1H), 8.56 (d, J=8.1, 2H), 7.91 (d, J=8.3, 2H), 4.47 (t, J=5.1, 1H), 4.11-3.93 (m, 2H), 3.53-3.42 (m, 1H), 3.39-3.33 (m, 1H), 2.45-2.32 (m, 2H), 1.92-1.74 (m, 1H), 0.92-0.81 (m, 6H).

Example 132

{1-[({2-[4-(trifluoromethyl)phenyl]pyrimidin-4-yl}methyl)amino]cyclobutyl}methanol To a solution of Example 91B (35 mg, 0.14 mmol) in 1:1 methanol:dichloromethane (1 mL) was added a solution of (1-aminocyclobutyl)methanol (17 mg, 1.2 equivalents, 0.17 mmol) in 1:1 methanol:dichloromethane (1 mL) followed by acetic acid (32 μL, 4.0 equivalents, 0.56 mmol). The mixture was stirred for 15 minutes at 50° C. then sodium cyanoborohydride (190 mg, 3 equivalents, 2.25 mmol) was added. The mixture was stirred overnight at 50° C. then filtered and concentrated. Purification by reverse phase HPLC (C18, 0-100% CH$_3$CN/water (0.1% TFA)) afforded the title compound. MS (ESI$^+$) m/z 338 (M+H).

Example 133

{1-[({2-[4-(trifluoromethyl)phenyl]pyrimidin-4-yl}methyl)amino]cyclopentyl}methanol The title compound was prepared according to Example 132, substituting (1-aminocyclopentyl)methanol for (1-aminocyclobutyl)methanol. MS (ESI$^+$) m/z 352 (M+H).

Example 134

{1-[({2-[4-(trifluoromethyl)phenyl]pyrimidin-4-yl}methyl)amino]cyclohexyl}methanol The title compound was prepared according to Example 132, substituting (1-aminocyclohexyl)methanol for (1-aminocyclobutyl)methanol. MS (ESI$^+$) m/z 366 (M+H).

Example 135

{1-[({2-[4-(trifluoromethyl)phenyl]pyrimidin-4-yl}methyl)amino]cyclopropyl}methanol The title compound was prepared according to Example 132, substituting (1-aminocyclopropyl)methanol for (1-aminocyclobutyl)methanol. MS (ESI$^+$) m/z 324 (M+H).

Example 136

2-methyl-2-[({2-[4-(trifluoromethyl)phenyl]pyrimidin-4-yl}methyl)amino]propan-1-ol The title compound was prepared according to Example 132, substituting 2-amino-2-methylpropan-1-ol for (1-aminocyclobutyl)methanol. MS (ESI$^+$) m/z 326 (M+H).

Example 137

(2R)-2-[({2-[4-(trifluoromethyl)phenyl]pyrimidin-4-yl}methyl)amino]propan-1-ol

The title compound was prepared according to Example 132, substituting (R)-2-aminopropan-1-ol for (1-aminocyclobutyl)methanol. MS (ESI$^+$) m/z 312 (M+H).

Example 138

(2R)-2-[({2-[4-(trifluoromethyl)phenyl]pyrimidin-4-yl}methyl)amino]butan-1-ol

The title compound was prepared according to Example 132, substituting (R)-2-aminobutan-1-ol for (1-aminocyclobutyl)methanol. MS (ESI$^+$) m/z 326 (M+H).

Example 139

(2R)-2-phenyl-2-[({2-[4-(trifluoromethyl)phenyl]pyrimidin-4-yl}methyl)amino]ethanol The title compound was prepared according to Example 132, substituting (R)-2-amino-2-phenylethanol for (1-aminocyclobutyl)methanol. MS (ESI$^+$) m/z 374 (M+H).

Example 140

(2R)-3-phenyl-2-[({2-[4-(trifluoromethyl)phenyl]pyrimidin-4-yl}methyl)amino]propan-1-ol The title compound was prepared according to Example 132, substituting (R)-2-amino-3-phenylpropanol for (1-aminocyclobutyl)methanol. MS (ESI$^+$) m/z 388 (M+H).

Example 141

(2R)-2-[({2-[4-(trifluoromethyl)phenyl]pyrimidin-4-yl}methyl)amino]pentan-1-ol

The title compound was prepared according to Example 132, substituting (R)-2-aminopentan-1-ol for (1-aminocyclobutyl)methanol. MS (ESI$^+$) m/z 340 (M+H).

Example 142

(2R)-4-methyl-2-[({2-[4-(trifluoromethyl)phenyl]pyrimidin-4-yl}methyl)amino]pentan-1-ol The title compound was prepared according to Example 132, substituting (R)-2-amino-4-methylpentan-1-ol for (1-aminocyclobutyl)methanol. MS (ESI$^+$) m/z 354 (M+H).

Example 143

3-methyl-2-[({2-[4-(trifluoromethyl)phenyl]pyrimidin-4-yl}methyl)amino]pentan-1-ol The title compound was prepared according to Example 132, substituting 2-amino-3-methylpentan-1-ol for (1-aminocyclobutyl)methanol. MS (ESI$^+$) m/z 354 (M+H).

Example 144

3-methoxy-2-[({2-[4-(trifluoromethyl)phenyl]pyrimidin-4-yl}methyl)amino]propan-1-ol The title compound was prepared according to Example 132, substituting 2-amino-3-methoxypropan-1-ol for (1-aminocyclobutyl)methanol. MS (ESI$^+$) m/z 342 (M+H).

Example 145

(2R)-2-cyclopropyl-2-[({2-[4-(trifluoromethyl)phenyl]pyrimidin-4-yl}methyl)amino]ethanol The title compound was prepared according to Example 132, substituting (R)-2-amino-2-cyclopropylethanol for (1-aminocyclobutyl)methanol. MS (ESI$^+$) m/z 338 (M+H).

Example 146

(2R)-2-cyclohexyl-2-[({2-[4-(trifluoromethyl)phenyl]pyrimidin-4-yl}methyl)amino]ethanol The title compound was prepared according to Example 132, substituting (R)-2-amino-2-cyclohexylethanol for (1-aminocyclobutyl)methanol. MS (ESI$^+$) m/z 380 (M+H).

Example 147

(2R)-3,3-dimethyl-2-[({2-[4-(trifluoromethyl)phenyl]pyrimidin-4-yl}methyl)amino]butan-1-ol The title compound was prepared according to Example 132, substituting (R)-2-amino-3,3-dimethylbutan-1-ol for (1-aminocyclobutyl)methanol. MS (ESI$^+$) m/z 354 (M+H).

Example 148

3-[({2-[4-(trifluoromethyl)phenyl]pyrimidin-4-yl}methyl)amino]butan-2-ol

The title compound was prepared according to Example 132, substituting 3-aminobutan-2-ol for (1-aminocyclobutyl)methanol. MS (ESI$^+$) m/z 326 (M+H).

Example 149

(2S,3S)-2-[({2-[4-(trifluoromethyl)phenyl]pyrimidin-4-yl}methyl)amino]butane-1,3-diol The title compound was prepared according to Example 132, substituting (2S,3S)-2-aminobutane-1,3-diol for (1-aminocyclobutyl)methanol. MS (ESI$^+$) m/z 342 (M+H).

Example 150

(2R,3R)-2-[({2-[4-(trifluoromethyl)phenyl]pyrimidin-4-yl}methyl)amino]butane-1,3-diol The title compound was prepared according to Example 132, substituting (2R,3R)-2-aminobutane-1,3-diol for (1-aminocyclobutyl)methanol. MS (ESI$^+$) m/z 342 (M+H).

Example 151

(2R,3S)-2-[({2-[4-(trifluoromethyl)phenyl]pyrimidin-4-yl}methyl)amino]butane-1,3-diol The title compound was prepared according to Example 132, substituting (2R,3S)-2-aminobutane-1,3-diol for (1-aminocyclobutyl)methanol. MS (ESI$^+$) m/z 342 (M+H).

Example 152

(2S,3R)-2-[({2-[4-(trifluoromethyl)phenyl]pyrimidin-4-yl}methyl)amino]butane-1,3-diol The title compound was prepared according to Example 132, substituting (2S,3R)-2-aminobutane-1,3-diol for (1-aminocyclobutyl)methanol. MS (ESI$^+$) m/z 342 (M+H).

Example 153

(1S,2S)-1-phenyl-2-[({2-[4-(trifluoromethyl)phenyl]pyrimidin-4-yl}methyl)amino]propane-1,3-diol The title compound was prepared according to Example 132, substituting (1S,2S)-2-amino-1-phenylpropane-1,3-diol for (1-aminocyclobutyl)methanol. MS (ESI$^+$) m/z 404 (M+H).

Example 154

(1R,2R)-1-phenyl-2-[({2-[4-(trifluoromethyl)phenyl]pyrimidin-4-yl}methyl)amino]propane-1,3-diol The title compound was prepared according to Example 132, substituting (1R,2R)-2-amino-1-phenylpropane-1,3-diol for (1-aminocyclobutyl)methanol. MS (ESI$^+$) m/z 404 (M+H).

Example 155

(2S)-3-methyl-2-[({2-[4-(trifluoromethyl)phenyl]pyrimidin-4-yl}methyl)amino]butan-1-ol The title compound was prepared according to Example 132, substituting (S)-2-amino-3-methylbutan-1-ol for (1-aminocyclobutyl)methanol. MS (ESI$^+$) m/z 340 (M+H).

Example 156

2,2-dimethyl-3-[({2-[4-(trifluoromethyl)phenyl]pyrimidin-4-yl}methyl)amino]propan-1-ol The title compound was prepared according to Example 132, substituting 3-amino-2,2-dimethylpropan-1-ol for (1-aminocyclobutyl)methanol. MS (ESI$^+$) m/z 340 (M+H).

Example 157

(1-{[({2-[4-(trifluoromethyl)phenyl]pyrimidin-4-yl}methyl)amino]methyl}cyclobutyl)methanol The title compound was prepared according to Example 132, substituting (1-(aminomethyl)cyclobutyl)methanol for (1-aminocyclobutyl)methanol. MS (ESI$^+$) m/z 352 (M+H).

Example 158

(1-{[({2-[4-(trifluoromethyl)phenyl]pyrimidin-4-yl}methyl)amino]methyl}cyclopentyl)methanol The title compound was prepared according to Example 132, substituting (1-(aminomethyl)cyclopentyl)methanol for (1-aminocyclobutyl)methanol. MS (ESI$^+$) m/z 366 (M+H).

Example 159

(1-{[({2-[4-(trifluoromethyl)phenyl]pyrimidin-4-yl}methyl)amino]methyl}cyclohexyl)methanol The title compound was prepared according to Example 132, substituting (1-(aminomethyl)cyclohexyl)methanol for (1-aminocyclobutyl)methanol. MS (ESI$^+$) m/z 380 (M+H).

Example 160

(3-{[({2-[4-(trifluoromethyl)phenyl]pyrimidin-4-yl}methyl)amino]methyl 1 oxetan-3-yl)methanol The title compound was prepared according to Example 132, substituting (3-(aminomethyl)oxetan-3-yl)methanol for (1-aminocyclobutyl)methanol. MS (ESI$^+$) m/z 354 (M+H).

Example 161

(4-{[({2-[4-(trifluoromethyl)phenyl]pyrimidin-4-yl}methyl)amino]methyl 1 tetrahydro-2H-pyran-4-yl)methanol The title compound was prepared according to Example 132, substituting (4-(aminomethyl)tetrahydro-2H-pyran-4-yl)methanol for (1-aminocyclobutyl)methanol. MS (ESI$^+$) m/z 382 (M+H).

Example 162

(3R)-3-phenyl-3-[({2-[4-(trifluoromethyl)phenyl]pyrimidin-4-yl}methyl)amino]propan-1-ol The title compound was prepared according to Example 132, substituting (R)-3-amino-3-phenylpropan-1-ol for (1-aminocyclobutyl)methanol. MS (ESI$^+$) m/z 388 (M+H).

Example 163

(3S)-3-phenyl-3-[({2-[4-(trifluoromethyl)phenyl]pyrimidin-4-yl}methyl)amino]propan-1-ol The title compound was prepared according to Example 132, substituting (S)-3-amino-3-phenylpropan-1-ol for (1-aminocyclobutyl)methanol. MS (ESI$^+$) m/z 388 (M+H).

Example 164

1-phenyl-3-[({2-[4-(trifluoromethyl)phenyl]pyrimidin-4-yl}methyl)amino]propan-1-ol The title compound was prepared according to Example 132, substituting 3-amino-1-phenylpropan-1-ol for (1-aminocyclobutyl)methanol. MS (ESI$^+$) m/z 388 (M+H).

Example 165

(1S,2R)-2-{[({2-[4-(trifluoromethyl)phenyl]pyrimidin-4-yl}methyl)amino]methyl}cyclohexanol The title compound was prepared according to Example 132, substituting (1S,2R)-2-(aminomethyl)cyclohexanol for (1-aminocyclobutyl)methanol. MS (ESI$^+$) m/z 366 (M+H).

Example 166

(1R,2R)-2-{[({2-[4-(trifluoromethyl)phenyl]pyrimidin-4-yl}methyl)amino]methyl}cyclohexanol The title compound was prepared according to Example 132, substituting (1R,2R)-2-(aminomethyl)cyclohexanol for (1-aminocyclobutyl)methanol. MS (ESI$^+$) m/z 366 (M+H).

Example 167

{(1S,2S)-2-[({2-[4-(trifluoromethyl)phenyl]pyrimidin-4-yl}methyl)amino]cyclohexyl}methanol The title compound was prepared according to Example 132, substituting ((1S, 2S)-2-aminocyclohexyl)methanol for (1-aminocyclobutyl)methanol. MS (ESI$^+$) m/z 366 (M+H).

Example 168

{(1R,2S)-2-[({2-[4-(trifluoromethyl)phenyl]pyrimidin-4-yl}methyl)amino]cyclohexyl}methanol The title compound was prepared according to Example 132, substituting ((1R,2S)-2-aminocyclohexyl)methanol for (1-aminocyclobutyl)methanol. MS (ESI$^+$) m/z 366 (M+H).

Example 169

{(1S,2R,3S,4R)-3-[({2-[4-(trifluoromethyl)phenyl]pyrimidin-4-yl}methyl)amino]bicyclo[2.2.1]hept-2-yl]methanol The title compound was prepared according to Example 132, substituting ((1S,2R,3S,4R)-3-aminobicyclo[2.2.1]heptan-2-yl)methanol for (1-aminocyclobutyl)methanol. MS (ESI$^+$) m/z 378 (M+H).

Example 170

{(1S,2S,3R,4R)-3-[({2-[4-(trifluoromethyl)phenyl]pyrimidin-4-yl}methyl)amino]bicyclo[2.2.1]hept-2-yl]methanol The title compound was prepared according to Example 132, substituting 41S,2S,3R,4R)-3-aminobicyclo[2.2.1]heptan-2-yl)methanol for (1-aminocyclobutyl)methanol. MS (ESI$^+$) m/z 378 (M+H).

Example 171

(1S,2S)-2-[({2-[4-(trifluoromethyl)phenyl]pyrimidin-4-yl}methyl)amino]cyclohexanol The title compound was prepared according to Example 132, substituting (1S,2S)-2-aminocyclohexanol for (1-aminocyclobutyl)methanol. MS (ESI$^+$) m/z 352 (M+H).

Example 172

(1R,2S)-2-[({2-[4-(trifluoromethyl)phenyl]pyrimidin-4-yl}methyl)amino]cyclohexanol The title compound was prepared according to Example 132, substituting (1R,2S)-2-aminocyclohexanol for (1-aminocyclobutyl)methanol. MS (ESI$^+$) m/z 352 (M+H).

Example 173

(1R,2S)-2-[({2-[4-(trifluoromethyl)phenyl]pyrimidin-4-yl}methyl)amino]cyclopentanol The title compound was prepared according to Example 132, substituting (1R,2S)-2-aminocyclopentanol for (1-aminocyclobutyl)methanol. MS (ESI+) m/z 338 (M+H).

Example 174

(1S,2S)-2-[({2-[4-(trifluoromethyl)phenyl]pyrimidin-4-yl}methyl)amino]cyclopentanol The title compound was prepared according to Example 132, substituting (1S,2S)-2-aminocyclopentanol for (1-aminocyclobutyl)methanol. MS (ESI+) m/z 338 (M+H).

Example 175

2-methyl-1-[({2-[4-(trifluoromethyl)phenyl]pyrimidin-4-yl}methyl)amino]propan-2-ol The title compound was prepared according to Example 132, substituting 1-amino-2-methylpropan-2-ol for (1-aminocyclobutyl)methanol. MS (ESI+) m/z 326 (M+H).

Example 176

1-{[({2-[4-(trifluoromethyl)phenyl]pyrimidin-4-yl}methyl)amino]methyl}cyclopropanol The title compound was prepared according to Example 132, substituting 1-(aminomethyl)cyclopropanol for (1-aminocyclobutyl)methanol. MS (ESI+) m/z 324 (M+H).

Example 177

1-{[({2-[4-(trifluoromethyl)phenyl]pyrimidin-4-yl}methyl)amino]methyl}cyclopentanol The title compound was prepared according to Example 132, substituting 1-(aminomethyl)cyclopentanol for (1-aminocyclobutyl)methanol. MS (ESI+) m/z 352 (M+H).

Example 178

1-{[({2-[4-(trifluoromethyl)phenyl]pyrimidin-4-yl}methyl)amino]methyl}cyclohexanol The title compound was prepared according to Example 132, substituting 1-(aminomethyl)cyclohexanol for (1-aminocyclobutyl)methanol. MS (ESI+) m/z 366 (M+H).

Example 179

1,1,1-trifluoro-3-[({2-[4-(trifluoromethyl)phenyl]pyrimidin-4-yl}methyl)amino]propan-2-ol The title compound was prepared according to Example 132, substituting 3-amino-1,1,1-trifluoropropan-2-ol for (1-aminocyclobutyl)methanol. MS (ESI+) m/z 366 (M+H).

Example 180

(2S)-1-[({2-[4-(trifluoromethyl)phenyl]pyrimidin-4-yl}methyl)amino]propan-2-ol

The title compound was prepared according to Example 132, substituting (S)-1-aminopropan-2-ol for (1-aminocyclobutyl)methanol. MS (ESI+) m/z 312 (M+H).

Example 181

1-[({2-[4-(trifluoromethyl)phenyl]pyrimidin-4-yl}methyl)amino]butan-2-ol

The title compound was prepared according to Example 132, substituting 1-aminobutan-2-ol for (1-aminocyclobutyl)methanol. MS (ESI+) m/z 326 (M+H).

Example 182

1-phenyl-2-[({2-[4-(trifluoromethyl)phenyl]pyrimidin-4-yl}methyl)amino]ethanol

The title compound was prepared according to Example 132, substituting 2-amino-1-phenylethanol for (1-aminocyclobutyl)methanol. MS (ESI+) m/z 374 (M+H).

Example 183

(2R)-1-[({2-[4-(trifluoromethyl)phenyl]pyrimidin-4-yl}methyl)amino]propan-2-ol

The title compound was prepared according to Example 132, substituting (R)-1-aminopropan-2-ol for (1-aminocyclobutyl)methanol. MS (ESI+) m/z 312 (M+H).

Example 184

(2R)-3-methyl-2-[({2-[6-(trifluoromethyl)pyridin-3-yl]pyrimidin-4-yl}methyl)amino]butan-1-ol The title compound was prepared according to Example 132, substituting 2-(6-(trifluoromethyl)pyridin-3-yl)pyrimidine-4-carbaldehyde for Example 91B and (R)-2-amino-3-methylbutan-1-ol for (1-aminocyclobutyl)methanol. MS (ESI+) m/z 341 (M+H).

Example 185

{1-[({2-[6-(trifluoromethyl)pyridin-3-yl]pyrimidin-4-yl}methyl)amino]cyclohexyl}methanol The title compound was prepared according to Example 132, substituting 2-(6-(trifluoromethyl)pyridin-3-yl)pyrimidine-4-carbaldehyde for Example 91B and (1-aminocyclohexyl)methanol for (1-aminocyclobutyl)methanol. MS (ESI+) m/z 367 (M+H).

Example 186

(2R)-2-[({2-[6-(trifluoromethyl)pyridin-3-yl]pyrimidin-4-yl}methyl)amino]butan-1-ol The title compound was prepared according to Example 132, substituting 2-(6-(trifluoromethyl)pyridin-3-yl)pyrimidine-4-carbaldehyde for Example 91B and (R)-2-aminobutan-1-ol for (1-aminocyclobutyl)methanol. MS (ESI⁺) m/z 327 (M+H).

Example 187

3-methoxy-2-[({2-[6-(trifluoromethyl)pyridin-3-yl]pyrimidin-4-yl}methyl)amino]propan-1-ol The title compound was prepared according to Example 132, substituting 2-(6-(trifluoromethyl)pyridin-3-yl)pyrimidine-4-carbaldehyde for Example 91B and 2-amino-3-methoxypropan-1-ol for (1-aminocyclobutyl)methanol. MS (ESI⁺) m/z 343 (M+H).

Example 188

(2R)-2-cyclopropyl-2-[({2-[6-(trifluoromethyl)pyridin-3-yl]pyrimidin-4-yl}methyl)amino]ethanol The title compound was prepared according to Example 132, substituting 2-(6-(trifluoromethyl)pyridin-3-yl)pyrimidine-4-carbaldehyde for Example 91B and (R)-2-amino-2-cyclopropylethanol for (1-aminocyclobutyl)methanol. MS (ESI⁺) m/z 339 (M+H).

Example 189

(2S)-3-methyl-2-[({2-[6-(trifluoromethyl)pyridin-3-yl]pyrimidin-4-yl}methyl)amino]butane-1,3-diol The title compound was prepared according to Example 132, substituting 2-(6-(trifluoromethyl)pyridin-3-yl)pyrimidine-4-carbaldehyde for Example 91B and (S)-2-amino-3-methylbutane-1,3-diol for (1-aminocyclobutyl)methanol. MS (ESI⁺) m/z 357 (M+H).

Example 190

3-[({2-[6-(trifluoromethyl)pyridin-3-yl]pyrimidin-4-yl}methyl)amino]butan-2-ol

The title compound was prepared according to Example 132, substituting 2-(6-(trifluoromethyl)pyridin-3-yl)pyrimidine-4-carbaldehyde for Example 91B and 3-aminobutan-2-ol for (1-aminocyclobutyl)methanol. MS (ESI⁺) m/z 327 (M+H).

Example 191

(2R,3R)-2-[({2-[6-(trifluoromethyl)pyridin-3-yl]pyrimidin-4-yl}methyl)amino]butane-1,3-diol The title compound was prepared according to Example 132, substituting 2-(6-(trifluoromethyl)pyridin-3-yl)pyrimidine-4-carbaldehyde for Example 91B and (2R,3R)-2-aminobutane-1,3-diol for (1-aminocyclobutyl)methanol. MS (ESI⁺) m/z 343 (M+H).

Example 192

(2R)-3-methyl-2-[({2-[5-(trifluoromethyl)pyridin-2-yl]pyrimidin-4-yl}methyl)amino]butan-1-ol The title compound was prepared according to Example 132, substituting 2-(5-(trifluoromethyl)pyridin-2-yl)pyrimidine-4-carbaldehyde for Example 91B and (R)-2-amino-3-methylbutan-1-ol for (1-aminocyclobutyl)methanol. MS (ESI⁺) m/z 341 (M+H).

Example 193

{1-[({2-[5-(trifluoromethyl)pyridin-2-yl]pyrimidin-4-yl}methyl)amino]cyclohexyl}methanol The title compound was prepared according to Example 132, substituting 2-(5-(trifluoromethyl)pyridin-2-yl)pyrimidine-4-carbaldehyde for Example 91B and (1-aminocyclohexyl)methanol for (1-aminocyclobutyl)methanol. MS (ESI⁺) m/z 327 (M+H).

Example 194

(2R)-2-[({2-[5-(trifluoromethyl)pyridin-2-yl]pyrimidin-4-yl}methyl)amino]butan-1-ol The title compound was prepared according to Example 132, substituting 2-(5-(trifluoromethyl)pyridin-2-yl)pyrimidine-4-carbaldehyde for Example 91B and (R)-2-aminobutan-1-ol for (1-aminocyclobutyl)methanol. MS (ESI⁺) m/z 327 (M+H).

Example 195

3-methoxy-2-[({2-[5-(trifluoromethyl)pyridin-2-yl]pyrimidin-4-yl}methyl)amino]propan-1-ol The title compound was prepared according to Example 132, substituting 2-(5-(trifluoromethyl)pyridin-2-yl)pyrimidine-4-carbaldehyde for Example 91B and 2-amino-3-methoxypropan-1-ol for (1-aminocyclobutyl)methanol. MS (ESI⁺) m/z 343 (M+H).

Example 196

(2R)-2-cyclopropyl-2-[({2-[5-(trifluoromethyl)pyridin-2-yl]pyrimidin-4-yl}methyl)amino]ethanol The title compound was prepared according to Example 132, substituting 2-(5-(trifluoromethyl)pyridin-2-yl)pyrimidine-4-carbaldehyde for Example 91B and (R)-2-amino-2-cyclopropylethanol for (1-aminocyclobutyl)methanol. MS (ESI⁺) m/z 339 (M+H).

Example 197

(2S)-3-methyl-2-[({2-[5-(trifluoromethyl)pyridin-2-yl]pyrimidin-4-yl}methyl)amino]butane-1.3-diol The title compound was prepared according to Example 132, substituting 2-(5-(trifluoromethyl)pyridin-2-yl)pyrimidine-4-carbaldehyde for Example 91B and (S)-2-amino-3-methylbutane-1,3-diol for (1-aminocyclobutyl)methanol. MS (ESI⁺) m/z 357 (M+H).

Example 198

(2R,3R)-2-[({2-[5-(trifluoromethyl)pyridin-2-yl]pyrimidin-4-yl}methyl)amino]butane-1,3-diol The title compound was prepared according to Example 132, substituting 2-(5-(trifluoromethyl)pyridin-2-yl)pyrimidine-4-carbaldehyde for Example 91B and (2R,3R)-2-aminobutane-1,3-diol for (1-aminocyclobutyl)methanol. MS (ESI⁺) m/z 343 (M+H).

Example 199

(2R)-2-({[6-(bicyclo[2.2.1]hept-2-yl)-3-fluoropyridin-2-yl]methyl}amino)-3-methylbutan-1-ol A microwave vial was charged with SiliaCat DPP-Pd (0.10 equivalent, 127 mg, purchased from Silicycle). A solution of Example 73A (100 mg, 0.30 mmol) in ethanol (1.0 mL) was added, followed by a solution of bicyclo[2.2.1]hept-2-en-2-ylboronic acid (41 mg, 0.30 mmol) in ethanol (1.0 mL) and 1 M aqueous $Cs_2CO_3$ (1.03 mL). The resulting mixture was heated in a microwave for 20 minutes at 120° C., filtered, and concentrated to provide (2R)-2-(((6-(bicyclo[2.2.1]hept-2-en-2-yl)-3-fluoropyridin-2-yl)methyl)amino)-3-methylbutan-1-ol. (2R)-2-(((6-(bicyclo[2.2.1]hept-2-en-2-yl)-3-fluoropyridin-2-yl)methyl)amino)-3-methylbutan-1-ol was subjected to hydrogenation ($H_2$ atmosphere, Pd/C catalyst) then purified by reverse phase HPLC to provide the title compound. MS (ESI+) m/z 307 (M+H)⁺.

Example 200

(2R)-2-({[3-fluoro-6-(4-methylcyclohexyl)pyridin-2-yl]methyl}amino)-3-methylbutan-1-ol (2R)-2-(((3-fluoro-6-(4-methylcyclohex-1-en-1-yl)pyridin-2-yl)methyl)amino)-3-methylbutan-1-ol was prepared according to Example 199, substituting 4-methylcyclohex-1-enylboronic acid for bicyclo[2.2.1]hept-2-en-2-ylboronic acid. (2R)-2-(((3-fluoro-6-(4-methylcyclohex-1-en-1-yl)pyridin-2-yl)methyl)amino)-3-methylbutan-1-ol was subjected to hydrogenation ($H_2$ atmosphere, Pd/C catalyst) to provide the title compound. MS (ESI⁺) m/z 309 (M+H)⁺.

Example 201

(2R)-2-({[6-(4-ethylcyclohexyl)-3-fluoropyridin-2-yl]methyl}amino)-3-methylbutan-1-ol (2R)-2-(((6-(4-ethylcyclohex-1-en-1-yl)-3-fluoropyridin-2-yl)methyl)amino)-3-methylbutan-1-ol was prepared according to Example 199, substituting 2-(4-ethylcyclohex-1-enyl)-4,4,5,5-tetramethyl-1,3,2-dioxaborolane for bicyclo[2.2.1]hept-2-en-2-ylboronic acid. (2R)-2-(((6-(4-ethylcyclohex-1-en-1-yl)-3-fluoropyridin-2-yl)methyl)amino)-3-methylbutan-1-ol was subjected to hydrogenation ($H_2$ atmosphere, Pd/C catalyst) to provide the title compound. MS (ESI+) m/z 323 (M+H)⁺.

Example 202

(2R)-2-({[6-(4,4-dimethylcyclohexyl)-3-fluoropyridin-2-yl]methyl}amino)-3-methylbutan-1-ol (R)-2-(((6-(4,4-dimethylcyclohex-1-en-1-yl)-3-fluoropyridin-2-yl)methyl)amino)-3-methylbutan-1-ol was prepared according to Example 199, substituting 2-(4,4-dimethylcyclohex-1-enyl)-4,4,5,5-tetramethyl-1,3,2-dioxaborolane for bicyclo[2.2.1]hept-2-en-2-ylboronic acid. (R)-2-(((6-(4,4-dimethylcyclohex-1-en-1-yl)-3-fluoropyridin-2-yl)methyl)amino)-3-methylbutan-1-ol was subjected to hydrogenation ($H_2$ atmosphere, Pd/C catalyst) to provide the title compound. MS (ESI+) m/z 323 (M+H)⁺.

Example 203

(2R)-2-({[6-(4,4-difluorocyclohexyl)-3-fluoropyridin-2-yl]methyl}amino)-3-methylbutan-1-ol (R)-2-(((6-(4,4-difluorocyclohex-1-en-1-yl)-3-fluoropyridin-2-yl)methyl)amino)-3-methylbutan-1-ol was prepared according to Example 199, substituting 2-(4,4-difluorocyclohex-1-enyl)-4,4,5,5-tetramethyl-1,3,2-dioxaborolane for bicyclo[2.2.1]hept-2-en-2-ylboronic acid. (R)-2-(((6-(4,4-difluorocyclohex-1-en-1-yl)-3-fluoropyridin-2-yl)methyl)amino)-3-methylbutan-1-ol was subjected to hydrogenation ($H_2$ atmosphere, Pd/C catalyst) to provide the title compound. MS (ESI+) m/z 331 (M+H)⁺.

Example 204

(2R)-2-({[3-fluoro-6-(tetrahydro-2H-pyran-4-yl)pyridin-2-yl]methyl}amino)-3-methylbutan-1-ol (R)-2-4(6-(3,6-dihydro-2H-pyran-4-yl)-3-fluoropyridin-2-yl)methyl)amino)-3-methylbutan-1-ol was prepared according to Example 199, substituting 2-(3,6-dihydro-2H-pyran-4-yl)-4,4,5,5-tetramethyl-1,3,2-dioxaborolane for bicyclo[2.2.1]hept-2-en-2-ylboronic acid. (R)-2-4(6-(3,6-dihydro-2H-pyran-4-yl)-3-fluoropyridin-2-yl)methyl)amino)-3-methylbutan-1-ol was subjected to hydrogenation ($H_2$ atmosphere, Pd/C catalyst) to provide the title compound. MS (ESI+) m/z 297 (M+H)⁺.

Example 205 tert-butyl 4-[5-fluoro-6-({[(2R)-1-hydroxy-3-methylbutan-2-yl]amino}methyl)pyridin-2-yl]piperidine-1-carboxylate (R)-tert-butyl 5-fluoro-6-4(1-hydroxy-3-methylbutan-2-yl)amino)methyl)-5',6'-dihydro-[2,4'-bipyridine]-1'(2'H)-carboxylate was prepared according to Example 199, substituting tert-butyl 4-(4,4,5,5-tetramethyl-1,3,2-dioxaborolan-2-yl)-5,6-dihydropyridine-1(2H)-carboxylate for bicyclo[2.2.1]hept-2-en-2-ylboronic acid. (R)-tert-butyl 5-fluoro-6-(((1-hydroxy-3-methylbutan-2-yl)amino)methyl)-5',6'-dihydro-[2,4'-bipyridine]-1'(2'H)-carboxylate was subjected to hydrogenation ($H_2$ atmosphere, Pd/C catalyst) to provide the title compound. MS (ESI⁺) m/z 396 (M+H)⁺.

Example 206

(2R)-2-{[(6-cycloheptyl-3-fluoropyridin-2-yl)methyl]amino 1-3-methylbutan-1-ol (R)-2-(((6-(cyclohept-1-en-1-yl)-3-fluoropyridin-2-yl)methyl)amino)-3-methylbutan-1-ol was prepared according to Example 199, substituting 2-cycloheptenyl-4,4,5,5-tetramethyl-1,3,2-dioxaborolane for bicyclo[2.2.1]hept-2-en-2-ylboronic acid. (R)-2-(((6-(cyclohept-1-en-1-yl)-3-fluoropyridin-2-yl)methyl)amino)-3-methylbutan-1-ol was subjected to hydrogenation ($H_2$ atmosphere, Pd/C catalyst) to provide the title compound. MS (ESI⁺) m/z 309 (M+H)⁺.

Example 207

(2R)-3-methyl-2-{[(2-{4-[(trifluoromethyl)sulfonyl]phenyl}pyrimidin-4-yl)methyl]amino}butan-1-ol The title compound was prepared according to Example 132, substituting 2-(4-((trifluoromethyl)sulfonyl)phenyl)pyrimidine-4-carbaldehyde for Example 91B and (R)-2-amino-3-methylbutan-1-ol for (1-aminocyclobutyl)methanol. MS (ESI⁺) m/z 404 (M+H).

Example 208

(1-{[(2-{4-[(trifluoromethyl)sulfonyl]phenyl}pyrimidin-4-yl)methyl]amino}cyclohexyl)methanol The title compound was prepared according to Example 132, substituting 2-(4-((trifluoromethyl)sulfonyl)phenyl)pyrimidine-4-carbaldehyde for Example 91B and (1-aminocyclohexyl)methanol for (1-aminocyclobutyl)methanol. MS (ESI⁺) m/z 430 (M+H).

Example 209

(2R)-2-{[(2-{4-[(trifluoromethyl)sulfonyl]phenyl}pyrimidin-4-yl)methyl]amino}butan-1-ol The title compound was prepared according to Example 132, substituting 2-(4-((trifluoromethyl)sulfonyl)phenyl)pyrimidine-4-carbaldehyde for Example 91B and (R)-2-aminobutan-1-ol for (1-aminocyclobutyl)methanol. MS (ESI⁺) m/z 390 (M+H).

Example 210

3-methoxy-2-{[(2-{4-[(trifluoromethyl)sulfonyl]phenyl}pyrimidin-4-yl)methyl]amino}propan-1-ol The title compound was prepared according to Example 132, substituting 2-(4-((trifluoromethyl)sulfonyl)phenyl)pyrimidine-4-carbaldehyde for Example 91B and 2-amino-3-methoxypropan-1-ol for (1-aminocyclobutyl)methanol. MS (ESI⁺) m/z 406 (M+H).

Example 211

(2S)-3-methyl-2-{[(2-{4-[(trifluoromethyl)sulfonyl]phenyl}pyrimidin-4-yl)methyl]amino}butane-1,3-diol The title compound was prepared according to Example 132, substituting 2-(4-((trifluoromethyl)sulfonyl)phenyl)pyrimidine-4-carbaldehyde for Example 91B and (S)-2-amino-3-methylbutane-1,3-diol for (1-aminocyclobutyl)methanol. MS (ESI⁺) m/z 420 (M+H).

Example 212

(2R,3R)-2-{[(2-{4-[(trifluoromethyl)sulfonyl]phenyl}pyrimidin-4-yl)methyl]amino}butane-1,3-diol The title compound was prepared according to Example 132, substituting 2-(4-((trifluoromethyl)sulfonyl)phenyl)pyrimidine-4-carbaldehyde for Example 91B and (2R,3R)-2-aminobutane-1,3-diol for (1-aminocyclobutyl)methanol. MS (ESI⁺) m/z 406 (M+H).

Example 213

(2R)-2-({[6-(4-tert-butylcyclohexyl)-3-fluoropyridin-2-yl]methyl}amino)-3-methylbutan-1-ol (2R)-2-(((6-(4-(tert-butyl)cyclohex-1-en-1-yl)-3-fluoropyridin-2-yl)methyl)amino)-3-methylbutan-1-ol was prepared according to Example 199, substituting 2-(4-tert-butylcyclohex-1-enyl)-4,4,5,5-tetramethyl-1,3,2-dioxaborolane for bicyclo[2.2.1]hept-2-en-2-ylboronic acid. (2R)-2-4(6-(4-(tert-butyl)cyclohex-1-en-1-yl)-3-fluoropyridin-2-yl)methyl)amino)-3-methylbutan-1-ol was subjected to hydrogenation (H₂ atmosphere, Pd/C catalyst) to provide the title compound. MS (ESI+) m/z 351 (M+H)⁺.

Example 214

(2R)-2-({[6-(1,4-dioxaspiro[4.5]dec-8-yl)-3-fluoropyridin-2-yl]methyl}amino)-3-methylbutan-1-ol (R)-2-(((3-fluoro-6-(1,4-dioxaspiro[4.5]dec-7-en-8-yl)pyridin-2-yl)methyl)amino)-3-methylbutan-1-ol was prepared according to Example 199, substituting 2-(4-tert-butylcyclohex-1-enyl)-4,4,5,5-tetramethyl-1,3,2-dioxaborolane for bicyclo[2.2.1]hept-2-en-2-ylboronic acid. (2R)-2-4(6-(4-(tert-butyl)cyclohex-1-en-1-yl)-3-fluoropyridin-2-yl)methyl)amino)-3-methylbutan-1-ol was subjected to hydrogenation (H₂ atmosphere, Pd/C catalyst) to provide the title compound. MS (ESI+) m/z 353 (M+H)⁺.

Example 215

(2R)-2-({[6-(1,4-dioxaspiro[4.5]dec-7-yl)-3-fluoropyridin-2-yl]methyl}amino)-3-methylbutan-1-ol (R)-2-(((3-fluoro-6-(1,4-dioxaspiro[4.5]dec-7-en-7-yl)pyridin-2-yl)methyl)amino)-3-methylbutan-1-ol was prepared according to Example 199, substituting 4,4,5,5-tetramethyl-2-(1,4-dioxaspiro[4.5]dec-7-en-7-yl)-1,3,2-dioxaborolane for bicyclo[2.2.1]hept-2-en-2-ylboronic acid. (R)-2-(((3-fluoro-6-(1,4-dioxaspiro[4.5]dec-7-en-7-yl)pyridin-2-yl)methyl)amino)-3-methylbutan-1-ol was subjected to hydrogenation (H₂ atmosphere, Pd/C catalyst) to provide the title compound. MS (ESI+) m/z 353 (M+H)⁺.

Example 216

(2R)-2-[({3-fluoro-6-[4-(trifluoromethyl)cyclohexyl]pyridin-2-yl}methyl)amino]-3-methylbutan-1-ol (2R)-2-(((3-fluoro-6-(4-(trifluoromethyl)cyclohex-1-en-1-yl)pyridin-2-yl)methyl)amino)-3-methylbutan-1-ol was prepared according to Example 199, substituting 4,4,5,5-tetramethyl-2-(4-(trifluoromethyl)cyclohex-1-enyl)-1,3,2-dioxaborolane for bicyclo[2.2.1]hept-2-en-2-ylboronic acid. (2R)-2-(((3-fluoro-6-(4-(trifluoromethyl)cyclohex-1-en-1-yl)pyridin-2-yl)methyl)amino)-3-methylbutan-1-ol was subjected to hydrogenation (H₂ atmosphere, Pd/C catalyst) to provide the title compound. MS (ESI+) m/z 363 (M+H)⁺.

Example 217

(2R)-2-({[3-fluoro-6-(1,2,3,4-tetrahydronaphthalen-2-yl)pyridin-2-yl]methyl}amino)-3-methylbutan-1-ol (R)-2-4(6-(3,4-dihydronaphthalen-2-yl)-3-fluoropyridin-2-yl)methyl)amino)-3-methylbutan-1-ol was prepared according to Example 199, substituting 3,4-dihydronaphthalen-2-ylboronic acid for bicyclo[2.2.1]hept-2-en-2-ylboronic acid. (R)-2-(((6-(3,4-dihydronaphthalen-2-yl)-3-fluoropyridin-2-yl)methyl)amino)-3-methylbutan-1-ol was subjected to hydrogenation (H₂ atmosphere, Pd/C catalyst) to provide the title compound. MS (ESI+) m/z 343 (M+H)⁺.

Example 218

(2R)-2-({[3-fluoro-6-(tetrahydro-2H-pyran-3-yl)pyridin-2-yl]methyl}amino)-3-methylbutan-1-ol (R)-2-4(6-(3,4-dihydro-2H-pyran-5-yl)-3-fluoropyridin-2-yl)methyl)amino)-3-methylbutan-1-ol was prepared according to Example 199, substituting 2-(3,4-dihydro-2H-pyran-5-yl)-4,4,5,5-tetramethyl-1,3,2-dioxaborolane for bicyclo[2.2.1]hept-2-en-2-ylboronic acid. (R)-2-4(6-(3,4-dihydro-2H-pyran-5-yl)-3-fluoropyridin-2-yl)methyl)amino)-3-methylbutan-1-ol was subjected to hydrogenation (H$_2$ atmosphere, Pd/C catalyst) to provide the title compound. MS (ESI+) m/z 297 (M+H)$^+$.

Example 219 tert-butyl 3-[5-fluoro-6-({[(2R)-1-hydroxy-3-methylbutan-2-yl]amino}methyl)pyridin-2-yl]piperidine-1-carboxylate (R)-tert-butyl 5-fluoro-6-4(1-hydroxy-3-methylbutan-2-yl)amino)methyl)-5',6'-dihydro-[2,3'-bipyridine]-1'(2'H)-carboxylate was prepared according to Example 199, substituting tert-butyl 3-(4,4,5,5-tetramethyl-1,3,2-dioxaborolan-2-yl)-5,6-dihydropyridine-1(2H)-carboxylate for bicyclo[2.2.1]hept-2-en-2-ylboronic acid. (R)-tert-butyl 5-fluoro-6-(((1-hydroxy-3-methylbutan-2-yl)amino)methyl)-5',6'-dihydro-[2,3'-bipyridine]-1'(2'H)-carboxylate was subjected to hydrogenation (H$_2$ atmosphere, Pd/C catalyst) to provide the title compound. MS (ESI+) m/z 396 (M+H)$^+$.

Example 220

(2R)-2-{[(6-cyclopentyl-3-fluoropyridin-2-yl)methyl]amino}-3-methylbutan-1-ol (R)-2-(((6-(cyclopent-1-en-1-yl)-3-fluoropyridin-2-yl)methyl)amino)-3-methylbutan-1-ol was prepared according to Example 199, substituting 2-cyclopentenyl-4,4,5,5-tetramethyl-1,3,2-dioxaborolane for bicyclo[2.2.1]hept-2-en-2-ylboronic acid. (R)-2-(((6-(cyclopent-1-en-1-yl)-3-fluoropyridin-2-yl)methyl)amino)-3-methylbutan-1-ol was subjected to hydrogenation (H$_2$ atmosphere, Pd/C catalyst) to provide the title compound. MS (ESI+) m/z 281 (M+H)$^+$.

Example 221

(2R)-2-({[3-fluoro-6-(tetrahydro furan-3-yl)pyridin-2-yl]methyl}amino)-3-methylbutan-1-ol (R)-2-(46-(4,5-dihydrofuran-3-yl)-3-fluoropyridin-2-yl)methyl)amino)-3-methylbutan-1-ol was prepared according to Example 199, substituting 2-(4,5-dihydrofuran-3-yl)-4,4,5,5-tetramethyl-1,3,2-dioxaborolane for bicyclo[2.2.1]hept-2-en-2-ylboronic acid.
(R)-2-4(6-(4,5-dihydrofuran-3-yl)-3-fluoropyridin-2-yl)methyl)amino)-3-methylbutan-1-ol was subjected to hydrogenation (H$_2$ atmosphere, Pd/C catalyst) to provide the title compound.
MS (ESI+) m/z 2813 (M+H)$^+$.

Example 222 tert-butyl 3-[5-fluoro-6-({[(2R)-1-hydroxy-3-methylbutan-2-yl]amino}methyl)pyridin-2-yl]pyrrolidine-1-carboxylate (R)-tert-butyl 4-(5-fluoro-6-(((1-hydroxy-3-methylbutan-2-yl)amino)methyl)pyridin-2-yl)-2,3-dihydro-1H-pyrrole-1-carboxylate was prepared according to Example 199, substituting tert-butyl 4-(4,4,5,5-tetramethyl-1,3,2-dioxaborolan-2-yl)-2,3-dihydro-1H-pyrrole-1-carboxylate for bicyclo[2.2.1]hept-2-en-2-ylboronic acid. (R)-tert-butyl 4-(5-fluoro-6-(((1-hydroxy-3-methylbutan-2-yl)amino)methyl)pyridin-2-yl)-2,3-dihydro-1H-pyrrole-1-carboxylate was subjected to hydrogenation (H$_2$ atmosphere, Pd/C catalyst) to provide the title compound. MS (ESI+) m/z 2813 (M+H)$^+$.

Example 223

(2R)-2-[({3-fluoro-6-[4-(trifluoromethyl)cyclohex-1-en-1-yl]pyridin-2-yl}methyl)amino]-3-methylbutan-1-ol The title compound was prepared according to Example 228, substituting (4-(trifluoromethyl)cyclohex-1-en-1-yl)boronic acid for 3,4-difluorophenylboronic acid. $^1$H NMR (300 MHz, CDCl$_3$) δ 7.61 (dd, J=9.4, 8.8 Hz, 1H), 7.48 (dd, J=8.6, 3.7 Hz, 1H), 6.69-6.64 (m, 1H), 4.41 (t, J=5.1 Hz, 1H), 3.86 (dd, J=22.9, 14.1 Hz, 2H), 3.49-3.39 (m, 1H), 2.86-2.71 (m, 1H), 2.66-2.55 (m, 1H), 2.48-2.41 (m, 1H), 2.38-2.17 (m, 3H), 2.15-2.04 (m, 1H), 1.92-1.76 (m, 1H), 1.56 (qd, J=12.1, 5.4 Hz, 1H), 0.85 (m, 6H). MS (ESI) m/z: 361.1 (M+H)$^+$.

Example 224

(2R)-2-({[6-(4,4-difluorocyclohex-1-en-1-yl)-3-fluoropyridin-2-yl]methyl}amino)-3-methylbutan-1-ol The title compound was prepared according to Example 228, substituting (4,4-difluorocyclohex-1-en-1-yl)boronic acid for 3,4-difluorophenylboronic acid. $^1$H NMR (300 MHz, DMSO-d$_6$) δ 7.70-7.58 (m, 1H), 7.53 (dd, J=8.7, 3.8 Hz, 1H), 6.53 (s, 1H), 4.42 (s, 1H), 3.97-3.76 (m, 2H), 3.51-3.39 (m, 1H), 3.31-3.23 (m, 2H), 2.86-2.67 (m, 4H), 2.40-2.27 (m, 1H), 2.28-2.07 (m, 2H), 1.94-1.73 (m, 1H), 0.91-0.77 (m, 6H). MS (ESI$^+$) m/z 329 (M+H)$^+$.

Example 225

(2R)-3-methyl-2-{[(6-phenylpyridin-2-yl)methyl]amino}butan-1-ol

To a solution of 6-phenylpicolinaldehyde (*Tetrahedron Lett.* 2010, 51, 5621-5623; 0.391 g, 2.133 mmol) in methanol (4 mL) at ambient temperature was added D-valinol (0.22 mL, 1.9 mmol) followed by acetic acid (0.4 mL, 8 mmol). After 5 min, MP-cyanoborohydride (2.5 mmol/g, 500 mg) was added and stirring continued overnight. The mixture was filtered and the filtrate partitioned between 1N NaOH and CH$_2$Cl$_2$. The organic phase extracted with 1N aqueous HCl. The organic layer was discarded and the aqueous phase was made basic with 1N NaOH and extracted with EtOAc. The organic extract dried, filtered and concentrated to provide 300 mg (57%) of the title compound. MS (DCI$^{30}$) m/z 271 (M+H); $^1$H NMR (300 MHz, CDCl$_3$) δ 8.04-7.93 (m, 2H), 7.73 (t, J=7.7 Hz, 1H), 7.62 (d, J=7.6 Hz, 1H), 7.53-7.35 (m, 3H), 7.21 (d, J=7.5 Hz, 1H), 4.06 (s, 2H), 3.72 (dd, J=11.0, 4.0 Hz, 1H), 3.52 (dd, J=11.0, 6.9 Hz, 1H), 2.55 (td, J=6.7, 4.0 Hz, 1H), 1.91 (td, J=13.6, 6.8 Hz, 1H), 1.05 (d, J=6.4 Hz, 3H), 0.96 (d, J=6.8 Hz, 3H).

Example 226

(2R)-3-methyl-2-[({6-[3-(trimethylsilyl)phenyl]pyridin-2-yl}methyl)amino]butan-1-ol

Example 226A 6-(3-(trimethylsilyl)phenyl)picolinaldehyde

To a solution of 6-bromopicolinaldehyde (1.00 g, 5.38 mmol) in dioxane (25 mL) at ambient temperature was added 3-trimethylsilylphenylboronic acid (1.04 g, 5.38 mmol), cesium carbonate (2.7 mL, 5.4 mmol) and 1,1'-bis(diphenylphosphino)ferrocene-palladium(II)dichloride dichloromethane complex (0.088 g, 0.11 mmol). The solution was degassed (3× vacuum/purge $N_2$) and heated to 80° C. overnight. The mixture was cooled to room temperature and partioned between water and $CH_2Cl_2$. The organic phase concentrated and purified by chromatography (10% EtOAc: hexanes) to provide 1.18 g (86%) of the title compound. MS (DCI$^{30}$) m/z 256 (M+H).

Example 226B (2R)-3-methyl-2-[({6-[3-(trimethylsilyl)phenyl]pyridin-2-yl}methyl)amino]butan-1-ol The title compound was prepared according to Example 225, substituting Example 226A for 6-phenylpicolinaldehyde. MS (DCI$^{30}$) m/z 343 (M+H); $^1$H NMR (300 MHz, CDCl$_3$) δ 8.18-8.09 (m, 1H), 8.00-7.90 (m, 1H), 7.74 (dd, J=9.2, 6.2 Hz, 1H), 7.67-7.55 (m, 2H), 7.53-7.42 (m, 1H), 7.21 (d, J=7.5 Hz, 1H), 4.06 (s, 2H), 3.77-3.68 (m, 1H), 3.58-3.47 (m, 1H), 2.62-2.48 (m, 1H), 2.01-1.81 (m, 2H), 1.06 (d, J=6.8 Hz, 3H), 0.98 (d, J=6.8 Hz, 3H), 0.05--0.03 (m, 10H).

Example 227

(2R)-2-{[(6-{5-[tert-butyl(dimethyl)silyl]thiophen-2-yl}pyridin-2-yl)methyl]amino}-3-methylbutan-1-ol

Example 227A (R)-2-((6-bromopyridin-2-yl)methylamino)-3-methylbutan-1-ol

To a solution of 6-bromopyridine-2-carbaldehyde (5.00 g, 26.9 mmol) in methanol (75 mL) at ambient temperature was added D-valinol (3.00 mL, 26.9 mmol) followed by acetic acid (6.2 mL, 110 mmol). After 5 minutes, MP-cyanoborohydride (2.49 mmol/g; 12 g) was added and stirred overnight. The mixture was filtered, concentrated. The residue was partitioned between 1N NaOH and $CH_2Cl_2$. The organic phase was dried (Na$_2$SO$_4$) and concentrated. The residue was purified by chromatography (50% ethyl acetate:CH$_2$Cl$_2$ to remove non polar impurites, then ethyl acetate to 20% acetone:ethyl acetate) to provide 4.39 g (60%) of the title compound. MS (DCI$^{30}$) m/z 273/275 (M+H).

Example 227B (2R)-2-{[(6-{5-[tert-butyl(dimethyl)silyl]thiophen-2-yl}pyridin-2-yl)methyl]amino}-3-methylbutan-1-ol To a solution of Example 227A (0.521 g, 1.91 mmol) in dioxane (10 mL) at ambient temperature was added 2-(t-butyldimethylsilyl)thiophene-5-boronic acid pinacol ester (0.619 g, 1.91 mmol), 2 molar cesium carbonate (0.9 mL, 1.9 mmol) and 1,1'-bis(diphenylphosphino)ferrocene-palladium(II)dichloride dichloromethane complex (0.031 g, 0.038 mmol). The solution was degassed (3× vacuum/purge $N_2$) and heated to 80° C. overnight. The mixture was cooled and partioned between water and $CH_2Cl_2$. The organic phase concentrated and the residue triturated with ether to provide 355 mg (41%) of the title compound. MS (DCI$^{30}$) m/z 391 (M+H); $^1$H NMR (300 MHz, CDCl$_3$) δ 7.69-7.60 (m, 2H), 7.54 (d, J=7.6 Hz, 1H), 7.25 (d, J=3.6 Hz, 1H), 7.12 (d, J=7.4 Hz, 1H), 3.99 (s, 2H), 3.70 (dd, J=10.9, 4.0 Hz, 1H), 3.50 (dd, J=10.9, 6.4 Hz, 1H), 2.51 (td, J=6.5, 4.0 Hz, 1H), 1.92 (td, J=13.6, 6.8 Hz, 1H), 1.06 (d, J=6.8 Hz, 3H), 1.00-0.92 (m, 12H), 0.37-0.28 (m, 6H).

Example 228

(2R)-2-({[6-(3,4-difluorophenyl)-3-fluoropyridin-2-yl]methyl}amino)-3-methylbutan-1-ol (2R)-2-{[(6-bromo-3-fluoropyridin-2-yl)methyl]amino}-3-methylbutan-1-ol Example 73A (0.197 g, 0.678 mmol), 3,4-difluorophenylboronic acid (0.117 g, 0.738 mmol), tetrakis(triphenylphosphine)palladium(0) (0.0176 g, 0.015 mmol) and sodium carbonate (0.155 g, 1.46 mmol) were combined in DME (3 mL)/water (1.5 mL). Nitrogen was bubbled through the reaction mixture for about 15 minutes and then the mixture was warmed to 80° C. for 3 hours. The reaction mixture was partitioned between 1 M NaOH and $CH_2Cl_2$ (15 mL each) and the layers separated. The aqueous phase was extracted with $CH_2Cl_2$ (15 mL). The combined organic extracts were washed with 1 M aqueous HCl (2×15 mL) then discarded. The combined acidic fractions were made basic with 2.5 M NaOH then extracted with EtOAc (3×15 mL). The combined EtOAc extracts were washed with brine (1×15 mL), dried (MgSO$_4$), and concentrated to provide the title compound (95.7 mg, 43%). $^1$H NMR (300 MHz, DMSO-d$_6$) δ 8.15 (ddd, J=12.4, 8.0, 2.2 Hz, 1H), 7.99 (dd, J=8.7, 3.7 Hz, 1H), 7/97-7/91 (m, 1H), 7.84-7.72 (m, 1H), 7.56 (dt, J=10.6, 8.6 Hz, 1H), 4.50 (s, 1H), 3.98 (q, J=14.7 Hz, 2H), 3.48 (dd, J=10.0, 3.7 Hz, 1H), 2.41 (s, 1H), 1.95-1.77 (m, 1H), 0.87 (dd, J=8.4, 7.0 Hz, 6H). MS (ESI$^+$) m/z 325 (M+H)$^+$.

Example 229

(2R)-2-({[6-(1-benzothiophen-2-yl)-3-fluoropyridin-2-yl]methyl}amino)-3-methylbutan-1-ol The title compound was prepared according to Example 228, substituting benzo[b]thiophen-2-ylboronic acid for 3,4-difluorophenylboronic acid. $^1$H NMR (300 MHz, DMSO-d$_6$) δ 8.12 (s, 1H), 8.07 (dd, J=8.6, 3.7 Hz, 1H), 8.03-7.95 (m, 1H), 7.91-7.84 (m, 1H), 7.84, −7.75 (m, 1H), 7.44-7.33 (m, 2H), 4.43 (t, J=5.2 Hz, 1H), 3.93 (s, 2H), 3.48 (dt, J=9.7, 4.8 Hz, 1H), 3.40-3.32 (m, 1H), 2.39 (dd, J=11.2, 4.8 Hz, 1H), 2.31 (s, 1H), 1.95-1.80 (m, 1H), 0.89 (t, J=6.8 Hz, 6H). MS (ESI$^+$) m/z 354 (M+H)$^+$.

Example 231

(2R)-2-({[2-(4,4-difluoropiperidin-1-yl)-5-fluoropyrimidin-4-yl]methyl}amino)-3-methylbutan-1-ol

Example 231A 2-(4,4-difluoropiperidin-1-yl)-5-fluoro-4-methylpyrimidine

A 5 mL microwave vial was charged with 2-chloro-5-fluoro-4-methylpyrimidine (*JOC* 2004, 69, 3943-3949) (0.19 g, 1.3 mmol), 4,4-difluoropiperidine hydrochloride (1.0 g, 6.5 mmol) and NMP (2.6 mL). The mixture was heated in a microwave oven at 120° C. for 24 hours then cooled to ambient temperature. The mixture was then diluted with EtOAc, washed with water (3×), and brine. The organic extract was concentrated and purified by chromatography (silica gel, 0-5% EtOAc/hexanes gradient) to afford the title compound. MS (ESI) m/z: 232.4 (M+H)$^+$.

Example 231B 2-(4,4-difluoropiperidin-1-yl)-5-fluoropyrimidine-4-carbaldehyde A 5 mL microwave vial was charged with Example 231A (0.072 g, 0.31 mmol), selenium dioxide (0.069 g, 0.62 mmol), dioxane (0.9 mL), and water (0.034 mL). The mixture was heated in a microwave at 160° C. for 40 minutes. The residue was diluted with EtOAc and washed with water and brine. Purification by chromatography (silica gel eluted with 0-10% EtOAc/hexanes gradient) afforded the title compound.

Example 231C (2R)-2-({[2-(4,4-difluoropiperidin-1-yl)-5-fluoropyrimidin-4-yl]methyl}amino)-3-methylbutan-1-ol The title compound was prepared according to Example 225, substituting Example 231B for 6-phenylpicolinaldehyde. $^1$H NMR (300 MHz, CDCl$_3$) δ 8.11 (d, J=1.6 Hz, 1H), 3.98-3.91 (m, 4H), 3.90 (d, J=1.7 Hz, 2H), 3.68 (dd, J=10.8, 4.0 Hz, 1H), 3.45 (dd, J=10.9, 6.7 Hz, 1H), 2.44 (td, J=6.6, 4.0 Hz, 1H), 2.10-1.92 (m, 4H), 1.86 (dq, J=13.5, 6.8 Hz, 1H), 1.00 (d, J=6.8 Hz, 3H), 0.94 (d, J=6.8 Hz, 3H). MS (ESI) m/z: 333.1 (M+H)$^+$.

Example 233

(2R)-2-[({3-fluoro-6-[(E)-2-(3-fluorophenyl)ethenyl]pyridin-2-yl}methyl)amino]-3-methylbutan-1-ol The title compound was prepared according to Example 228, substituting (E)-(3-fluorostyryl)boronic acid for 3,4-difluorophenylboronic acid. $^1$H NMR (300 MHz, DMSO-d$_6$) δ 7.74-7.33 (m, 7H), 7.21-7.09 (m, 1H), 4.48 (t, J=5.2 Hz, 1H), 3.90 (q, J=14.2 Hz, 2H), 3.47 (dt, J=9.7, 4.7 Hz, 1H), 3.40-3.33 (m, 1H), 2.42-2.27 (m, 2H), 1.94-1.77 (m, 1H), 0.87 (dd, J=8.1, 7.3 Hz, 6H). MS (ESI$^+$) m/z 333 (M+H)$^+$.

Example 234

(2R)-2-({[6-[1,3-benzothiazol-5-yl)-3-fluoropyridin-2-yl]methyl}amino)-3-methylbutan-1-ol The title compound was prepared according to Example 228, substituting benzo[d]thiazol-5-ylboronic acid for 3,4-difluorophenylboronic acid. $^1$H NMR (300 MHz, DMSO-d$_6$) δ 9.46 (s, 1H), 8.78 (d, J=1.1 Hz, 1H), 8.28 (d, J=8.4 Hz, 1H), 8.23 (dd, J=8.5, 1.5 Hz, 1H), 8.10 (dd, J=8.6, 3.6 Hz, 1H), 7.84-7.74 (m, 1H), 4.48 (t, J=5.0 Hz, 1H), 4.07-3.90 (m, 2H), 3.49 (dt, J=9.3, 4.6 Hz, 1H), 3.40-3.33 (m, 1H), 2.46-2.36 (m, 2H), 1.96-1.80 (m, 1H), 0.88 (dd, J=8.2, 7.0 Hz, 6H). MS (ESI$^+$) m/z 346 (M+H)$^+$.

Example 235

(2R)-2-[({3-fluoro-6-[(4-methoxyphenyl)ethynyl]pyridin-2-yl}methyl)amino]-3-methylbutan-1-ol Example 73A (0.203 g, 0.697 mmol), 1-ethynyl-4-methoxybenzene (0.10 mL, 0.77 mmol), PdCl$_2$(PPh$_3$)$_2$ (7.1 mg, 10 μmol), copper(I) iodide (4.5 mg, 0.024 mmol) and triethylamine (0.15 mL, 1.08 mmol) were combined in acetonitrile (4 mL) and the mixture was warmed to 80° C. for 17 hours. After cooling to ambient temperature, the mixture was partitioned between 1 M NaOH and CH$_2$Cl$_2$ (15 mL each) and the layers separated. The aqueous phase was extracted with CH$_2$Cl$_2$ (15 mL). The combined organic extractes were washed with 1 N aqueous HCl (2×15 mL) then discarded. The combined acidic fractions were made basic with 15 mL of 2.5 M aquoues NaOH and extracted with EtOAc (3×15 mL). The combined EtOAc extracts were washed with brine (1×20 mL), dried (MgSO$_4$), and concentrated. The residue was diluted with CH$_2$Cl$_2$ and filtered through a PL-Thiol MP SPE tube (StratoSpheres™, to remove residual metals) then concentrated to afford the title compound (0.194 g, 82%). $^1$H NMR (300 MHz, DMSO-d$_6$) δ 7.77-7.67 (m, 1H), 7.60 (dd, J=8.5, 3.9 Hz, 1H), 7.57-7.52 (m, 2H), 7.05-6.98 (m, 2H), 4.50 (s, 1H), 3.89 (q, J=14.0 Hz, 2H), 3.81 (s, 3H), 3.52-3.41 (m, 1H), 3.39-3.31 (m, 1H), 2.44-2.27 (m, 2H), 1.91-1.73 (m, 1H), 0.85 (dd, J=9.7, 6.9 Hz, 6H). MS (ESI$^+$) m/z 343 (M+H)$^+$.

Example 236

(2R)-2-({[6-(3-cyclohexylprop-1-yn-1-yl)-3-fluoropyridin-2-yl]methyl}amino)-3-methylbutan-1-ol The title compound was prepared according to Example 235, substituting prop-2-yn-1-ylcyclohexane for 1-ethynyl-4-methoxybenzene. $^1$H NMR (300 MHz, DMSO-d$_6$) δ 7.65 (dd, J=9.3, 8.7 Hz, 1H), 7.43 (dd, J=8.5, 3.9 Hz, 1H), 4.51 (s, 1H), 3.88 (q, J=13.7 Hz, 2H), 3.53-3.41 (m, 1H), 3.39-3.33 (m, 1H), 2.35 (d, J=6.6 Hz, 3H), 1.91-1.76 (m, 3H), 1.75-1.45 (m, 4H), 1.33-0.97 (m, 6H), 0.92-0.78 (m, 6H). MS (ESI+) m/z 333 (M+H)$^+$.

Example 237

2-methyl-2-[({6-[3-(trimethylsilyl)phenyl]pyridin-2-yl}methyl)amino]propan-1-ol

To a solution of Example 226A (1.00 g, 3.92 mmol) in methanol (20 mL) at ambient temperature was added 2-amino-2-methyl-1-propanol (0.349 g, 3.92 mmol), acetic acid (0.90 mL, 15.7 mmol) followed by MP-cyanoborohydride (2.49 mmol/g; 1.5 g). After 2 hours, the mixture was filtered, concentrated and the residue partitioned between ether and 1N NaOH. The organic layer was extracted with 1N aquoues HCl (×2) and the organic phase discarded. The aqueous layer was neutralized with 1N NaOH and extracted with EtOAc. The EtOAc extract was dried and concentrated to provide 700 mg (54%) of the title compound. MS (DCI+) m/z 329 (M+H); $^1$H NMR (300 MHz, CDCl$_3$) δ 8.10 (s, 1H), 7.97-7.90 (m, 1H), 7.73 (t, J=7.7 Hz, 1H), 7.64-7.54 (m, 2H), 7.48 (t, J=7.5 Hz, 1H), 7.22 (d, J=7.7 Hz, 1H), 3.95 (s, 2H), 3.42 (s, 2H), 1.18 (s, 6H), 0.39-0.25 (m, 9H).

Example 238

(2R)-2-[({3-fluoro-6-[(4-fluorophenyl)ethynyl]pyridin-2-yl}methyl)amino]-3-methylbutan-1-ol The title compound was prepared according to Example 235, substituting 1-ethynyl-4-fluorobenzene for 1-ethynyl-4-methoxybenzene. $^1$H NMR (300 MHz, DMSO-d$_6$) δ 7.80-7.60 (m, 4H), 7.37-7.25 (m, 2H), 4.46 (t, J=5.2 Hz, 1H), 3.88 (q, J=13.3 Hz, 2H), 3.46 (dt, J=10.4, 4.7 Hz, 1H), 3.36-3.25 (m, 1H) under water peak, 2.33 (dd, J=11.3, 4.8 Hz, 1H), 2.13 (s, 1H), 1.89-1.73 (m, 1H), 0.85 (dd, J=9.5, 6.9 Hz, 6H). MS (ESI$^+$) m/z 331 (M+H)$^+$.

Example 239

(2R)-2-[({6-[(3,4-difluorophenyl)ethynyl]-3-fluoropyridin-2-yl}methyl)amino]-3-methylbutan-1-ol The title compound was prepared according to Example 235, substituting 4-ethynyl-1,2-difluorobenzene for 1-ethynyl-4-methoxybenzene. $^1$H NMR (300 MHz, DMSO-d$_6$) δ 7.83-7.72 (m, 2H), 7.66 (dd, J=8.5, 4.0 Hz, 1H), 7.60-7.46 (m, 2H), 4.46 (t, J=5.2 Hz, 1H), 3.88 (q, J=13.7 Hz, 2H), 3.51-3.41 (m, 1H), 3.37-3.22 (m, 1H) under water peak, 2.33 (dd, J=11.4, 4.8 Hz, 1H), 2.13 (s, 1H), 1.88-1.73 (m, 1H), 0.84 (dd, J=9.8, 6.9 Hz, 6H). MS (ESI$^+$) m/z 349 (M+H)$^+$.

Example 240

(2R)-2-({[6-(cyclohexylethynyl)-3-fluoropyridin-2-yl]methyl}amino)-3-methylbutan-1-ol The title compound was prepared according to Example 235, substituting ethynylcyclohexane for 1-ethynyl-4-methoxybenzene. $^1$H NMR (300 MHz, DMSO-d$_6$) δ 7.63 (dd, J=9.3, 8.7 Hz, 1H), 7.41 (dd, J=8.5, 3.8 Hz, 1H), 4.45 (t, J=5.2 Hz, 1H), 3.83 (q, J=13.7 Hz, 2H), 3.50-3.38 (m, 1H), 3.30-3.22 (m, 1H), 2.71-2.59 (m, 1H), 2.30 (dd, J=11.4, 4.8 Hz, 1H), 2.11 (s, 1H), 1.91-1.76 (m, 3H), 1.76-1.61 (m, 2H), 1.56-1.41 (m, 3H), 1.41-1.22 (m, 3H), 0.84 (dd, J=9.4, 6.9 Hz, 6H). MS (ESI$^+$) m/z 319 (M+H)$^+$.

Example 241

(2R)-2-[({6-[(4-tert-butylphenyl)ethynyl]-3-fluoropyridin-2-yl}methyl)amino]-3-methylbutan-1-ol The title compound was prepared according to Example 235, substituting 1-(tert-butyl)-4-ethynylbenzene for 1-ethynyl-4-methoxybenzene. $^1$H NMR (300 MHz, DMSO-d$_6$) δ 7.78-7.69 (m, 1H), 7.62 (dd, J=8.5, 4.0 Hz, 1H), 7.58-7.51 (m, 2H), 7.51-7.44 (m, 2H), 4.47 (t, J=5.2 Hz, 1H), 3.88 (q, J=13.7 Hz, 2H), 3.51-3.40 (m, 1H), 3.35-3.24 (m, 1H) under water peak, 2.33 (dd, J=11.4, 4.8 Hz, 1H), 2.14 (s, 1H), 1.88-1.73 (m, 1H), 1.30 (s, 9H), 0.85 (dd, J=9.5, 6.9 Hz, 6H). MS (ESI$^+$) m/z 369 (M+H)$^+$.

Example 242

(2R)-2-({[6-[5-chlorothiophen-2-yl)-3-fluoropyridin-2-yl]methyl}amino)-3-methylbutan-1-ol The title compound was prepared according to Example 228, substituting (5-chlorothiophen-2-yl)boronic acid for 3,4-difluorophenylboronic acid. $^1$H NMR (300 MHz, DMSO-d$_6$) δ 7.89 (dd, J=8.6, 3.7 Hz, 1H), 7.74 (dd, J=9.3, 8.8 Hz, 1H), 7.65 (d, J=4.0 Hz, 1H), 7.17 (d, J=4.0 Hz, 1H), 4.41 (t, J=5.1 Hz, 1H), 3.97-3.80 (m, 2H), 3.45 (dt, J=9.6, 4.7 Hz, 1H), 3.38-3.23 (m, 1H) under water peak, 2.35 (dt, J=6.5, 4.8 Hz, 1H), 2.27 (s, 1H), 1.94-1.76 (m, 1H), 0.86 (t, J=6.7 Hz, 6H). MS (ESI$^+$) m/z 329 (M+H)$^+$.

Example 243

(2R)-2-({[3-fluoro-6-(5-methylthiophen-2-yl)pyridin-2-yl]methyl}amino)-3-methylbutan-1-ol The title compound was prepared according to Example 228, substituting (5-methylthiophen-2-yl)boronic acid for 3,4-difluorophenylboronic acid. $^1$H NMR (300 MHz, CDCl$_3$) δ 7.51 (dd, J=8.6, 3.7 Hz, 1H), 7.37 (t, J=8.7, Hz, 1H), 7.32 (d, J=3.7 Hz, 1H), 6.78-6.71 (m, 1H), 4.27 (dd, J=15.4, 1.8 Hz, 1H), 4.13 (dd, J=15.4, 1.8 Hz, 1H), 3.80 (dd, J=11.6, 3.8 Hz, 1H), 3.68 (dd, J=11.6, 6.6 Hz, 1H), 2.62 (td, J=6.6, 3.8 Hz, 1H), 2.01 (dq, J=13.6, 6.7 Hz, 1H), 1.08 (d, J=6.8 Hz, 3H), 1.02 (d, J=6.8 Hz, 3H). MS (ESI) m/z: 309.1 (M+H)$^+$.

Example 244

(2R)-2-({[3-fluoro-6-(3,4,5-trifluorophenyl)pyridin-2-yl]methyl}amino)-3-methylbutan-1-ol The title compound was prepared according to Example 245, substituting (3,4,5-trifluorophenyl)boronic acid for (3,4-difluorophenyl)boronic acid.

Example 245

(2R)-2-({[3-fluoro-6-(2,3,4-trifluorophenyl)pyridin-2-yl]methyl}amino)-3-methylbutan-1-ol A 4 mL vial was charged with SiliaCat DPP-Pd (0.1 equivalent., 26 mg, purchased from Silicycle). Solutions of Example 73A (20 mg, 0.07 mmol) in ethanol (1.0 mL) and 2,3,4-trifluorophenylboronic acid (14 mg, 0.08 mmol) in ethanol (0.3 mL) were added followed by 1 M aqueous Cs$_2$CO$_3$ (0.21 mL). The mixture was heated (Synthos 3000 Anton Paar microwave reaction system) for 30 minutes at 120° C., then filtered and concentrated. The residue was purified by reverse phase HPLC to provide the title compound. MS (ESI+) m/z 343 (M+H)$^+$.

Example 246

(2R)-2-({[3-fluoro-6-(2,4,5-trifluorophenyl)pyridin-2-yl]methyl}amino)-3-methylbutan-1-ol The title compound was prepared according to Example 245, substituting (2,4,5-trifluorophenyl)boronic acid for 2,3,4-trifluorophenylboronic acid. MS (ESI+) m/z 343 (M+H)$^+$.

Example 247

(2R)-2-({[6-(3,5-difluorophenyl)-3-fluoropyridin-2-yl]methyl}amino)-3-methylbutan-1-ol The title compound was prepared according to Example 245, substituting (3,5-difluorophenyl)boronic acid for 2,3,4-trifluorophenylboronic acid. MS (ESI+) m/z 325 (M+H)$^+$.

Example 248

(2R)-2-({[3-fluoro-6-(1-methyl-1H-indol-5-yl)pyridin-2-yl]methyl}amino)-3-methylbutan-1-ol The title compound was prepared according to Example 245, substituting 1-methyl-1H-indol-5-ylboronic acid for 2,3,4-trifluorophenylboronic acid. MS (ESI+) m/z 342 (M+H)+.

Example 249

(2R)-2-({[3-fluoro-6-(1-methyl-1H-indol-2-yl)pyridin-2-yl]methyl}amino)-3-methylbutan-1-ol The title compound was prepared according to Example 228, substituting (1-methyl-1H-indol-2-yl)boronic acid for 3,4-difluorophenylboronic acid. $^1$H NMR (300 MHz, CDCl$_3$) δ 8.18 (d, J=1.5, Hz, 1H), 7.86 (dd, J=8.6, 1.7 Hz, 1H), 7.68 (dd, J=8.6, 3.7 Hz, 1H), 7.47-7.37 (m, 2H), 7.09 (d, J=3.1 Hz, 1H), 6.56 (d, J=3.0, Hz, 1H), 4.27-4.08 (m, 2H), 3.83 (s, 3H), 3.75 (dd, J=11.2, 3.8 Hz, 1H), 3.57 (dd, J=11.2, 6.7 Hz, 1H), 2.56 (td, J=6.7, 3.9 Hz, 1H), 1.94 (dq, J=13.6, 6.8 Hz, 1H), 1.04 (d, J=6.8 Hz, 3H), 0.97 (d, J=6.8 Hz, 3H).
MS (ESI) m/z: 342 (M+H)+.

Example 250

(2R)-2-[({6-[1-(1,3-dioxolan-2-ylmethyl)-1H-pyrazol-4-yl]-3-fluoropyridin-2-yl}methyl)amino]-3-methylbutan-1-ol The title compound was prepared according to Example 228, substituting (14(1,3-dioxolan-2-yl)methyl)-1H-pyrazol-4-yl)boronic acid for 3,4-difluorophenylboronic acid. $^1$H NMR (300 MHz, CDCl$_3$) δ 8.02 (s, 1H), 7.94 (s, 1H), 7.38-7.28 (m, 2H), 5.26 (t, J=3.9, Hz, 1H), 4.34 (d, J=3.8 Hz, 1H), 4.05 (d, J=2.0 Hz, 1H), 3.94-3.87 (m, 4H), 3.70 (dd, J=10.9, 3.9 Hz, 1H), 3.48 (dd, J=10.9, 6.8 Hz, 1H), 2.47 (td, J=6.7, 3.8 Hz, 1H), 1.86 (dq, J=13.5, 6.8 Hz, 1H), 1.02 (d, J=6.8 Hz, 3H), 0.95 (d, J=6.8 Hz, 3H). MS (ESI) m/z: 365 (M+H)+.

Example 251

(2R)-2-({[3-fluoro-6-(furan-3-yl)pyridin-2-yl]methyl}amino)-3-methylbutan-1-ol

The title compound was prepared according to Example 228, substituting furan-3-ylboronic acid for 3,4-difluorophenylboronic acid. $^1$H NMR (300 MHz, CDCl$_3$) δ 8.01-7.96 (m, 1H), 7.48 (t, J=1.7 Hz, 1H), 7.36 (d, J=6.6 Hz, 1H), 6.86 (dd, J=1.9, 0.9 Hz, 1H), 4.07 (d, J=2.0 Hz, 1H), 3.70 (dd, J=10.9, 3.9 Hz, 1H), 3.48 (dd, J=10.9, 6.8 Hz, 1H), 2.48 (td, J=6.7, 3.8 Hz, 1H), 1.86 (dq, J=13.5, 6.8 Hz, 1H), 1.02 (d, J=6.8 Hz, 3H), 0.95 (d, J=6.8 Hz, 3H). MS (ESI) m/z: 279 (M+H)+.

Example 252

(2R)-2-({[3-fluoro-6-(1-methyl-1H-pyrazol-5-yl)pyridin-2-yl]methyl}amino)-3-methylbutan-1-ol The title compound was prepared according to Example 228, substituting (1-methyl-1H-pyrazol-5-yl)boronic acid for 3,4-difluorophenylboronic acid. $^1$H NMR (300 MHz, CDCl$_3$) δ 7.55-7.42 (m, 3H), 6.55 (d, J=2.0 Hz, 1H), 4.20 (s, 3H), 4.15 (dd, J=3.4, 2.0 Hz, 1H), 3.75 (dd, J=11.1, 4.0 Hz, 1H), 3.54 (dd, J=11.1, 7.0 Hz, 1H), 2.59 (td, J=6.7, 4.0 Hz, 1H), 1.94 (dq, J=13.5, 6.8 Hz, 1H), 1.01 (d, J=6.8 Hz, 3H), 0.96 (d, J=6.8 Hz, 3H). MS (ESI) m/z: 293 (M+H)+.

Example 253

(2R)-2-({[5-fluoro-5'-methyl-6'-(morpholin-4-yl)-2,3'-bipyridin-6-yl]methyl}amino)-3-methylbutan-1-ol The title compound was prepared according to Example 228, substituting (5-methyl-6-morpholinopyridin-3-yl)boronic acid for 3,4-difluorophenylboronic acid. $^1$H NMR (300 MHz, CDCl$_3$) δ 8.68 (d, J=2.4 Hz, 1H), 8.02 (d, J=2.4 Hz, 1H), 7.58 (dd, J=8.6, 3.7 Hz, 1H), 7.43 (t, J=8.7 Hz, 1H), 4.22-4.06 (m, 2H), 3.95-3.78 (m, 4H), 3.74 (dd, J=11.0, 3.9 Hz, 1H), 3.54 (dd, J=11.1, 6.8 Hz, 1H), 3.30-3.20 (m, 4H), 2.54 (td, J=6.7, 3.9 Hz, 1H), 2.37 (s, 3H), 1.92 (td, J=13.6, 6.8 Hz, 1H), 1.03 (d, J=6.8 Hz, 3H), 0.97 (d, J=6.8 Hz, 3H). MS (ESI) m/z: 389 (M+H)+.

Example 254

(2R)-2-({[5-fluoro-6'-(4-methylpiperazin-1-yl)-2,3'-bipyridin-6-yl]methyl}amino)-3-methylbutan-1-ol The title compound was prepared according to Example 228, substituting (6-(4-methylpiperazin-1-yl)pyridin-3-yl)boronic acid for 3,4-difluorophenylboronic acid. $^1$H NMR (300 MHz, CDCl$_3$) δ 8.74 (d, J=2.5 Hz, 1H), 8.11 (dd, J=8.9, 2.5 Hz, 1H), 7.51 (dd, J=8.6, 3.7 Hz, 1H), 7.38 (t, J=8.8 Hz, 1H), 6.73 (d, J=8.9 Hz, 1H), 4.07 (d, J=2.0 Hz, 1H), 3.82-3.54 (m, 5H), 3.47 (dd, J=10.8, 6.7 Hz, 1H), 2.58-2.51 (m, 4H), 2.48 (td, J=6.7, 4.0 Hz, 1H), 2.37 (s, 3H), 1.87 (td, J=13.6, 6.8 Hz, 1H), 1.01 (d, J=6.8 Hz, 3H), 0.96 (d, J=6.8 Hz, 3H). MS (ESI) m/z: 388 (M+H)+.

Example 255

(2R)-2-({[6-(1-benzothiophen-5-yl)-3-fluoropyridin-2-yl]methyl}amino)-3-methylbutan-1-ol The title compound was prepared according to Example 228, substituting benzo[b]thiophen-5-ylboronic acid for 3,4-difluorophenylboronic acid. $^1$H NMR (300 MHz, CDCl$_3$) δ 8.39 (d, J=1.2 Hz, 1H), 7.98-7.93 (m, 2H), 7.70 (dd, J=8.6, 3.6 Hz, 1H), 7.52-7.39 (m, 3H), 4.15-4.11 (m, 2H), 3.72 (dd, J=10.9, 3.9 Hz, 1H), 3.50 (dd, J=10.9, 6.6 Hz, 1H), 2.52 (td, J=6.6, 3.9 Hz, 1H), 1.90 (dq, J=13.6, 6.8 Hz, 1H), 1.03 (d, J=6.8 Hz, 3H), 0.96 (d, J=6.8 Hz, 3H). MS (ESI) m/z: 345 (M+H)+.

Example 256

(2R)-2-({[6-(1-benzofuran-5-yl)-3-fluoropyridin-2-yl]methyl}amino)-3-methylbutan-1-ol The title compound was prepared according to Example 228, substituting benzofuran-5-ylboronic acid for 3,4-difluorophenylboronic acid. $^1$H NMR (300 MHz, CDCl$_3$) δ 8.17 (d, J=1.9 Hz, 1H), 7.90 (dd, J=8.6, 1.9 Hz, 1H), 7.71-7.62 (m, 2H), 7.58 (d, J=8.7, Hz, 1H), 7.44 (t, J=8.8 Hz, 1H), 6.85 (dd, J=2.2, 0.9 Hz, 1H), 4.21-4.08 (m, 2H), 3.73 (dd, J=11.0, 3.9 Hz, 1H), 3.52 (dd, J=11.0, 6.7 Hz, 1H), 2.54 (td, J=6.7, 3.9

Hz, 1H), 1.91 (td, J=13.6, 6.8 Hz, 1H), 1.03 (d, J=6.8 Hz, 3H), 0.96 (d, J=6.8 Hz, 3H). MS (ESI) m/z: 329 (M+H)+.

Example 257

(2R)-2-[({3-fluoro-6-[cis-4-(trifluoromethyl)cyclohexyl]pyridin-2-yl}methyl)amino]-3-methylbutan-1-ol Example 223 (1.20 g, 3.33 mmol) and MeOH (20 mL) were added to 5% wet Pd/C (0.240 g, 2.26 mmol) and stirred under 30 psi of hydrogen for 4 hours at ambient temperature. The mixture was filtered through a nylon membrane then concentrated under reduced pressure and purified by chromatography (silica gel eluted with 30-100% EtOAc/hexanes gradient) to provide a mixture of the title compound and Example 258.

Separation of the isomers was achieved by preparative HPLC (Chiralpak® AS, 25 cm×2.0 cm, 1% 2-propanol/hexanes, 10 mL/min, UV 220 and 254 nm) to provide Example 258 (retention time 15.8 min) and the title compound (retention time 16.6 min). Characterization data for Example 257: $^1$H NMR (300 MHz, DMSO-$d_6$) δ 7.57 (dd, J=9.8, 8.5 Hz, 1H), 7.29 (dd, J=8.6, 3.7 Hz, 1H), 4.37 (t, J=5.2 Hz, 2H), 3.86 (d, J=1.7 Hz, 2H), 3.42 (dt, J=9.9, 4.9 Hz, 1H), 3.34-3.23 (m, 1H), 2.99 (p, J=5.2 Hz, 1H), 2.48-2.35 (m, 1H), 2.32 (dt, J=6.2, 4.9 Hz, 1H), 2.28-2.17 (m, 1H), 2.17-2.04 (m, 2H), 1.89-1.58 (m, 7H), 0.84 (d, J=2.4 Hz, 3H), 0.82 (d, J=2.4 Hz, 3H). MS (ESI) m/z: 363 (M+H)+.

Example 258

(2R)-2-[({3-fluoro-6-[trans-4-(trifluoromethyl)cyclohexyl]pyridin-2-yl}methyl)amino]-3-methylbutan-1-ol The title compound was prepared and isolated as described in Example 257. $^1$H NMR (300 MHz, DMSO-$d_6$) δ 7.57 (dd, J=9.8, 8.5 Hz, 1H), 7.29 (dd, J=8.6, 3.7 Hz, 1H), 4.37 (t, J=5.2 Hz, 2H), 3.86 (d, J=1.7 Hz, 2H), 3.42 (dt, J=9.9, 4.9 Hz, 1H), 3.34-3.23 (m, 1H), 2.99 (p, J=5.2 Hz, 1H), 2.48-2.35 (m, 1H), 2.32 (dt, J=6.2, 4.9 Hz, 1H), 2.28-2.17 (m, 1H), 2.17-2.04 (m, 2H), 1.89-1.58 (m, 7H), 0.84 (d, J=2.4 Hz, 3H), 0.82 (d, J=2.4 Hz, 3H). MS (ESI) m/z: 363.1 (M+H)+.

Example 259 tert-butyl 4-(benzyloxy)-2-[5-fluoro-6-({[(2R)-1-hydroxy-3-methylbutan-2-yl]amino}methyl)pyridin-2-yl]-1H-indole-1-carboxylate The title compound was prepared according to Example 228, substituting (4-(benzyloxy)-1-(tert-butoxycarbonyl)-1H-indol-2-yl)boronic acid for (3,4-difluorophenyl)boronic acid. $^1$H NMR (300 MHz, DMSO-$d_6$) δ 7.77 (dd, J=9.5, 8.6 Hz, 1H), 7.70-7.62 (m, 2H), 7.54-7.48 (m, 2H), 7.44-7.34 (m, 2H), 7.34-7.30 (m, 1H), 7.27 (d, J=8.3 Hz, 1H), 6.95 (d, J=0.4 Hz, 1H), 6.91 (d, J=8.0 Hz, 1H), 5.28 (s, 2H), 4.40 (t, J=5.1 Hz, 1H), 4.00-3.86 (m, 2H), 3.44 (dt, J=9.5, 4.7 Hz, 1H), 3.35-3.23 (m, 1H) under water peak, 2.35 (dd, J=11.1, 4.8 Hz, 1H), 2.14 (s, 1H), 1.88-1.73 (m, 1H), 1.30 (s, 9H), 0.83 (t, J=6.8 Hz, 6H). MS (ESI+) m/z 534 (M+H)+.

Example 260

(2R)-2-[({3-fluoro-6-[3-(1H-pyrazol-1-yl)phenyl]pyridin-2-yl}methyl)amino]-3-methylbutan-1-ol The title compound was prepared according to Example 228, substituting (3-(1H-pyrazol-1-yl)phenyl)boronic acid for (3,4-difluorophenyl)boronic acid. $^1$H NMR (300 MHz, DMSO-$d_6$) δ 8.61 (d, J=2.4 Hz, 1H), 8.50 (t, J=1.8 Hz, 1H), 8.06 (dd, J=8.7, 3.6 Hz, 1H), 8.03-7.98 (m, 1H), 7.94-7.88 (m, 1H), 7.82 (d, J=9.3 Hz, 1H), 7.80-7.76 (m, 1H), 7.61 (t, J=7.9 Hz, 1H), 6.59 (dd, J=3.0, 1.3 Hz, 1H), 4.48 (t, J=5.2 Hz, 1H), 4.06-3.90 (m, 2H), 3.53-3.43 (m, 1H), 3.40-3.28 (m, 1H), 2.47-2.34 (m, 2H), 1.94-1.80 (m, 1H), 0.88 (t, J=7.1 Hz, 6H). MS (ESI+) m/z 355 (M+H)+.

Example 261

(2R)-2-[({6-[2-(dimethylamino)pyrimidin-5-yl]-3-fluoropyridin-2-yl}methyl)amino]-3-methylbutan-1-ol The title compound was prepared according to Example 228, substituting (2-(dimethylamino)pyrimidin-5-yl)boronic acid for (3,4-difluorophenyl)boronic acid. $^1$H NMR (300 MHz, DMSO-$d_6$) δ 9.02 (s, 2H), 7.83 (dd, J=8.7, 3.7 Hz, 1H), 7.77-7.66 (m, 1H), 4.48 (t, J=5.2 Hz, 1H), 3.91 (qd, J=14.5, 1.5 Hz, 2H), 3.51-3.40 (m, 1H), 3.39-3.25 (m, 1H), 3.19 (s, 6H), 2.46 (s, 1H), 2.37 (dt, J=6.8, 4.7 Hz, 1H), 1.93-1.77 (m, 1H), 0.93-0.80 (m, 6H). MS (ESI+) m/z 334 (M+H)+.

Example 262

(2R)-2-({[6-(4-butoxy-3-chlorophenyl)pyridin-2-yl]methyl}amino)-3-methylbutan-1-ol Example 262A 6-(4-butoxy-3-chlorophenyl)picolinaldehyde To a solution of 6-bromopicolinaldehyde (4.07 g, 21.88 mmol) in dioxane (40 mL) at ambient temperature was added 4-butoxy-3-chlorophenylboronic acid (5.00 g, 21.9 mmol), 2M cesium carbonate (22.0 mL, 43.8 mmol) and 1,1'-bis(diphenylphosphino)ferrocene-palladium(II)dichloride dichloromethane complex (0.357 g, 0.438 mmol). The mixture was degassed (3× vacuum/purge $N_2$) then heated at 80° C. overnight. The mixture was cooled to room temperature then partioned between water and $CH_2Cl_2$. The organic phase was concentrated and purified by chromatography (silica gel, 10% ethyl acetate:hexanes) to provide 5.20 g (82%) of the title compound. MS (DCI+) m/z 290 (M+H).

Example 262B (2R)-2-({[6-(4-butoxy-3-chlorophenyl)pyridin-2-yl]methyl}amino)-3-methylbutan-1-ol To a solution of Example 262A (0.500 g, 1.73 mmol) in MeOH (10 mL) at ambient temperature was added D-valinol (0.20 mL, 1.7 mmol), acetic acid (0.40 ml, 6.9 mmol) followed by MP-cyanoborohydride (2.49 mmol/g; 1.00 g). After 2 hours, the mixture was filtered and concentrated. The residue was partitioned between 1N HCl and ethyl acetate. The organic layer was discarded. The aqueous layer made basic with 1N NaOH and extracted with ethyl acetate. The EtOAc extract was dried ($Na_2SO_4$) and concentrated to give 420 mg (65%) of the title compound. MS (DCI+) m/z 377 (M+H); $^1$H NMR (300 MHz, CDCl$_3$) δ 8.03 (d, J=2.3 Hz, 1H), 7.87 (dd, J=8.6, 2.2 Hz, 1H), 7.68 (t, J=7.7 Hz, 1H), 7.53 (d, J=7.8 Hz, 1H), 7.17 (d, J=7.6 Hz, 1H), 7.00 (d, J=4.4 Hz, 1H), 4.09 (t, J=6.5 Hz, 2H), 4.06-3.92 (m, 2H), 3.69 (dd, J=10.8, 4.0 Hz, 1H), 3.47 (dd, J=10.8, 6.8 Hz, 1H), 2.51 (td, J=6.7, 4.0 Hz, 1H), 1.95-1.78 (m, 4H), 1.63-1.46 (m, 2H), 0.99 (m, 9H).

Example 263

(2R)-3-methyl-2-{[(6-{[4-(pentafluoro-$\lambda^6$-sulfanyl) phenyl]ethynyl}pyridin-2-yl)methyl]amino}butan-1-ol Example 263A 6-((4-(pentafluorothio)phenyl)ethynyl)picolinaldehyde To a solution of 6-ethynylpicolinaldehyde (*Chem. Lett.* 2004, 33, 1298; 0.500 g, 3.81 mmol) in acetonitrile (30 mL) and triethylamine (30 mL) at ambient temperature was added 4-iodophenylsulfur pentafluoride (1.26 g, 3.81 mmol), Pd(PPh$_3$)$_2$Cl$_2$ (0.054 g, 0.076 mmol) and copper(I) iodide (0.029 g, 0.15 mmol). The mixture was heated at 80° C. for 30 minutes; cooled to ambient temperature, concentrated and purified by chromatography (silica gel, 0% to 10% ethyl acetate:hexanes) to provide 730 mg (57%) of the title compound. MS (DCI+) m/z 334 (M+H).

Example 263B (2R)-3-methyl-2-{[(6-{[4-(pentafluoro-$\lambda^6$-sulfanyl) phenyl]ethynyl}pyridin-2-yl)methyl]amino}butan-1-ol To a solution of Example 263A (0.730 g, 2.19 mmol) in CH$_2$Cl$_2$ (5 mL) and MeOH (5 mL) at ambient temperature was added D-valinol (0.24 mL, 2.2 mmol), acetic acid (0.50 g, 8.8 mmol) and MP-cyanoborohydride (2.49 mmol/g; 1.10 g). After stirring overnight, the mixture was filtered and concentrated. The residue was partitioned between ether and 1N NaOH and the organic extract was dried (Na$_2$SO$_4$) and concentrated to give 480 mg (47%) of the title compound. MS (DCI+) m/z 421 (M+H); $^1$H NMR (300 MHz, CDCl$_3$) δ 7.80-7.61 (m, 6H), 7.49-7.42 (m, 1H), 7.36-7.29 (m, 1H), 4.10-3.93 (m, 2H), 3.73-3.63 (m, 1H), 3.51-3.40 (m, 1H), 2.54-2.42 (m, 1H), 1.93-1.79 (m, 1H), 1.01 (d, J=6.8 Hz, 3H), 0.94 (d, J=6.8 Hz, 3H).

Example 264

(2R)-2-[({6-[(4-fluorophenyl)ethynyl]pyridin-2-yl}methyl)amino]-3-methylbutan-1-ol Example 264A 6-((4-fluorophenyl)ethynyl)picolinaldehyde The title compound was prepared according to Example 235, substituting 1-ethynyl-4-fluorobenzene for 1-ethynyl-4-methoxybenzene and substituting 6-bromopicolinaldehyde for Example 73A. MS (DCI+) m/z 226 (M+H).

Example 264B (2R)-2-[({6-[(4-fluorophenyl)ethynyl]pyridin-2-yl}methyl)amino]-3-methylbutan-1-ol The title compound was prepared according to Example 262B, substituting Example 264A for Example 262A. $^1$H NMR (400 MHz, CDCl$_3$) δ 7.80 (t, J=7.8 Hz, 1H), 7.71-7.62 (m, 2H), 7.49 (d, J=7.9 Hz, 2H), 7.34-7.24 (m, 2H), 4.45 (s, 1H), 3.90-3.74 (m, 2H), 3.51-3.40 (m, 1H), 2.36-2.24 (m, 1H), 1.86-1.73 (m, 1H), 0.86 (dd, J=10.9, 6.9 Hz, 6H), −2H under water peak and NH/OH. MS (DCI$^{30}$) m/z 313 (M+H)$^+$.

Example 265

(2R)-2-[({6-[(3,4-difluorophenyl)ethynyl]pyridin-2-yl}methyl)amino]-3-methylbutan-1-ol Example 265A 6-((3,4-difluorophenyl)ethynyl)picolinaldehyde The title compound was prepared according to Example 235, substituting 4-ethynyl-1,2-difluorobenzene for 1-ethynyl-4-methoxybenzene and substituting 6-bromopicolinaldehyde for Example 73A. MS (DCI+) m/z 244 (M+H).

Example 265B (2R)-2-[({6-[(3,4-difluorophenyl)ethynyl]pyridin-2-yl}methyl)amino]-3-methylbutan-1-ol The title compound was prepared according to Example 262B, substituting Example 265A for Example 262A. $^1$H NMR (300 MHz, CDCl$_3$) δ 7.73-7.63 (m, 1H), 7.47-7.39 (m, 2H), 7.39-7.32 (m, 1H), 7.32-7.28 (m, 1H), 7.24-7.09 (m, 1H), 4.12-3.94 (m, 2H), 3.69 (dd, J=11.0, 3.9 Hz, 1H), 3.54-3.44 (m, 1H), 2.73-2.55 (m, 2H), 2.50 (ddd, J=13.2, 8.4, 5.1 Hz, 1H), 1.95-1.78 (m, 1H), 1.06-0.91 (m, 6H). MS (DCI$^{30}$) m/z 331 (M+H)$^+$.

Example 266

[1-({[6-(3-chloro-4-fluorophenyl)pyridin-2-yl]methyl}amino)cyclopentyl]methanol

Example 266A 6-(3-chloro-4-fluorophenyl)picolinaldehyde

To a solution of 6-bromopicolinaldehyde (1.07 g, 5.74 mmol) in dioxane (30 mL) at ambient temperature was added 3-chloro-4-fluorophenylboronic acid (1.00 g, 5.74 mmol), 2M cesium carbonate (8.60 mL, 17.2 mmol) and 1,1'-bis (diphenylphosphino)ferrocene-palladium(II)dichloride dichloromethane complex (0.234 g, 0.287 mmol). The mixture was degassed (3× vacuum/purge N$_2$), then heated at 80° C. overnight. After cooling to ambient temperature the mixture was concentrated and the residue was partitioned between water and CH$_2$Cl$_2$. The organic extract was concentrated and purified by chromatography (10% ethyl acetate: hexanes) to provide the title compound. MS (DCI+) m/z 236 (M+H).

Example 266B (1-((6-(3-chloro-4-fluorophenyl)pyridin-2-yl)methylamino)cyclopentyl)methanol To a solution of Example 266A (0.500 g, 2.12 mmol) in methanol (20 mL) and CH$_2$Cl$_2$ (20 mL) at ambient temperature was added cycloleucinol (0.244 g, 2.12 mmol), acetic acid (0.50 mL, 8.5 mmol) followed by MP-cyanoborohydride (2.49 mmol/g; 1.0 g). After 2 hours, the mixture was filtered, concentrated and the residue partitioned between ether and 1N NaOH. The organic extract was concentrated and purified by chromatography to provide 418 mg (59%) of the title compound. MS (DCI+) m/z 335 (M+H); $^1$H NMR (500 MHz, CDCl$_3$) δ 8.03 (dd, J=7.1, 2.2 Hz, 1H), 7.86 (ddd, J=8.6, 4.6, 2.3 Hz, 1H), 7.73 (t, J=7.8 Hz, 1H), 7.55 (d, J=7.8 Hz, 1H), 7.30-7.19 (m, 2H), 3.95 (s, 2H), 3.48 (s, 2H), 1.87-1.52 (m, 8H).

Example 267

(2R)-2-[({6-[4-fluoro-3-(trifluoromethyl)phenyl]pyridin-2-yl}methyl)amino]-3-methylbutan-1-ol

Example 267A 6-(4-fluoro-3-(trifluoromethyl)phenyl)picolinaldehyde

To a solution of 6-bromopicolinaldehyde (1.00 g, 5.38 mmol) in dioxane (30 mL) at ambient temperature was added 4-fluoro-3-(trifluoromethyl)phenylboronic acid (1.11 g, 5.38 mmol), 2M cesium carbonate (8.0 mL, 16 mmol) and 1,1'-bis(diphenylphosphino)ferrocene-palladium(II)dichloride dichloromethane complex (0.220 g, 0.269 mmol). The mixture was degassed (3× vacuum/purge N$_2$), then heated at 80° C. overnight. After cooling to room temperature the mixture was concentrated and the residue partitioned between water and CH$_2$Cl$_2$. The organic extract was concentrated and purified by chromatography (10% ethyl acetate:hexanes) to provide 1.31 g (91%) of the title compound. MS (DCI+) m/z 270 (M+H).

Example 267B (2R)-2-[({6-[4-fluoro-3-(trifluoromethyl)phenyl]pyridin-2-yl}methyl)amino]-3-methylbutan-1-ol To a solution of Example 267A (0.500 g, 1.86 mmol) in methanol (20 mL) at ambient temperature was added D-valinol (0.20 mL, 1.9 mmol) and acetic acid (0.40 mL, 7.4 mmol) followed by MP-cyanoborohydride (2.49 mmol/g; 1.0 g). After 2 hours, the mixture was filtered, concentrated and the residue partitioned between ether and 1M NaOH. The organic extract was concentrated and purified by chromatography to provide 390 mg (59%) of the title compound. MS (DCI+) m/z 270 (M+H); $^1$H NMR (500 MHz, CDCl$_3$) δ 8.28 (dd, J=6.8, 2.0 Hz, 1H), 8.24-8.15 (m, 1H), 7.76 (t, J=7.7 Hz, 1H), 7.61 (d, J=7.8 Hz, 1H), 7.34-7.25 (m, 2H), 4.04 (q, J=14.5 Hz, 2H), 3.70 (dd, J=10.9, 4.0 Hz, 1H), 3.49 (dd, J=10.8, 6.9 Hz, 1H), 2.53 (td, J=6.7, 4.1 Hz, 1H), 1.97-1.85 (m, 1H), 1.04 (d, J=6.8 Hz, 3H), 0.97 (d, J=6.9 Hz, 3H).

Example 268

{1-[({6-[4-fluoro-3-(trifluoromethyl)phenyl]pyridin-2-yl}methyl)amino]cyclopentyl}methanol The title compound was prepared according to Example 266B, substituting Example 267A for Example 266A. MS (DCI+) m/z 369 (M+H); $^1$H NMR (500 MHz, DMSO-d$_6$) δ 8.50-8.42 (m, 2H), 7.93 (d, J=7.7 Hz, 1H), 7.90-7.84 (m, 1H), 7.65 (dd, J=13.3, 6.5 Hz, 1H), 7.50 (d, J=7.6 Hz, 1H), 4.65-4.55 (m, 1H), 3.84 (s, 2H), 3.36 (d, J=5.8 Hz, 2H), 2.41-2.15 (m, 1H), 1.76-1.42 (m, 8H).

Example 269

2-fluoro-5-[6-({[(2R)-1-hydroxy-3-methylbutan-2-yl]amino}methyl)pyridin-2-yl]benzonitrile To a solution of 6-bromopicolinaldehyde (1.00 g, 5.38 mmol) in dioxane (30 mL) at ambient temperature was added 3-cyano-4-fluorophenylboronic acid (0.887 g, 5.38 mmol), 2M cesium carbonate (8.1 mL, 16.2 mmol) and 1,1'-bis(diphenylphosphino)ferrocene-palladium(II)dichloride dichloromethane complex (0.220 g, 0.269 mmol). The mixture was degassed (3× vacuum/purge N$_2$), then heated at 80° C. overnight. The mixture was cooled, concentrated and partitioned between water and CH$_2$Cl$_2$. The organic layer was concentrated and purified by chromatography (30% ethyl acetate:hexanes) to provide 2-fluoro-5-(6-formylpyridin-2-yl)benzonitrile. To a solution of 2-fluoro-5-(6-formylpyridin-2-yl)benzonitrile (0.500 g, 2.21 mmol) in methanol (20 mL) at ambient temperature was added D-valinol (0.25 mL, 2.2 mmol), acetic acid (0.50 mL, 8.8 mmol) followed by MP-cyanoborohydride (2.49 mmol/g; 1.0 g). After 2 hours, the mixture was filtered, concentrated, and the residue partitioned between ether and 1M NaOH. The organic layer was concentrated and purified by chromatography to provide 362 mg (52%) of the title compound. MS (DCI+) m/z 314 (M+H); $^1$H NMR (400 MHz, DMSO-d$_6$) δ 8.62 (dd, J=6.3, 2.3 Hz, 1H), 8.52 (ddd, J=8.9, 5.3, 2.4 Hz, 1H), 7.97-7.84 (m, 2H), 7.66 (t, J=9.0 Hz, 1H), 7.49 (dd, J=7.4, 1.1 Hz, 1H), 3.92 (d, J=3.6 Hz, 2H), 3.52-3.43 (m, 1H), 2.40-2.22 (m, 2H), 1.93-1.76 (m, 1H), 0.89 (dd, J=9.5, 6.9 Hz, 6H).

Example 270

(2R)-2-[({6-[2,4-bis(trifluoromethyl)phenyl]pyridin-2-yl}methyl)amino]-3-methylbutan-1-ol

Example 270A 6-(2,4-bis(trifluoromethyl)phenyl)picolinaldehyde

To a solution of 6-bromopicolinaldehyde (1.00 g, 5.38 mmol) in dioxane (30 mL) at ambient temperature was added 2,4-bis(trifluoromethyl)phenylboronic acid (1.38 g, 5.38 mmol), 2M cesium carbonate (8.0 mL, 16 mmol) and 1,1'-bis(diphenylphosphino)ferrocene-palladium(II)dichloride dichloromethane complex (0.220 g, 0.269 mmol). The mixture was degassed (3× vacuum/purge N$_2$), then heated at 80° C. overnight. The mixture was cooled to room temperature and concentrated and the residue then partitioned between water and CH$_2$Cl$_2$. The organic layer concentrated and purified by chromatography (20% ethyl acetate:hexanes) to provide the title compound.

Example 270B (2R)-2-[({6-[2,4-bis(trifluoromethyl)phenyl]pyridin-2-yl}methyl)amino]-3-methylbutan-1-ol The title compound was prepared according to Example 266B, substituting Example 270A for Example 266A, and substituting D-valinol for cycloleucinol. MS (DCI+) m/z 407 (M+H); $^1$H NMR (400 MHz, CDCl$_3$) δ 8.04 (s, 1H), 7.93-7.86 (m, 1H), 7.82-7.73 (m, 1H), 7.66 (d, J=8.1 Hz, 1H), 7.36 (dd, J=17.0, 7.7 Hz, 2H), 4.13-4.05 (m, 1H), 4.06-3.98 (m, 1H), 3.71-3.63 (m, 1H), 3.46 (dd, J=10.9, 6.9 Hz, 1H), 2.55-2.45 (m, 1H), 1.91-1.80 (m, 1H), 0.98 (d, J=6.8 Hz, 3H), 0.93 (d, J=6.8 Hz, 3H).

Example 271

{1-[({6-[2,4-bis(trifluoromethyl)phenyl]pyridin-2-yl}methyl)amino]cyclopentyl}methano 1

The title compound was prepared according to Example 266B, substituting Example 270A for Example 266A. MS (DCI+) m/z 419 (M+H); $^1$H NMR (500 MHz, CDCl$_3$) δ 8.04 (s, 1H), 7.90 (d, J=8.0 Hz, 1H), 7.77 (t, J=7.8 Hz, 1H), 7.66 (d, J=8.0 Hz, 1H), 7.35 (dd, J=20.4, 7.7 Hz, 2H), 3.96 (s, 2H), 3.43 (s, 2H), 1.83-1.51 (m, 8H).

Example 272

{1-[({6-[3,5-bis(trifluoromethyl)phenyl]pyridin-2-yl}methyl)amino]cyclopentyl}methano 1

Example 272A 6-(3,5-bis(trifluoromethyl)phenyl)picolinaldehyde

To a solution of 6-bromopicolinaldehyde (1.00 g, 5.38 mmol) in dioxane (30 mL) at ambient temperature was added 3,5-bis(trifluoromethyl)phenylboronic acid (1.39 g, 5.38 mmol), 2M cesium carbonate (8.0 mL, 16 mmol) and 1,1'-bis(diphenylphosphino)ferrocene-palladium(II)dichloride dichloromethane complex (0.220 g, 0.269 mmol). The mixture was degassed (3× vacuum/purge N$_2$), then heated at 80° C. overnight. The mixture was cooled, concentrated and the residue partitioned between water and CH$_2$Cl$_2$. The organic layer concentrated and purified by chromatography (10% ethyl acetate:hexanes) to provide 1.36 g (79%) of the title compound.

Example 272B

{1-[({6-[3,5-bis(trifluoromethyl)phenyl]pyridin-2-yl}methyl)amino]cyclopentyl}methanol The title compound was prepared according to Example 266B, substituting Example 272A for Example 266A. MS (DCI+) m/z 419 (M+H); $^1$H NMR (500 MHz, CDCl$_3$) δ 8.47 (s, 2H), 7.92 (s, 1H), 7.82 (td, J=7.7, 1.3 Hz, 1H), 7.70 (d, J=7.8 Hz, 1H), 7.39 (d, J=7.6 Hz, 1H), 3.98 (s, 2H), 3.50 (s, 2H), 1.92-1.52 (m, 8H).

Example 273 tert-butyl 2-[5-fluoro-6-({[(2R)-1-hydroxy-3-methylbutan-2-yl]amino}methyl)pyridin-2-yl]-1H-indole-1-carboxylate The title compound was prepared according to Example 228, substituting (1-(tert-butoxycarbonyl)-1H-indol-2-yl)boronic acid for 3,4-difluorophenylboronic acid. $^1$H NMR (300 MHz, CDCl$_3$) δ 8.16 (dd, J=8.3, 1.0 Hz, 1H), 7.62-7.55 (m, 1H), 7.47-7.33 (m, 3H), 7.26 (s, 1H), 6.75 (s, 1H), 4.09 (d, J=1.6 Hz, 2H), 3.67 (dd, J=10.8, 3.9 Hz, 1H), 3.43 (dd, J=11.0, 6.8 Hz, 1H), 2.48 (td, J=6.7, 3.9 Hz, 1H), 1.83 (dq, J=13.5, 6.8 Hz, 1H), 1.41 (s, 9H), 0.97 (d, J=6.8 Hz, 3H), 0.92 (d, J=6.8 Hz, 3H). MS (ESI) m/z: 428 (M+H)$^+$.

Example 274

(2R)-2-({[3-fluoro-6-(1H-indol-2-yl)pyridin-2-yl]methyl}amino)-3-methylbutan-1-ol Example 273 was treated with acid (1 N aquoues HCl) to remove the tert-butoxy carbonyl group and provide the title compound. $^1$H NMR (400 MHz, CDCl$_3$) δ 10.19 (s, 1H), 7.64-7.57 (m, 2H), 7.48 (dd, J=8.1, 1.1 Hz, 1H), 7.30-7.24 (m, 1H), 7.21 (ddd, J=8.2, 7.1, 1.1 Hz, 1H), 7.09 (td, I=7.6, 1.0 Hz, 1H), 6.88 (d, I=0.9 Hz, 1H), 4.22 (dd, I=15.6, 1.9 Hz, 1H), 4.06 (dd, I=15.7, 1.9 Hz, 1H), 3.84 (dd, J=10.9, 3.9 Hz, 1H), 3.60 (dd, J=10.8, 8.2 Hz, 1H), 2.76-2.68 (m, 1H), 1.94 (dq, J=13.5, 6.8 Hz, 1H), 1.05 (d, J=6.9 Hz, 3H), 0.99 (d, J=6.8 Hz, 3H). MS (ESI) m/z: 328 (M+H)$^+$.

Example 275

{4-[5-fluoro-6-({[(2R)-1-hydroxy-3-methylbutan-2-yl]amino}methyl)pyridin-2-yl]phenyl}(4-methylpiperidin-1-yl)methanone The title compound was prepared according to Example 228, substituting (4-(4-methylpiperidine-1-carbonyl)phenyl)boronic acid for 3,4-difluorophenylboronic acid. $^1$H NMR (300 MHz, CDCl$_3$) δ 8.12 (d, J=8.3 Hz, 2H), 7.96 (dd, J=8.6, 3.6 Hz, 1H), 7.77 (t, J=9.0 Hz, 1H), 7.47 (d, J=8.3 Hz, 2H), 4.48-4.42 (m, 2H), 4.01-3.88 (m, 2H), 3.68-3.51 (m, 1H), 3.47 (dt, J=9.5, 4.6 Hz, 1H), 3.36-3.30 (m, 1H), 3.13-2.64 (m, 2H), 2.42-2.34 (m, 2H), 1.92-1.79 (m, 1H), 1.76-1.47 (m, 3H), 1.18-1.00 (m, 2H), 0.93 (d, J=6.4 Hz, 3H), 0.88 (d, J=6.9 Hz, 3H), 0.85 (d, J=6.9 Hz, 3H). MS (ESI) m/z: 414 (M+H)$^+$.

Example 276

{4-[5-fluoro-6-({[(2R)-1-hydroxy-3-methylbutan-2-yl]amino}methyl)pyridin-2-yl]phenyl}(pyrrolidin-1-yl)methanone The title compound was prepared according to Example 228, substituting (4-(pyrrolidine-1-carbonyl)phenyl)boronic acid for 3,4-difluorophenylboronic acid. $^1$H NMR (300 MHz, CDCl$_3$) δ 7.99 (d, J=8.3 Hz, 2H), 7.66 (dd, J=8.7, 3.7 Hz, 1H), 7.63 (d, J=8.3 Hz, 2H), 7.45 (t, J=8.7 Hz, 1H), 4.17-4.07 (m, 2H), 3.72 (dd, J=10.9, 4.0 Hz, 1H), 3.69-3.64 (m, 2H), 3.50 (dd, J=11.1, 6.8 Hz, 1H), 3.47 (t, J=6.6 Hz, 2H), 2.52 (td, J=6.7, 4.0 Hz, 1H), 2.10-1.79 (m, 5H), 1.02 (d, J=6.8 Hz, 3H), 0.96 (d, J=6.8 Hz, 3H). MS (ESI) m/z: 386 (M+H)$^+$.

Example 277

4-[5-fluoro-6-({[(2R)-1-hydroxy-3-methylbutan-2-yl]amino}methyl)pyridin-2-yl]-N,N-dipropylbenzamide The title compound was prepared according to Example 228, substituting (4-(dipropylcarbamoyl)phenyl)boronic acid for 3,4-difluorophenylboronic acid. $^1$H NMR (300 MHz, CDCl$_3$) δ 7.98 (d, J=8.3 Hz, 2H), 7.65 (dd, J=8.6, 3.6 Hz, 1H), 7.49-7.41 (m, 3H), 4.14-4.09 (m, 2H), 3.76-3.68 (m, 1H), 3.50 (dd, J=10.9, 6.7 Hz, 1H), 3.50-3.43 (m, 2H), 3.27-3.14 (m, 2H), 2.52 (td, J=6.6, 4.0 Hz, 1H), 1.90 (h, J=6.8 Hz, 1H), 1.78-1.50 (m, 4H), 1.02 (d, J=6.8 Hz, 3H), 1.02-0.95 (m, 3H), 0.96 (d, J=6.8 Hz, 3H), 0.82-0.70 (m, 3H). MS (ESI) m/z: 416 (M+H)$^+$.

Example 278

(2R)-2-{[(5'-chloro-5-fluoro-2,3'-bipyridin-6-yl)methyl]amino}-3-methylbutan-1-ol The title compound was prepared according to Example 228, substituting (5-chloropyridin-3-yl)boronic acid for 3,4-difluorophenylboronic acid. $^1$H NMR (300 MHz, CDCl$_3$) δ

9.04 (d, J=1.9 Hz, 1H), 8.60 (d, J=2.3 Hz, 1H), 8.30 (t, J=2.1 Hz, 1H), 7.67 (dd, J=8.5, 3.6 Hz, 1H), 7.49 (t, J=8.7 Hz, 1H), 4.11 (d, J=1.9 Hz, 2H), 3.72 (dd, J=10.8, 4.0 Hz, 1H), 3.49 (dd, J=10.8, 6.7 Hz, 1H), 2.51 (td, J=6.6, 4.0 Hz, 1H), 1.90 (h, J=6.8 Hz, 1H), 1.02 (d, J=6.8 Hz, 3H), 0.96 (d, J=6.8 Hz, 3H). MS (ESI) m/z: 324 (M+H)+.

Example 279

2-fluoro-5-[5-fluoro-6-({[(2R)-1-hydroxy-3-methylbutan-2-yl]amino}methyl)pyridin-2-yl]benzonitrile The title compound was prepared according to Example 228, substituting (3-cyano-4-fluorophenyl)boronic acid for 3,4-difluorophenylboronic acid. $^1$H NMR (300 MHz, CDCl$_3$) δ 8.30-8.16 (m, 2H), 7.60 (dd, J=8.6, 3.6 Hz, 1H), 7.48 (t, J=8.7 Hz, 1H), 7.32 (t, J=8.6 Hz, 1H), 4.15-4.06 (m, 2H), 3.70 (dd, J=10.8, 4.0 Hz, 1H), 3.47 (dd, J=10.8, 6.9 Hz, 1H), 2.74-2.32 (m, 2H), 2.50 (td, J=6.7, 4.0 Hz, 1H), 1.89 (dq, J=13.6, 6.8 Hz, 1H), 1.02 (d, J=6.8 Hz, 3H), 0.96 (d, J=6.8 Hz, 3H). MS (ESI) m/z: 332 (M+H)+.

Example 280

(2R)-2-({[3-fluoro-6-(4-fluoro-3-methylphenyl)pyridin-2-yl]methyl}amino)-3-methylbutan-1-ol The title compound was prepared according to Example 228, substituting (4-fluoro-3-methylphenyl)boronic acid for 3,4-difluorophenylboronic acid. $^1$H NMR (300 MHz, CDCl$_3$) δ 7.78 (dd, J=7.4, 2.0 Hz, 1H), 7.75-7.69 (m, 1H), 7.57 (dd, J=8.6, 3.7 Hz, 1H), 7.42 (t, J=8.7 Hz, 1H), 7.09 (t, J=8.9 Hz, 1H), 4.20-4.05 (m, 2H), 3.72 (dd, J=11.0, 3.9 Hz, 1H), 3.52 (dd, J=11.0, 6.7 Hz, 1H), 2.52 (td, J=6.6, 3.9 Hz, 1H), 2.35 (d, J=1.9 Hz, 3H), 1.91 (dq, J=13.6, 6.8 Hz, 1H), 1.03 (d, J=6.8 Hz, 3H), 0.96 (d, J=6.8 Hz, 3H). MS (ESI) m/z: 321 (M+H)+.

Example 281

(2R)-2-[({3-fluoro-6-[4-fluoro-3-(trifluoromethyl)phenyl]pyridin-2-yl}methyl)amino]-3-methylbutan-1-ol The title compound was prepared according to Example 228, substituting (4-fluoro-3-(trifluoromethyl)phenyl)boronic acid for 3,4-difluorophenylboronic acid. $^1$H NMR (300 MHz, CDCl$_3$) δ 8.22 (dd, J=6.8, 2.3 Hz, 1H), 8.19-8.11 (m, 1H), 7.63 (dd, J=8.6, 3.6 Hz, 1H), 7.47 (t, J=8.7 Hz, 1H), 7.30 (t, J=9.3 Hz, 1H), 4.17-4.06 (m, 2H), 3.72 (dd, J=10.9, 4.0 Hz, 1H), 3.50 (dd, J=10.8, 6.6 Hz, 1H), 2.88-2.57 (m, 2H), 2.52 (td, J=6.6, 4.0 Hz, 1H), 1.91 (h, J=6.8 Hz, 1H), 1.02 (d, J=6.8 Hz, 3H), 0.96 (d, J=6.8 Hz, 3H). MS (ESI) m/z: 375 (M+H)+.

Example 282

(2R)-2-[({3-fluoro-6-[2-fluoro-5-(trifluoromethyl)phenyl]pyridin-2-yl}methyl)amino]-3-methylbutan-1-ol The title compound was prepared according to Example 228, substituting (2-fluoro-5-(trifluoromethyl)phenyl)boronic acid for 3,4-difluorophenylboronic acid. $^1$H NMR (300 MHz, CDCl$_3$) δ 8.33 (dd, J=7.2, 2.5 Hz, 1H), 7.78 (ddd, J=8.6, 3.7, 1.9 Hz, 1H), 7.72-7.59 (m, 1H), 7.48 (t, J=8.7 Hz, 1H), 7.28 (dd, J=9.8, 8.7 Hz, 1H), 4.15 (qd, J=15.0, 1.8 Hz, 2H), 3.74 (dd, J=11.0, 3.9 Hz, 1H), 3.53 (dd, J=11.0, 6.4 Hz, 1H), 2.54 (td, J=6.5, 3.9 Hz, 1H), 2.02-1.83 (m, 1H), 1.03 (d, J=6.8 Hz, 3H), 0.97 (d, J=6.8 Hz, 3H). MS (ESI) m/z: 375 (M+H)+.

Example 283

(2R)-2-({[6-(3,4-difluoro-5-methoxyphenyl)-3-fluoropyridin-2-yl]methyl}amino)-3-methylbutan-1-ol The title compound was prepared according to Example 228, substituting (3,4-difluoro-5-methoxyphenyl)boronic acid for 3,4-difluorophenylboronic acid. $^1$H NMR (300 MHz, CDCl$_3$) δ 7.57 (dd, J=8.6, 3.7 Hz, 1H), 7.49-7.40 (m, 2H), 7.32 (ddd, J=10.9, 6.6, 2.1 Hz, 1H), 4.11 (d, J=1.9 Hz, 2H), 4.00 (s, 3H), 3.72 (dd, J=10.9, 3.9 Hz, 1H), 3.50 (dd, J=10.9, 6.7 Hz, 1H), 2.52 (td, J=6.6, 4.0 Hz, 1H), 1.99-1.82 (m, 1H), 1.02 (d, J=6.8 Hz, 3H), 0.96 (d, J=6.8 Hz, 3H). MS (ESI) m/z: 355 (M+H)+.

Example 284

(2R)-2-[({6-[(2,4-difluorophenyl)ethynyl]pyridin-2-yl}methyl)amino]-3-methylbutan-1-ol

Example 284A 6-((2,4-difluorophenyl)ethynyl)picolinaldehyde

The title compound was prepared according to Example 235, substituting 1-ethynyl-2,4-difluorobenzene for 1-ethynyl-4-methoxybenzene, and substituting 6-bromopicolinaldehyde for Example 73A. MS (DCI+) m/z 244 (M+H).

Example 284B (2R)-2-[({6-[(2,4-difluorophenyl)ethynyl]pyridin-2-yl}methyl)amino]-3-methylbutan-1-ol The title compound was prepared according to Example 262B, substituting Example 284A for Example 262A. $^1$H NMR (300 MHz, DMSO-d$_6$) δ 7.83 (t, J=7.8 Hz, 1H), 7.77 (td, J=8.5, 6.5 Hz, 1H), 7.52 (dd, J=10.8, 4.0 Hz, 2H), 7.45 (dd, J=9.8, 2.5 Hz, 1H), 7.27-7.16 (m, 1H), 4.43 (t, J=5.2 Hz, 1H), 3.93-3.77 (m, 2H), 3.46 (dt, J=9.9, 4.8 Hz, 1H), 3.34 (dd, J=11.3, 5.7 Hz, 1H), 2.30 (dd, J=11.0, 5.0 Hz, 1H), 2.15 (s, 1H), 1.89-1.71 (m, 1H), 0.87 (dd, J=7.8, 7.0 Hz, 6H). MS (DCI+) m/z 331 (M+H)+.

Example 285

(2R)-2-[({6-[(2-fluorophenyl)ethynyl]pyridin-2-yl}methyl)amino]-3-methylbutan-1-ol

Example 285A 6-((2-fluorophenyl)ethynyl)picolinaldehyde

The title compound was prepared according to Example 235, substituting 1-ethynyl-2-fluorobenzene for 1-ethynyl-4-methoxybenzene, and substituting 6-bromopicolinaldehyde for Example 73A. MS (DCI+) m/z 226 (M+H).

Example 285B (2R)-2-[({6-[(2-fluorophenyl)ethynyl]pyridin-2-yl}methyl)amino]-3-methylbutan-1-ol The title compound was prepared according to Example 262B, substituting Example 285A for Example 262A. $^1$H NMR (300 MHz, DMSO-d$_6$) δ 7.83 (t, J=7.8 Hz, 1H), 7.69 (td, J=7.5, 1.7 Hz, 1H), 7.58-7.49 (m, 3H), 7.37 (ddd, J=9.6, 8.5, 1.0 Hz, 1H), 7.30 (td, J=7.5, 1.1 Hz, 1H), 4.44 (t, J=5.3 Hz, 1H), 3.93-3.78 (m, 2H), 3.46 (dt, J=9.9, 4.9 Hz, 1H), 3.35 (dd, J=10.4, 4.8 Hz, 1H), 2.30 (dd, J=11.0, 5.0 Hz, 1H), 2.16 (s, 1H), 1.88-1.74 (m, 1H), 0.87 (dd, J=7.8, 7.1 Hz, 6H). MS (DCI+) m/z 313 (M+H)$^+$.

Example 286

(2R)-2-[({6-[(4-chlorophenyl)ethynyl]pyridin-2-yl}methyl)amino]-3-methylbutan-1-ol

Example 286A 6-((4-chlorophenyl)ethynyl)picolinaldehyde

The title compound was prepared according to Example 235, substituting 1-chloro-4-ethynylbenzene for 1-ethynyl-4-methoxybenzene, and substituting 6-bromopicolinaldehyde for Example 73A. MS (DCI+) m/z 242 (M+H).

Example 286B (2R)-2-[({6-[(4-chlorophenyl)ethynyl]pyridin-2-yl}methyl)amino]-3-methylbutan-1-ol The title compound was prepared according to Example 262B, substituting Example 286A for Example 262A. $^1$H NMR (300 MHz, DMSO-d$_6$) δ 7.82 (t, J=7.8 Hz, 1H), 7.67-7.61 (m, 2H), 7.57-7.48 (m, 4H), 4.44 (t, J=5.3 Hz, 1H), 3.92-3.77 (m, 2H), 3.46 (dt, J=10.0, 4.9 Hz, 1H), 3.34 (dd, J=11.6, 5.9 Hz, 1H), 2.30 (dd, J=10.9, 5.0 Hz, 1H), 2.14 (s, 1H), 1.88-1.72 (m, 1H), 0.87 (dd, J=8.0, 7.0 Hz, 6H). MS (DCI$^+$) m/z 329 (M+H)$^+$.

Example 287

(2R)-2-({[3-fluoro-6-(4-methyl-2-phenyl-1,3-thiazol-5-yl)pyridin-2-yl]methyl}amino)-3-methylbutan-1-ol The title compound was prepared according to Example 228, substituting (4-methyl-2-phenylthiazol-5-yl)boronic acid for 3,4-difluorophenylboronic acid. $^1$H NMR (300 MHz, CDCl$_3$) δ 8.01-7.84 (m, 2H), 7.52 (dd, J=8.6, 3.8 Hz, 1H), 7.49-7.38 (m, 4H), 4.14 (qd, J=15.0, 1.6 Hz, 2H), 3.75 (dd, J=11.1, 4.1 Hz, 1H), 3.57 (dd, J=11.1, 6.6 Hz, 1H), 2.73 (s, 3H), 2.57 (td, J=6.6, 4.0 Hz, 1H), 1.95 (dq, J=13.5, 6.7 Hz, 1H), 1.05 (d, J=6.8 Hz, 3H), 0.99 (d, J=6.8 Hz, 3H). MS (ESI) m/z: 386 (M+H)$^+$.

Example 288

(2R)-2-({[6-(4-cyclohexylbut-1-yn-1-yl)-3-fluoropyridin-2-yl]methyl}amino)-3-methylbutan-1-ol The title compound was prepared according to Example 235, substituting but-3-yn-1-ylcyclohexane for 1-ethynyl-4-methoxybenzene. $^1$H NMR (300 MHz, DMSO-d$_6$) δ 7.63 (dd, J=9.5, 8.6 Hz, 1H), 7.40 (dd, J=8.5, 3.8 Hz, 1H), 4.43 (t, J=5.2 Hz, 1H), 3.91-3.75 (m, 2H), 3.49-3.39 (m, 1H), 3.34-3.23 (m, 1H), 2.45 (t, J=7.3 Hz, 2H), 2.34-2.25 (m, 1H), 2.11 (bs, 1H), 1.87-1.51 (m, 6H), 1.46 (dd, J=14.2, 7.1 Hz, 2H), 1.42-1.11 (m, 4H), 0.97-0.84 (m, 2H), 0.85 (d, J=6.9 Hz, 3H), 0.82 (d, J=6.9 Hz, 3H). MS (ESI) m/z: 347 (M+H)$^+$.

Example 289

(2R)-2-({[3-fluoro-6-(phenylethynyl)pyridin-2-yl]methyl}amino)-3-methylbutan-1-ol The title compound was prepared according to Example 235, substituting ethynylbenzene for 1-ethynyl-4-methoxybenzene. $^1$H NMR (300 MHz, CDCl$_3$) δ 7.62-7.56 (m, 2H), 7.50 (dd, J=8.5, 4.0 Hz, 1H), 7.46-7.32 (m, 4H), 4.32 (d, J=15.8 Hz, 1H), 4.20 (d, J=15.8 Hz, 1H), 3.81 (dd, J=11.7, 3.5 Hz, 1H), 3.69 (dd, J=11.3, 7.3 Hz, 1H), 2.67-2.57 (m, 1H), 2.05-1.92 (m, 1H), 1.80-1.34 (m, 2H), 1.08 (d, J=6.8 Hz, 3H), 1.01 (d, J=6.8 Hz, 3H). MS (ESI) m/z: 313 (M+H)$^+$.

Example 290

(2R)-2-[({3-fluoro-6-[5-(trifluoromethyl)thiophen-2-yl]pyridin-2-yl}methyl)amino]-3-methylbutan-1-ol The title compound was prepared according to Example 228, substituting (5-(trifluoromethyl)thiophen-2-yl)boronic acid for 3,4-difluorophenylboronic acid. $^1$H NMR (300 MHz, CDCl$_3$) δ 7.60 (dd, J=8.5, 3.7 Hz, 1H), 7.52-7.38 (m, 3H), 4.12 (qd, J=15.1, 1.5 Hz, 2H), 3.74 (dd, J=11.1, 3.9 Hz, 1H), 3.56 (dd, J=11.1, 6.6 Hz, 1H), 2.55 (td, J=6.6, 4.0 Hz, 1H), 2.03-1.86 (m, 1H), 1.05 (d, J=6.8 Hz, 3H), 0.99 (d, J=6.8 Hz, 3H). MS (ESI) m/z: 363 (M+H)$^+$.

Example 291

(2R)-2-[({3-fluoro-6-[1-methyl-3-(trifluoromethyl)-1H-pyrazol-5-yl]pyridin-2-yl}methyl)amino]-3-methylbutan-1-ol The title compound was prepared according to Example 228, substituting (1-methyl-3-(trifluoromethyl)-1H-pyrazol-5-yl)boronic acid for 3,4-difluorophenylboronic acid. $^1$H NMR (300 MHz, CDCl$_3$) δ 7.56-7.44 (m, 2H), 6.78 (s, 1H), 4.24 (s, 3H), 4.09 (d, J=2.0 Hz, 2H), 3.71 (dd, J=10.7, 4.1 Hz, 1H), 3.45 (dd, J=10.7, 6.9 Hz, 1H), 2.51 (td, J=6.7, 4.1 Hz, 1H), 1.88 (td, J=13.6, 6.8 Hz, 1H), 0.99 (d, J=6.8 Hz, 3H), 0.94 (d, J=6.8 Hz, 3H). MS (ESI) m/z: 361. (M+H)$^+$.

Example 292

(2R)-2-({[5-fluoro-5'-(trifluoromethyl)-2,3'-bipyridin-6-yl]methyl}amino)-3-methylbutan-1-ol The title compound was prepared according to Example 228, substituting (5-(trifluoromethyl)pyridin-3-yl)boronic acid for 3,4-difluorophenylboronic acid. $^1$H NMR (300 MHz, CDCl$_3$) δ 9.36 (d, J=2.1 Hz, 1H), 8.92 (d, J=2.1 Hz, 1H), 8.57-8.53 (m, 1H), 7.75 (dd, J=8.5, 3.6 Hz, 1H), 7.54 (t, J=8.6 Hz, 1H), 4.24-4.11 (m, 2H), 3.75 (dd, J=10.9, 3.9 Hz, 1H), 3.54 (dd, J=10.9, 6.7 Hz, 1H), 2.57 (td, J=6.6, 3.9 Hz, 1H), 1.95 (dq, J=13.5, 6.8 Hz, 1H), 1.04 (d, J=6.8 Hz, 3H), 0.98 (d, J=6.8 Hz, 3H). MS (ESI) m/z: 358 (M+H)$^+$.

Example 293

(2R)-2-[({6-[2,4-bis(trifluoromethyl)phenyl]-3-fluoropyridin-2-yl}methyl)amino]-3-methylbutan-1-ol The title compound was prepared according to Example 228, substituting (2,4-bis(trifluoromethyl)phenyl)boronic acid for 3,4-difluorophenylboronic acid. ¹H NMR (300 MHz, CDCl₃) δ 8.04 (s, 1H), 7.93 (d, J=8.2 Hz, 1H), 7.74 (d, J=8.1 Hz, 1H), 7.57 (t, J=8.6 Hz, 1H), 7.47 (dd, J=8.5, 3.8 Hz, 1H), 4.55 (d, J=15.7 Hz, 1H), 4.41 (d, J=15.6 Hz, 1H), 3.93-3.78 (m, 2H), 2.87-2.78 (m, 1H), 2.18-1.99 (m, 2H), 1.01 (d, J=3.9 Hz, 3H), 0.98 (d, J=3.8 Hz, 3H). MS (ESI) m/z: 425 (M+H)⁺.

Example 294

(2R)-2-({[6-(3-chloro-4-fluorophenyl)-3-fluoropyridin-2-yl]methyl}amino)-3-methylbutan-1-ol The title compound was prepared according to Example 228, substituting (3-chloro-4-fluorophenyl)boronic acid for 3,4-difluorophenylboronic acid. ¹H NMR (300 MHz, DMSO-d₆) δ 8.29 (dd, J=7.3, 2.3 Hz, 1H), 8.10 (ddd, J=8.7, 4.7, 2.3 Hz, 1H), 8.00 (dd, J=8.6, 3.6 Hz, 1H), 7.78 (dd, J=9.4, 8.7 Hz, 1H), 7.54 (t, J=9.0 Hz, 1H), 4.44 (t, J=5.2 Hz, 1H), 4.03-3.86 (m, 2H), 3.52-3.41 (m, 1H), 3.38-3.26 (m, 1H), 2.43-2.32 (m, 2H), 1.85 (pd, J=6.9, 4.7 Hz, 1H), 0.88 (d, J=7.0 Hz, 3H), 0.85 (d, J=7.0 Hz, 3H). MS (ESI) m/z: 341 (M+H)⁺.

Example 295

(2R)-2-({[3-fluoro-6-(6-methoxynaphthalen-2-yl)pyridin-2-yl]methyl}amino)-3-methylbutan-1-ol The title compound was prepared according to Example 245, substituting 6-methoxynaphthalen-2-ylboronic acid for 2,3,4-trifluorophenylboronic acid. MS (ESI⁺) m/z 369 (M+H)⁺.

Example 296

(2R)-2-({[3-fluoro-6-(4-methylnaphthalen-1-yl)pyridin-2-yl]methyl}amino)-3-methylbutan-1-ol The title compound was prepared according to Example 245, substituting 4-methylnaphthalen-1-ylboronic acid for 2,3,4-trifluorophenylboronic acid. MS (ESI⁺) m/z 353 (M+H)⁺.

Example 297

(2R)-2-({[6-(9H-carbazol-2-yl)-3-fluoropyridin-2-yl]methyl}amino)-3-methylbutan-1-ol The title compound was prepared according to Example 245, substituting 2-(4,4,5,5-tetramethyl-1,3,2-dioxaborolan-2-yl)-9H-carbazole for 2,3,4-trifluorophenylboronic acid. MS (ESI⁺) m/z 378 (M+H)⁺.

Example 298

(2R)-2-({[3-fluoro-6-(naphthalen-2-yl)pyridin-2-yl]methyl}amino)-3-methylbutan-1-ol The title compound was prepared according to Example 245, substituting 6-methyl-2-(naphthalen-2-yl)-1,3,6,2-dioxazaborocane-4,8-dione for 2,3,4-trifluorophenylboronic acid. MS (ESI⁺) m/z 339 (M+H)⁺.

Example 299

{4-[5-fluoro-6-({[(2R)-1-hydroxy-3-methylbutan-2-yl]amino}methyl)pyridin-2-yl]phenyl}(phenyl)methanone The title compound was prepared according to Example 245, substituting phenyl(4-(4,4,5,5-tetramethyl-1,3,2-dioxaborolan-2-yl)phenyl)methanone for 2,3,4-trifluorophenylboronic acid. MS (ESI⁺) m/z 393 (M+H)⁺.

Example 300

(2R)-2-({[6-(3,4-dihydronaphthalen-2-yl)-3-fluoropyridin-2-yl]methyl}amino)-3-methylbutan-1-ol The title compound was prepared according to Example 228, substituting (3,4-dihydronaphthalen-2-yl)boronic acid for 3,4-difluorophenylboronic acid. ¹H NMR (300 MHz, DMSO-d₆) δ 7.73 (dd, J=8.7, 4.0 Hz, 1H), 7.67 (t, J=9.0 Hz, 1H), 7.44 (s, 1H), 7.28-7.13 (m, 4H), 4.44 (t, J=5.2 Hz, 1H), 3.90 (qd, J=14.2, 1.8 Hz, 2H), 3.46 (dt, J=9.5, 4.6 Hz, 1H), 3.40-3.23 (m, 1H) under water peak, 2.96-2.75 (m, 4H), 2.46-2.32 (m, 2H), 1.93-1.78 (m, 1H), 0.87 (t, J=6.9 Hz, 6H). MS (DCI⁺) m/z 341 (M+H)⁺.

Example 301

(2R)-2-({[3-fluoro-6-(prop-1-en-2-yl)pyridin-2-yl]methyl}amino)-3-methylbutan-1-ol The title compound was prepared according to Example 228, substituting prop-1-en-2-ylboronic acid for 3,4-difluorophenylboronic acid. ¹H NMR (300 MHz, DMSO-d₆) δ 7.68-7.60 (m, 1H), 7.57 (dd, J=8.6, 4.0 Hz, 1H), 5.87 (s, 1H), 5.32-5.24 (m, 1H), 4.41 (t, J=5.1 Hz, 1H), 3.88 (qd, J=14.3, 2.0 Hz, 2H), 3.44 (dt, J=9.2, 4.5 Hz, 1H), 3.36-3.24 (m, 1H) under water peak, 2.45-2.29 (m, 2H), 2.14 (s, 3H), 1.91-1.76 (m, 1H), 0.91-0.80 (m, 6H). MS (DCI⁺) m/z 253 (M+H)⁺.

Example 302

(2R)-2-({[6-(1-benzyl-1H-pyrazol-4-yl)-3-fluoropyridin-2-yl]methyl}amino)-3-methylbutan-1-ol The title compound was prepared according to Example 228, substituting (1-benzyl-1H-pyrazol-4-yl)boronic acid for 3,4-difluorophenylboronic acid. ¹H NMR (300 MHz, DMSO-d₆) δ 8.35 (s, 1H), 8.02 (s, 1H), 7.69-7.56 (m, 2H), 7.41-7.23 (m, 5H), 5.37 (s, 2H), 4.45 (t, J=5.2 Hz, 1H), 3.86 (qd, J=13.9, 1.2 Hz, 2H), 3.44 (dt, J=9.9, 4.8 Hz, 1H), 3.39-3.22 (m, 1H) under water peak, 2.39-2.23 (m, 2H), 1.92-1.75 (m, 1H), 0.85 (t, J=7.2 Hz, 6H). MS (DCI⁺) m/z 369 (M+H)⁺.

Example 303

(2R)-2-[({6-[(1E)-3-cyclopentylprop-1-en-1-yl]-3-fluoropyridin-2-yl}methyl)amino]-3-methylbutan-1-ol The title compound was prepared according to Example 228, substituting (E)-(3-cyclopentylprop-1-en-1-yl)boronic acid for 3,4-difluorophenylboronic acid. ¹H NMR (300 MHz, CDCl₃) δ 7.27 (dd, J=10.3, 7.2 Hz, 1H), 7.16 (dd, J=8.5, 3.9

Hz, 1H), 6.63 (dt, J=15.3, 7.1 Hz, 1H), 6.45 (d, J=15.7 Hz, 1H), 4.03 (d, J=1.9 Hz, 2H), 3.68 (dd, J=10.9, 3.8, 1H), 3.48 (dd, J=10.9, 6.8 Hz, 1H), 2.45 (td, J=6.7, 3.8, 1H), 2.26 (t, J=7.1 Hz, 2H), 2.11-1.72 (m, 4H), 1.28-1.05 (m, 2H), 1.01 (d, J=6.8 Hz, 3H), 0.95 (d, J=6.8 Hz, 3H). MS (ESI) m/z: 321 (M+H)$^+$.

Example 304

(2R)-2-({[6-(3,4-dihydro-2H-1,5-benzodioxepin-7-yl)-3-fluoropyridin-2-yl]methyl}amino)-3-methylbutan-1-ol The title compound was prepared according to Example 228, substituting (3,4-dihydro-2H-benzo[b][1,4]dioxepin-7-yl)boronic acid for 3,4-difluorophenylboronic acid. $^1$H NMR (300 MHz, CDCl$_3$) δ 7.62-7.46 (m, 3H), 7.39 (t, J=8.8 Hz, 1H), 7.05 (d, J=8.3 Hz, 1H), 4.27 (t, J=5.7 Hz, 4H), 4.15-4.02 (m, 2H), 3.71 (dd, J=10.9, 3.9, 1H), 3.49 (dd, J=10.9, 6.7 Hz, 1H), 2.50 (td, J=6.7, 4.0, 1H), 2.28-2.18 (m, 2H), 1.89 (dq, J=13.6, 6.8 Hz, 1H), 1.02 (d, J=6.9 Hz, 3H), 0.95 (d, J=6.8 Hz, 3H). MS (ESI) m/z: 361 (M+H)$^+$.

Example 306

(2R)-2-({[3-fluoro-6-(3-fluoro-4-methoxyphenyl)pyridin-2-yl]methyl}amino)-3-methylbutan-1-ol The title compound was prepared according to Example 245, substituting (3-fluoro-4-methoxyphenyl)boronic acid for 2,3,4-trifluorophenylboronic acid. MS (ESI$^+$) m/z 337 (M+H)$^+$.

Example 307

(2R)-2-[({6-[4-(ethylsulfanyl)phenyl]-3-fluoropyridin-2-yl}methyl)amino]-3-methylbutan-1-ol The title compound was prepared according to Example 245, substituting 4-(ethylthio)phenylboronic acid for 2,3,4-trifluorophenylboronic acid. MS (ESI$^+$) m/z 349 (M+H)$^+$.

Example 308

(2R)-2-({[3-fluoro-6-(3-fluoro-4-methylphenyl)pyridin-2-yl]methyl}amino)-3-methylbutan-1-ol The title compound was prepared according to Example 245, substituting 3-fluoro-4-methylphenylboronic acid for 2,3,4-trifluorophenylboronic acid. MS (ESI$^+$) m/z 321 (M+H)$^+$.

Example 309

(2R)-2-[({3-fluoro-6-[2-(propan-2-yl)phenyl]pyridin-2-yl}methyl)amino]-3-methylbutan-1-ol The title compound was prepared according to Example 245, substituting 2-isopropylphenylboronic acid for 2,3,4-trifluorophenylboronic acid. MS (ESI$^+$) m/z 331 (M+H)$^+$.

Example 310

(2R)-2-({[6-(4-cyclopropylphenyl)-3-fluoropyridin-2-yl]methyl}amino)-3-methylbutan-1-ol The title compound was prepared according to Example 245, substituting 4-cyclopropylphenylboronic acid for 2,3,4-trifluorophenylboronic acid. MS (ESI$^+$) m/z 329 (M+H)$^+$.

Example 311

(2R)-2-[({6-[4-(butan-2-yl)phenyl]-3-fluoropyridin-2-yl}methyl)amino]-3-methylbutan-1-ol The title compound was prepared according to Example 245, substituting 4-sec-butylphenylboronic acid for 2,3,4-trifluorophenylboronic acid. MS (ESI$^+$) m/z 345 (M+H)$^+$.

Example 312

(2R)-2-({[3-fluoro-6-(2,3,5-trifluorophenyl)pyridin-2-yl]methyl}amino)-3-methylbutan-1-ol The title compound was prepared according to Example 245, substituting 2,3,5-trifluorophenylboronic acid for 2,3,4-trifluorophenylboronic acid. MS (ESI$^+$) m/z 343 (M+H)$^+$.

Example 313

(2R)-2-[({3-fluoro-6-[4-(propan-2-yl)phenyl]pyridin-2-yl}methyl)amino]-3-methylbutan-1-ol The title compound was prepared according to Example 245, substituting 4-isopropylphenylboronic acid for 2,3,4-trifluorophenylboronic acid. MS (ESI$^+$) m/z 331 (M+H)$^+$.

Example 314

(2R)-2-({[3-fluoro-6-(4-propylphenyl)pyridin-2-yl]methyl}amino)-3-methylbutan-1-ol The title compound was prepared according to Example 245, substituting 4-propylphenylboronic acid for 2,3,4-trifluorophenylboronic acid. MS (ESI$^+$) m/z 331 (M+H)$^+$.

Example 315

(2R)-2-[({6-[3-(ethylsulfanyl)phenyl]-3-fluoropyridin-2-yl}methyl)amino]-3-methylbutan-1-ol The title compound was prepared according to Example 245, substituting 3-(ethylthio)phenylboronic acid for 2,3,4-trifluorophenylboronic acid. MS (ESI$^+$) m/z 349 (M+H)$^+$.

Example 316

(2R)-2-[({6-[2-(ethylsulfanyl)phenyl]-3-fluoropyridin-2-yl}methyl)amino]-3-methylbutan-1-ol The title compound was prepared according to Example 245, substituting 2-(ethylthio)phenylboronic acid for 2,3,4-trifluorophenylboronic acid. MS (ESI$^+$) m/z 349 (M+H)$^+$.

Example 317

(2R)-2-({[6-(4-chloro-3-methylphenyl)-3-fluoropyridin-2-yl]methyl}amino)-3-methylbutan-1-ol The title compound was prepared according to Example 245, substituting 4-chloro-3-methylphenylboronic acid for 2,3,4-trifluorophenylboronic acid. MS (ESI+) m/z 337 (M+H)+.

Example 318

(2R)-2-({[6-(biphenyl-4-yl)-3-fluoropyridin-2-yl]methyl}amino)-3-methylbutan-1-ol The title compound was prepared according to Example 245, substituting biphenyl-4-ylboronic acid for 2,3,4-trifluorophenylboronic acid. MS (ESI+) m/z 365 (M+H)+.

Example 319

(2R)-2-[({6-[2-(benzyloxy)phenyl]-3-fluoropyridin-2-yl}methyl)amino]-3-methylbutan-1-ol The title compound was prepared according to Example 245, substituting ((benzyloxy)phenyl)-4,4,5,5-tetramethyl-1,3,2-dioxaborolane for 2,3,4-trifluorophenylboronic acid. MS (ESI+) m/z 395 (M+H)+.

Example 320

(2R)-2-({[6-(2-ethenylphenyl)-3-fluoropyridin-2-yl]methyl}amino)-3-methylbutan-1-ol The title compound was prepared according to Example 245, substituting 2-vinylphenylboronic acid for 2,3,4-trifluorophenylboronic acid. MS (ESI+) m/z 315 (M+H)+.

Example 321

(2R)-2-({[3-fluoro-6-(4-methyl-3-nitrophenyl)pyridin-2-yl]methyl}amino)-3-methylbutan-1-ol The title compound was prepared according to Example 245, substituting 4-methyl-3-nitrophenylboronic acid for 2,3,4-trifluorophenylboronic acid. MS (ESI+) m/z 348 (M+H)+.

Example 322

(2R)-2-[({6-[2-chloro-4-(trifluoromethyl)phenyl]-3-fluoropyridin-2-yl}methyl)amino]-3-methylbutan-1-ol The title compound was prepared according to Example 245, substituting 2-chloro-4-(trifluoromethyl)phenylboronic acid for 2,3,4-trifluorophenylboronic acid. MS (ESI+) m/z 391 (M+H)+.

Example 323

(2R)-2-[({3-fluoro-6-[2-(trifluoromethoxy)phenyl]pyridin-2-yl}methyl)amino]-3-methylbutan-1-ol The title compound was prepared according to Example 245, substituting 2-(trifluoromethoxy)phenylboronic acid for 2,3,4-trifluorophenylboronic acid. MS (ESI+) m/z 373 (M+H)+.

Example 324

(2R)-2-({[6-(5-chloro-2-methylphenyl)-3-fluoropyridin-2-yl]methyl}amino)-3-methylbutan-1-ol The title compound was prepared according to Example 245, substituting 5-chloro-2-methylphenylboronic acid for 2,3,4-trifluorophenylboronic acid. MS (ESI+) m/z 337 (M+H)+.

Example 325

4-[5-fluoro-6-({[(2R)-1-hydroxy-3-methylbutan-2-yl]amino}methyl)pyridin-2-yl]-N-(2-methylpropyl)benzamide The title compound was prepared according to Example 245, substituting 4-(isobutylcarbamoyl)phenylboronic acid for 2,3,4-trifluorophenylboronic acid. MS (ESI+) m/z 388 (M+H)+.

Example 326

(2R)-2-({[6-(4-bromo-3-fluorophenyl)-3-fluoropyridin-2-yl]methyl}amino)-3-methylbutan-1-ol The title compound was prepared according to Example 245, substituting 4-bromo-3-fluorophenylboronic acid for 2,3,4-trifluorophenylboronic acid. MS (ESI+) m/z 385 (M+H)+.

Example 327

(2R)-2-[({3-fluoro-6-[3-(propan-2-yl)phenyl]pyridin-2-yl}methyl)amino]-3-methylbutan-1-ol The title compound was prepared according to Example 245, substituting 3-isopropylphenylboronic acid for 2,3,4-trifluorophenylboronic acid. MS (ESI+) m/z 331 (M+H)+.

Example 328

(2R)-2-({[6-(2,4-difluorophenyl)-3-fluoropyridin-2-yl]methyl}amino)-3-methylbutan-1-ol The title compound was prepared according to Example 245, substituting 2,4-difluorophenylboronic acid for 2,3,4-trifluorophenylboronic acid. MS (ESI+) m/z 325 (M+H)+.

Example 329

(2R)-2-({[6-(biphenyl-3-yl)-3-fluoropyridin-2-yl]methyl}amino)-3-methylbutan-1-ol The title compound was prepared according to Example 245, substituting biphenyl-3-ylboronic acid for 2,3,4-trifluorophenylboronic acid. MS (ESI+) m/z 365 (M+H)+.

Example 330

(2R)-2-({[3-fluoro-6-(2,4,5-trimethylphenyl)pyridin-2-yl]methyl}amino)-3-methylbutan-1-ol The title compound was prepared according to Example 245, substituting 2,4,5-trimethylphenylboronic acid for 2,3,4-trifluorophenylboronic acid. MS (ESI+) m/z 331 (M+H)+.

Example 331

(2R)-2-[({3-fluoro-6-[4-(propan-2-ylsulfanyl)phenyl]pyridin-2-yl}methyl)amino]-3-methylbutan-1-ol The title compound was prepared according to Example 245, substituting 4-(isopropylthio)phenylboronic acid for 2,3,4-trifluorophenylboronic acid. MS (ESI⁺) m/z 363 (M+H)⁺.

Example 332

(2R)-2-({[6-(4-chloro-3-fluorophenyl)-3-fluoropyridin-2-yl]methyl}amino)-3-methylbutan-1-ol The title compound was prepared according to Example 245, substituting 4-chloro-3-fluorophenylphenylboronic acid for 2,3,4-trifluorophenylboronic acid. MS (ESI⁺) m/z 340 (M+H)⁺.

Example 333

(2R)-2-({[3-fluoro-6-(4-sulfanylphenyl)pyridin-2-yl]methyl}amino)-3-methylbutan-1-ol The title compound was prepared according to Example 245, substituting 4-mercaptophenylphenylboronic acid for 2,3,4-trifluorophenylboronic acid. MS (ESI⁺) m/z 321 (M+H)⁺.

Example 334

(2R)-2-({[6-(2-chloro-4-fluorophenyl)-3-fluoropyridin-2-yl]methyl}amino)-3-methylbutan-1-ol The title compound was prepared according to Example 245, substituting 2-chloro-4-fluorophenylphenylboronic acid for 2,3,4-trifluorophenylboronic acid. MS (ESI⁺) m/z 341 (M+H)⁺.

Example 335

(2R)-2-[({3-fluoro-6-[2-(methylsulfanyl)phenyl]pyridin-2-yl}methyl)amino]-3-methylbutan-1-ol The title compound was prepared according to Example 245, substituting 2-methylthiophenylphenylboronic acid for 2,3,4-trifluorophenylboronic acid. MS (ESI⁺) m/z 335 (M+H)⁺.

Example 336

(2R)-2-({[3-fluoro-6-(2,3,5,6-tetramethylphenyl)pyridin-2-yl]methyl}amino)-3-methylbutan-1-ol The title compound was prepared according to Example 245, substituting 2,3,5,6-tetramethylphenylphenylboronic acid for 2,3,4-trifluorophenylboronic acid. MS (ESI⁺) m/z 345 (M+H)⁺.

Example 337

(2R)-2-({[6-(2-ethylphenyl)-3-fluoropyridin-2-yl]methyl}amino)-3-methylbutan-1-ol The title compound was prepared according to Example 245, substituting 2-ethylphenylphenylboronic acid for 2,3,4-trifluorophenylboronic acid. MS (ESI⁺) m/z 317 (M+H)⁺.

Example 338

(2R)-2-({[3-fluoro-6-(4-fluoro-2-methylphenyl)pyridin-2-yl]methyl}amino)-3-methylbutan-1-ol The title compound was prepared according to Example 245, substituting 2-(4-fluoro-2-methylphenyl)-4,4,5,5-tetramethyl-1,3,2-dioxaborolane for 2,3,4-trifluorophenylboronic acid. MS (ESI⁺) m/z 321 (M+H)⁺.

Example 339

(2R)-2-({[3-fluoro-6-(5-fluoro-2-methylphenyl)pyridin-2-yl]methyl}amino)-3-methylbutan-1-ol The title compound was prepared according to Example 245, substituting 5-fluoro-2-methylphenylboronic acid for 2,3,4-trifluorophenylboronic acid. MS (ESI⁺) m/z 321 (M+H)⁺.

Example 340

(2R)-2-({[6-(2,6-dimethylphenyl)-3-fluoropyridin-2-yl]methyl}amino)-3-methylbutan-1-ol The title compound was prepared according to Example 245, substituting 2,6-dimethylphenylboronic acid for 2,3,4-trifluorophenylboronic acid. MS (ESI⁺) m/z 317 (M+H)⁺.

Example 341

(2R)-2-({[6-[2,3-difluorophenyl)-3-fluoropyridin-2-yl]methyl}amino)-3-methylbutan-1-ol The title compound was prepared according to Example 245, substituting 2,3-difluorophenylboronic acid for 2,3,4-trifluorophenylboronic acid. MS (ESI⁺) m/z 325 (M+H)⁺.

Example 342

(2R)-2-[({3-fluoro-6-[2-fluoro-4-(trifluoromethyl)phenyl]pyridin-2-yl}methyl)amino]-3-methylbutan-1-ol The title compound was prepared according to Example 245, substituting 2-fluoro-4-(trifluoromethyl)phenylboronic acid for 2,3,4-trifluorophenylboronic acid. MS (ESI⁺) m/z 375 (M+H)⁺.

Example 343

(2R)-2-({[6-[2,5-difluorophenyl)-3-fluoropyridin-2-yl]methyl}amino)-3-methylbutan-1-ol The title compound was prepared according to Example 245, substituting 2,5-difluorophenylboronic acid for 2,3,4-trifluorophenylboronic acid. MS (ESI⁺) m/z 325 (M+H)⁺.

Example 344

(2R)-2-({[6-(4-ethylphenyl)-3-fluoropyridin-2-yl]methyl}amino)-3-methylbutan-1-ol The title compound was prepared according to Example 245, substituting 4-ethylphenylboronic acid for 2,3,4-trifluorophenylboronic acid. MS (ESI⁺) m/z 317 (M+H)⁺.

Example 345

(2R)-2-({[6-(4-tert-butylphenyl)-3-fluoropyridin-2-yl]methyl}amino)-3-methylbutan-1-ol The title compound was prepared according to Example 245, substituting 4-tert-butylphenylboronic acid for 2,3,4-trifluorophenylboronic acid. MS (ESI$^+$) m/z 345 (M+H)$^+$.

Example 346

(2R)-2-({[3-fluoro-6-(2,4,6-trimethylphenyl)pyridin-2-yl]methyl}amino)-3-methylbutan-1-ol The title compound was prepared according to Example 245, substituting mesitylphenylboronic acid for 2,3,4-trifluorophenylboronic acid. MS (ESI+) m/z 331 (M+H)$^+$.

Example 347

N-{2-[5-fluoro-6-({[(2R)-1-hydroxy-3-methylbutan-2-yl]amino}methyl)pyridin-2-yl]phenyl}-2,2-dimethylpropanamide The title compound was prepared according to Example 245, substituting 2-pivalamidophenylboronic acid for 2,3,4-trifluorophenylboronic acid. MS (ESI+) m/z 388 (M+H)$^+$.

Example 348

(2R)-2-[({3-fluoro-6-[4-(2-methylpropyl)phenyl]pyridin-2-yl}methyl)amino]-3-methylbutan-1-ol The title compound was prepared according to Example 245, substituting 2-(4-isobutylphenyl)-4,4,5,5-tetramethyl-1,3,2-dioxaborolane for 2,3,4-trifluorophenylboronic acid. MS (ESI+) m/z 345 (M+H)$^+$.

Example 349

(2R)-2-({[3-fluoro-6-(4-methylphenyl)pyridin-2-yl]methyl}amino)-3-methylbutan-1-ol The title compound was prepared according to Example 245, substituting 4,4,5,5-tetramethyl-2-p-tolyl-1,3,2-dioxaborolane for 2,3,4-trifluorophenylboronic acid. MS (ESI+) m/z 303 (M+H)$^+$.

Example 350

(2R)-2-[({6-[4-(benzyloxy)phenyl]-3-fluoropyridin-2-yl}methyl)amino]-3-methylbutan-1-ol The title compound was prepared according to Example 245, substituting 2-(4-(benzyloxy)phenyl)-4,4,5,5-tetramethyl-1,3,2-dioxaborolane for 2,3,4-trifluorophenylboronic acid. MS (ESI+) m/z 395 (M+H)$^+$.

Example 351

(2R)-2-({[3-fluoro-6-(3-methylphenyl)pyridin-2-yl]methyl}amino)-3-methylbutan-1-ol The title compound was prepared according to Example 245, substituting 4,4,5,5-tetramethyl-2-m-tolyl-1,3,2-dioxaborolane for 2,3,4-trifluorophenylboronic acid. MS (ESI+) m/z 303 (M+H)$^+$.

Example 352

(2R)-2-({[6-(2-chlorophenyl)-3-fluoropyridin-2-yl]methyl}amino)-3-methylbutan-1-ol The title compound was prepared according to Example 245, substituting 2-(2-chlorophenyl)-4,4,5,5-tetramethyl-1,3,2-dioxaborolane for 2,3,4-trifluorophenylboronic acid. MS (ESI+) m/z 323 (M+H)$^+$.

Example 353

(2R)-2-({[6-(3-bromo-5-methylphenyl)-3-fluoropyridin-2-yl]methyl}amino)-3-methylbutan-1-ol The title compound was prepared according to Example 245, substituting 3-bromo-5-methylphenylboronic acid for 2,3,4-trifluorophenylboronic acid. MS (ESI+) m/z 381 (M+H)$^+$.

Example 354

(2R)-2-({[6-(3-chloro-2-methylphenyl)-3-fluoropyridin-2-yl]methyl}amino)-3-methylbutan-1-ol The title compound was prepared according to Example 245, substituting 3-chloro-2-methylphenylboronic acid for 2,3,4-trifluorophenylboronic acid. MS (ESI$^+$) m/z 337 (M+H)$^+$.

Example 355

(2R)-2-({[6-(4-bromo-2,5-dimethylphenyl)-3-fluoropyridin-2-yl]methyl}amino)-3-methylbutan-1-ol The title compound was prepared according to Example 245, substituting 4-bromo-2,5-dimethyl phenylboronic acid for 2,3,4-trifluorophenylboronic acid.

Example 356

(2R)-2-({[6-(3-chloro-2-fluorophenyl)-3-fluoropyridin-2-yl]methyl}amino)-3-methylbutan-1-ol The title compound was prepared according to Example 245, substituting 3-chloro-2-fluorophenylboronic acid for 2,3,4-trifluorophenylboronic acid. MS (ESI$^+$) m/z 341 (M+H)$^+$.

Example 357

N-butyl-4-[5-fluoro-6-({[(2R)-1-hydroxy-3-methylbutan-2-yl]amino}methyl)pyridin-2-yl]benzamide The title compound was prepared according to Example 245, substituting 4-(butylcarbamoylphenylboronic acid for 2,3,4-trifluorophenylboronic acid. MS (ESI$^+$) m/z 388 (M+H)$^+$.

Example 358

(2R)-2-({[6-(3-bromo-5-fluorophenyl)-3-fluoropyridin-2-yl]methyl}amino)-3-methylbutan-1-ol The title compound was prepared according to Example 245, substituting 3-bromo-5-fluorophenylboronic acid for 2,3,4-trifluorophenylboronic acid.

Example 359

(2R)-2-[({6-[4-(dimethylamino)phenyl]-3-fluoropyridin-2-yl}methyl)amino]-3-methylbutan-1-ol The title compound was prepared according to Example 245, substituting N,N-dimethyl-4-(4,4,5,5-tetramethyl-1,3,2-dioxaborolan-2-yl)aniline for 2,3,4-trifluorophenylboronic acid. MS (ESI$^+$) m/z 332 (M+H)$^+$.

Example 360

(2R)-2-({[6-(5-bromo-2-fluorophenyl)-3-fluoropyridin-2-yl]methyl}amino)-3-methylbutan-1-ol The title compound was prepared according to Example 245, substituting 5-bromo-2-fluorophenylboronic acid for 2,3,4-trifluorophenylboronic acid.

Example 361

(2R)-2-({[6-(3-bromo-2-fluorophenyl)-3-fluoropyridin-2-yl]methyl}amino)-3-methylbutan-1-ol The title compound was prepared according to Example 245, substituting 3-bromo-2-fluorophenylboronic acid for 2,3,4-trifluorophenylboronic acid.

Example 362

(2R)-2-({[6-(5-chloro-2-fluorophenyl)-3-fluoropyridin-2-yl]methyl}amino)-3-methylbutan-1-ol The title compound was prepared according to Example 245, substituting 5-chloro-2-fluorophenylboronic acid for 2,3,4-trifluorophenylboronic acid. MS (ESI$^+$) m/z 341 (M+H)$^+$.

Example 363

(2R)-2-({[3-fluoro-6-(2-fluoro-4-methylphenyl)pyridin-2-yl]methyl}amino)-3-methylbutan-1-ol The title compound was prepared according to Example 245, substituting 2-fluoro-4-methylphenylboronic acid for 2,3,4-trifluorophenylboronic acid. MS (ESI$^+$) m/z 321 (M+H)$^+$.

Example 364

(2R)-2-[({6-[2-(dimethylamino)phenyl]-3-fluoropyridin-2-yl}methyl)amino]-3-methylbutan-1-ol The title compound was prepared according to Example 245, substituting N,N-dimethyl-2-(4,4,5,5-tetramethyl-1,3,2-dioxaborolan-2-yl)aniline for 2,3,4-trifluorophenylboronic acid. MS (ESI$^+$) m/z 332 (M+H)$^+$.

Example 365

(2R)-2-({[3-fluoro-6-(4-fluoro-2-methoxyphenyl)pyridin-2-yl]methyl}amino)-3-methylbutan-1-ol The title compound was prepared according to Example 245, substituting 4-fluoro-2-methoxyphenylboronic acid for 2,3,4-trifluorophenylboronic acid. MS (ESI$^+$) m/z 337 (M+H)$^+$.

Example 366

(2R)-2-[({3-fluoro-6-[3-fluoro-5-(trifluoromethyl)phenyl]pyridin-2-yl}methyl)amino]-3-methylbutan-1-ol The title compound was prepared according to Example 245, substituting 3-fluoro-5-(trifluoromethyl)phenylboronic acid for 2,3,4-trifluorophenylboronic acid. MS (ESI$^+$) m/z 375 (M+H)$^+$.

Example 367

(2R)-2-({[6-(9H-fluoren-2-yl)-3-fluoropyridin-2-yl]methyl}amino)-3-methylbutan-1-ol The title compound was prepared according to Example 245, substituting 9H-fluoren-2-ylboronic acid for 2,3,4-trifluorophenylboronic acid. MS (ESI$^+$) m/z 377 (M+H)$^+$.

Example 368

(2R)-2-[({3-fluoro-6-[2-fluoro-3-(trifluoromethyl)phenyl]pyridin-2-yl}methyl)amino]-3-methylbutan-1-ol The title compound was prepared according to Example 245, substituting 2-fluoro-3-(trifluoromethyl)phenylboronic acid for 2,3,4-trifluorophenylboronic acid. MS (ESI$^+$) m/z 375 (M+H)$^+$.

Example 369

(2R)-2-[({3-fluoro-6-[2-fluoro-5-(trifluoromethoxy)phenyl]pyridin-2-yl}methyl)amino]-3-methylbutan-1-ol The title compound was prepared according to Example 245, substituting 2-fluoro-5-(trifluoromethoxy)phenylboronic acid for 2,3,4-trifluorophenylboronic acid. MS (ESI$^+$) m/z 391 (M+H)$^+$.

Example 370

(2R)-2-({[6-(2-chloro-5-methylphenyl)-3-fluoropyridin-2-yl]methyl}amino)-3-methylbutan-1-ol The title compound was prepared according to Example 245, substituting 2-chloro-5-methylphenylboronic acid for 2,3,4-trifluorophenylboronic acid. MS (ESI$^+$) m/z 337 (M+H)$^+$.

Example 371

(2R)-2-({[3-fluoro-6-(2-methylphenyl)pyridin-2-yl]methyl}amino)-3-methylbutan-1-ol The title compound was prepared according to Example 245, substituting 4,4,5,5-tetramethyl-2-o-tolyl-1,3,2-dioxaborolane for 2,3,4-trifluorophenylboronic acid. MS (ESI$^+$) m/z 303 (M+H)$^+$.

Example 372

(2R)-2-({[3-fluoro-6-(3-fluoro-5-methylphenyl)pyridin-2-yl]methyl}amino)-3-methylbutan-1-ol The title compound was prepared according to Example 245, substituting 3-fluoro-5-methylphenylboronic acid for 2,3,4-trifluorophenylboronic acid. MS (ESI$^+$) m/z 321 (M+H)$^+$.

Example 373

(2R)-2-[({6-[2-(ethoxymethyl)phenyl]-3-fluoropyridin-2-yl}methyl)amino]-3-methylbutan-1-ol The title compound was prepared according to Example 245, substituting 2-(ethoyxymethyl)phenylboronic acid for 2,3,4-trifluorophenylboronic acid. MS (ESI$^+$) m/z 347 (M+H)$^+$.

Example 374

(2R)-2-[({3-fluoro-6-[2-(trifluoromethyl)phenyl]pyridin-2-yl}methyl)amino]-3-methylbutan-1-ol The title compound was prepared according to Example 245, substituting 4,4,5,5-tetramethyl-2-(2-(trifluoromethyl)phenyl)-1,3,2-dioxaborolane for 2,3,4-trifluorophenylboronic acid. MS (ESI$^+$) m/z 357 (M+H)$^+$.

Example 375

(2R)-2-({[6-(3-chloro-5-fluorophenyl)-3-fluoropyridin-2-yl]methyl}amino)-3-methylbutan-1-ol The title compound was prepared according to Example 245, substituting 3-chloro-5-fluorophenylboronic acid for 2,3,4-trifluorophenylboronic acid. MS (ESI$^+$) m/z 341 (M+H)$^+$.

Example 376

(2R)-2-{[(3-fluoro-6-{4-[(phenylamino)methyl]phenyl}pyridin-2-yl)methyl]amino 1-3-methylbutan-1-ol The title compound was prepared according to Example 245, substituting N-(4-(4,4,5,5-tetramethyl-1,3,2-dioxaborolan-2-yl)benzyl)aniline for 2,3,4-trifluorophenylboronic acid. MS (ESI$^+$) m/z 394 (M+H)$^+$.

Example 377

(2R)-2-[({3-fluoro-6-[3-(1-methoxyethyl)phenyl]pyridin-2-yl}methyl)amino]-3-methylbutan-1-ol The title compound was prepared according to Example 245, substituting 3-(1-methoxyethyl)phenylboronic acid for 2,3,4-trifluorophenylboronic acid. MS (ESI$^+$) m/z 347 (M+H)$^+$.

Example 378

(2R)-2-[({3-fluoro-6-[4-(1-methoxyethyl)phenyl]pyridin-2-yl}methyl)amino]-3-methylbutan-1-ol The title compound was prepared according to Example 245, substituting 4-(1-methoxyethyl)phenylboronic ac id for 2,3,4-trifluorophenylboronic acid. MS (ESI$^+$) m/z 347 (M+H)$^+$.

Example 379

(2R)-2-{[(6-{4-[1-(dimethylamino)ethyl]phenyl}-3-fluoropyridin-2-yl)methyl]amino 1-3-methylbutan-1-ol The title compound was prepared according to Example 245, substituting 4-(1-(dimethylamino)ethyl)phenylboronic acid for 2,3,4-trifluorophenylboronic acid. MS (ESI$^+$) m/z 360 (M+H)$^+$.

Example 380

(2R)-2-[({3-fluoro-6-[3-fluoro-4-(trifluoromethoxy)phenyl]pyridin-2-yl}methyl)amino]-3-methylbutan-1-ol The title compound was prepared according to Example 245, substituting 3-fluoro-4-(trifluoromethoxy)phenylboronic acid for 2,3,4-trifluorophenylboronic acid. MS (ESI$^+$) m/z 391 (M+H)$^+$.

Example 381

(2R)-2-({[3-fluoro-6-(2-methoxynaphthalen-1-yl)pyridin-2-yl]methyl}amino)-3-methylbutan-1-ol The title compound was prepared according to Example 245, substituting 2-methoxynaphthalen-1-ylboronic acid for 2,3,4-trifluorophenylboronic acid. MS (ESI$^+$) m/z 369 (M+H)$^+$.

Example 382

(2R)-2-({[6'-(dimethylamino)-5-fluoro-2,3'-bipyridin-6-yl]methyl}amino)-3-methylbutan-1-ol The title compound was prepared according to Example 228, substituting (6-(dimethylamino)pyridin-3-yl)boronic acid for 3,4-difluorophenylboronic acid. $^1$H NMR (300 MHz, CDCl$_3$) δ 8.74 (d, J=2.5 Hz, 1H), 8.09 (dd, J=8.9, 2.6 Hz, 1H), 7.51 (dd, J=8.6, 3.7 Hz, 1H), 7.37 (t, J=8.7 Hz, 1H), 6.60 (d, J=8.9 Hz, 1H), 4.07 (m, 2H), 3.70 (dd, J=10.9, 3.9, 1H), 3.48 (dd, J=10.8, 6.7 Hz, 1H), 3.15 (s, 6H), 2.49 (td, J=6.7, 3.9, 1H), 1.88 (dq, J=13.5, 6.7 Hz, 1H), 1.01 (d, J=6.8 Hz, 3H), 0.95 (d, J=6.8 Hz, 3H). MS (ESI) m/z: 333 (M+H)$^+$.

Example 383

(2R)-2-[({3-fluoro-6-[4-(1H-pyrazol-1-yl)phenyl]pyridin-2-yl}methyl)amino]-3-methylbutan-1-ol The title compound was prepared according to Example 228, substituting (4-(1H-pyrazol-1-yl)phenyl)boronic acid for 3,4-difluorophenylboronic acid. $^1$H NMR (300 MHz, CDCl$_3$) δ 8.09-8.02 (m, 2H), 7.99 (d, J=2.5 Hz, 1H), 7.85-7.78 (m, 2H), 7.76 (d, J=1.8 Hz, 1H), 7.67 (dd, J=8.6, 3.6 Hz, 1H), 7.46 (t, J=8.7 Hz, 1H), 6.50 (d, J=2.1 Hz, 1H), 4.14 (t, J=2.0 Hz, 2H), 3.74 (dd, J=11.0, 3.9, 1H), 3.53 (dd, J=11.0, 6.7 Hz, 1H), 2.54 (td, J=6.7, 3.9, 1H), 1.92 (dq, J=13.5, 6.8 Hz, 1H), 1.03 (d, J=6.8 Hz, 3H), 0.97 (d, J=6.8 Hz, 3H). MS (ESI) m/z: 355 (M+H)+.

Example 384

(2R)-2-({[6'-(cyclopropylmethoxy)-5-fluoro-2,3'-bipyridin-6-yl]methyl}amino)-3-methylbutan-1-ol The title compound was prepared according to Example 228, substituting (6-(cyclopropylmethoxy)pyridin-3-yl)boronic acid for 3,4-difluorophenylboronic acid. $^1$H NMR (300 MHz, CDCl$_3$) δ 8.69 (d, J=2.5 Hz, 1H), 8.18 (dd, J=8.6, 2.5 Hz, 1H), 7.55 (dd, J=8.6, 3.7 Hz, 1H), 7.42 (t, J=8.8 Hz, 1H), 6.86 (d, J=8.7 Hz, 1H), 4.19 (d, J=7.1 Hz, 2H), 4.08 (d, J=2.0 Hz, 2H), 3.70 (dd, J=10.8, 4.0, 1H), 3.46 (dd, J=10.8, 6.7 Hz, 1H), 2.49 (td, J=6.7, 4.0, 1H), 1.87 (dh, J=13.8, 6.9 Hz, 1H), 1.40-1.21 (m, 1H), 1.01 (d, J=6.8 Hz, 3H), 0.95 (d, J=6.8 Hz, 3H), 0.68-0.59 (m, 2H), 0.42-0.33 (m, 2H). MS (ESI) m/z: 360 (M+H)+.

Example 385

N-butyl-3-[5-fluoro-6-({[(2R)-1-hydroxy-3-methylbutan-2-yl]amino}methyl)pyridin-2-yl]benzamide The title compound was prepared according to Example 228, substituting (3-(butylcarbamoyl)phenyl)boronic acid for 3,4-difluorophenylboronic acid. $^1$H NMR (300 MHz, CDCl$_3$) δ 8.49 (t, J=1.8 Hz, 1H), 7.97-7.92 (m, 1H), 7.92-7.88 (m, 1H), 7.67 (dd, J=8.6, 3.7 Hz, 1H), 7.52 (t, J=7.7 Hz, 1H), 7.45 (t, J=8.8 Hz, 1H), 7.39-7.29 (m, 1H), 4.33 (dd, J=16.4, 2.0 Hz, 1H), 4.09 (dd, J=16.4, 2.0 Hz, 1H), 3.76 (dd, J=10.7, 3.8, 1H), 3.55-3.39 (m, 3H), 2.61 (ddd, J=8.4, 6.3, 3.8, 1H), 1.87 (dq, J=13.4, 6.8 Hz, 1H), 1.75-1.56 (m, 2H), 1.45 (dq, J=14.2, 7.2 Hz, 2H), 1.04 (d, J=6.9 Hz, 3H), 1.00-0.93 (m, 6H).
MS (ESI) m/z: 388 (M+H)+.

Example 386

(2R)-2-{[(3-fluoro-6-{4-[5-(methylamino)-1,3,4-thiadiazol-2-yl]phenyl}pyridin-2-yl)methyl]amino}-3-methylbutan-1-ol The title compound was prepared according to Example 228, substituting (4-(5-(methylamino)-1,3,4-thiadiazol-2-yl)phenyl)boronic acid for 3,4-difluorophenylboronic acid. $^1$H NMR (300 MHz, CDCl$_3$) δ 8.06-7.99 (m, 2H), 7.94-7.87 (m, 2H), 7.68 (dd, J=8.6, 3.6 Hz, 1H), 7.45 (t, J=8.8 Hz, 1H), 5.36-5.25 (m, 1H), 4.12 (d, J=1.9 Hz, 2H), 3.72 (dd, J=10.9, 3.9, 1H), 3.50 (dd, J=10.9, 6.7 Hz, 1H), 3.13 (s, 3H), 2.52 (td, J=6.6, 3.9 Hz, 1H), 1.90 (dq, J=13.5, 6.7 Hz, 1H), 1.03 (d, J=6.8 Hz, 3H), 0.96 (d, J=6.8 Hz, 3H). MS (ESI) m/z: 402 (M+H)+.

Example 387

(2R)-2-({[3-fluoro-6-(3-methylthiophen-2-yl)pyridin-2-yl]methyl}amino)-3-methylbutan-1-ol The title compound was prepared according to Example 228, substituting (3-methylthiophen-2-yl)boronic acid for 3,4-difluorophenylboronic acid. $^1$H NMR (300 MHz, CDCl$_3$) δ 7.52 (d, J=3.3 Hz, 1H), 7.44-7.37 (m, 2H), 7.06-7.00 (m, 1H), 4.18-4.04 (m, 2H), 3.72 (dd, J=11.0, 3.9, 1H), 3.50 (dd, J=11.0, 6.8 Hz, 1H), 2.53 (td, J=6.7, 3.9 Hz, 1H), 2.42 (d, J=1.0 Hz, 3H), 1.89 (dq, J=13.6, 6.8 Hz, 1H), 1.00 (d, J=6.8 Hz, 3H), 0.95 (d, J=6.8 Hz, 3H). MS (ESI) m/z: 309 (M+H)+.

Example 388

(2R)-2-{[(6-{3-chloro-4-[(3-chlorobenzyl)oxy]phenyl}-3-fluoropyridin-2-yl)methyl]amino}-3-methylbutan-1-ol The title compound was prepared according to Example 228, substituting (3-chloro-4-((3-chlorobenzyl)oxy)phenyl)boronic acid for 3,4-difluorophenylboronic acid. $^1$H NMR (300 MHz, CDCl$_3$) δ 8.01 (d, J=2.2 Hz, 1H), 7.81 (dd, J=8.6, 2.3 Hz, 1H), 7.56 (dd, J=8.6, 3.6 Hz, 1H), 7.48 (s, 1H), 7.43 (d, J=8.8 Hz, 1H) 7.40-7.29 (m, 3H), 7.02 (d, J=8.6, 1H), 5.18 (s, 2H), 4.20-4.06 (m, 2H), 3.73 (dd, J=11.0, 3.9, 1H), 3.53 (dd, J=11.0, 6.7 Hz, 1H), 2.54 (td, J=6.7, 3.9 Hz, 1H), 1.92 (dq, J=13.6, 6.8 Hz, 1H), 1.03 (d, J=6.8 Hz, 3H), 0.97 (d, J=6.8 Hz, 3H). MS (ESI) m/z: 463 (M+H)+.

Example 389

(2R)-2-{[(6-{4-[(3-chlorobenzyl)oxy]phenyl}-3-fluoropyridin-2-yl)methyl]amino}-3-methylbutan-1-ol The title compound was prepared according to Example 228, substituting (4-((3-chlorobenzyl)oxy)phenyl)boronic acid for 3,4-difluorophenylboronic acid. $^1$H NMR (300 MHz, CDCl$_3$) δ 7.67-7.57 (m, 3H), 7.57-7.51 (m, 1H), 7.48-7.33 (m, 3H), 7.32-7.24 (m, 2H), 7.04 (ddd, J=8.2, 2.6, 0.9 Hz, 1H), 5.26 (s, 2H), 4.21-4.06 (m, 2H), 3.73 (dd, J=10.9, 3.9, 1H), 3.52 (dd, J=11.0, 6.7 Hz, 1H), 2.52 (td, J=6.8, 3.9 Hz, 1H), 1.91 (dq, J=13.6, 6.8 Hz, 1H), 1.02 (d, J=6.8 Hz, 3H), 0.96 (d, J=6.8 Hz, 3H). MS (ESI) m/z: 429 (M+H)+.

Example 390

(2R)-2-{[(6-{4-[(4-chlorobenzyl)oxy]phenyl}-3-fluoropyridin-2-yl)methyl]amino}-3-methylbutan-1-ol The title compound was prepared according to Example 228, substituting (4-((4-chlorobenzyl)oxy)phenyl)boronic acid for 3,4-difluorophenylboronic acid. $^1$H NMR (300 MHz, CDCl$_3$) δ 7.66-7.58 (m, 2H), 7.55-7.49 (m, 1H), 7.45 (d, J=8.8 Hz, 1H), 7.42-7.33 (m, 5H), 7.00 (ddd, J=8.2, 2.6, 1.0 Hz, 1H), 5.12 (s, 2H), 4.19-4.06 (m, 2H), 3.76-3.68 (m, 1H), 3.51 (dd, J=11.0, 6.7 Hz, 1H), 2.53 (td, J=6.6, 3.9 Hz, 1H), 1.99-1.82 (m, 1H), 1.02 (d, J=6.8 Hz, 3H), 0.96 (d, J=6.8 Hz, 3H). MS (ESI) m/z: 429 (M+H)+.

Example 391

(2R)-2-({[6-(4-{[(4-chloronaphthalen-1-yl)oxy]methyl}phenyl)-3-fluoropyridin-2-yl]methyl}amino)-3-methylbutan-1-ol The title compound was prepared according to Example 228, substituting (4-((4-chloronaphthalen-1-yl)methoxy)phenyl)boronic acid for 3,4-difluorophenylboronic acid. $^1$H NMR (300 MHz, CDCl$_3$) δ 8.43-8.35 (m, 1H), 8.26-8.18 (m, 1H), 8.03-7.96 (m, 2H), 7.75-7.33 (m, 7H), 6.81 (dd, J=8.2, 1.0 Hz, 1H), 5.30 (s, 2H), 4.27-4.13 (m, 2H), 3.76 (dd, J=11.2, 3.8 Hz, 1H), 3.58 (dd, J=11.2, 6.8 Hz, 1H), 2.58 (td, J=6.7, 3.8

Hz, 1H), 1.95 (dq, J=13.5, 6.8 Hz, 1H), 1.04 (d, J=6.8 Hz, 3H), 0.98 (d, J=6.8 Hz, 3H). MS (ESI) m/z: 479 (M+H)⁺.

Example 392

(2R)-2-{[(3-fluoro-6-{4-[(naphthalen-1-yloxy)methyl]phenyl}pyridin-2-yl)methyl]amino}-3-methylbutan-1-ol The title compound was prepared according to Example 228, substituting 4-((naphthalen-1-yloxy)methyl)phenylboronic acid for 3,4-difluorophenylboronic acid. ¹H NMR (300 MHz, CDCl₃) δ 8.40-8.33 (m, 1H), 8.03-7.96 (m, 2H), 7.85-7.78 (m, 1H), 7.69-7.60 (m, 3H), 7.56-7.41 (m, 4H), 7.40-7.33 (m, 1H), 6.90 (dd, J=7.5, 1.1 Hz, 1H), 5.32 (s, 2H), 4.22-4.08 (m, 2H), 3.73 (dd, J=11.0, 3.9 Hz, 1H), 3.52 (dd, J=11.0, 6.8 Hz, 1H), 2.54 (td, J=6.7, 3.9 Hz, 1H), 1.91 (dq, J=13.6, 6.8 Hz, 1H), 1.03 (d, J=6.8 Hz, 3H), 0.97 (d, J=6.8 Hz, 3H). MS (ESI) m/z: 445 (M+H)⁺.

Example 393

(2R)-2-{[(6-{3-[(3-chlorobenzyl)oxy]phenyl}-3-fluoropyridin-2-yl)methyl]amino}-3-methylbutan-1-ol The title compound was prepared according to Example 228, substituting (3-((3-chlorobenzyl)oxy)phenyl)boronic acid for 3,4-difluorophenylboronic acid. ¹H NMR (300 MHz, CDCl₃) δ 7.64-7.59 (m, 2H), 7.53 (d, J=7.9 1H), 7.48 (s, 1H), 7.46-7.38 (m, 2H), 7.36-7.29 (m, 3H), 7.01 (dd, J=7.9, 2.3 Hz, 1H), 5.13 (s, 2H), 4.09 (d, J=1.9 Hz, 2H), 3.70 (dd, J=10.8, 4.0 Hz, 1H), 3.47 (dd, J=10.9, 6.7 Hz, 1H), 2.50 (td, J=6.6, 4.0 Hz, 1H), 1.88 (dq, J=13.5, 6.8 Hz, 1H), 1.02 (d, J=6.8 Hz, 3H), 0.95 (d, J=6.8 Hz, 3H). MS (ESI) m/z: 429 (M+H)⁺.

Example 394

(2R)-2-({[5-fluoro-6'-(trifluoromethyl)-2,3'-bipyridin-6-yl]methyl}amino)-2-phenylethanol To a solution of Example 28A (27 mg, 0.10 mmol) in 1:1 methanol/dichloromethane (1.0 mL) was added a solution of (R)-2-amino-2-phenylethanol (14 mg, 0.12 mmol) in 1:1 ethanol/dichloromethane (0.4 mL) followed by acetic acid (58 μL, 1.0 mmol). The mixture was shaken for 2 hours at room temperature then MP-cyanoborohydride resin (135 mg, 2.17 mmol/g) was added. The resulting mixture was shaken at room temperature overnight then filtered and concentrated. The residue purified by reverse phase HPLC to provide the title compound. MS (ESI⁺) m/z 392 (M+H)⁺.

Example 395

N²-{[5-fluoro-6'-(trifluoromethyl)-2,3'-bipyridin-6-yl]methyl}-L-leucinamide

The title compound was prepared according to Example 394, substituting (S)-2-amino-4-methylpentanamide hydrochloride for (R)-2-amino-2-phenylethanol. MS (ESI⁺) m/z 385 (M+H)⁺.

Example 396

(2S)-2-({[5-fluoro-6'-(trifluoromethyl)-2,3'-bipyridin-6-yl]methyl}amino)-4-methylpentan-1-ol The title compound was prepared according to Example 394, substituting (S)-2-amino-4-methylpentan-1-ol for (R)-2-amino-2-phenylethanol. MS (ESI⁺) m/z 372 (M+H)⁺.

Example 397

(2S)-2-({[5-fluoro-6'-(trifluoromethyl)-2,3'-bipyridin-6-yl]methyl}amino)-2-phenylethanol The title compound was prepared according to Example 394, substituting (S)-2-amino-2-phenylethanol for (R)-2-amino-2-phenylethanol. MS (ESI⁺) m/z 392 (M+H)⁺.

Example 398

N-cyclopropyl-3-[5-fluoro-6-({[(2R)-1-hydroxy-3-methylbutan-2-yl]amino}methyl)pyridin-2-yl]benzenesulfonamide The title compound was prepared according to Example 228, substituting (3-(N-cyclopropylsulfamoyl)phenyl)boronic acid for 3,4-difluorophenylboronic acid. ¹H NMR (300 MHz, DMSO-d₆) δ 8.51 (t, J=1.8 Hz, 1H), 8.33 (dt, J=7.8, 1.4 Hz, 1H), 8.00 (dd, J=8.7, 3.7 Hz, 1H), 7.95 (s, 1H), 7.92-7.78 (m, 2H), 7.74 (t, J=7.8 Hz, 1H), 4.42 (t, J=5.2 Hz, 1H), 4.04-3.95 (m, 7H), 3.50-3.42 (m, 1H), 3.37-3.31 (m, 1H), 3.28 (s, 3H), 2.41-2.32 (m, 1H), 2.20-2.10 (m, 1H), 1.92-1.78 (m, 1H), 0.90-0.81 (m, 6H), 0.54-0.45 (m, 2H), 0.44-0-35 (m, 2H). MS (ESI) m/z: 408 (M+H)⁺.

Example 399

3-[5-fluoro-6-({[(2R)-1-hydroxy-3-methylbutan-2-yl]amino}methyl)pyridin-2-yl]-N-(1,3-thiazol-2-yl)benzamide The title compound was prepared according to Example 228, substituting (3-(thiazol-2-ylcarbamoyl)phenyl)boronic acid for 3,4-difluorophenylboronic acid. ¹H NMR (300 MHz, DMSO-d₆) δ 13.26-12.14 (m, 1H), 8.76 (t, J=1.5 Hz, 1H), 8.36 (d, J=7.8 Hz, 1H), 8.17-8.06 (m, 2H), 7.84 (dd, J=9.3, 8.9 Hz, 1H), 7.68 (t, J=7.8 Hz, 1H), 7.59 (d, J=3.6 Hz, 1H), 7.31 (d, J=3.6 Hz, 1H), 4.59-4.39 (m, 1H), 4.08-3.89 (m, 2H), 3.48 (dd, J=10.9, 4.5 Hz, 1H), 3.40-3.23 (m, 1H), 2.46-2.33 (m, 1H), 1.93-1.78 (m, 1H), 0.88 (d, J=7.0 Hz, 3H), 0.86 (d, J=7.0 Hz, 3H). MS (ESI) m/z: 415 (M+H)⁺.

Example 400

(2R)-2-({[3-fluoro-6-(4-methoxy-3-methylphenyl)pyridin-2-yl]methyl}amino)-3-methylbutan-1-ol The title compound was prepared according to Example 245, substituting 4-methoxy-3-methylphenylboronic acid for 2,3,4-trifluorophenylboronic acid. MS (ESI⁺) m/z 333 (M+H)⁺.

Example 401

(2R)-2-({[6-(4-ethoxyphenyl)-3-fluoropyridin-2-yl]methyl}amino)-3-methylbutan-1-ol The title compound was prepared according to Example 245, substituting 4-ethoxyphenylboronic acid for 2,3,4-trifluorophenylboronic acid. MS (ESI+) m/z 333 (M+H)+.

Example 402

(2R)-2-[({6-[3-(benzyloxy)phenyl]-3-fluoropyridin-2-yl}methyl)amino]-3-methylbutan-1-ol The title compound was prepared according to Example 245, substituting 3-(benzyloxy)phenylboronic acid for 2,3,4-trifluorophenylboronic acid. MS (ESI+) m/z 395 (M+H)+.

Example 403

(2R)-2-({[6-(2-butoxyphenyl)-3-fluoropyridin-2-yl]methyl}amino)-3-methylbutan-1-ol The title compound was prepared according to Example 245, substituting 2-butoxyphenylboronic acid for 2,3,4-trifluorophenylboronic acid. MS (ESI+) m/z 361 (M+H)+.

Example 404

(2R)-2-({[6-(4-ethoxy-3,5-dimethylphenyl)-3-fluoropyridin-2-yl]methyl}amino)-3-methylbutan-1-ol The title compound was prepared according to Example 245, substituting 4-ethoxy-3,5-dimethylphenylboronic acid for 2,3,4-trifluorophenylboronic acid. MS (ESI+) m/z 361 (M+H)+.

Example 405

(2R)-2-({[6-(3-butoxyphenyl)-3-fluoropyridin-2-yl]methyl}amino)-3-methylbutan-1-ol The title compound was prepared according to Example 245, substituting 3-butoxyphenylboronic acid for 2,3,4-trifluorophenylboronic acid. MS (ESI+) m/z 361 (M+H)+.

Example 406 propan-2-yl 3-[5-fluoro-6-({[(2R)-1-hydroxy-3-methylbutan-2-yl]amino}methyl)pyridin-2-yl]benzoate The title compound was prepared according to Example 245, substituting 3-(isopropoxycarbonyl)phenylboronic acid for 2,3,4-trifluorophenylboronic acid. MS (ESI+) m/z 375 (M+H)+.

Example 407

4-[5-fluoro-6-({[(2R)-1-hydroxy-3-methylbutan-2-yl]amino}methyl)pyridin-2-yl]-2,6-dimethylphenol The title compound was prepared according to Example 245, substituting 2,6-dimethyl-4-(4,4,5,5-tetramethyl-1,3,2-dioxaborolan-2-yl)phenol for 2,3,4-trifluorophenylboronic acid. MS (ESI+) m/z 333 (M+H)+.

Example 408

(2R)-2-({[6-(4-butoxyphenyl)-3-fluoropyridin-2-yl]methyl}amino)-3-methylbutan-1-ol The title compound was prepared according to Example 245, substituting 4-butoxyphenylboronic acid for 2,3,4-trifluorophenylboronic acid. MS (ESI+) m/z 361 (M+H)+.

Example 409

(2R)-2-({[6-(3,5-dimethoxyphenyl)-3-fluoropyridin-2-yl]methyl}amino)-3-methylbutan-1-ol The title compound was prepared according to Example 245, substituting 3,5-dimethoxyphenylboronic acid for 2,3,4-trifluorophenylboronic acid. MS (ESI+) m/z 349 (M+H)+.

Example 410

(2R)-2-[({3-fluoro-6-[4-methoxy-2-(trifluoromethyl)phenyl]pyridin-2-yl}methyl)amino]-3-methylbutan-1-ol The title compound was prepared according to Example 245, substituting 4-methoxy-2-(trifluoromethyl)phenylboronic acid for 2,3,4-trifluorophenylboronic acid. MS (ESI+) m/z 387 (M+H)+.

Example 411

(2R)-2-({[6-(3,5-difluoro-2-methoxyphenyl)-3-fluoropyridin-2-yl]methyl}amino)-3-methylbutan-1-ol The title compound was prepared according to Example 245, substituting 3,5-difluoro-2-methoxyphenylboronic acid for 2,3,4-trifluorophenylboronic acid. MS (ESI+) m/z 355 (M+H)+.

Example 412

(2R)-2-({[6-(6-ethoxynaphthalen-2-yl)-3-fluoropyridin-2-yl]methyl}amino)-3-methylbutan-1-ol The title compound was prepared according to Example 245, substituting 6-ethoxynaphthalen-2-ylboronic acid for 2,3,4-trifluorophenylboronic acid. MS (ESI+) m/z 383 (M+H)+.

Example 413

(2R)-2-({[6-(2,3-dimethoxyphenyl)-3-fluoropyridin-2-yl]methyl}amino)-3-methylbutan-1-ol The title compound was prepared according to Example 245, substituting 2,3-dimethoxyphenylboronic acid for 2,3,4-trifluorophenylboronic acid. MS (ESI+) m/z 349 (M+H)+.

Example 414

(2R)-2-({[3-fluoro-6-(2-methoxy-5-methylphenyl)pyridin-2-yl]methyl}amino)-3-methylbutan-1-ol The title compound was prepared according to Example 245, substituting 2-methoxy-5-methylphenylboronic acid for 2,3,4-trifluorophenylboronic acid. MS (ESI+) m/z 333 (M+H)+.

Example 415

(2R)-2-({[6-(2-ethoxy-5-methylphenyl)-3-fluoropyridin-2-yl]methyl}amino)-3-methylbutan-1-ol The title compound was prepared according to Example 245, substituting 2-ethoxy-5-methylphenylboronic acid for 2,3,4-trifluorophenylboronic acid. MS (ESI$^+$) m/z 347 (M+H)$^+$.

Example 416

(2R)-2-({[3-fluoro-6-(4-methoxy-2-methylphenyl)pyridin-2-yl]methyl}amino)-3-methylbutan-1-ol The title compound was prepared according to Example 245, substituting 4-methoxy-2-methylphenylboronic acid for 2,3,4-trifluorophenylboronic acid. MS (ESI$^+$) m/z 333 (M+H)$^+$.

Example 417

(2R)-2-({[6-(2-ethoxyphenyl)-3-fluoropyridin-2-yl]methyl}amino)-3-methylbutan-1-ol The title compound was prepared according to Example 245, substituting 2-ethoxyphenylboronic acid for 2,3,4-trifluorophenylboronic acid. MS (ESI$^+$) m/z 333 (M+H)$^+$.

Example 418

(2R)-2-[({3-fluoro-6-[2-(propan-2-yloxy)phenyl]pyridin-2-yl}methyl)amino]-3-methylbutan-1-ol The title compound was prepared according to Example 245, substituting 2-isopropoxyphenylboronic acid for 2,3,4-trifluorophenylboronic acid. MS (ESI$^+$) m/z 347 (M+H)$^+$.

Example 419

(2R)-2-({[3-fluoro-6-(5-fluoro-2-methoxyphenyl)pyridin-2-yl]methyl}amino)-3-methylbutan-1-ol The title compound was prepared according to Example 245, substituting 5-fluoro-2-methoxyphenylboronic acid for 2,3,4-trifluorophenylboronic acid. MS (ESI$^+$) m/z 337 (M+H)$^+$.

Example 420

(2R)-2-({[3-fluoro-6-(2-fluoro-3-methoxyphenyl)pyridin-2-yl]methyl}amino)-3-methylbutan-1-ol The title compound was prepared according to Example 245, substituting 2-fluoro-3-methoxyphenylboronic acid for 2,3,4-trifluorophenylboronic acid. MS (ESI$^+$) m/z 337 (M+H)$^+$.

Example 421

(2R)-2-({[6-(2-ethoxy-4-fluorophenyl)-3-fluoropyridin-2-yl]methyl}amino)-3-methylbutan-1-ol The title compound was prepared according to Example 245, substituting 4-fluoro-2-ethoxyphenylboronic acid for 2,3,4-trifluorophenylboronic acid. MS (ESI$^+$) m/z 351 (M+H)$^+$.

Example 422

(2R)-2-({[6-(2,6-dimethoxyphenyl)-3-fluoropyridin-2-yl]methyl}amino)-3-methylbutan-1-ol The title compound was prepared according to Example 245, substituting 2,6-dimethoxyphenylboronic acid for 2,3,4-trifluorophenylboronic acid. MS (ESI$^+$) m/z 349 (M+H)$^+$.

Example 423

(2R)-2-({[6-(3-chloro-4-propoxyphenyl)-3-fluoropyridin-2-yl]methyl}amino)-3-methylbutan-1-ol The title compound was prepared according to Example 245, substituting 3-chloro-4-propoxyphenylboronic acid for 2,3,4-trifluorophenylboronic acid. MS (ESI$^+$) m/z 381 (M+H)$^+$.

Example 424

(2R)-2-({[6-(4-ethoxy-3-fluorophenyl)-3-fluoropyridin-2-yl]methyl}amino)-3-methylbutan-1-ol The title compound was prepared according to Example 245, substituting 4-ethoxy-3-fluorophenylboronic acid for 2,3,4-trifluorophenylboronic acid. MS (ESI$^+$) m/z 351 (M+H)$^+$.

Example 425

(2R)-2-({[3-fluoro-6-(3-propoxyphenyl)pyridin-2-yl]methyl}amino)-3-methylbutan-1-ol The title compound was prepared according to Example 245, substituting 3-propoxyphenylboronic acid for 2,3,4-trifluorophenylboronic acid. MS (ESI$^+$) m/z 347 (M+H)$^+$.

Example 426

(2R)-2-({[3-fluoro-6-(5-fluoro-2-propoxyphenyl)pyridin-2-yl]methyl}amino)-3-methylbutan-1-ol The title compound was prepared according to Example 245, substituting 5-fluoro-2-propoxyphenylboronic acid for 2,3,4-trifluorophenylboronic acid. MS (ESI$^+$) m/z 365 (M+H)$^+$.

Example 427

(2R)-2-({[3-fluoro-6-(3-fluoro-4-propoxyphenyl)pyridin-2-yl]methyl}amino)-3-methylbutan-1-ol The title compound was prepared according to Example 245, substituting 3-fluoro-4-propoxyphenylboronic acid for 2,3,4-trifluorophenylboronic acid. MS (ESI$^+$) m/z 365 (M+H)$^+$.

Example 428

(2R)-2-[({3-fluoro-6-[3-(2-methylpropoxy)phenyl]pyridin-2-yl}methyl)amino]-3-methylbutan-1-ol The title compound was prepared according to Example 245, substituting 3-isobutoxyphenylboronic acid for 2,3,4-trifluorophenylboronic acid. MS (ESI$^+$) m/z 361 (M+H)$^+$.

Example 429

(2R)-2-({[3-fluoro-6-(2-fluoro-6-propoxyphenyl)pyridin-2-yl]methyl}amino)-3-methylbutan-1-ol The title compound was prepared according to Example 245, substituting 6-fluoro-2-propoxyphenylboronic acid for 2,3,4-trifluorophenylboronic acid.

Example 430

(2R)-2-({[3-fluoro-6-(2-methyl-4-propoxyphenyl)pyridin-2-yl]methyl}amino)-3-methylbutan-1-ol The title compound was prepared according to Example 245, substituting 2-methyl-4-propoxyphenylboronic acid for 2,3,4-trifluorophenylboronic acid. MS (ESI$^+$) m/z 361 (M+H)$^+$.

Example 431

(2R)-2-({[6-(5-chloro-2-propoxyphenyl)-3-fluoropyridin-2-yl]methyl}amino)-3-methylbutan-1-ol The title compound was prepared according to Example 245, substituting 5-chloro-2-propoxyphenylboronic acid for 2,3,4-trifluorophenylboronic acid. MS (ESI$^+$) m/z 381 (M+H)$^+$.

Example 432

(2R)-2-[({6-[5-chloro-2-(propan-2-yloxy)phenyl]-3-fluoropyridin-2-yl}methyl)amino]-3-methylbutan-1-ol The title compound was prepared according to Example 245, substituting 5-chloro-2-isopropoxyphenylboronic acid for 2,3,4-trifluorophenylboronic acid. MS (ESI$^+$) m/z 381 (M+H)$^+$.

Example 433

(2R)-2-({[6-(2-ethoxynaphthalen-1-yl)-3-fluoropyridin-2-yl]methyl}amino)-3-methylbutan-1-ol The title compound was prepared according to Example 245, substituting 2-ethoxynaphthalen-1-ylboronic acid for 2,3,4-trifluorophenylboronic acid. MS (ESI$^+$) m/z 383 (M+H)$^+$.

Example 434

(2R)-2-[({3-fluoro-6-[4-(methylsulfanyl)phenyl]pyridin-2-yl}methyl)amino]-3-methylbutan-1-ol The title compound was prepared according to Example 245, substituting 4,4,5,5-tetramethyl-2-(4-(methylthio)phenyl)-1,3,2-dioxaborolane for 2,3,4-trifluorophenylboronic acid. MS (ESI$^+$) m/z 335 (M+H)$^+$.

Example 435

(2R)-2-({[6-(3,4-dimethoxyphenyl)-3-fluoropyridin-2-yl]methyl}amino)-3-methylbutan-1-ol The title compound was prepared according to Example 245, substituting 2-(3,4-dimethoxyphenyl)-4,4,5,5-tetramethyl-1,3,2-dioxaborolane for 2,3,4-trifluorophenylboronic acid. MS (ESI$^+$) m/z 349 (M+H)$^+$.

Example 436

(2R)-2-({[6-(5-butoxy-2-fluorophenyl)-3-fluoropyridin-2-yl]methyl}amino)-3-methylbutan-1-ol The title compound was prepared according to Example 245, substituting 5-butoxy-2-fluorophenylboronic acid for 2,3,4-trifluorophenylboronic acid. MS (ESI$^+$) m/z 379 (M+H)$^+$.

Example 437

(2R)-2-({[3-fluoro-6-(4-methoxyphenyl)pyridin-2-yl]methyl}amino)-3-methylbutan-1-ol The title compound was prepared according to Example 245, substituting 2-(4-methoxyphenyl)-4,4,5,5-tetramethyl-1,3,2-dioxaborolane for 2,3,4-trifluorophenylboronic acid. MS (ESI$^+$) m/z 319 (M+H)$^+$.

Example 438

(2R)-2-({[3-fluoro-6-(2-propoxyphenyl)pyridin-2-yl]methyl}amino)-3-methylbutan-1-ol The title compound was prepared according to Example 245, substituting 2-propoxyphenylboronic acid for 2,3,4-trifluorophenylboronic acid. MS (ESI$^+$) m/z 347 (M+H)$^+$.

Example 439

(2R)-2-({[3-fluoro-6-(3-methoxyphenyl)pyridin-2-yl]methyl}amino)-3-methylbutan-1-ol The title compound was prepared according to Example 245, substituting 2-(3-methoxyphenyl)-4,4,5,5-tetramethyl-1,3,2-dioxaborolane for 2,3,4-trifluorophenylboronic acid. MS (ESI$^+$) m/z 319 (M+H)$^+$.

Example 440

(2R)-2-({[3-fluoro-6-(4-propoxyphenyl)pyridin-2-yl]methyl}amino)-3-methylbutan-1-ol The title compound was prepared according to Example 245, substituting 4-propoxyphenylboronic acid for 2,3,4-trifluorophenylboronic acid. MS (ESI$^+$) m/z 347 (M+H)$^+$.

Example 441

(2R)-2-[({3-fluoro-6-[2-(2-methylpropoxy)phenyl]pyridin-2-yl}methyl)amino]-3-methylbutan-1-ol The title compound was prepared according to Example 245, substituting 2-isobutoxyphenylboronic acid for 2,3,4-trifluorophenylboronic acid. MS (ESI$^+$) m/z 361 (M+H)$^+$.

Example 442

(2R)-2-[({3-fluoro-6-[5-fluoro-2-(propan-2-yloxy)phenyl]pyridin-2-yl}methyl)amino]-3-methylbutan-1-ol The title compound was prepared according to Example 245, substituting 5-fluoro-2-isopropoxyphenylboronic acid for 2,3,4-trifluorophenylboronic acid. MS (ESI$^+$) m/z 365 (M+H)$^+$.

Example 443

(2R)-2-({[3-fluoro-6-(5-methyl-2-propoxyphenyl)pyridin-2-yl]methyl}amino)-3-methylbutan-1-ol The title compound was prepared according to Example 245, substituting 5-methyl-2-propoxyphenylboronic acid for 2,3,4-trifluorophenylboronic acid. MS (ESI$^+$) m/z 361 (M+H)$^+$.

Example 444

(2R)-2-({[6-(2-butoxy-5-fluorophenyl)-3-fluoropyridin-2-yl]methyl}amino)-3-methylbutan-1-ol The title compound was prepared according to Example 245, substituting 2-butoxy-5-fluorophenylboronic acid for 2,3,4-trifluorophenylboronic acid. MS (ESI$^+$) m/z 379 (M+H)$^+$.

Example 445

(2R)-2-({[6-(4-butoxy-3-fluorophenyl)-3-fluoropyridin-2-yl]methyl}amino)-3-methylbutan-1-ol The title compound was prepared according to Example 245, substituting 4-butoxy-3-fluorophenylboronic acid for 2,3,4-trifluorophenylboronic acid. MS (ESI$^+$) m/z 379 (M+H)$^+$.

Example 446

(2R)-2-({[3-fluoro-6-(2-methoxyphenyl)pyridin-2-yl]methyl}amino)-3-methylbutan-1-ol The title compound was prepared according to Example 245, substituting 2-(2-methoxyphenyl)-4,4,5,5-tetramethyl-1,3,2-dioxaborolane for 2,3,4-trifluorophenylboronic acid. MS (ESI$^+$) m/z 319 (M+H)$^+$.

Example 447

(2R)-2-[({3-fluoro-6-[5-methyl-2-(propan-2-yloxy)phenyl]pyridin-2-yl}methyl)amino]-3-methylbutan-1-ol The title compound was prepared according to Example 245, substituting 2-isopropoxy-5-methylphenylboronic acid for 2,3,4-trifluorophenylboronic acid. MS (ESI$^+$) m/z 361 (M+H)$^+$.

Example 448

(2R)-2-({[6-(4-ethoxy-2-methylphenyl)-3-fluoropyridin-2-yl]methyl}amino)-3-methylbutan-1-ol The title compound was prepared according to Example 245, substituting 4-ethoxy-2-methylphenylboronic acid for 2,3,4-trifluorophenylboronic acid. MS (ESI$^+$) m/z 347 (M+H)$^+$.

Example 449

(2R)-2-({[6-(5-chloro-2-ethoxyphenyl)-3-fluoropyridin-2-yl]methyl}amino)-3-methylbutan-1-ol The title compound was prepared according to Example 245, substituting 5-chloro-2-ethoxyphenylboronic acid for 2,3,4-trifluorophenylboronic acid. MS (ESI$^+$) m/z 367 (M+H)$^+$.

Example 450

(2R)-2-({[6-(2-ethoxy-5-fluorophenyl)-3-fluoropyridin-2-yl]methyl}amino)-3-methylbutan-1-ol The title compound was prepared according to Example 245, substituting 2-ethoxy-5-fluorophenylboronic acid for 2,3,4-trifluorophenylboronic acid. MS (ESI$^+$) m/z 351 (M+H)$^+$.

Example 451

(2R)-2-({[6-(2-ethoxy-6-fluorophenyl)-3-fluoropyridin-2-yl]methyl}amino)-3-methylbutan-1-ol The title compound was prepared according to Example 245, substituting 2-ethoxy-6-fluorophenylboronic acid for 2,3,4-trifluorophenylboronic acid. MS (ESI$^+$) m/z 351 (M+H)$^+$.

Example 452

(2R)-2-({[6-(5-ethoxy-2-fluorophenyl)-3-fluoropyridin-2-yl]methyl}amino)-3-methylbutan-1-ol The title compound was prepared according to Example 245, substituting 5-ethoxy-2-fluorophenylboronic acid for 2,3,4-trifluorophenylboronic acid. MS (ESI$^+$) m/z 351 (M+H)$^+$.

Example 453

(2R)-2-({[3-fluoro-6-(2-fluoro-5-methoxyphenyl)pyridin-2-yl]methyl}amino)-3-methylbutan-1-ol The title compound was prepared according to Example 245, substituting 2-fluoro-5-methoxyphenylboronic acid for 2,3,4-trifluorophenylboronic acid. MS (ESI$^+$) m/z 337 (M+H)$^+$.

Example 454

(2R)-2-({[6-(2-chloro-6-methoxyphenyl)-3-fluoropyridin-2-yl]methyl}amino)-3-methylbutan-1-ol The title compound was prepared according to Example 245, substituting 2-chloro-6-methoxyphenylboronic acid for 2,3,4-trifluorophenylboronic acid.

Example 455

(2R)-2-({[6-(2,5-difluoro-4-methoxyphenyl)-3-fluoropyridin-2-yl]methyl}amino)-3-methylbutan-1-ol The title compound was prepared according to Example 245, substituting 2,5-difluoro-4-methoxyphenylboronic acid for 2,3,4-trifluorophenylboronic acid. MS (ESI$^+$) m/z 355 (M+H)$^+$.

Example 456

(2R)-2-({[3-fluoro-6-(2-fluoro-5-propoxyphenyl)pyridin-2-yl]methyl}amino)-3-methylbutan-1-ol The title compound was prepared according to Example 245, substituting 2-fluoro-5-propoxyphenylboronic acid for 2,3,4-trifluorophenylboronic acid. MS (ESI$^+$) m/z 365 (M+H)$^+$.

Example 457

(2R)-2-({[6-(3-chloro-4-ethoxyphenyl)-3-fluoropyridin-2-yl]methyl}amino)-3-methylbutan-1-ol The title compound was prepared according to Example 245, substituting 3-chloro-4-ethoxyphenylboronic acid for 2,3,4-trifluorophenylboronic acid. MS (ESI$^+$) m/z 367 (M+H)$^+$.

Example 458

(2R)-2-({[6-(3-ethoxy-2-fluorophenyl)-3-fluoropyridin-2-yl]methyl}amino)-3-methylbutan-1-ol The title compound was prepared according to Example 245, substituting 3-ethoxy-2-fluorophenylboronic acid for 2,3,4-trifluorophenylboronic acid. MS (ESI$^+$) m/z 351 (M+H)$^+$.

Example 459

(2R)-2-[({3-fluoro-6-[3-methoxy-5-(trifluoromethyl)phenyl]pyridin-2-yl}methyl)amino]-3-methylbutan-1-ol The title compound was prepared according to Example 245, substituting 3-methoxy-5-(trifluoromethyl)phenylboronic acid for 2,3,4-trifluorophenylboronic acid. MS (ESI$^+$) m/z 387 (M+H)$^+$.

Example 460

(2R)-2-({[6-(4-ethoxy-3-methylphenyl)-3-fluoropyridin-2-yl]methyl}amino)-3-methylbutan-1-ol The title compound was prepared according to Example 245, substituting 4-ethoxy-3-methylphenylboronic acid for 2,3,4-trifluorophenylboronic acid. MS (ESI$^+$) m/z 347 (M+H)$^+$.

Example 461

(2R)-2-[({3-fluoro-6-[4-methoxy-3-(trifluoromethyl)phenyl]pyridin-2-yl}methyl)amino]-3-methylbutan-1-ol The title compound was prepared according to Example 245, substituting 4-methoxy-3-(trifluoromethyl)phenylboronic acid for 2,3,4-trifluorophenylboronic acid. MS (ESI$^+$) m/z 387 (M+H)$^+$.

Example 462

(2R)-2-{[(6-{3-[(cyclopropylmethyl)sulfanyl]phenyl}-3-fluoropyridin-2-yl)methyl]amino}-3-methylbutan-1-ol The title compound was prepared according to Example 245, substituting 3-(cyclopropylmethylthio)phenylboronic acid for 2,3,4-trifluorophenylboronic acid. MS (ESI$^+$) m/z 375 (M+H)$^+$.

Example 463

(2R)-2-[({3-fluoro-6-[4-(2-methylpropoxy)phenyl]pyridin-2-yl}methyl)amino]-3-methylbutan-1-ol The title compound was prepared according to Example 245, substituting 4-isobutoxyphenylboronic acid for 2,3,4-trifluorophenylboronic acid. MS (ESI$^+$) m/z 361 (M+H)$^+$.

Example 464

(2R)-2-[({6-[3,5-dimethyl-4-(propan-2-yloxy)phenyl]-3-fluoropyridin-2-yl}methyl)amino]-3-methylbutan-1-ol The title compound was prepared according to Example 245, substituting (4-isopropoxy-3,5-dimethylphenyl)boronic acid for 2,3,4-trifluorophenylboronic acid. MS (ESI$^+$) m/z 375 (M+H)$^+$.

Example 465

(2R)-2-({[6-(2-ethoxy-4,5-difluorophenyl)-3-fluoropyridin-2-yl]methyl}amino)-3-methylbutan-1-ol The title compound was prepared according to Example 245, substituting 2-ethoxy-4,5-difluoroboronic acid for 2,3,4-trifluorophenylboronic acid. MS (ESI$^+$) m/z 369 (M+H)$^+$.

Example 466

(2R)-2-({[6-(2,4-diethoxyphenyl)-3-fluoropyridin-2-yl]methyl}amino)-3-methylbutan-1-ol The title compound was prepared according to Example 245, substituting 2,4-diethoxyphenylboronic acid for 2,3,4-trifluorophenylboronic acid. MS (ESI$^+$) m/z 377 (M+H)$^+$.

Example 467

(2R)-2-({[6-(2-butoxy-6-fluorophenyl)-3-fluoropyridin-2-yl]methyl}amino)-3-methylbutan-1-ol The title compound was prepared according to Example 245, substituting 2-butoxy-6-fluorophenylboronic acid for 2,3,4-trifluorophenylboronic acid. MS (ESI$^+$) m/z 379 (M+H)$^+$.

Example 468

(2R)-2-({[6-(3-ethoxy-5-fluorophenyl)-3-fluoropyridin-2-yl]methyl}amino)-3-methylbutan-1-ol The title compound was prepared according to Example 245, substituting 3-ethoxy-5-fluorophenylboronic acid for 2,3,4-trifluorophenylboronic acid. MS (ESI$^+$) m/z 351 (M+H)$^+$.

Example 469

(2R)-2-[({3-fluoro-6-[2-methoxy-6-(propan-2-yloxy)phenyl]pyridin-2-yl}methyl)amino]-3-methylbutan-1-ol The title compound was prepared according to Example 245, substituting 2-isopropoxy-6-methoxyphenylboronic acid for 2,3,4-trifluorophenylboronic acid. MS (ESI$^+$) m/z 377 (M+H)$^+$.

Example 470

(2R)-2-[({3-fluoro-6-[2-fluoro-6-(propan-2-yloxy)phenyl]pyridin-2-yl}methyl)amino]-3-methylbutan-1-ol The title compound was prepared according to Example 245, substituting 2-fluoro-6-isopropoxyphenylboronic acid for 2,3,4-trifluorophenylboronic acid. MS (ESI$^+$) m/z 365 (M+H)$^+$.

Example 471

(2R)-2-[({3-fluoro-6-[2-methoxy-6-(2-methylpropoxy)phenyl]pyridin-2-yl}methyl)amino]-3-methylbutan-1-ol The title compound was prepared according to Example 245, substituting 2-isobutoxy-6-methoxyphenylboronic acid for 2,3,4-trifluorophenylboronic acid. MS (ESI$^+$) m/z 391 (M+H)$^+$.

Example 472

(2R)-2-({[3-fluoro-6-(4-fluoro-3-methoxyphenyl)pyridin-2-yl]methyl}amino)-3-methylbutan-1-ol The title compound was prepared according to Example 245, substituting 4-fluoro-3-methoxyphenylboronic acid for 2,3,4-trifluorophenylboronic acid. MS (ESI$^+$) m/z 337 (M+H)$^+$.

Example 473

(2R)-2-[({3-fluoro-6-[3-fluoro-5-(propan-2-yloxy)phenyl]pyridin-2-yl}methyl)amino]-3-methylbutan-1-ol The title compound was prepared according to Example 245, substituting 3-fluoro-5-isopropoxyphenylboronic acid for 2,3,4-trifluorophenylboronic acid. MS (ESI$^+$) m/z 365 (M+H)$^+$.

Example 474

(2R)-2-[({3-fluoro-6-[5-methyl-2-(2-methylpropoxy)phenyl]pyridin-2-yl}methyl)amino]-3-methylbutan-1-ol The title compound was prepared according to Example 245, substituting 2-isobutoxy-5-methylphenylboronic acid for 2,3,4-trifluorophenylboronic acid. MS (ESI$^+$) m/z 375 (M+H)$^+$.

Example 475

(2R)-2-({[644,5-difluoro-2-methoxyphenyl)-3-fluoropyridin-2-yl]methyl}amino)-3-methylbutan-1-ol The title compound was prepared according to Example 245, substituting 3,4-difluoro-2-methoxyphenylboronic acid for 2,3,4-trifluorophenylboronic acid. MS (ESI$^+$) m/z 355 (M+H)$^+$.

Example 476

2-ethoxy-3-[5-fluoro-6-({[(2R)-1-hydroxy-3-methylbutan-2-yl]amino}methyl)pyridin-2-yl]-5-methylbenzaldehyde The title compound was prepared according to Example 245, substituting 2-ethoxy-3-formyl-5-methylphenylboronic acid for 2,3,4-trifluorophenylboronic acid. MS (ESI$^+$) m/z 375 (M+H)$^+$.

Example 477

(2R)-2-[({6-[4-(benzyloxy)-3-chlorophenyl]-3-fluoropyridin-2-yl}methyl)amino]-3-methylbutan-1-ol The title compound was prepared according to Example 228, substituting (4-(benzyloxy)-3-chlorophenyl)boronic acid for 3,4-difluorophenylboronic acid. $^1$H NMR (300 MHz, CDCl$_3$) δ 8.01 (d, J=2.3 Hz, 1H), 7.79 (dd, J=8.6, 2.2 Hz, 1H), 7.58-7.51 (m, 1H), 7.48 (d, J=7.3 Hz, 2H), 7.45-7.29 (m, 4H), 7.05 (d, J=8.6 Hz, 1H), 5.33 (d, J=64.1 Hz, 2H), 4.08 (s, 2H), 3.70 (dd, J=10.9, 4.0 Hz, 1H), 3.48 (dd, J=10.9, 6.7 Hz, 1H), 2.64-2.42 (m, 3H), 1.89 (dq, J=13.6, 6.8 Hz, 1H), 0.99 (dd, J=19.6, 6.8 Hz, 6H). MS (DCI$^+$) m/z 429 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:
1. A compound of formula (I)

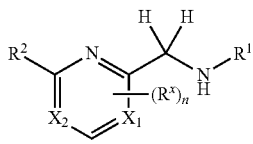

or a pharmaceutically acceptable salt, solvate, or salt of a solvate thereof, wherein $X_1$ and $X_2$ are each CH;

each $R^x$ is an optional substituent on any substitutable carbon atom, and is independently selected from the group consisting of alkyl, alkenyl, alkynyl, halogen, CN, $O(R^{1a})$, $N(R^{1a})(R^{1b})$, $NO_2$, haloalkyl, —($C_1$-$C_6$ alkylenyl)-$O(R^{1a})$, and —($C_1$-$C_6$ alkylenyl)-$N(R^{1a})(R^{1b})$;

n is 0, 1, 2, or 3;

$R^1$ is a monocyclic cycloalkyl, a monocyclic heterocycle, or —$CH_2$-(monocyclic cycloalkyl); wherein the monocyclic cycloalkyl, the monocyclic heterocycle, or the monocyclic cycloalkyl moiety of the —$CH_2$-(monocyclic cycloalkyl), is substituent, with one substituent, $R^y$, selected from the group consisting of OH, —($CH_2$)—OH, and —$C(O)N(R^5)_2$, and is optionally further substituted with 1, 2, 3, 4, or 5 substituents, $R^z$, selected from the group consisting of alkyl, halogen, haloalkyl, and oxo; or $R^1$ is

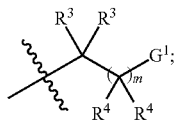

$G^1$ is OH or —$C(O)N(R^5)_2$;

m is 0, 1, or 2; with the proviso that m is 1 or 2 when $G^1$ is OH;

each $R^3$ is independently hydrogen, alkyl, halogen, haloalkyl, —$C(O)R^{3a}$, —$C(O)OR^{3a}$, —$C(O)N(R^{3a})(R^{3b})$, $G^{3a}$, —($C_1$-$C_6$ alkylenyl)-$G^{3a}$, hydroxyalkyl, alkoxyalkyl, or haloalkoxyalkyl; wherein $G^{3a}$ is cycloalkyl, cycloalkenyl, heterocycle, aryl, or heteroaryl; or two $R^3$ together with the carbon atom to which they are attached, form a 3-, 4-, 5-, or 6-membered monocyclic ring wherein said ring optionally contains 1, 2, or 3 heteroatoms selected from the group consisting of S, O, N, and NH, and optionally contains one double bond; said ring is unsubstituted or substituted on any substitutable ring atoms with 1, 2, 3, 4, or 5 substituents independently selected from the group consisting of alkyl, halogen, haloalkyl, and oxo;

$R^{3a}$, at each occurrence, is independently hydrogen, alkyl, or haloalkyl;

$R^{3b}$ is hydrogen, alkyl, haloalkyl, or aryl wherein the aryl is optionally substituted with 1, 2, 3, 4, or 5 substituents independently selected from the group consisting of alkyl, halogen, and haloalkyl;

each $R^4$ is independently hydrogen, alkyl, halogen, phenyl, or haloalkyl; two $R^4$ together with the carbon atom to which they are attached, optionally form a 3-, 4-, 5-, or 6-membered monocyclic ring, said ring optionally contains 1, 2, or 3 heteroatoms selected from the group consisting of S, O, N, and NH, and optionally contains one double bond; said ring is unsubstituted or substituted on any substitutable ring atoms with 1, 2, 3, 4, or 5 substituents independently selected from the group consisting of alkyl, halogen, haloalkyl, and oxo;

each $R^5$ is independently hydrogen or alkyl, or two $R^5$ together with the nitrogen atom to which they are attached, form 3-, 4-, 5-, or 6-membered monocyclic heterocycle ring; wherein said ring optionally contains one additional heteroatom selected from the group consisting of N, NH, O, S, S(O), and $S(O)_2$ and optionally a double bond, and is optionally fused with a monocyclic ring selected from the group consisting of benzo, heteroaryl, heterocycle, cycloalkyl, and cycloalkenyl; said ring is optionally substituted with 1, 2, 3, 4, or 5 substituents independently selected from the group consisting of alkyl, alkenyl, alkynyl, oxo, halogen, and haloalkyl;

$R^2$ is $G^{2a}$;

$G^{2a}$, at each occurrence, is independently heteroaryl, and is optionally substituted with 1, 2, 3, 4, or 5 substituents independently selected from the group consisting of alkyl, alkenyl, alkynyl, halogen, haloalkyl, oxo, $G^a$, $NO_2$, CN, —$OR^f$, —$OC(O)R^f$, —$OC(O)N(R^f)_2$, —Si(alkyl)$_3$, —$SF_5$, —$SR^f$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^e$, —$N(R^f)S(O)_2R^e$, —$N(R^f)C(O)O(R^e)$, —$N(R^f)C(O)N(R^f)_2$, —($C_1$-$C_6$ alkylenyl)-$G^a$, —($C_1$-$C_6$ alkylenyl)-$OR^f$, —($C_1$-$C_6$ alkylenyl)-$OC(O)R^f$, —($C_1$-$C_6$ alkylenyl)-$OC(O)N(R^f)_2$, —($C_1$-$C_6$ alkylenyl)-$S(O)_2R^e$, —($C_1$-$C_6$ alkylenyl)-$S(O)_2N(R^f)_2$, —($C_1$-$C_6$ alkylenyl)-$C(O)R^f$, —($C_1$-$C_6$ alkylenyl)-$C(O)OR^f$, —($C_1$-$C_6$ alkylenyl)-$C(O)N(R^f)_2$, —($C_1$-$C_6$ alkylenyl)-$N(R^f)_2$ —($C_1$-$C_6$ alkylenyl)-$N(R^f)C(O)R^e$, —($C_1$-$C_6$ alkylenyl)-$N(R^f)S(O)_2 R^e$, —($C_1$-$C_6$ alkylenyl)-$N(R^f)C(O)O(R^e)$, —($C_1$-$C_6$ alkylenyl)-$N(R^f)C(O)N(R^f)_2$, and —($C_1$-$C_6$ alkylenyl)-CN;

$R^f$, at each occurrence, is independently hydrogen, alkyl, haloalkyl, —($C_1$-$C_6$ alkylenyl)-$OR^g$, $G^a$, or —($C_1$-$C_6$ alkylenyl)-$G^a$;

$R^e$, at each occurrence, is independently alkyl, haloalkyl, —($C_1$-$C_6$ alkylenyl)-$OR^g$, $G^a$, or —($C_1$-$C_6$ alkylenyl)-$G^a$;

$R^g$, at each occurrence, is independently hydrogen, alkyl, haloalkyl, monocyclic cycloalkyl, or —($C_1$-$C_6$ alkylenyl)-(monocyclic cycloalkyl); wherein the monocyclic cycloakyl, alone or as part of the group, is optionally substituted with 1, 2, 3, 4, or 5 substituents independently selected from the group consisting of alkyl, haloalkyl, oxo, OH, and alkoxy;

$G^a$, at each occurrence, is independently aryl, heteroaryl, cycloalkyl, cycloalkenyl, or heterocycle;

$G^{3a}$ and $G^a$, are each independently unsubstituted or substituted with 1, 2, 3, 4, or 5 substituents independently selected from the group consisting of alkyl, alkenyl, alkynyl, halogen, haloalkyl, oxo, $NO_2$, CN, —$OR^{1a}$, —$OC(O)R^{1c}$, —$OC(O)N(R^{1a})(R^{1b})$, —$SR^{1a}$, —$S(O)_2R^{1a}$, —$S(O)_2N(R^{1a})(R^{1b})$, —$C(O)R^{1a}$, —$C(O)OR^{1a}$, —$C(O)N(R^{1a})(R^{1b})$, —$N(R^{1a})(R^{1b})$, —$N(R^{1a})C(O)R^{1c}$, —$N(R^{1a})S(O)_2R^{1c}$, —$N(R^{1a})C(O)O(R^{1c})$, —$N(R^{1a})C(O)N(R^{1a})(R^{1b})$, —($C_1$-$C_6$ alkylenyl)-$OR^{1a}$—($C_1$-$C_6$ alkylenyl)-$OC(O)R^{1c}$, —($C_1$-$C_6$ alkylenyl)-$OC(O)N(R^{1a})(R^{1b})$, —($C_1$-$C_6$ alkylenyl)-$S(O)_2 R^{1a}$, —($C_1$-$C_6$ alkylenyl)-$S(O)_2N(R^{1a})(R^{1b})$, —($C_1$-$C_6$ alkylenyl)-$C(O)R^{1a}$, —($C_1$-$C_6$ alkylenyl)-$C(O)OR^{1a}$, —($C_1$-$C_6$ alkylenyl)-$C(O)N(R^{1a})(R^{1b})$, —($C_1$-$C_6$ alkylenyl)-$N(R^{1a})(R^{1b})$, —($C_1$-$C_6$ alkylenyl)-$N(R^{1a})C(O)

$R^{1c}$, —($C_1$-$C_6$ alkylenyl)-N($R^{1a}$)S(O)$_2$$R^{1c}$, —($C_1$-$C_6$ alkylenyl)-N($R^{1a}$)C(O)O($R^{1c}$), —($C_1$-$C_6$ alkylenyl)-N($R^{1a}$)C(O)N($R^{1a}$)($R^{1b}$), and —($C_1$-$C_6$ alkylenyl)-CN;

$R^{1a}$ and $R^{1b}$, at each occurrence, are each independently hydrogen, alkyl, or haloalkyl; and $R^{1c}$, at each occurrence, is each independently alkyl or haloalkyl.

2. The compound of formula (I-a) according to claim 1 or a pharmaceutically acceptable salt, solvate, or salt of a solvate thereof,

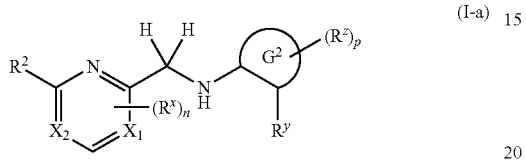

(I-a)

wherein $G^2$ is a $C_3$-$C_6$ cycloalkyl wherein two non-adjacent atoms of the $G^2$ ring are optionally linked by an alkylenyl bridge of 1 or 2 carbon atoms;

$R^y$ is OH or —(CH$_2$)—OH;

p is 0, 1, 2, 3, 4, or 5; and $R^x$, $R^2$, n, and $R^z$ are as set forth in claim 1.

3. The compound of formula (I) according to claim 1 or a pharmaceutically acceptable salt, solvate, or salt of a solvate thereof, wherein $R^1$ is

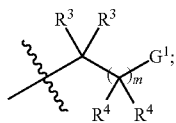

and $G^1$ is OH.

4. The compound of formula (I) according to claim 3 or a pharmaceutically acceptable salt, solvate, or salt of a solvate thereof, wherein each $R^4$ is independently hydrogen, alkyl, phenyl, or haloalkyl; two $R^4$ together with the carbon atom to which they are attached optionally form $C_3$-$C_6$ cycloalkyl, oxetanyl, or tetrahydropyranyl, each of which is optionally substituted.

5. The compound of formula (I) according to claim 4 or a pharmaceutically acceptable salt, solvate, or salt of a solvate thereof, wherein m is 1, and each $R^4$ is independently hydrogen or $C_1$-$C_4$ alkyl.

6. The compound of formula (I-b) according to claim 1 or a pharmaceutically acceptable salt, solvate, or salt of a solvate thereof,

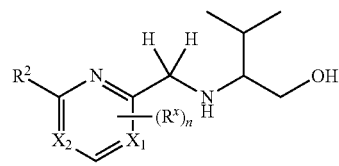

(I-b)

wherein $X_1$, $X_2$, $R^x$, $R^2$, and n are as set forth in claim 1.

7. The compound according to claim 1 or a pharmaceutically acceptable salt, solvate, or salt of a solvate thereof, wherein the compound is selected from the group consisting of:

(2R)-2-({[5-fluoro-6'-(trifluoromethyl)-2,3'-bipyridin-6-yl]methyl}amino)-3-methylbutan-1-ol;

(2R)-2-({[5-fluoro-2'-(trifluoromethyl)-2,4'-bipyridin-6-yl]methyl}amino)-3-methylbutan-1-ol;

(2S)-2-({[5-fluoro-6'-(trifluoromethyl)-2,3'-bipyridin-6-yl]methyl}amino)-3-methylbutan-1-ol;

(2R)-2-{[(5,5'-difluoro-2,2'-bipyridin-6-yl)methyl]amino}-3-methylbutan-1-ol;

(2R)-2-{[(6'-choloro-5-fluoro-2,3'-bipyridin-6-yl)methyl]amino}-3-methylbutan-1-ol;

(2R)-2-({[5-fluoro-2'-(morpholin-4-yl)-2,4'-bipyridin-6-yl]methyl}amino)-3-methylbutan-1-ol;

(2R)-2-({[5-fluoro-6'-(propan-2-yloxy)-2,3'-bipyridin-6-yl]methyl}amino)-3-methylbutan-1-ol;

(2R)-2-({[3-fluoro-6-(1-methyl-1H-indol-4-yl)pyridin-2-yl]methyl}amino)-3-methylbutan-1-ol;

(2R)-2-({[3-fluoro-6-(1-methyl-1H-indol-6-yl)pyridin-2-yl]methyl}amino)-3-methylbutan-1-ol;

(2R)-2-({[5-fluoro-6'-(2,2,2-trifluoroethoxy)-2,3'-bipyridin-6-yl]methyl}amino)-3-methylbutan-1-ol;

(2R)-3-methyl-2-({[6'-(trifluoromethyl)-2,3'-bipyridin-6-yl]methyl}amino)butan-1-ol;

(2R)-2-({[3-fluoro-6-(quinolin-3-yl)pyridin-2-yl]methyl}amino)-3-methylbutan-1-ol;

(2R)-2-({[5-fluoro-5'-(trifluoromethyl)-2,2'-bipyridin-6-yl]methyl}amino)-3-methylbutan-1-ol;

(2R)-2-cyclopropyl-2-({[5-fluoro-6'-(trifluoromethyl)-2,3'-bipyridin-6-yl]methyl}amino)-ethanol;

(2R)-2-cyclopropyl-2-({[5-fluoro-6'-(2,2,2-trifluoroethoxy)-2,3'-bipyridin-6-yl]methyl}-amino )ethanol;

(2R)-2-({[5-fluoro-6'-(trifluoromethyl)-2,3'-bipyridin-6-yl]methyl}amino)butan-1-ol;

(2R)-2-({[5-fluoro-6'-(trifluoromethyl)-2,3'-bipyridin-6-yl]methyl}amino)pentan-1-ol;

(2R)-2-cyclohexyl-2-({[5-fluoro-6'-(trifluoromethyl)-2,3'-bipyridin-6-yl]methyl}amino)-ethanol;

(2R)-2-({[5-fluoro-6'-(trifluoromethyl)-2,3'-bipyridin-6-yl]methyl}amino)-3,3-dimethylbutan-1-ol;

3-({[5-fluoro-6'-(trifluoromethyl)-2,3'-bipyridin-6-yl]methyl}amino)butan-2-ol;

(3R)-3-({[5-fluoro-6'-(trifluoromethyl)-2,3'-bipyridin-6-yl]methyl}amino)-2,4-dimethylpentan-2-ol;

3-({[5-fluoro-6'-(trifluoromethyl)-2,3'-bipyridin-6-yl]methyl}amino)-4-methylpentan-2-ol;

(2R)-2-({[5-fluoro-6'-(trifluoromethyl)-2,3'-bipyridin-6-yl]methyl}amino)-3-methylbutan-1-ol;
(2R)-2-({[5-chloro-6'-(trifluoromethyl)-2,3'-bipyridin-6-yl]methyl}amino)-3-methylbutan-1-ol;
(2R)-3-methyl-2-({[5-methyl-6'-(trifluoromethyl)-2,3'-bipyridin-6-yl]methyl}amino)butan-1-ol;
(2R)-2-({[5-methoxy-6'-(trifluoromethyl)-2,3'-bipyridin-6-yl]methyl}amino)-3-methylbutan-1-ol;
(2R)-2-[({3-fluoro-6-[2-(trifluoromethyl)pyrimidin-5-yl]pyridin-2-yl}methyl)amino]-3-methylbutan-1-ol;
(2R)-2-[({3-fluoro-6-[2-(2,2,2-trifluoroethoxy)pyrimidin-5-yl]pyridin-2-yl}methyl)amino]-3-methylbutan-1-ol;
(3R)-3-({[5-fluoro-6'-(trifluoromethyl)-2,3'-bipyridin-6-yl]methyl}amino)pentan-2-ol;
(R)-2-((5-fluoro-6'-(trifluoromethyl)-2,3'-bipyridin-6-yl)methylamino)-3-methylbutanamide;
(2R)-2-({[4,6'-bis(trifluoromethyl)-2,3'-bipyridin-6-yl]methyl}amino)-3-methylbutan-1-ol;
(S)-2-((5-fluoro-6'-(trifluoromethyl)-2,3'-bipyridin-6-yl)methylamino)-3-methylbutanamide;
(2S,3R)-2-((5-fluoro-6'-(trifluoromethyl)-2,3'-bipyridin-6-yl)methylamino)-3-hydroxybutanamide;
(2R,3R)-2-({[5-fluoro-6'-(trifluoromethyl)-2,3'-bipyridin-6-yl]methyl}amino)butane-1,3-diol;
(1S,2S)-2-({[5-fluoro-6'-(trifluoromethyl)-2,3'-bipyridin-6-yl]methyl}amino)cyclohexanol;
(1R,2S)-2-({[5-fluoro-6'-(trifluoromethyl)-2,3'-bipyridin-6-yl]methyl}amino)cyclohexanol;
$N^2$-{[5-fluoro-6'-(trifluoromethyl)-2,3'-bipyridin-6-yl]methyl}-N-naphthalen-2-yl-L-threoninamide;
(2R)-2-({[6-(1-benzothiophen-2-yl)-3-fluoropyridin-2-yl]methyl}amino)-3-methylbutan-1-ol;
(2R)-2-({[6-(1,3-benzothiazol-5-yl)-3-fluoropyridin-2-yl]methyl}amino)-3-methylbutan-1-ol;
(2R)-2-({[6-(5-chlorothiophen-2-yl)-3-fluoropyridin-2-yl]methyl}amino)-3-methylbutan-1-ol;
(2R)-2-({[3-fluoro-6-(5-methylthiophen-2-yl)pyridin-2-yl]methyl}amino)-3-methylbutan-1-ol;
(2R)-2-({[3-fluoro-6-(1-methyl-1H-indol-5-yl)pyridin-2-yl]methyl}amino)-3-methylbutan-1-ol;
(2R)-2-({[3-fluoro-6-(1-methyl-1H-indol-2-yl)pyridin-2-yl]methyl}amino)-3-methylbutan-1-ol;
(2R)-2-[({6-[1-(1,3-dioxolan-2-ylmethyl)-1H-pyrazol-4-yl]-3-fluoropyridin-2-yl}methyl)-amino]-3-methylbutan-1-ol;
(2R)-2-({[3-fluoro-6-(furan-3-yl)pyridin-2-yl]methyl}amino)-3-methylbutan-1-ol;
(2R)-2-({[3-fluoro-6-(1-methyl-1H-pyrazol-5-yl)pyridin-2-yl]methyl}amino)-3-methylbutan-1-ol;
(2R)-2-({[5-fluoro-5'-methyl-6'-(morpholin-4-yl)-2,3'-bipyridin-6-yl]methyl}amino)-3-methylbutan-1-ol;
(2R)-2-({[5-fluoro-6'-(4-methylpiperazin-1-yl)-2,3'-bipyridin-6-yl]methyl}amino)-3-methylbutan-1-ol;
(2R)-2-({[6-(1-benzothiophen-5-yl)-3-fluoropyridin-2-yl]methyl}amino)-3-methylbutan-1-ol;
(2R)-2-({[6-(1-benzofuran-5-yl)-3-fluoropyridin-2-yl]methyl}amino)-3-methylbutan-1-ol;
tert-butyl 4-(benzyloxy)-2-[5-fluoro-6-({[(2R)-1-hydroxy-3-methylbutan-2-yl]amino}methyl)pyridin-2-yl]-1H-indole-1-carboxylate;
(2R)-2-[({6-[2-(dimethylamino)pyrimidin-5-yl]-3-fluoropyridin-2-yl}methyl)amino]-3-methylbutan-1-ol;
tert-butyl 2-[5-fluoro-6-({[(2R)-1-hydroxy-3-methylbutan-2-yl]amino}methyl)pyridin-2-yl]-1H-indole-1-carboxylate;
(2R)-2-({[3-fluoro-6-(1H-indol-2-yl)pyridin-2-yl]methyl}amino)-3-methylbutan-1-ol;
(2R)-2-{[(5'-chloro-5-fluoro-2,3'-bipyridin-6-yl)methyl]amino}-3-methylbutan-1-ol;
(2R)-2-({[3-fluoro-6-(4-methyl-2-phenyl-1,3-thiazol-5-yl)pyridin-2-yl]methyl}amino)-3-methylbutan-1-ol;
(2R)-2-[({3-fluoro-6-[5-(trifluoromethyl)thiophen-2-yl]pyridin-2-yl}methyl)amino]-3-methylbutan-1-ol;
(2R)-2-[({3-fluoro-6-[1-methyl-3-(trifluoromethyl)-1H-pyrazol-5-yl]pyridin-2-yl}methyl)amino]-3-methylbutan-1-ol;
(2R)-2-({[5-fluoro-5'-(trifluoromethyl)-2,3'-bipyridin-6-yl]methyl}amino)-3-methylbutan-1-ol;
(2R)-2-({[6-(1-benzyl-1H-pyrazol-4-yl)-3-fluoropyridin-2-yl]methyl}amino)-3-methylbutan-1-ol;
(2R)-2-({[6'-(dimethylamino)-5-fluoro-2,3'-bipyridin-6-yl]methyl}amino)-3-methylbutan-1-ol;
(2R)-2-({[6'-(cyclopropylmethoxy)-5-fluoro-2,3'-bipyridin-6-yl]methyl}amino)-3-methylbutan-1-ol;
(2R)-2-({[3-fluoro-6-(3-methylthiophen-2-yl)pyridin-2-yl]methyl}amino)-3-methylbutan-1-ol;
(2R)-2-({[5-fluoro-6'-(trifluoromethyl)-2,3'-bipyridin-6-yl]methyl}amino)-2-phenylethanol;
$N^2$-{[5-fluoro-6'-(trifluoromethyl)-2,3'-bipyridin-6-yl]methyl}-L-leucinamide;
(2S)-2-({[5-fluoro-6'-(trifluoromethyl)-2,3'-bipyridin-6-yl]methyl}amino)-4-methylpentan-1-ol ; and
(2S)-2-({[5-fluoro-6'-(trifluoromethyl)-2,3'-bipyridin-6-yl]methyl}amino)-2-phenylethanol.

8. A pharmaceutical composition comprising a therapeutically effective amount of a compound of formula (I) according to claim 1 or a pharmaceutically acceptable salt, solvate, or salt of a solvate thereof, in combination with a pharmaceutically acceptable carrier.

9. A method for treating pain in a subject in need of such treatment comprising administering to the subject a therapeutically effective amount of a compound of formula (I) according to claim 1, or a pharmaceutically acceptable salt, solvate, or salt of a solvate thereof.

\* \* \* \* \*